(12) United States Patent
Galemmo, Jr. et al.

(10) Patent No.: US 6,271,237 B1
(45) Date of Patent: Aug. 7, 2001

(54) NITROGEN CONTAINING HEROMATICS WITH ORTHO-SUBSTITUTED P1S AS FACTOR XA INHABITORS

(75) Inventors: Robert A. Galemmo, Jr., Collegeville, PA (US); Lori L. Bostrom, Newark, DE (US); Donald J. P. Pinto, Newark, DE (US); Karen A. Rossi, Newark, DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/217,336

(22) Filed: Dec. 21, 1998

Related U.S. Application Data
(60) Provisional application No. 60/068,491, filed on Dec. 22, 1997, and provisional application No. 60/101,075, filed on Sep. 18, 1998.

(51) Int. Cl.[7] ............ A61K 31/415; A61K 31/506; C07D 231/14; C07D 403/12
(52) U.S. Cl. .............. 514/256; 514/235.8; 514/236.5; 514/341; 514/397; 514/400; 514/406; 544/139; 544/140; 544/333; 546/274.7; 546/275.1; 548/111; 548/251; 548/254; 548/312.7; 548/314.7; 548/333.5; 548/364.1; 548/365.1; 548/374.1
(58) Field of Search .................. 514/406, 235.8, 514/236.5, 256, 341, 397, 400; 548/251, 254, 111, 312.7, 314.7, 333.5, 364.1, 365.1, 374.1; 544/134, 140, 333; 546/274.7, 375.1

(56) References Cited

U.S. PATENT DOCUMENTS

| | | | |
|---|---|---|---|
| 4,214,090 | 7/1980 | Huppatz | 548/377 |
| 4,950,668 | 8/1990 | Okada et al. | 514/232.2 |
| 5,082,949 | 1/1992 | Sohn et al. | 548/378 |
| 5,463,071 | 10/1995 | Himmelsbach et al. | 548/251 |
| 5,550,147 | 8/1996 | Matsuo et al. | 514/406 |
| 5,612,353 | 3/1997 | Ewing et al. | 514/309 |
| 5,658,909 | 8/1997 | DeBernardis et al. | 514/252 |

FOREIGN PATENT DOCUMENTS

| | | |
|---|---|---|
| 0554829 | 8/1993 | (EP) . |
| 4247081 | 3/1992 | (JP) . |
| 9518111 | 7/1995 | (WO) . |
| 9732583 | 9/1997 | (WO) . |
| 9747299 | 12/1997 | (WO) . |
| 9857937 | 12/1998 | (WO) . |
| 9828269 | 7/1999 | (WO) . |

*Primary Examiner*—Richard L. Raymond
(74) *Attorney, Agent, or Firm*—David H. Vance

(57) ABSTRACT

The present application describes nitrogen containing heteroaromatics with ortho-substituted P1's and derivatives thereof of formula I:

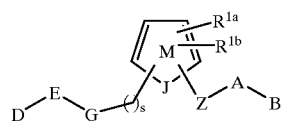

or pharmaceutically acceptable salt or prodrug forms thereof, wherein J is N or NH and D is substituted ortho to G on E and may be $CH_2NH_2$, which are useful as inhibitors of factor Xa.

42 Claims, No Drawings

NITROGEN CONTAINING HETEROMATICS WITH ORTHO-SUBSTITUTED P1S AS FACTOR XA INHABITORS

This application claims the benefit of U.S. Provisional Application No. 60/068,491, filed Dec. 22, 1997 and U.S. Provisional Application No. 60/101,075, filed Sep. 18, 1998.

FIELD OF THE INVENTION

This invention relates generally to nitrogen containing heteroaromatics, with ortho-substituted P1 groups, which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

WO 95/18111 addresses fibrinogen receptor antagonists, containing basic and acidic termini, of the formula:

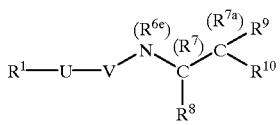

wherein $R^1$ represents the basic termini, U is an alkylene or heteroatom linker, V may be a heterocycle, and the right hand portion of the molecule represents the acidic termini. The presently claimed compounds do not contain the acidic termini of WO 95/18111.

In U.S. Pat. No. 5,463,071, Himmelsbach et al depict cell aggregation inhibitors which are 5-membered heterocycles of the formula:

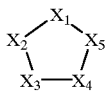

wherein the heterocycle may be aromatic and groups A—B—C— and F—E—D— are attached to the ring system. A—B—C— can be a wide variety of substituents including a basic group attached to an aromatic ring. The F—E—D— group, however, would appear to be an acidic functionality which differs from the present invention. Furthermore, use of these compounds as inhibitors of factor Xa is not discussed.

Baker et al, in U.S. Pat. No. 5,317,103, discuss 5-HT$_1$ agonists which are indole substituted five-membered heteroaromatic compounds of the formula:

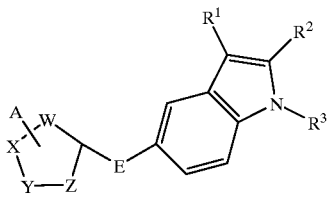

wherein $R^1$ may be pyrrolidine or piperidine and A may be a basic group including amino and amidino. Baker et al, however, do not indicate that A can be a substituted ring system like that contained in the presently claimed heteroaromatics.

Baker et al, in WO 94/02477, discuss 5-HT$_1$ agonists which are imidazoles, triazoles, or tetrazoles of the formula:

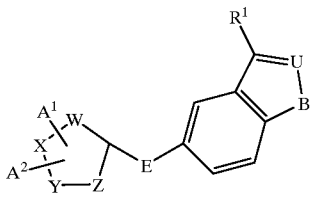

wherein $R^1$ represents a nitrogen containing ring system or a nitrogen substituted cyclobutane, and A may be a basic group including amino and amidino. Baker et al, however, do not indicate that A can be a substituted ring system like that contained in the presently claimed heteroaromatics.

Illig et al, in WO 97/47299, illustrate amidino and guanidino heterocycle protease inhibitors of the formula:

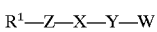

wherein $R^1$ can be a substituted aryl group, Z is a two carbon linker containing at least one heteroatome, X is a heterocycle, Y is an optional linker and W is an amidino or guanidino containing group. Compounds of this sort are not considered part of the present invention.

Jackson et al, in WO 97/32583, describe cytokine inhibitors useful for inhibiting angiogenesis. These inhibitors include imidazoles of the formula:

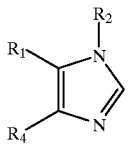

wherein $R_1$ is a variety of heteroaryl groups, $R_4$ is phenyl, naphthyl, or a heteroaryl group, and $R_2$ can be a wide variety of groups. Jackson et al do not teach inhibition of factor Xa. Furthermore, the imidazoles of Jackson et al are not considered part of the present invention.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel nitrogen containing aromatic heterocycles, with ortho-substituted P1 groups, which are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

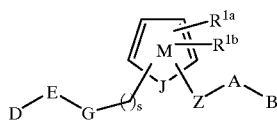

I or pharmaceutically acceptable salt or prodrug forms thereof, wherein A, B, D, E, G, J, M, $R^{1a}$, $R^{1b}$, and s are defined below, are effective factor Xa inhibitors.

DETAILED DESCRIPTION OF PREFERRED EMBODIMENTS

[1] Thus, in a first embodiment, the present invention provides novel compounds of formula I:

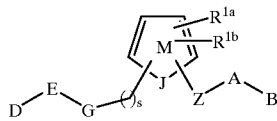

I or a stereoisomer or pharmaceutically acceptable salt thereof, wherein;

ring M contains, in addition to J, 0–3 N atoms, provided that if M contains 2 N atoms then $R^{1b}$ is not present and if M contains 3 N atoms then $R^{1a}$ and $R^{1b}$ are not present;

J is N or NH;

D is selected from CN, C(=$NR^8$)$NR^7R^9$, NHC(=$NR^8$)$NR^7R^9$, $NR^8$CH(=$NR^7$), C(O)$NR^7R^8$, and (C$R^8R^9$)$_t$$NR^7R^8$, provided that D is substituted ortho to G on E;

E is selected from phenyl, pyridyl, pyrimidyl, pyrazinyl, pyridazinyl, and piperidinyl substituted with 1–2 R;

R is selected from H, Cl, F, Br, I, (CH$_2$)$_r$OR$^3$, C$_{1-4}$ alkyl, OCF$_3$, CF$_3$, C(O)$NR^7R^8$, and (C$R^8R^9$)$_t$$NR^7R^8$;

G is absent or is selected from NHCH$_2$, OCH$_2$, and SCH$_2$, provided that when s is 0, then G is attached to a carbon atom on ring M;

Z is selected from a C$_{1-4}$ alkylene, (CH$_2$)$_r$O(CH$_2$)$_r$, (CH$_2$)$_r$ NR$^3$(CH$_2$)$_r$, (CH$_2$)$_r$C(O)(CH$_2$)$_r$, (CH$_2$)$_r$C(O)O(CH$_2$)$_r$, (CH$_2$)$_r$OC(O)(CH$_2$)$_r$, (CH$_2$)$_r$C(O)NR$^3$(CH$_2$)$_r$, (CH$_2$)$_r$ NR$^3$C(O)(CH$_2$)$_r$, (CH$_2$)$_r$OC(O)O(CH$_2$)$_r$, (CH$_2$)$_r$ OC(O)NR$^3$(CH$_2$)$_r$, (CH$_2$)$_r$NR$^3$C(O)O(CH$_2$)$_r$, (CH$_2$)$_r$ NR$^3$C(O)NR$^3$(CH$_2$)$_r$, (CH$_2$)$_r$S(O)$_p$(CH$_2$)$_r$, (CH$_2$)$_r$ SO$_2$NR$^3$(CH$_2$)$_r$, (CH$_2$)$_r$NR$^3$SO$_2$(CH$_2$)$_r$, and (CH$_2$)$_r$ NR$^3$SO$_2$NR$^3$(CH$_2$)$_r$, provided that Z does not form a N—N, N—O, N—S, NCH$_2$N, NCH$_2$O, or NCH$_2$S bond with ring M or group A;

$R^{1a}$ and $R^{1b}$ are independently absent or selected from —(CH$_2$)$_r$—$R^{1'}$, —CH=CH—$R^{1'}$, NCH$_2$$R^{1''}$, OCH$_2$$R^{1''}$, SCH$_2$$R^{1''}$, NH(CH$_2$)$_2$(CH$_2$)$_r$$R^{1'}$, O(CH$_2$)$_2$ (CH$_2$)$_r$$R^{1'}$, and S(CH$_2$)$_2$(CH$_2$)$_r$$R^{1'}$;

alternatively, $R^{1a}$ and $R^{1b}$, when attached to adjacent carbon atoms, together with the atoms to which they are attached form a 5–8 membered saturated, partially saturated or unsaturated ring substituted with 0–2 $R^4$ and which contains from 0–2 heteroatoms selected from the group consisting of N, O and S;

$R^{1'}$ is selected from H, C$_{1-3}$ alkyl, F, Cl, Br, I, —CN, —CHO, (CF$_2$)$_r$CF$_3$, (CH$_2$)$_r$OR$^2$, NR$^2R^{2a}$, C(O)R$^{2c}$, OC(O)R$^2$, (CF$_2$)$_r$CO$_2$R$^{2c}$, S(O)$_p$R$^{2b}$, NR$^2$(CH$_2$)$_r$OR$^2$, CH(=NR$^{2c}$)NR$^2R^{2a}$, NR$^2$C(O)R$^{2b}$, NR$^2$C(O)NHR$^{2b}$, NR$^2$C(O)$_2$R$^{2a}$, OC(O)NR$^{2a}R^{2b}$, C(O)NR$^2R^{2a}$, C(O)NR$^2$(CH$_2$)$_r$OR$^2$, SO$_2$NR$^2R^{2a}$, NR$^2$SO$_2$R$^{2b}$, C$_{3-6}$ carbocyclic residue substituted with 0–2 R$^4$, and 5–10 membered heterocyclic system containing from 1–4 heteroatoms selected from the group consisting of N, O, and S substituted with 0–2 R$^4$;

$R^{1''}$ is selected from H, CH(CH$_2$OR$^2$)$_2$, C(O)R$^{2c}$, C(O)NR$^2R^{2a}$, S(O)R$^{2b}$, S(O)$_2$R$^{2b}$, and SO$_2$NR$^2R^{2a}$;

$R^2$, at each occurrence, is selected from H, CF$_3$, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

$R^{2a}$, at each occurrence, is selected from H, CF$_3$, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

$R^{2b}$, at each occurrence, is selected from CF$_3$, C$_{1-4}$ alkoxy, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

$R^{2c}$, at each occurrence, is selected from CF$_3$, OH, C$_{1-4}$ alkoxy, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

alternatively, $R^2$ and $R^{2a}$ combine to form a 5 or 6 membered saturated, partially saturated or unsaturated ring substituted with 0–2 R$^{4b}$ which contains from 0–1 additional heteroatoms selected from the group consisting of N, O, and S;

alternatively, $R^2$ and $R^{2a}$, together with the atom to which they are attached, combine to form a 5 or 6 membered saturated, partially saturated or unsaturated ring substituted with 0–2 R$^{4b}$ and containing from 0–1 additional heteroatoms selected from the group consisting of N, O, and S;

$R^3$, at each occurrence, is selected from H, C$_{1-4}$ alkyl, and phenyl;

$R^{3a}$, at each occurrence, is selected from H, C$_{1-4}$ alkyl, and phenyl;

$R^{3b}$, at each occurrence, is selected from H, C$_{1-4}$ alkyl, and phenyl;

$R^{3c}$, at each occurrence, is selected from C$_{1-4}$ alkyl, and phenyl;

A is selected from:

C$_{3-10}$ carbocyclic residue substituted with 0–2 R$^4$, and

5–10 membered heterocyclic system containing from 1–4 heteroatoms selected from the group consisting of N, O, and S substituted with 0–2 $R^4$;

B is selected from:
X—Y, $NR^2R^{2a}$, $C(=NR^2)NR^2R^{2a}$, $NR^2C(=NR^2)NR^2R^{2a}$,
$C_{3-10}$ carbocyclic residue substituted with 0–2 $R^{4a}$, and
5–10 membered heterocyclic system containing from 1–4 heteroatoms selected from the group consisting of N, O, and S substituted with 0–2 $R^{4a}$;

X is selected from $C_{1-4}$ alkylene, $-CR^2(CR^2R^{2b})(CH_2)_t-$, $-C(O)-$, $-C(=NR^{1''})-$, $-CR^2(NR^{1''}R^2)-$, $-CR^2(OR^2)-$, $-CR^2(SR^2)-$, $-C(O)CR^2R^{2a}-$, $-CR^2R^{2a}C(O)-$, $-S(O)_p-$, $-S(O)_pCR^2R^{2a}-$, $-CR^2R^{2a}S(O)_p-$, $-S(O)_2NR^2-$, $-NR^2S(O)_2-$, $-NR^2S(O)_2CR^2R^{2a}-$, $-CR^2R^{2a}S(O)_2NR^2-$, $-NR^2S(O)_2NR^2-$, $-C(O)NR^2-$, $-NR^2C(O)-$, $-C(O)NR^2CR^2R^{2a}-$, $-NR^2C(O)CR^2R^{2a}-$, $-CR^2R^{2a}C(O)NR^2-$, $-CR^2R^{2a}NR^2C(O)-$, $-NR^2C(O)O-$, $-OC(O)NR^2-$, $-NR^2C(O)NR^2-$, $-NR^2-$, $-NR^2CR^2R^{2a}-$, $-CR^2R^{2a}NR^2-$, O, $-CR^2R^{2a}O-$, and $-OCR^2R^{2a}-$;

Y is selected from:
$(CH_2)_rNR^2R^{2a}$, provided that X—Y do not form a N—N, O—N, or S—N bond,
$C_{3-10}$ carbocyclic residue substituted with 0–2 $R^{4a}$, and
5–10 membered heterocyclic system containing from 1–4 heteroatoms selected from the group consisting of N, O, and S substituted with 0–2 $R^{4a}$;

$R^4$, at each occurrence, is selected from H, =O, $(CH_2)_rOR^2$, F, Cl, Br, I, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)NR^2R^{2a}$, $CH(=NR^2)NR^2R^{2a}$, $CH(=NS(O)_2R^5)NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2-C_{1-4}$ alkyl, $NR^2SO_2R^5$, $S(O)_pR^5$, $(CF_2)_rCF_3$, $NCH_2R^{1''}$, $OCH_2R^{1''}$, $SCH_2R^{1''}$, $N(CH_2)_2(CH_2)_tR^{1''}$, $O(CH_2)_2(CH_2)_tR^{1''}$, and $S(CH_2)_2(CH_2)_tR^{1''}$,
alternatively, one $R^4$ is a 5–6 membered aromatic heterocycle containing from 1–4 heteroatoms selected from the group consisting of N, O, and S;

$R^{4a}$, at each occurrence, is selected from H, =O, $(CH_2)_rOR^2$, $(CH_2)_r-F$, $(CH_2)_r-Br$, $(CH_2)_r-Cl$, Cl, Br, F, I, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $C(O)NH(CH_2)_2NR^2R^{2a}$, $NR^2C(O)NR^2R^{2a}$, $CH(=NR^2)NR^2R^{2a}$, $NHC(=NR^2)NR^2R^{2a}$, $SO_2NR^2R^{2a}$, $NR^2SO_2NR^2R^{2a}$, $NR^2SO_2-C_{1-4}$ alkyl, $C(O)NHSO_2-C_{1-4}$ alkyl, $NR^2SO_2R^5$, $S(O)_pR^5$, and $(CF_2)_rCF_3$;
alternatively, one $R^{4a}$ is a 5–6 membered aromatic heterocycle containing from 1–4 heteroatoms selected from the group consisting of N, O, and S substituted with 0–1 $R^5$;

$R^{4b}$, at each occurrence, is selected from H, =O, $(CH_2)_rOR^3$, F, Cl, Br, I, $C_{1-4}$ alkyl, —CN, $NO_2$, $(CH_2)_rNR^3R^{3a}$, $(CH_2)_rC(O)R^3$, $(CH_2)_rC(O)OR^{3c}$, $NR^3C(O)R^{3a}$, $C(O)NR^3R^{3a}$, $NR^3C(O)NR^3R^{3a}$, $CH(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2-C_{1-4}$ alkyl, $NR^3SO_2CF_3$, $NR^3SO_2$-phenyl $S(O)_pCF_3$, $S(O)_p-C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

alternatively, $R^7$ and $R^8$ combine to form a 5 or 6 membered saturated, ring which contains from 0–1 additional heteroatoms selected from the group consisting of N, O, and S;

$R^9$, at each occurrence, is selected from H, $C_{1-6}$ alkyl and $(CH_2)_n$-phenyl;

n, at each occurrence, is selected from 0, 1, 2, and 3;
m, at each occurrence, is selected from 0, 1, and 2;
p, at each occurrence, is selected from 0, 1, and 2;
r, at each occurrence, is selected from 0, 1, 2, and 3;
s, at each occurrence, is selected from 0, 1, and 2; and,
t, at each occurrence, is selected from 0, 1, 2, and 3;

provided that D—E—G—$(CH_2)_s-$ and —Z—A—B are not both benzamidines.

[2] In a preferred embodiment, the present invention provides novel compounds of formulae Ia–Ih:

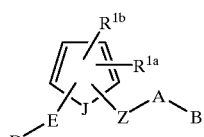

Ia

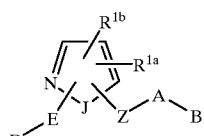

Ib

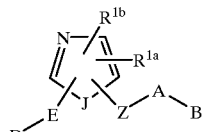

Ic

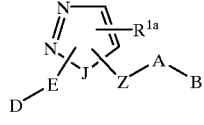

Id

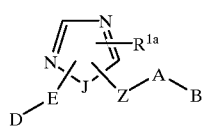

Ie

-continued

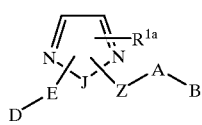

If

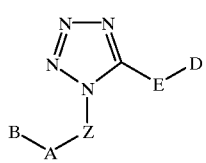

Ig

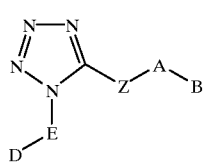

Ih wherein, groups D—E— and —Z—A—B are attached to adjacent atoms on the ring;

R is selected from H, Cl, F, Br, I, $(CH_2)_rOR^3$, $C_{1-4}$ alkyl, $OCF_3$, $CF_3$, $C(O)NR^7R^8$, and $(CR^8R^9)_rNR^7R^8$;

Z is selected from a $CH_2O$, $OCH_2$, $CH_2NH$, $NHCH_2$, $C(O)$, $CH_2C(O)$, $C(O)CH_2$, $NHC(O)$, $C(O)NH$, $CH_2S(O)_2$, $S(O)_2(CH_2)$, $SO_2NH$, and $NHSO_2$, provided that Z does not form a N—N, N—O, $NCH_2N$, or $NCH_2O$ bond with ring M or group A;

A is selected from one of the following carbocyclic and heterocyclic systems which are substituted with 0–2 $R^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is selected from: Y, X—Y, $NR^2R^{2a}$, $C(=NR^2)NR^2R^{2a}$, and $NR^2C(=NR^2)NR^2R^{2a}$;

X is selected from $C_{1-4}$ alkylene, —C(O)—, —C(=NR)—, —$CR^2(NR^2R^{2a})$—, —$C(O)CR^2R^{2a}$—, —$CR^2R^{2a}C(O)$, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is $NR^2R^{2a}$, provided that X—Y do not form a N—N or O—N bond;

alternatively, Y is selected from one of the following carbocyclic and heterocyclic systems which are substituted with 0–2 $R^{4a}$;

cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic roaryl ring systems:

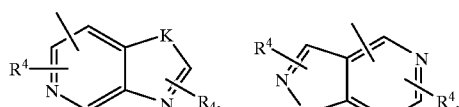

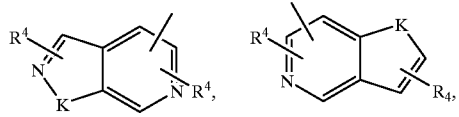

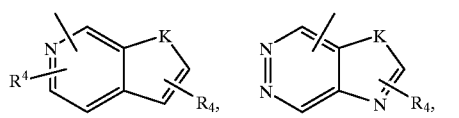

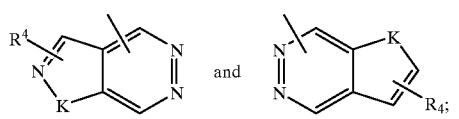

K is selected from O, S, NH, and N.

[3] In a more preferred embodiment, the present invention provides novel compounds of formulae IIa–IIf:

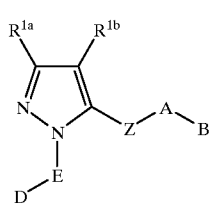

IIa

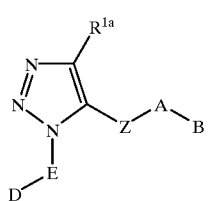

IIb

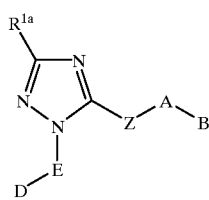

IIc

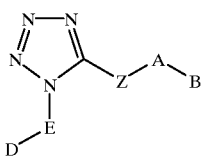

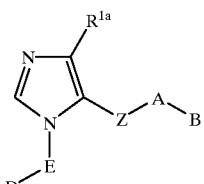

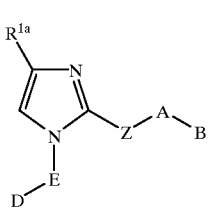

wherein;

Z is selected from a C(O), CH$_2$C(O), C(O)CH$_2$, NHC(O), C(O)NH, C(O)N(CH$_3$), CH$_2$S(O)$_2$, S(O)$_2$(CH$_2$), SO$_2$NH, and NHSO$_2$, provided that Z does not form a N—N or NCH$_2$N bond with ring M or group A.

[4] In an even more preferred embodiment, the present invention provides novel compounds of formulae IIa–IIf, wherein;

E is phenyl substituted with R or 2-pyridyl substituted with R;

D is selected from NH$_2$, NHCH$_3$, CH$_2$NH$_2$, CH$_2$NHCH$_3$, CH(CH$_3$)NH$_2$, and C(CH$_3$)$_2$NH$_2$, provided that D is substituted ortho to ring M on E; and, R is selected from H, OCH$_3$, Cl, and F.

[5] In a further preferred embodiment, the present invention provides novel compounds of formulae IIa–IIf, wherein;

D—E is selected from 2-aminophenyl, 2-methylaminophenyl, 2-aminomethylphenyl, 4-methoxy-2-aminophenyl, 4-methoxy-2-(methylamino)phenyl, 4-methoxy-2-aminomethylphenyl, 4-methoxy-2-(methylaminomethyl)phenyl, 4-methoxy-2-(1-aminoethyl)phenyl, 4-methoxy-2-(2-amino-2-propyl)phenyl, 4-Cl-2-aminophenyl, 4-Cl-2-(methylamino)phenyl, 4-Cl-2-aminomethylphenyl, 4-Cl-2-(methylaminomethyl)phenyl, 4-Cl-2-(1-aminoethyl)phenyl, 4-Cl-2-(2-amino-2-propyl)phenyl, 4-F-2-aminophenyl, 4-F-2-(methylamino)phenyl, 4-F-2-aminomethylphenyl, 4-F-2-(methylaminomethyl)phenyl, 4-F-2-(1-aminoethyl)phenyl, and 4-F-2-(2-amino-2-propyl)phenyl.

[6] In another even more preferred embodiment, the present invention provides novel compounds of formulae IIa–IIf, wherein;

Z is C(O)CH$_2$ and CONH, provided that Z does not form a N—N bond with group A;

A is selected from phenyl, pyridyl, and pyrimidyl, and is substituted with 0–2 R$^4$; and, B is selected from X—Y, phenyl, pyrrolidino, morpholino, 1,2,3-triazolyl, and imidazolyl, and is substituted with 0–1 R$^{4a}$;

R$^4$, at each occurrence, is selected from OH, (CH$_2$)$_r$OR$^2$, halo, C$_{1-4}$ alkyl, (CH$_2$)$_r$NR$^2$R$^{2a}$, and (CF$_2$)$_r$CF$_3$;

R$^{4a}$ is selected from C$_{1-4}$ alkyl, CF$_3$, S(O)$_p$R$^5$, SO$_2$NR$^2$R$^{2a}$, and 1-CF$_3$-tetrazol-2-yl;

R$^5$, at each occurrence, is selected from CF$_3$, C$_{1-6}$ alkyl, phenyl, and benzyl;

X is CH$_2$ or C(O); and,

Y is selected from pyrrolidino and morpholino.

[7] In another further preferred embodiment, the present invention provides novel compounds of formulae IIa–IIf, wherein;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-CF$_3$-phenyl, 2-(aminosulfonyl)phenyl, 2-(methylaminosulfonyl)phenyl, 2-(dimethylaminosulfonyl)phenyl, 1-pyrrolidinocarbonyl, 2-(methylsulfonyl)phenyl, 4-morpholino, 2-(1'-CF$_3$-tetrazol-2-yl)phenyl, 4-morpholinocarbonyl, 2-methyl-1-imidazolyl, 5-methyl-1-imidazolyl, 2-methylsulfonyl-1-imidazolyl and, 5-methyl-1,2,3-triazolyl.

[8] In another even more preferred embodiment, the present invention provides novel compounds of formulae IIa–IIf, wherein;

E is phenyl substituted with R or 2-pyridyl substituted with R;

D is selected from NH$_2$, NHCH$_3$, CH$_2$NH$_2$, CH$_2$NHCH$_3$, CH(CH$_3$)NH$_2$, and C(CH$_3$)$_2$NH$_2$, provided that D is substituted ortho to ring M on E; and, R is selected from H, OCH$_3$, Cl, and F;

Z is C(O)CH$_2$ and CONH, provided that Z does not form a N—N bond with group A;

A is selected from phenyl, pyridyl, and pyrimidyl, and is substituted with 0–2 R$^4$; and, B is selected from X—Y, phenyl, pyrrolidino, morpholino, 1,2,3-triazolyl, and imidazolyl, and is substituted with 0–1 R$^{4a}$;

R$^4$, at each occurrence, is selected from OH, (CH$_2$)$_r$OR$^2$, halo, C$_{1-4}$ alkyl, (CH$_2$)$_r$NR$^2$R$^{2a}$, and (CF$_2$)$_r$CF$_3$;

R$^{4a}$ is selected from C$_{1-4}$ alkyl, CF$_3$, S(O)$_p$R$^5$, SO$_2$NR$^2$R$^{2a}$, and 1-CF$_3$-tetrazol-2-yl;

R$^5$, at each occurrence, is selected from CF$_3$, C$_{1-6}$ alkyl, phenyl, and benzyl;

X is CH$_2$ or C(O); and,

Y is selected from pyrrolidino and morpholino.

[9] In another further preferred embodiment, the present invention provides novel compounds of formulae IIa–IIf, wherein;

D—E is selected from 2-aminophenyl, 2-methylaminophenyl, 2-aminomethylphenyl, 4-methoxy-2-aminophenyl, 4-methoxy-2-(methylamino)phenyl, 4-methoxy-2-aminomethylphenyl, 4-methoxy-2-(methylaminomethyl)phenyl, 4-methoxy-2-(1-aminoethyl)phenyl, 4-methoxy-2-(2-amino-2-propyl)phenyl, 4-Cl-2-aminophenyl, 4-Cl-2-(methylamino)phenyl, 4-Cl-2-aminomethylphenyl, 4-Cl-2-(methylaminomethyl)phenyl, 4-Cl-2-(1-aminoethyl)phenyl, 4-Cl-2-(2-amino-2-propyl)phenyl, 4-F-2-aminophenyl, 4-F-2-(methylamino)phenyl, 4-F-2-aminomethylphenyl, 4-F-2-(methylaminomethyl)phenyl, 4-F-2-(1-aminoethyl) phenyl, and 4-F-2-(2-amino-2-propyl)phenyl;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-$CF_3$-phenyl, 2-(aminosulfonyl)phenyl, 2-(methylaminosulfonyl) phenyl, 2-(dimethylaminosulfonyl)phenyl, 1-pyrrolidinocarbonyl, 2-(methylsulfonyl)phenyl, 4-morpholino, 2-(1'-$CF_3$-tetrazol-2-yl)phenyl, 4-morpholinocarbonyl, 2-methyl-1-imidazolyl, 5-methyl-1-imidazolyl, 2-methylsulfonyl-1-imidazolyl and, 5-methyl-1,2,3-triazolyl.

[10] In a still further preferred embodiment, the present invention provides a novel compound of formula IIa.

[11] In another still further preferred embodiment, the present invention provides a novel compound of formula IIb.

[12] In another still further preferred embodiment, the present invention provides a novel compound of formula IIc.

[13] In another still further preferred embodiment, the present invention provides a novel compound of formula IId.

[14] In another still further preferred embodiment, the present invention provides a novel compound of formula IIe.

[15] In another still further preferred embodiment, the present invention provides a novel compound of formula IIf.

[16] In another even more preferred embodiment, the present invention provides novel compounds of formulae IIa–IIf, wherein;

D is selected from —CN, C(=$NR^8$)$NR^7R^9$, C(O)$NR^7R^8$, $NR^7R^8$, and $CH_2NR^7R^8$, provided that D is substituted ortho to ring M on E;

E is phenyl substituted with R or pyridyl substituted with R;

R is selected from H, Cl, F, $OR^3$, $CH_3$, $CH_2CH_3$, $OCF_3$, $CF_3$, $NR^7R^8$, and $CH_2NR^7R^8$;

Z is selected from C(O), $CH_2$C(O), C(O)$CH_2$, NHC(O), and C(O)NH, provided that Z does not form a N—N bond with ring M or group A;

$R^{1a}$ and $R^{1b}$ are independently absent or selected from —($CH_2$)$_r$—$R^{1'}$, $NCH_2R^{1'}$, $OCH_2R^{1'}$, $SCH_2R^{1'}$, N($CH_2$)$_2$($CH_2$)$_rR^{1'}$, O($CH_2$)$_2$($CH_2$)$_rR^{1'}$, and S($CH_2$)$_2$($CH_2$)$_rR^{1'}$, or combined to form a 5–8 membered saturated, partially saturated or unsaturated ring substituted with 0–2 $R^4$ and which contains from 0–2 heteroatoms selected from the group consisting of N, O, and S;

$R^{1'}$, at each occurrence, is selected from H, $C_{1-3}$ alkyl, halo, ($CF_2$)$_rCF_3$, $OR^2$, $NR^2R^{2a}$, C(O)$R^{2c}$, ($CF_2$)$_r$$CO_2R^{2c}$, S(O)$_pR^{2b}$, $NR^2$($CH_2$)$_rOR^2$, $NR^2$C(O)$R^{2b}$, $NR^2$C(O)$_2R^{2b}$, C(O)$NR^2R^{2a}$, $SO_2NR^2R^{2a}$, and $NR^2SO_2R^{2b}$;

A is selected from one of the following carbocyclic and heterocyclic systems which are substituted with 0–2 $R^4$;
 phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, and imidazolyl;

B is selected from: Y, X—Y, $NR^2R^{2a}$, C(=$NR^2$)$NR^2R^{2a}$, and $NR^2$C(=$NR^2$)$NR^2R^{2a}$;

X is selected from $CH_2$, —$CR^2$($CR^2R^{2b}$)($CH_2$)$_t$—, —C(O)—, —C(=NR)—, —CH($NR^2R^{2a}$)—, —C(O) $NR^2$—, —$NR^2$C(O)—, —$NR^2$C(O)$NR^2$—, —$NR^2$—, and O;

Y is $NR^2R^{2a}$, provided that X—Y do not form a N—N or O—N bond;

alternatively, Y is selected from one of the following carbocyclic and heterocyclic systems which are substituted with 0–2 $R^{4a}$;
 phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

$R^4$, at each occurrence, is selected from =O, OH, Cl, F, $C_{1-4}$ alkyl, ($CH_2$)$_rNR^2R^{2a}$, ($CH_2$)$_rC(O)R^{2b}$, $NR^2C(O)R^{2b}$, C(O)$NR^2R^{2a}$, CH(=NH)$NH_2$, NHC(=NH)$NH_2$, $SO_2NR^2R^{2a}$, $NR^2SO_2$—$C_{1-4}$ alkyl, $NR^2SO_2R^5$, S(O)$_pR^5$, and ($CF_2$)$_rCF_3$;

$R^{4a}$, at each occurrence, is selected from =O, OH, Cl, F, $C_{1-4}$ alkyl, ($CH_2$)$_rNR^2R^{2a}$, ($CH_2$)$_rC(O)R^{2b}$, $NR^2C(O)R^{2b}$, C(O)$NR^2R^{2a}$, CH(=NH)$NH_2$, NHC(=NH)$NH_2$, $SO_2NR^2R^{2a}$, $NR^2SO_2$—$C_{1-4}$ alkyl, $NR^2SO_2R^5$, S(O)$_pR^5$, ($CF_2$)$_rCF_3$, and 1-$CF_3$-tetrazol-2-yl;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, =O, OH, $OR^2$, Cl, F, $CH_3$, CN, $NO_2$, ($CH_2$)$_rNR^2R^{2a}$, ($CH_2$)$_rC(O)R^{2b}$, $NR^2C(O)R^{2b}$, CH(=NH)$NH_2$, NHC(=NH) $NH_2$, and $SO_2NR^2R^{2a}$;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, benzyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and benzyl; and alternatively, $R^7$ and $R^8$ combine to form a morpholino group; and, $R^9$, at each occurrence, is selected from H, $C_{1-6}$ alkyl and benzyl.

[17] In a another further preferred embodiment, the present invention provides novel compounds of formulae IIa–IIf, wherein;

E is phenyl substituted with R or 2-pyridyl substituted with R;

R is selected from H, Cl, F, $OCH_3$, $CH_3$, $OCF_3$, $CF_3$, $NH_2$, and $CH_2NH_2$;

Z is selected from a C(O)$CH_2$ and C(O)NH, provided that Z does not form a N—N bond with group A;

$R^{1a}$ is selected from H, $CH_3$, $CH_2CH_3$, Cl, F, $CF_3$, $OCH_3$, $NR^2R^{2a}$, S(O)$_pR^{2b}$, $CH_2S(O)_pR^{2b}$, $CH_2NR^2S(O)_pR^{2b}$, C(O)$R^{2c}$, $CH_2$C(O)$R^{2c}$, C(O)$NR^2R^{2a}$, and $SO_2NR^2R^{2a}$;

$R^{1b}$ is selected from H, $CH_3$, $CH_2CH_3$, Cl, F, $CF_3$, $OCH_3$, $NR^2R^{2a}$, S(O)$_pR^{2b}$, $CH_2S(O)_pR^{2b}$, $CH_2NR^2S(O)_pR^{2b}$, C(O)$R^{2c}$, $CH_2$C(O)$R^{2c}$, C(O)$NR^2R^{2a}$, and $SO_2NR^2R^{2a}$;

A is selected from one of the following carbocyclic and heterocyclic systems which are substituted with 0–2 $R^4$;

phenyl, pyridyl, pyrimidyl, furanyl, thiophenyl, pyrrolyl, oxazolyl, isoxazolyl, thiazolyl, isothiazolyl, pyrazolyl, and imidazolyl;

B is selected from: Y and X—Y;

X is selected from $CH_2$, —$CR^2(CR^2R^{2b})$—, —C(O)—, —C(=NR)—, —$CH(NR^2R^{2a})$—, —$C(O)NR^2$—, —$NR^2C(O)$—, —$NR^2C(O)NR^2$—, —$NR^2$—, and O;

Y is $NR^2R^{2a}$, provided that X—Y do not form a N—N or O—N bond;

alternatively, Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

$R^2$, at each occurrence, is selected from H, $CF_3$, $CH_3$, benzyl, and phenyl;

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^{2a}$ combine to form a 5 or 6 membered saturated, partially unsaturated, or unsaturated ring which contains from 0–1 additional heteroatoms selected from the group consisting of N, O, and S;

$R^3$, at each occurrence, is selected from H, $CH_3$, $CH_2CH_3$, and phenyl;

$R^{3a}$, at each occurrence, is selected from H, $CH_3$, $CH_2CH_3$, and phenyl;

$R^4$, at each occurrence, is selected from OH, Cl, F, $CH_3$, $CH_2CH_3$, $NR^2R^{2a}$, $CH_2NR^2R^{2a}$, $C(O)R^{2b}$, $NR^2C(O)R^{2b}$, $C(O)NR^2R^{2a}$, and $CF_3$;

$R^{4a}$, at each occurrence, is selected from OH, Cl, F, $CH_3$, $CH_2CH_3$, $NR^2R^{2a}$, $CH_2NR^2R^{2a}$, $C(O)R^{2b}$, $C(O)NR^2R^{2a}$, $SO_2NR^2R^{2a}$, $S(O)_pR^5$, $CF_3$, and 1-$CF_3$-tetrazol-2-yl;

$R^5$, at each occurrence, is selected from $CF_3$, $C_{1-6}$ alkyl, phenyl substituted with 0–2 $R^6$, and benzyl substituted with 1 $R^6$;

$R^6$, at each occurrence, is selected from H, OH, $OCH_3$, Cl, F, $CH_3$, CN, $NO_2$, $NR^2R^{2a}$, $CH_2NR^2R^{2a}$, and $SO_2NR^2R^{2a}$;

$R^7$, at each occurrence, is selected from H and $C_{1-3}$ alkyl;

$R^8$, at each occurrence, is selected from H, $CH_3$, and benzyl;

$R^9$, at each occurrence, is selected from H, $CH_3$, and benzyl; and, t, at each occurrence, is selected from 0 and 1.

[18] In a another still further preferred embodiment, the present invention provides novel compounds of formulae IIa–IIf, wherein;

D is selected from $NR^7R^8$, and $CH_2NR^7R^8$, provided that D is substituted ortho to ring M on E;

$R^{1a}$ is absent or is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $CH_2NR^2S(O)_pR^{2b}$, $C(O)R^{2c}$, $CH_2C(O)R^{2c}$, and $SO_2NR^2R^{2a}$;

$R^{1b}$ is absent or is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $CH_2NR^2S(O)_pR^{2b}$, $C(O)R^{2b}$, $CH_2C(O)R^{2b}$, and $SO_2NR^2R^{2a}$;

A is selected from one of the following carbocyclic and heterocyclic systems which are substituted with 0–2 $R^4$;

phenyl, pyridyl, and pyrimidyl;

B is selected from: Y and X—Y;

X is selected from —C(O)— and O;

Y is $NR^2R^{2a}$, provided that X—Y do not form a O—N bond;

alternatively, Y is selected from one of the following carbocyclic and heterocyclic systems which are substituted with 0–2 $R^{4a}$;

phenyl, piperazinyl, pyridyl, pyrimidyl, morpholinyl, pyrrolidinyl, imidazolyl, and 1,2,3-triazolyl;

$R^2$, at each occurrence, is selected from H, $CF_3$, $CH_3$, benzyl, and phenyl;

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^{2a}$ combine to form a ring system selected from pyrrolidinyl, piperazinyl and morpholino;

$R^4$, at each occurrence, is selected from Cl, F, $CH_3$, $NR^2R^{2a}$, and $CF_3$;

$R^{4a}$, at each occurrence, is selected from Cl, F, $CH_3$, $SO_2NR^2R^{2a}$, $S(O)_pR^5$, and $CF_3$;

$R^5$, at each occurrence, is selected from $CF_3$ and $CH_3$;

$R^7$, at each occurrence, is selected from H, $CH_3$, and $CH_2CH_3$; and, $R^8$, at each occurrence, is selected from H and $CH_3$.

[19] Specifically preferred compounds of the present invention are selected from the group:

3-Methyl-1-(2-aminomethyl-4-methoxyphenyl)-1H-pyrazole-5-(N-(2'-sulfamido-[1,1']-biphen-4-yl))carboxyamide;

3-Ethyl-1-(2-aminomethyl-4-methoxyphenyl)-1H-pyrazole-5-(N-(2'-sulfamido-[1,1']-biphen-4-yl))carboxyamide;

3-Trifluoromethyl-1-(2-aminomethyl-4-methoxyphenyl)-1H-pyrazole-5-(N-(2'-sulfamido-[1,1']-biphen-4-yl))carboxyamide;

3-Methyl-1-(2-N-methylaminomethyl-4-methoxyphenyl)-1H-pyrazole-5-(N-(2'-sulfamido-[1,1']-biphen-4-yl))carboxyamide;

3-Ethyl-1-(2-N-methylaminomethyl-4-methoxyphenyl)-1H-pyrazole-5-(N-(2'-sulfamido-[1,1']-biphen-4-yl))carboxyamide;

3-Trifluoromethyl-1-(2-N-methylaminomethyl-4-methoxyphenyl)-1H-pyrazole-5-(N-(2'-sulfamido-[1,1']-biphen-4-yl))carboxyamide;

3-Methyl-1-(2-aminomethyl-4-methoxyphenyl)-1H-pyrazole-5-(N-(2'-methylsulfonyl-[1,1']-biphen-4-yl))carboxyamide;

3-Ethyl-1-(2-aminomethyl-4-methoxyphenyl)-1H-pyrazole-5-(N-(2'-methylsulfonyl-[1,1']-biphen-4-yl))carboxyamide;

3-Trifluoromethyl-1-(2-aminomethyl-4-methoxyphenyl)-1H-pyrazole-5-(N-(2'-methylsulfonyl-[1,1']-biphen-4-yl))carboxyamide;

3-Methyl-1-(2-N-methylaminomethyl-4-methoxyphenyl)-1H-pyrazole-5-(N-(2'-methylsulfonyl-[1,1']-biphen-4-yl))carboxyamide;

3-Ethyl-1-(2-N-methylaminomethyl-4-methoxyphenyl)-1H-pyrazole-5-(N-(2'-methylsulfonyl-[1,1']-biphen-4-yl))carboxyamide;

3-Trifluoromethyl-1-(2-N-methylaminomethyl-4-methoxyphenyl)-1H-pyrazole-5-(N-(2'-methylsulfonyl-[1,1']-biphen-4-yl))carboxyamide;

3-Methyl-1-(2-aminomethyl-4-methoxyphenyl)-1H-pyrazole-5-(N-(3-fluoro-2'-sulfamido-[1,1']-biphen-4-yl))carboxyamide;

3-Ethyl-1-(2-aminomethyl-4-methoxyphenyl)-1H-pyrazole-5-(N-(3-fluoro-2'-sulfamido-[1,1']-biphen-4-yl))carboxyamide;

3-Trifluoromethyl-1-(2-aminomethyl-4-methoxyphenyl)-1H-pyrazole-5-(N-(3-fluoro-2'-sulfamido-[1,1']-biphen-4-yl))carboxyamide;

3-Methyl-1-(2-N-methylaminomethyl-4-methoxyphenyl)-1H-pyrazole-5-(N-(3-fluoro-2'-sulfamido-[1,1']-biphen-4-yl))carboxyamide;

3-Ethyl-1-(2-N-methylaminomethyl-4-methoxyphenyl)-1H-pyrazole-5-(N-(3-fluoro-2'-sulfamido-[1,1']-biphen-4-yl))carboxyamide;

3-Trifluoromethyl-1-(2-N-methylaminomethyl-4-methoxyphenyl)-1H-pyrazole-5-(N-(3-fluoro-2'-sulfamido-[1,1']-biphen-4-yl))carboxyamide;

3-Methyl-1-(2-aminomethyl-4-methoxyphenyl)-1H-pyrazole-5-(N-(3-fluoro-2'-methylsulfonyl-[1,1']-biphen-4-yl))carboxyamide;

3-Ethyl-1-(2-aminomethyl-4-methoxyphenyl)-1H-pyrazole-5-(N-(3-fluoro-2'-methylsulfonyl-[1,1']-biphen-4-yl))carboxyamide;

3-Trifluoromethyl-1-(2-aminomethyl-4-methoxyphenyl)-1H-pyrazole-5-(N-(3-fluoro-2'-methylsulfonyl-[1,1']-biphen-4-yl))carboxyamide;

3-Methyl-1-(2-N-methylaminomethyl-4-methoxyphenyl)-1H-pyrazole-5-(N-(3-fluoro-2'-methylsulfonyl-[1,1']-biphen-4-yl))carboxyamide;

3-Ethyl-1-(2-N-methylaminomethyl-4-methoxyphenyl)-1H-pyrazole-5-(N-(3-fluoro-2'-methylsulfonyl-[1,1']-biphen-4-yl))carboxyamide;

3-Trifluoromethyl-1-(2-N-methylaminomethyl-4-methoxyphenyl)-1H-pyrazole-5-(N-(3-fluoro-2'-methylsulfonyl-[1,1']-biphen-4-yl))carboxyamide;

3-Methyl-1-(2-aminomethyl-4-methoxyphenyl)-1H-pyrazole-5-(N-(4-(1-pyrrolidinocarbonyl)phenyl)carboxyamide;

3-Ethyl-1-(2-aminomethyl-4-methoxyphenyl)-1H-pyrazole-5-(N-(4-(1-pyrrolidinocarbonyl)phenyl)carboxyamide;

3-Trifluoromethyl-1-(2-aminomethyl-4-methoxyphenyl)-1H-pyrazole-5-(N-(4-(1-pyrrolidinocarbonyl)phenyl)carboxyamide;

3-Methyl-1-(2-N-methylaminomethyl-4-methoxyphenyl)-1H-pyrazole-5-(N-(4-(1-pyrrolidinocarbonyl)phenyl)carboxyamide;

3-Ethyl-1-(2-N-methylaminomethyl-4-methoxyphenyl)-1H-pyrazole-5-(N-(4-(1-pyrrolidinocarbonyl)phenyl)carboxyamide;

3-Trifluoromethyl-1-(2-N-methylaminomethyl-4-methoxyphenyl)-1H-pyrazole-5-(N-(4-(1-pyrrolidinocarbonyl)phenyl)carboxyamide;

3-Methyl-1-(2-aminomethyl-4-methoxyphenyl)-1H-pyrazole-5-(N-(2-fluoro-4-(1-pyrrolidinocarbonyl)phenyl)carboxyamide;

3-Ethyl-1-(2-aminomethyl-4-methoxyphenyl)-1H-pyrazole-5-(N-(2-fluoro-4-(1-pyrrolidinocarbonyl)phenyl)carboxyamide;

3-Trifluoromethyl-1-(2-aminomethyl-4-methoxyphenyl)-1H-pyrazole-5-(N-(2-fluoro-4-(1-pyrrolidinocarbonyl)phenyl)carboxyamide;

3-Methyl-1-(2-N-methylaminomethyl-4-methoxyphenyl)-1H-pyrazole-5-(N-(2-fluoro-4-(1-pyrrolidinocarbonyl)phenyl)carboxyamide;

3-Ethyl-1-(2-N-methylaminomethyl-4-methoxyphenyl)-1H-pyrazole-5-(N-(2-fluoro-4-(1-pyrrolidinocarbonyl)phenyl)carboxyamide;

3-Trifluoromethyl-1-(2-N-methylaminomethyl-4-methoxyphenyl)-1H-pyrazole-5-(N-(2-fluoro-4-(1-pyrrolidinocarbonyl)phenyl)carboxyamide;

3-Methyl-1-(2-aminomethyl-4-methoxyphenyl)-1H-pyrazole-5-(N-(5-((2-sulfamido)phenyl)pyridin-2-yl)carboxyamide;

3-Ethyl-1-(2-aminomethyl-4-methoxyphenyl)-1H-pyrazole-5-(N-(5-((2-sulfamido)phenyl)pyridin-2-yl)carboxyamide;

3-Trifluoromethyl-1-(2-aminomethyl-4-methoxyphenyl)-1H-pyrazole-5-(N-(5-((2-sulfamido)phenyl)pyridin-2-yl)carboxyamide;

3-Methyl-1-(2-N-methylaminomethyl-4-methoxyphenyl)-1H-pyrazole-5-(N-(5-((2-sulfamido)phenyl)pyridin-2-yl)carboxyamide;

3-Ethyl-1-(2-N-methylaminomethyl-4-methoxyphenyl)-1H-pyrazole-5-(N-(5-((2-sulfamido)phenyl)pyridin-2-yl)carboxyamide;

3-Trifluoromethyl-1-(2-N-methylaminomethyl-4-methoxyphenyl)-1H-pyrazole-5-(N-(5-((2-sulfamido)phenyl)pyridin-2-yl)carboxyamide;

3-Methyl-1-(2-aminomethyl-4-methoxyphenyl)-1H-pyrazole-5-(N-(5-((2-methylsulphenyl)phenyl)pyridin-2-yl)carboxyamide;

3-Ethyl-1-(2-aminomethyl-4-methoxyphenyl)-1H-pyrazole-5-(N-(5-(2-methylsulphenyl)phenyl)pyridin-2-yl)carboxyamide;

3-Trifluoromethyl-1-(2-aminomethyl-4-methoxyphenyl)-1H-pyrazole-5-(N-(5-((2-methylsulphenyl)phenyl)pyridin-2-yl)carboxyamide;

3-Methyl-1-(2-N-methylaminomethyl-4-methoxyphenyl)-1H-pyrazole-5-(N-(5-((2-methylsulphonyl)phenyl)pyridin-2-yl)carboxyamide;

3-Ethyl-1-(2-N-methylaminomethyl-4-methoxyphenyl)-1H-pyrazole-5-(N-(5-((2-methylsulphonyl)phenyl)pyridin-2-yl)carboxyamide;

3-Trifluoromethyl-1-(2-N-methylaminomethyl-4-methoxyphenyl)-1H-pyrazole-5-(N-(5-((2-methylsulphonyl)phenyl)pyridin-2-yl)carboxyamide;

3-Methyl-1-(2-aminomethyl-4-methoxyphenyl)-1H-pyrazole-5-(N-(5-((2-sulfamido) phenyl)pyrimidin-2-yl)carboxyamide;

3-Ethyl-1-(2-aminomethyl-4-methoxyphenyl)-1H-pyrazole-5-(N-(5-((2-sulfamido)phenyl)pyrimidin-2-yl)carboxyamide;

3-Trifluoromethyl-1-(2-aminomethyl-4-methoxyphenyl)-1H-pyrazole-5-(N-(5-((2-sulfamido)phenyl)pyrimidin-2-yl)carboxyamide;

3-Methyl-1-(2-N-methylaminomethyl-4-methoxyphenyl)-1H-pyrazole-5-(N-(5-((2-sulfamido)phenyl)pyrimidin-2-yl)carboxyamide;

3-Ethyl-1-(2-N-methylaminomethyl-4-methoxyphenyl)-1H-pyrazole-5-(N-(5-((2-sulfamido)phenyl)pyrimidin-2-yl)carboxyamide;

3-Trifluoromethyl-1-(2-N-methylaminomethyl-4-methoxyphenyl)-1H-pyrazole-5-(N-(5-((2-sulfamido) phenyl)pyrimidin-2-yl)carboxyamide;

3-Methyl-1-(2-aminomethyl-4-methoxyphenyl)-1H-pyrazole-5-(N-(5-((2-methylsulphonyl)phenyl)pyrimidin-2-yl)carboxyamide;

3-Ethyl-1-(2-aminomethyl-4-methoxyphenyl)-1H-pyrazole-5-(N-(5-(2-methylsulphonyl)phenyl)pyrimidin-2-yl) carboxyamide;
3-Trifluoromethyl-1-(2-aminomethyl-4-methoxyphenyl)-1H-pyrazole-5-(N-(5-((2-methylsulphonyl)phenyl) pyrimidin-2-yl)carboxyamide;
3-Methyl-1-(2-N-methylaminomethyl-4-methoxyphenyl)-1H-pyrazole-5-(N-(5-((2-methylsulphonyl)phenyl) pyrimidin-2-yl)carboxyamide;
3-Ethyl-1-(2-N-methylaminomethyl-4-methoxyphenyl)-1H-pyrazole-5-(N-(5-((2-methylsulphonyl)phenyl) pyrimidin-2-yl)carboxyamide;
3-Trifluoromethyl-1-(2-N-methylaminomethyl-4-methoxyphenyl)-1H-pyrazole-5-(N-(5-((2-methylsulphonyl)phenyl)pyrimidin-2-yl)carboxyamide;
3-Methyl-1-(2-aminomethyl-4-methoxyphenyl)-1H-pyrazole-5-(N-(4-((2-methyl)imidazo-1-yl)phenyl) carboxyamide;
3-Ethyl-1-(2-aminomethyl-4-methoxyphenyl)-1H-pyrazole-5-(N-(4-((2-methyl)imidazo-1-yl)phenyl)carboxyamide;
3-Trifluoromethyl-1-(2-aminomethyl-4-methoxyphenyl)-1H-pyrazole-5-(N-(4-((2-methyl)imidazo-1-yl)phenyl) carboxyamide;
3-Methyl-1-(2-N-methylaminomethyl-4-methoxyphenyl)-1H-pyrazole-5-(N-(4-((2-methyl)imidazo-1-yl)phenyl) carboxyamide;
3-Ethyl-1-(2-N-methylaminomethyl-4-methoxyphenyl)-1H-pyrazole-5-(N-(4-((2-methyl)imidazo-1-yl)phenyl) carboxyamide;
3-Trifluoromethyl-1-(2-N-methylaminomethyl-4-methoxyphenyl)-1H-pyrazole-5-(N-(4-((2-methyl) imidazo-1-yl)phenyl)carboxyamide;
3-Methyl-1-(2-aminomethyl-4-methoxyphenyl)-1H-pyrazole-5-(N-(4-((5-methyl)imidazo-1-yl)phenyl) carboxyamide;
3-Ethyl-1-(2-aminomethyl-4-methoxyphenyl)-1H-pyrazole-5-(N-(4-((5-methyl)imidazo-1-yl)phenyl)carboxyamide;
3-Trifluoromethyl-1-(2-aminomethyl-4-methoxyphenyl)-1H-pyrazole-5-(N-(4-((5-methyl)imidazo-1-yl)phenyl) carboxyamide;
3-Methyl-1-(2-N-methylaminomethyl-4-methoxyphenyl)-1H-pyrazole-5-(N-(4-((5-methyl)imidazo-1-yl)phenyl) carboxyamide;
3-Ethyl-1-(2-N-methylaminomethyl-4-methoxyphenyl)-1H-pyrazole-5-(N-(4-((5-methyl)imidazo-1-yl)phenyl) carboxyamide;
3-Trifluoromethyl-1-(2-N-methylaminomethyl-4-methoxyphenyl)-1H-pyrazole-5-(N-(4-((5-methyl) imidazo-1-yl)phenyl)carboxyamide;
3-Methyl-1-(2-aminomethyl-4-methoxyphenyl)-1H-pyrazole-5-(N-(2-fluoro-4-((2-methyl)imidazo-1-yl) phenyl)carboxyamide;
3-Ethyl-1-(2-aminomethyl-4-methoxyphenyl)-1H-pyrazole-5-(N-(2-fluoro-4-((2-methyl)imidazo-1-yl)phenyl) carboxyamide;
3-Trifluoromethyl-1-(2-aminomethyl-4-methoxyphenyl)-1H-pyrazole-5-(N-(2-fluoro-4-((2-methyl)imidazo-1-yl) phenyl)carboxyamide;
3-Methyl-1-(2-N-methylaminomethyl-4-methoxyphenyl)-1H-pyrazole-5-(N-(2-fluoro-4-((2-methyl)imidazo-1-yl) phenyl)carboxyamide;
3-Ethyl-1-(2-N-methylaminomethyl-4-methoxyphenyl)-1H-pyrazole-5-(N-(2-fluoro-4-((2-methyl)imidazo-1-yl) phenyl)carboxyamide;
3-Trifluoromethyl-1-(2-N-methylaminomethyl-4-methoxyphenyl)-1H-pyrazole-5-(N-(2-fluoro-4-((2-methyl)imidazo-1-yl)phenyl)carboxyamide;
3-Methyl-1-(2-aminomethyl-4-methoxyphenyl)-1H-pyrazole-5-(N-(2-fluoro-4-((5-methyl)imidazo-1-yl) phenyl)carboxyamide;
3-Ethyl-1-(2-aminomethyl-4-methoxyphenyl)-1H-pyrazole-5-(N-(2-fluoro-4-((5-methyl)imidazo-1-yl)phenyl) carboxyamide;
3-Trifluoromethyl-1-(2-aminomethyl-4-methoxyphenyl)-1H-pyrazole-5-(N-(2-fluoro-4-((5-methyl)imidazo-1-yl) phenyl)carboxyamide;
3-Methyl-1-(2-N-methylaminomethyl-4-methoxyphenyl)-1H-pyrazole-5-(N-(2-fluoro-4-((5-methyl)imidazo-1-yl) phenyli)carboxyamide;
3-Ethyl-1-(2-N-methylaminomethyl-4-methoxyphenyl)-1H-pyrazole-5-(N-(2-fluoro-4-((5-methyl)imidazo-1-yl) phenyl)carboxyamide; and,
3-Trifluoromethyl-1-(2-N-methylaminomethyl-4-methoxyphenyl)-1H-pyrazole-5-(N-(2-fluoro-4-((5-methyl)imidazo-1-yl) phenyl) carboxyamide; and pharmaceutically acceptable salts thereof.

[20] More specifically preferred compounds of the present invention are selected from the group:
3-Methyl-1-(2-aminomethyl-4-methoxyphenyl)-1H-pyrazole-5- (N-(2'-sulfamido-[1,1']-biphen-4-yl)) carboxyamide;
5-Methyl-1-(2-aminomethyl-4-methoxyphenyl)-1H-pyrazole-3-(N-(2'-sulfamido-[1,1']-biphen-4-yl)) carboxyamide;
3-Methyl-1-(2-N,N-dimethylaminomethyl-4-methoxyphenyl)-1H-pyrazole-5-(N-(2'-N-methylsulfamido-[1,1']-biphen-4-yl))carboxyamide;
3-Trifluoromethyl-1-(2-aminomethyl-4-methoxyphenyl)-1H-pyrazole-5-(N-(3-fluoro-2'-sulfamido-[1,1]-biphen-4-yl))carboxyamide;
3-Trifluoromethyl-1-(2-aminomethyl-4-methoxyphenyl)-1H-pyrazole-5-(N-(3-fluoro-2'-methylsulfonyl-[1,1]-biphen-4-yl))carboxyamide;
3-Trifluoromethy-1-(2-aminomethyl-4-methoxyphenyl)-1H-pyrazole-5-(N-(2'-methylsulfonyl-[1,1]-biphen-4-yl)) carboxyamide;
3-Trifluoromethyl-1-(2-aminomethyl-4-methoxyphenyl)-1H-pyrazole-5-(N-(2'-sulfamido-[1,1]-biphen-4-yl)) carboxyamide;
3-Trifluoromethyl-1-(2-aminomethyl-4-methoxyphenyl)-1H-pyrazole-5-(N-(4-N-pyrrolidinocarbonyl)phenyl) carboxyamide;
N-Benzylsulfonyl-4-(3-trifluoromethyl-1-(2-aminomethyl-4-methoxyphenyl)-1H-pyrazole-5-carboxyamido) piperidine;
3-Trifluoromethyl-1-(2-aminomethyl-4-methoxyphenyl)-1H-pyrazole-5-(N-(5-(2'-sulfonamido)phenyl)pyrid-2-yl) carboxyamide;
3-Trifluoromethyl-1-(2-aminomethyl-4-methoxyphenyl)-1H-pyrazole-5-(N-(5-(pyrid-2-yl))pyrid-2-yl) carboxyamide;
N-Benzyl-4-(3-trifluoromethyl-1-(2-aminomethyl-4-methoxyphenyl)-1H-pyrazole-5-carboxyamido) piperidine;
N-Phenylsulfonyl-4-(3-trifluoromethyl-1-(2-aminomethyl-4-methoxyphenyl)-1H-pyrazole-5-carboxyamido) piperidine;
3-Trifluoromethyl-1-(2-aminomethyl-4-chlorophenyl)-1H-pyrazole-5-(N-(3-fluoro-2'-methylsulfonyl-[1,1']-biphen-4-yl))carboxyamide;
3-Trifluoromethyl-1-(2-aminomethyl-4-chlorophenyl)-1H-pyrazole-5-(N-(3-fluoro-2'-sulfamido-[1,1']-biphen-4-; yl))carboxyamide;
3-Trifluoromethyl-1-(2-aminomethyl-5-chlorophenyl)-1H-pyrazole-5-(N-(3-fluoro-2'-methylsulfonyl-[1,1']-biphen-4-yl))carboxyamide;

3-Trifluoromethyl-1-(2-aminomethyl-4-chlorophenyl)-1H-pyrazole-5-(N-(3-fluoro-2'-sulfamido-[1,1']-biphen-4-yl))carboxyamide;
3-Trifluoromethyl-1-(2-aminomethyl-4-fluorophenyl)-1H-pyrazole-5-(N-(3-fluoro-2'-methylsulfonyl-[1,1']-biphen-4-yl))carboxyamide;
3-Trifluoromethyl-1-(2-aminomethyl-4-fluorophenyl)-1H-pyrazole-5-(N-(3-fluoro-2'-sulfamido-[1,1']-biphen-4-yl))carboxyamide;
3-Trifluoromethyl-1-(2-aminomethyl-5-fluorophenyl)-1H-pyrazole-5-(N-(3-fluoro-2'-methylsulfonyl-[1,1']-biphen-4-yl))carboxyamide;
3-Trifluoromethyl-1-(2-aminomethyl-5-fluorophenyl)-1H-pyrazole-5-(N-(3-fluoro-2'-sulfamido-[1,1']-biphen-4-yl))carboxyamide;
3-Trifluoromethyl-1-(2-aminomethyl-4,5-difluorophenyl)-1H-pyrazole-5-(N-(3-fluoro-2'-methylsulfonyl-[1,1']-biphen-4-yl))carboxyamide;
3-Trifluoromethyl-1-(2-aminomethyl-4,5-difluorophenyl)-1H-pyrazole-5-(N-(3-fluoro-2'-sulfamido-[1,1']-biphen-4-yl))carboxyamide;
3-Trifluoromethyl-1-(2-aminomethyl-3-fluorophenyl)-1H-pyrazole-5-(N-(3-fluoro-2'-methylsulfonyl-[1,1']-biphen-4-yl))carboxyamide;
3-Trifluoromethyl-1-(2-aminomethyl-3-fluorophenyl)-1H-pyrazole-5-(N-(3-fluoro-2'-sulfamido-[1,1']-biphen-4-yl))carboxyamide;
3-Trifluoromethyl-1-(2-aminomethyl-4-fluorophenyl)-1H-pyrazole-5-(N-(4-(2-methylsulfonyl-[1,1']-biphen-4-yl))carboxyamide;
3-Trifluoromethyl-1-(2-aminomethyl-4-fluorophenyl)-1H-pyrazole-5-(N-(4-(2-sulfamido-[1,1']-biphen-4-yl))carboxyamide;
3-Trifluoromethyl-1-(2-aminomethyl-4-fluorophenyl)-1H-pyrazole-5-(N-(4-(N-((N'-methylsulfonyl)iminoly)pyrrolidino))phenyl)carboxyamide;
3-Trifluoromethyl-1-(2-(N-glycyl)aminomethyl-4-methoxyphenyl)-1H-pyrazole-5-(N-(3-fluoro-2'-methylsulfonyl-[1,1']-biphen-4-yl))carboxyamide;
3-Trifluoromethyl-1-(2-(N-phenylacetyl)aminomethyl-4-methoxyphenyl)-1H-pyrazole-5-(N-(3-fluoro-2'-methylsulfonyl-[1,1']-biphen-4-yl))carboxyamide;
3-(Trifluoromethyl)-1-(2-(aminomethyl)phenyl)-1H-pyrazole-5-(N-(2'-methylsulfonyl-[1,1']-biphen-4-yl))carboxyamide;
3-Trifluoromethyl-1-(2-(aminomethyl)phenyl)-1H-pyrazole-5-(N-(2'-aminosulfonyl-[1,1']-biphen-4-yl))carboxyamide;
3-Trifluoromethyl-1-(2-(aminomethyl)phenyl)-1H-pyrazole-5-(N-(3-fluoro-2'-aminosulfonyl-[1,1']-biphen-4-yl))carboxyamide;
3-Trifluoromethyl-1-(2-(aminomethyl)phenyl)-1H-pyrazole-5-(N-(3-fluoro-2'-methylsulfonyl-[1,1']-biphen-4-yl))carboxyamide;
3-Trifluoromethyl-1-(2-(N-(glycyl)aminomethyl)phenyl)-1H-pyrazole-5-(N-(3-fluoro-2'-methylsulfonyl-[1,1']-biphen-4-yl))carboxyamide;
3-Trifluoromethyl-1-(2-((N-(N-methylglycyl)aminomethyl)phenyl)-1H-pyrazole-5-(N-(3-fluoro-2'-methylsulfonyl-[1,1']-biphen-4-yl))carboxyamide;
3-Trifluoromethyl-1-(2-carboxamidophenyl)-1H-pyrazole-5-(N-(3-fluoro-2'-methylsulfonyl-[1,1']-biphen-4-yl))carboxyamide;
3-Trifluoromethyl-1-(2-cyanophenyl)-1H-pyrazole-5-(N-(3-fluoro-2'-methylsulfonyl-[1,1']-biphen-4-yl))carboxyamide;
1-(2'-Aminomethylphenyl)-5-[[(2'-methylsulfonyl)-3-fluoro-[1,1')-biphen-4-yl]aminocarbonyl]-tetrazole;
1-(2'-Aminomethylphenyl)-5-[(2'-aminosulfonyl-[1,1']-biphen-4-yl)aminocarbonyl]-tetrazole;
1-[2-(Aminomethyl)phenyl]-3-thiomethoxy-5-[(2-fluoro)-(2'-methylsulfonyl-[1,1']-biphen-4-yl)aminocarbonyl]pyrazole;
1-[2-(Aminomethyl)phenyl]-3-methysulfonyl-5-(2-fluoro)-(2'-methylsulfonyl-[1,1']-biphen-4-yl)aminocarbonyl]pyrazole;
1-[2-(Aminomethyl)phenyl]-5-[(2-fluoro)-(2'-methylsulfonyl-[1,1']-biphen-4-yl)aminocarbonyl]triazole;
1-[2-(Aminomethyl)phenyl]-5-[(2-fluoro)-(2'-methylsulfonyl-[1,1']-biphen-4-yl)aminocarbonyl]pyrazole;
1-[2-(Aminomethyl)phenyl]-3-trifluoromethyl-5-[((2-fluoro)-(2'-pyrrolidinomethyl)-[1,1']-biphen-4-yl)aminocarbonyl]pyrazole; and,
1-[2-(Aminomethyl)phenyl]-3-trifluoromethyl-5-[((2-fluoro)-(2'-hydroxymethyl)-[1,1']-biphen-4-yl)aminocarbonyl]pyrazole;
and pharmaceutically acceptable salts thereof.

In a second embodiment, the present invention provides novel pharmaceutical compositions, comprising: a pharmaceutically acceptable carrier and a therapeutically effective amount of a compound of formula (I) or a pharmaceutically acceptable salt form thereof.

In a third embodiment, the present invention provides a novel method for treating or preventing a thromboembolic disorder, comprising: administering to a patient in need thereof a therapeutically effective amount of a compound of formula (I) or a pharmaceutically acceptable salt form thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example $-C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. Alkenyl" is intended to include hydrocarbon chains of either a straight or branched configuration and one or more unsaturated carbon-carbon bonds which may occur in any stable point along the chain, such as ethenyl and propenyl. "Alkynyl" is intended to include hydrocarbon chains of either a straight or branched configuration and one or more triple carbon-carbon bonds which may occur in any stable point along the chain, such as ethynyl and propynyl.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3- to 7-membered monocyclic or bicyclic or 7-to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5-to 7-membered monocyclic or bicyclic or 7-to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5-to 7-membered monocyclic or bicyclic or 7-to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like. Preferred prodrugs are amidine prodrugs wherein D is $C(=NR^7)NH_2$ or its tautomer $C(=NH)NHR^7$ and $R^7$ is selected from OH, $C_{1-4}$ alkoxy, $C_{6-10}$ aryloxy, $C_{1-4}$ alkoxycarbonyl, $C_{6-10}$ aryloxycarbonyl, $C_{6-10}$ arylmethylcarbonyl, $C_{1-4}$ alkylcarbonyloxy $C_{1-4}$ alkoxycarbonyl, and $C_{6-10}$ arylcarbonyloxy $C_{1-4}$ alkoxycarbonyl. More preferred prodrugs are where $R^7$ is OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, *Adv. Enzyme Regul.* 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis,* Wiley and Sons, 1991). All references cited herein are hereby incorporated in their entirety herein by reference.

The compounds of Formula I in which ring M is pyrrole can be prepared by the procedures described in Schemes 1–9. In Scheme 1 is shown how to prepare pyrroles in which the group Q—E is attached to the pyrrole nitrogen, wherein Q is a functionality that can be converted into D of Formula I, Re is functionality that can be converted into Z—A—B of Formula I and $R^f$ is or can be converted into $R^{1a}$ of Formula I. Oxidation of a furan with bromine in acetic acid can afford a 2,5-diacetoxydihydrofuran which can react with amine Q—E—NH2 to afford a pyrrole. Vilsmeier-Haack formulation with phosphorous oxychloride and DMF preferentially can acylate the pyrrole ring at C-2. Oxidation of the resulting aldehyde can give a carboxylic acid. The carboxylic acid can then be converted into amine derivatives using either the Hofmann degradation of the derived primary amide (Huisgen et. al. *Chem. Ber.* 1960, 93, 65) or the Curtius rearrangement of the derived acyl azide (*J. Prakt. Chem.* 1909, 42, 477). Derivatives which contain a sulfur atom attached to the pyrrole ring can be obtained by direct sulfonation with pyridine sulfur trioxide complex to give the sulfonic acids or treatment with copper (II) thiocyanate (*J. Het. Chem.* 1988, 25, 431) followed by the reduction of the intermediate thiocyanate with sodium borohydride to give a mercaptan.

Scheme 1

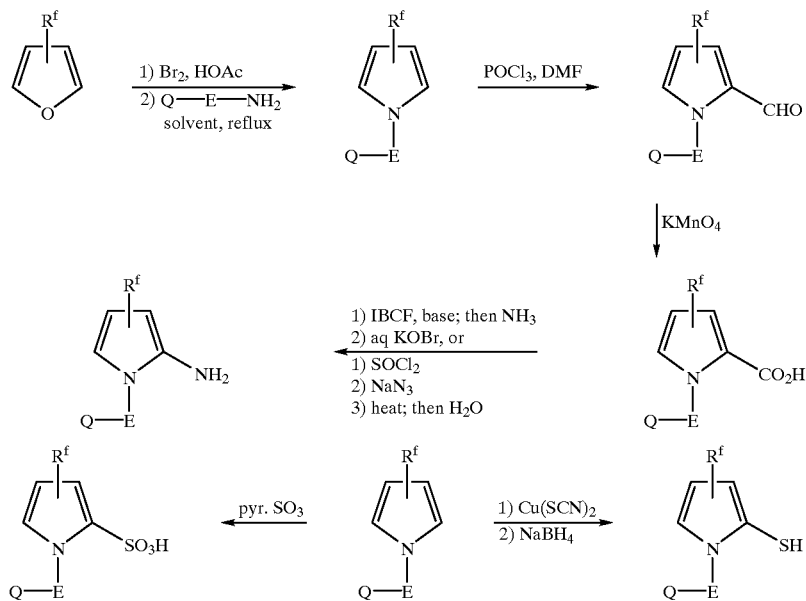

In Scheme 2 is shown how to prepare pyrroles in which Q—E is attached to the 2-position, wherein $R^f$ and $R^g$ collectively are hydrogen or a group that can be converted into $R^{1a}$ and $R^{1b}$ of Formula I. The Hantzsch pyrrole synthesis is a versatile reaction involving the cyclization of an appropriate β-ketoester with an α-halo ketone or aldehyde in the presence of a primary amine (*Ber. Dtsch Chem. Ges.* 1890, 23, 1474). The β-ketoesters can be prepared from acid chlorides (X=Cl) by the addition of the magnesium anion of potassium alkylmalonate followed by decarboxylation (*Synthesis* 1993, 290). Alternatively, β-ketoesters can be prepared from an appropriate aldehyde (R=H) by Reformatsky reaction with an α-bromoacetate followed by oxidation. Cyclization with an α-halo ketone or aldehyde in the presence of a primary amine can afford pyrroles. Acidic hydrolysis of the 3-carboalkoxy pyrrole can afford the carboxylic acids. Pyrroles which contain a 3-amino substituent can be prepared from the acids by treatment with phosphoryl azide and triethylamine to effect a Curtius rearrangement to afford the isocyanates (*J. Med. Chem.* 1981, 24, 33) which upon hydrolysis can yield 3-aminopyrroles. Pyrroles which contain a sulfur atom at C-3 can be prepared from the acids by employing the Hunsdiecker procedure to give the 3-bromo derivatives. Halogen-metal exchange at low temperature with an alkyllithium reagent can afford the 3-lithio derivative which can be quenched with a variety of electrophiles, such as S8 to afford thiols directly or $Cu(SCN)_2$ to afford a thiocyanate which can be reduced with sodium borohydride. The thiols can further be oxidized to the sulfonic acid derivatives by an oxidant such as $KMnO_4$.

Scheme 2

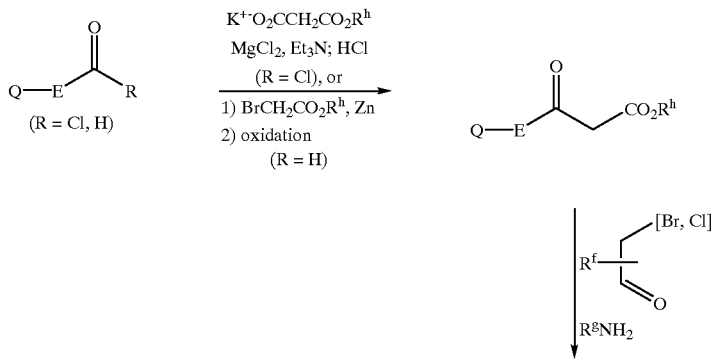

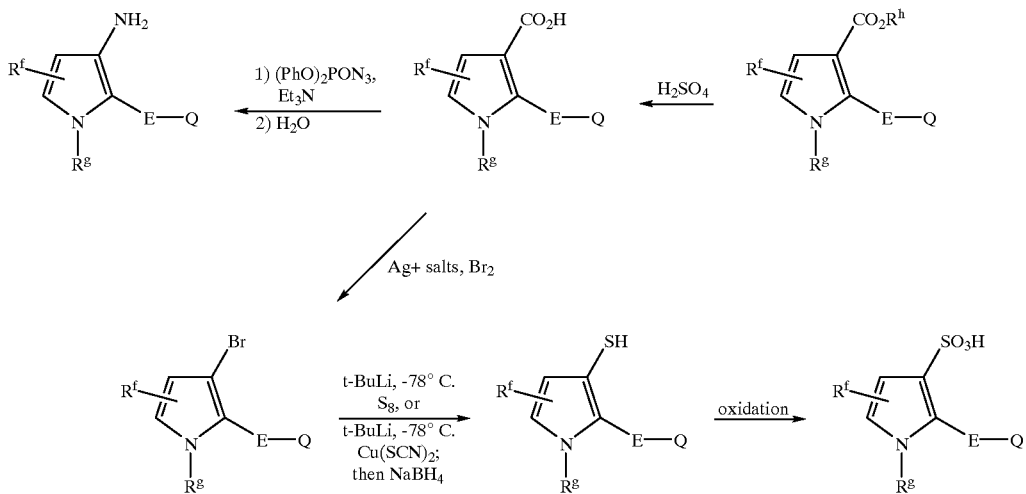

In Scheme 3 is shown how to prepare pyrroles in which Q—E is attached to the 3-position. This scheme relies upon the extremely versatile Knorr pyrrole synthesis, which involves condensation of α-aminoketones with β-ketoesters. The α-aminoketones can be prepared from β-ketoesters (Scheme 2) by nitrosation followed by reduction with zinc/acetic acid. Condensation of α-aminoketones with appropriate β-ketoesters can afford good yields of pyrroles. These intermediates are very versatile and can be converted into pyrroles with a wide variety of substituents with varying substitution patterns. For cases wherein $R^e$ (Z—A—B precursor) is at the 2-position, acidic hydrolysis can selectively hydrolyze the C-3 ester. Heating should then effect decarboxylation. Hydrolysis of the 2-carboxylic acid can be achieved under basic conditions. Curtius rearrangement of the acid as described previously can afford the amino derivatives. To prepare compounds with a sulfur atom attached to C-2, basic hydrolysis and decarboxylation can afford the C-2 unsubstituted pyrroles. These pyrroles can undergo electrophilic substitution to afford thiols (Cu(SCN)$_2$, then NaBH$_4$) and sulfonic acids (pyridine SO$_3$ complex or chlorosulfonic acid). The $R^{1a}$ group contained in Formula I can be derived either from the remaining ester or from $R^f$. Alternatively, the thiol and sulfonic acid derivatives can also be derived form the C-2 acids by manipulation of the carboxylic acid group as described previously.

Scheme 3

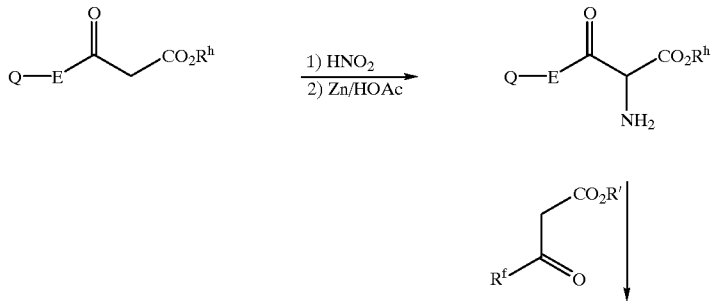

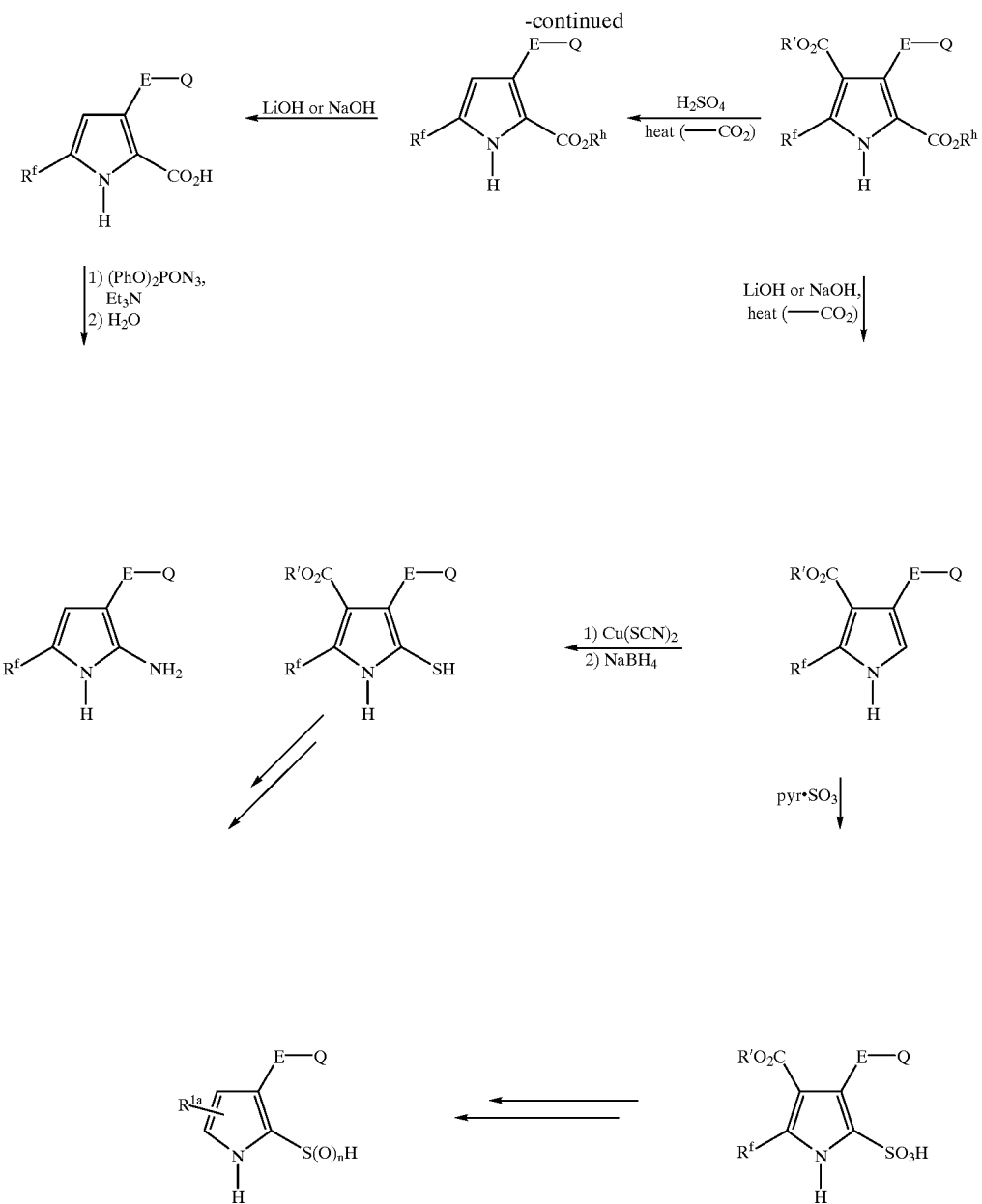

In Scheme 4 is shown how to prepare pyrroles in which Q—E is attached to the 3-position. Cyclization of α-aminoketones as described previously with β-ketoesters can afford pyrroles. Hydrolysis under basic conditions can selectively hydrolyze the C-2 ester which upon heating should undergo decarboxylation to afford 2-unsubstituted pyrroles. The C-3 ester can then be hydrolyzed under acidic conditions to afford the 3-carboxypyrroles. Curtius rearrangement under conditions described previously can afford the 3-aminopyrroles. The carboxylic acids can be used to prepare the 3-mercapto and 3-sulfonic acid derivatives. The Hunsdiecker procedure can be used to prepare the 3-bromopyrroles. Halogen metal exchange with t-BuLi at low temperature followed by quenching with copper isocyanate should introduce an isocyanate group at C-3. This intermediate can be reduced with sodium borohydride to afford the 3-mercaptopyrroles. Alternatively, the carboxylic acids can be decarboxylated to afford pyrroles which can be N-protected with a bulky protecting group such as triisopropylsilyl (TIPS). This bulky group directs electrophilic substitution to C-3 of the pyrrole ring. Thus, reaction with copper isocyanate followed by sodium borohydride reduction and then fluoride induced TIPS deprotection can afford 3-mercaptopyrroles. Sulfonation of N-protected pyrrole with pyridine sulfur trioxide complex can again be directed to C-3 of the pyrrole to afford, after TIPS deprotection, the 3-sulfonic acids.

Scheme 4

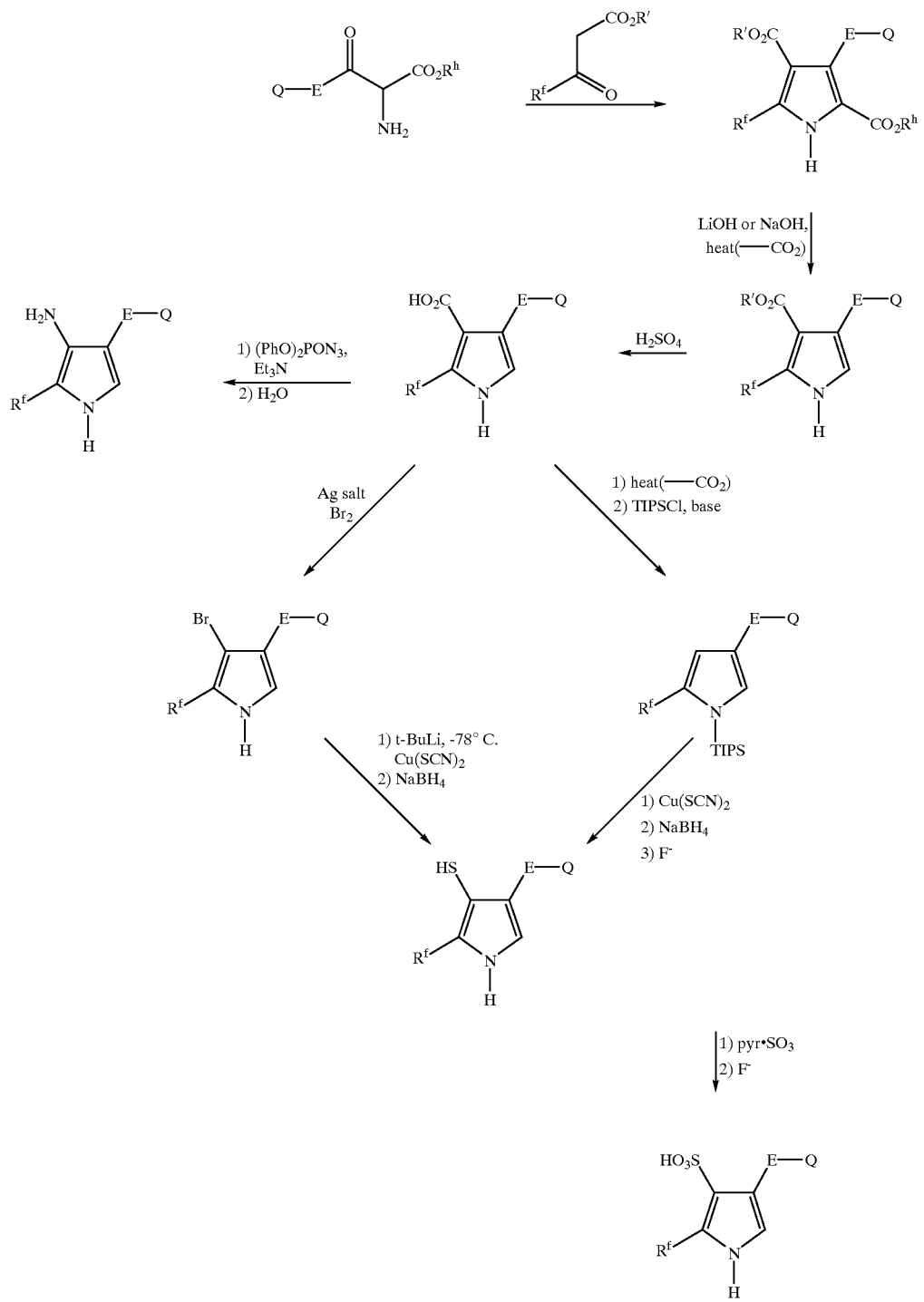

Another general method of pyrrole synthesis that can be used to prepare compounds of the present invention is shown in Scheme 5. This approach (Cushman et. al. *J. Org. Chem.* 1996, 61, 4999) uses N-protected α-aminoketones and N-protected α-aminoaldehydes which are readily available from α-amino acids by initial preparation of the N-methoxy-N-methylamides followed by addition of an alkyl Grignard reagent (to produce ketones) or by reduction with a hydride reducing agent such as lithium aluminum hydride or diisobutylaluminum hydride. These aldehydes and ketones can be allowed to react with the enolates of additional ketones to afford intermediate aldol addition products which under acidic conditions cyclize to form pyrroles. The reacting partners in this approach can be of wide scope and can be chosen so that one skilled in the art will be able to prepare varied pyrroles.

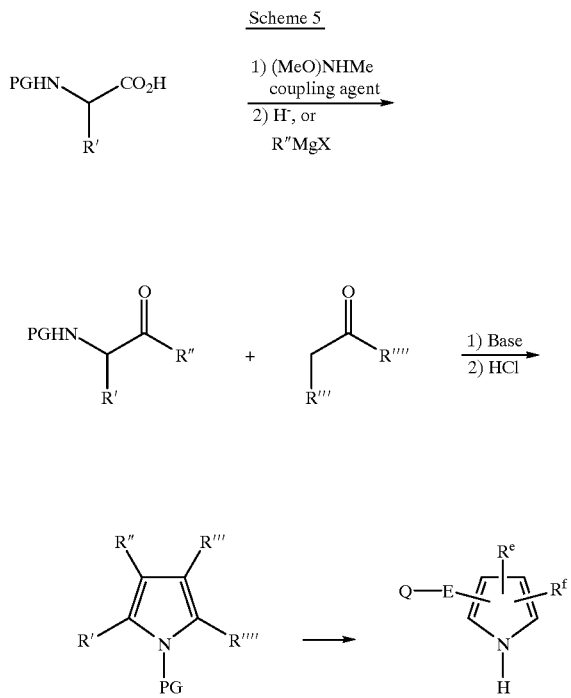

(PG = protecting group)

Another very general method of pyrrole synthesis useful A for preparing compounds of the present invention is the Paal-Knorr reaction shown in Scheme 6. This reaction involves the reacting 1,4-diketones or 1,4-ketoaldehydes with primary amines to afford pyrroles. The starting 1,4-diketones and 1,4-ketoaldehydes can be prepared using standard enolate chemistry or by other procedures which are familiar to those skilled in the art of organic synthesis. The reaction is of wide scope and the starting materials can be chosen so that a variety of pyrroles can be prepared.

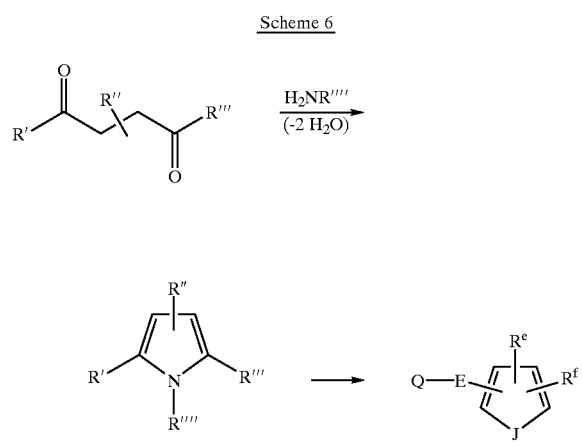

(J = NH, N—E—Q, NR$^g$)

In Scheme 7 is shown how the compounds of Schemes 1–6 wherein R$^e$ is a carboxylic ester group can be converted into compounds containing the Z—A—B residue. For the amide linker (Formula I, Z=—CONH—), when R$^e$=carboalkoxy, it can be hydrolyzed to the acid under either basic or acidic conditions depending on the substitution pattern, as described previously. Formation of the acid chloride with thionyl chloride followed by the addition of an appropriate amine H$_2$N—A—B can afford the amide-linked compounds. Alternatively, the acid can be combined with amine H$_2$N—A—B in the presence of a suitable peptide coupling agent, such as BOP-Cl, HBTU or DCC. In another method the ester can be directly coupled with an aluminum reagent, prepared by the addition of trimethylaluminum to the amine H$_2$N—A—B.

To form ether- or thioether-linked compounds of Formula I (Z=—CH$_2$O—, —CH$_2$S—) the acid can be reduced to the alcohol. Preferred procedures for this transformation are reduction with borane THF complex, or a procedure involving the reduction of the mixed anhydride with sodium borohydride (IBCF=isobutyl chloroformate and NMM=N-methylmorpholine). Completion of the ether and thioether linked compounds of Formula I can readily be accomplished by the Mitsonobu protocol with an appropriate phenol, thiophenol or hydroxy- or mercaptoheterocycle HX—A—B (X=O, S) (Formula I, A=aryl or heteroaryl). Other ethers or thioethers (X=O,S) can be prepared following initial conversion of the alcohol to a suitable leaving group, such as tosylate. Where X=S, thioethers can be further oxidized to prepare the sulfones (Formula I, Z=—CH$_2$SO$_2$—).

To prepare the amine-linked compounds of Formula I (Z=—CH$_2$NH—) the alcohol can be oxidized to the aldehyde by a number of procedures, two preferred methods of which are the Swern oxidation and oxidation with pyridinium chlorochromate (PCC). Alternatively, the aldehyde may be directly prepared by direct formylation of the pyrrole ring by the Vilsmeier-Haack procedure in certain cases, as described in previous schemes. Reductive amination of the aldehyde with an appropriate amine H$_2$N—A—B and sodium cyanoborohydride can then afford the amine linked compounds.

The aldehyde also can be used to prepare the ketone-linked compounds of Formula I (Z=—COCH$_2$—). Treatment with an organometallic species can afford the alcohol. The organometallic species (wherein M=magnesium or zinc) can preferably be prepared from the corresponding halide by treatment with metallic magnesium or zinc. These reagents should readily react with aldehydes to afford alcohols. Oxidation of the alcohol by any of a number of procedures, such as the Swern oxidation or PCC oxidation, can afford the ketones-linked compounds.

Scheme 7

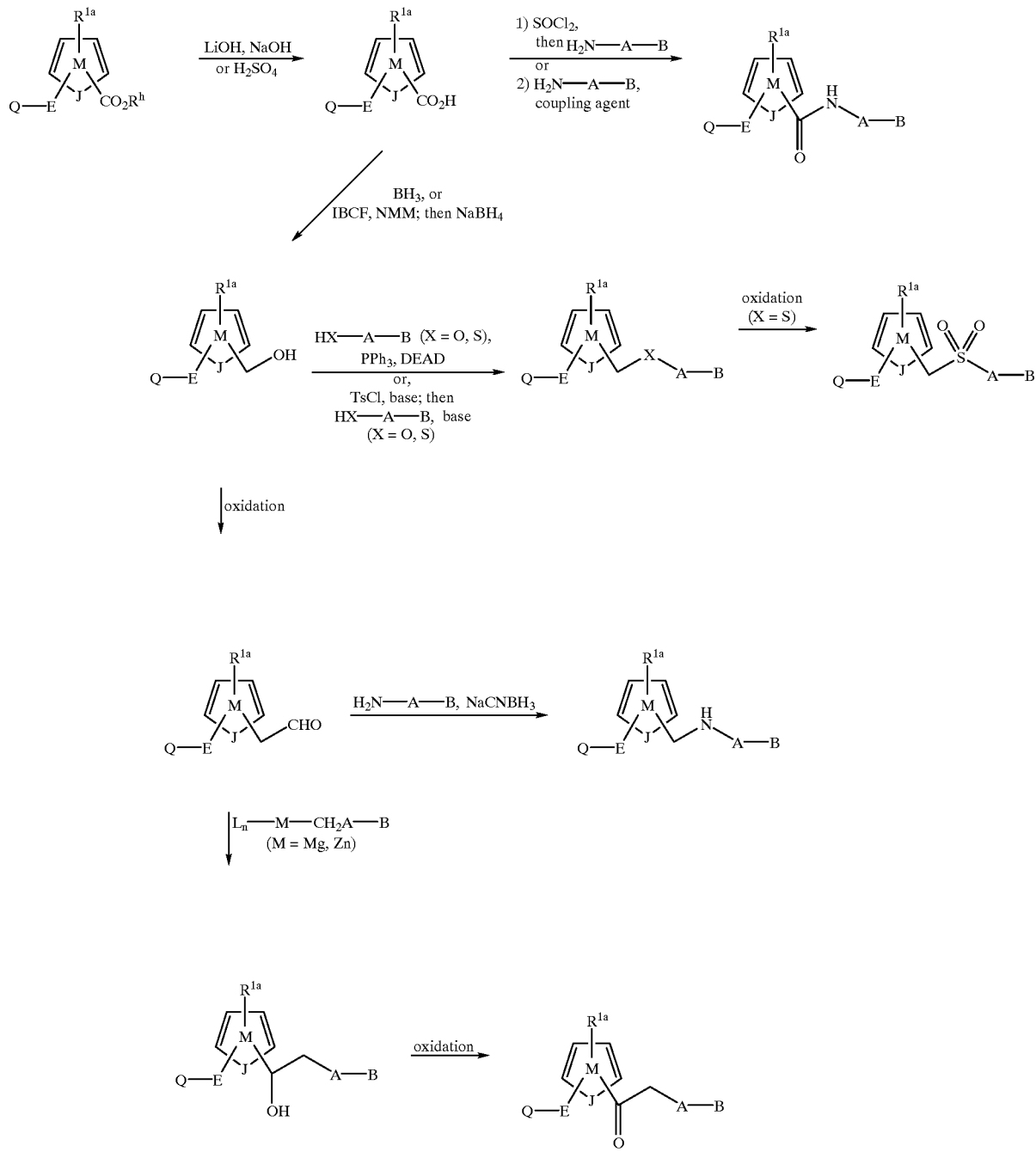

Additional compounds of Formula I in which the linking group m/z contains a nitrogen atom attached to ring M can be prepared by the procedures described in Scheme 8. The amines can be converted to sulfonamides (Formula I, m/z—NHSO$_2$—) by treatment with an appropriate sulfonyl chloride B—A—SO$_2$Cl in the presence of a base such as triethylamine. The amines can be converted into amides (Formula I, Z=—NHCO—) by treatment with an appropriate acid chloride Cl—CO—A—B in the presence of a base or by treatment with an appropriate carboxylic acid HO—CO—A—B in the presence of a suitable peptide coupling agent, such as DCC, HBTU or BOP. The amines can also be converted into amine-linked compounds (Formula I, Z=—NHCH$_2$—) by reductive amination with an appropriate aldehyde OHC—A—B.

Scheme 8

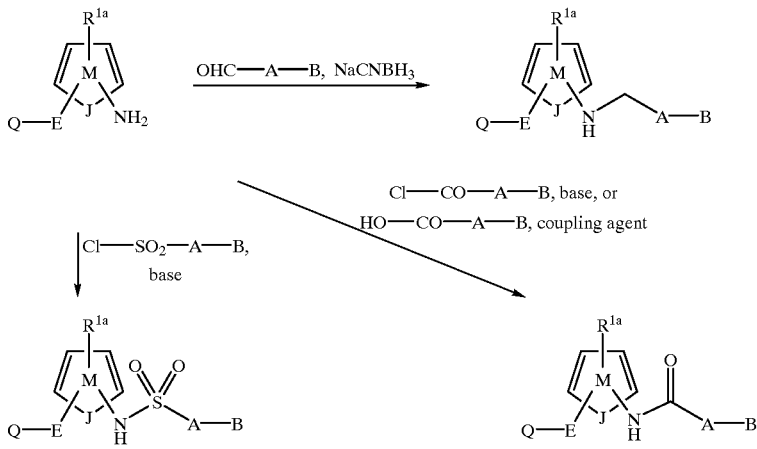

Additional compounds of Formula I in which the linking group Z contains a sulfur atom attached to ring M can be prepared by the procedures described in Scheme 9. Treatment of sulfonic acids with phosphorous pentachloride followed by treatment with an appropriate amine $H_2N$—A—B can afford sulfonamide-linked compounds (Formula I, Z=—$SO_2NH$—). The thiols can be alkylated with a suitable alkylating reagent in the presence of a base to afford thioethers (Formula I, Z=—$SCH_2$—). These compounds can be further oxidized by a variety of reagents to afford the sulfone-linked compounds (Formula I, Z=—$SO_2CH_2$—).

Scheme 9

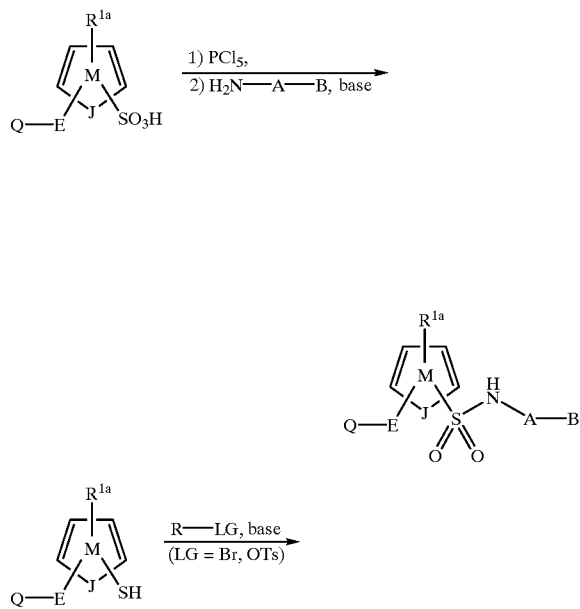

-continued

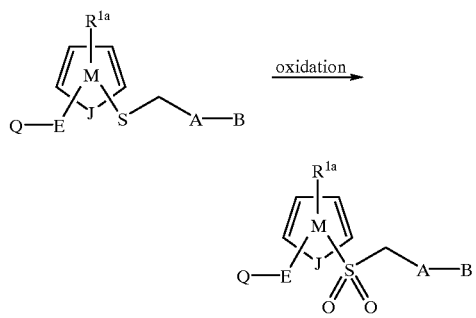

Compounds of Formula I wherein ring M is an imidazole can be formed using procedures described in Schemes 10–16. N-Substituted imidazole derivatives can be made by the general procedure shown in Scheme 10, wherein V' is either V or a precursor of $(CH_2)_nV$, V is nitro, amino, thio, hydroxy, sulfonic acid, sulfonic ester, sulfonyl chloride, ester, acid, or halide, n is 0 and 1, and PG is either a hydrogen or a protecting group. Substitution can be achieved by coupling an imidazole with a halogen containing fragment Q—E—G—Hal in the presence of a catalyst, such as base, Cu/CuBr/base, or Pd/base, followed by conversion of V' to $(CH_2)_nV$. Then, Q can be converted to D, and finally V can be converted to —Z—A—B following the procedures outlined in Schemes 7–9. Alternatively, V can be converted to Z—A—B followed by deprotection of N. This product can then be coupled as before to obtain the desired imidazole.

Scheme 10

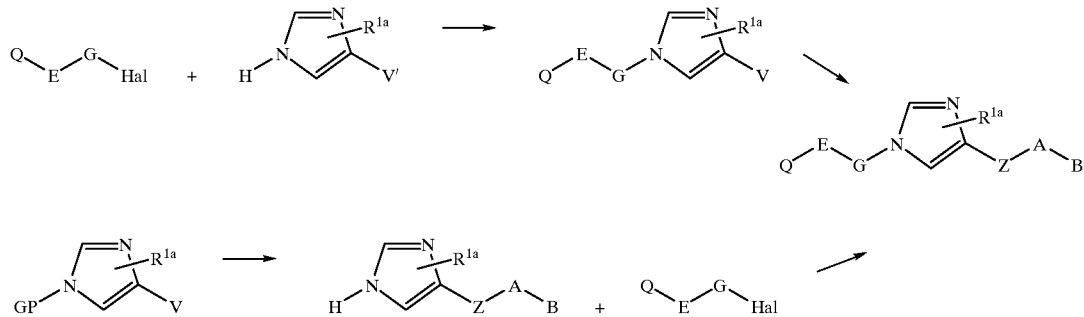

One way to make amidino-phenyl-imidazole derivatives is shown in Scheme 11. 4-Imidazole carboxylic acid can be treated with thionyl chloride and then coupled with $H_2N$—A—B in the presence of a base and then be heated with 3-fluorobenzonitrile in the presence of a base. The Pinner reaction using standard procedures known to those of skill in the art can be used to form the amidino group.

Route b1 when $R^{1b}$ is $CH_3$, it can be oxidized with $SeO_2$, $MnO_2$, $NaIO_4$/cat. $RhCl_3$, or NBS to form U. When $R^{1b}$ is hydrogen, sequential deprotonation and quenching with a lithium base and trimethysilyl chloride, followed by a second deprotonation with a lithium base and quenching with formate, formamide, carbon dioxide, sulfonyl chloride (sulfur dioxide and then chlorine), or isocyanate can afford

Scheme 11

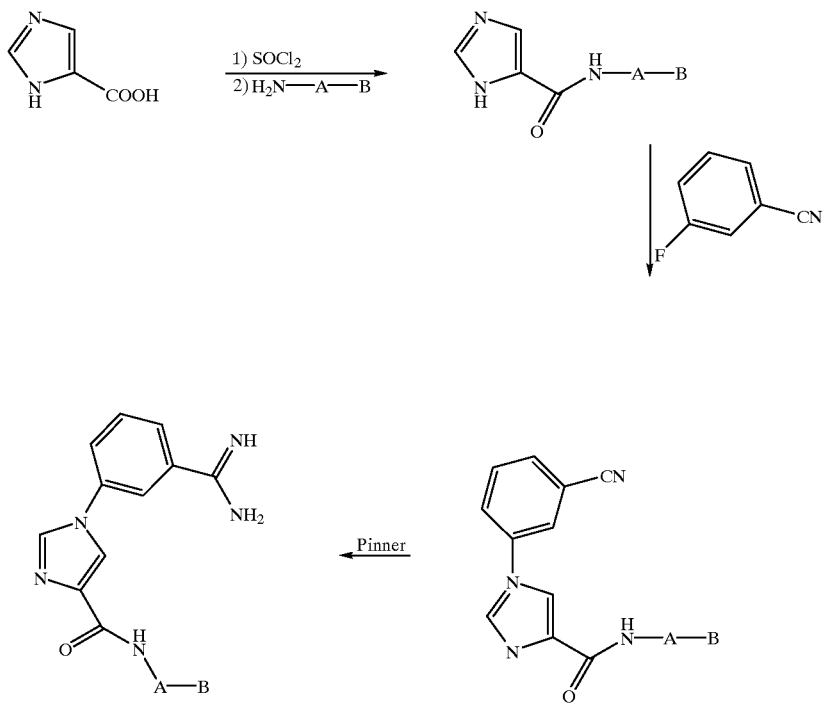

1,2-Disubstituted and 1,5-disubstituted imidazole derivatives can be made by the general procedures described in Scheme 12, wherein $R^{1b}$ is either a hydrogen or an alkyl group and U is aldehyde, ester, acid, amide, amino, thiol, hydroxy, sulfonic acid, sulfonic ester, sulfonyl chloride, or methylene halide. Step a involves coupling in the presence of a catalyst, such as base, Cu/CuBr/base, or Pd/base. When $R^{1b}$ is a hydrogen, it can be deprotonated with a lithium base and trapped by formate, formamide, carbon dioxide, sulfonyl chloride (sulfur dioxide and then chlorine), or isocyanate to give 1,2-disubstituted imidazoles (Route b1). Also, in 1,5-disubstituted imidazoles (Route b2). When $R^{1b}$ is not hydrogen, the procedure of Route b2 can again be used to form 1,5-disubstituted imidazoles (Route b3).

Scheme 12

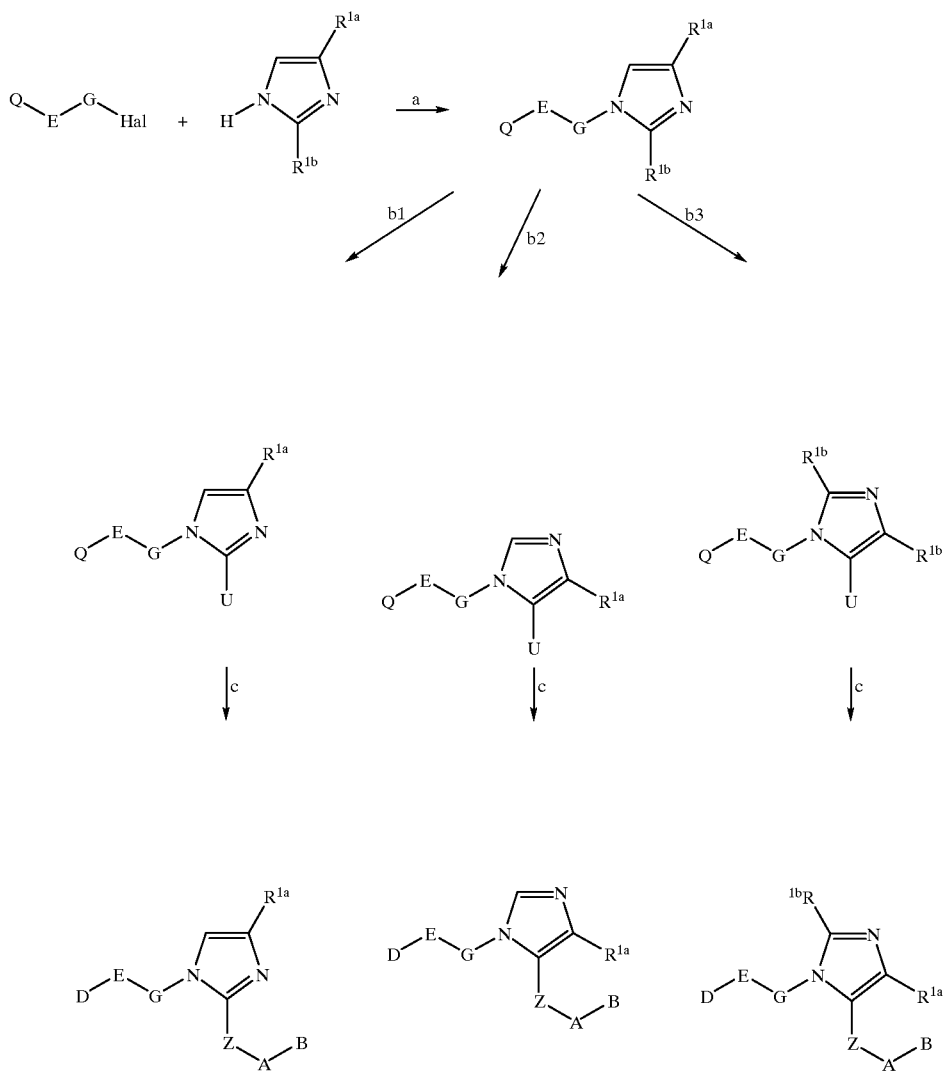

A preferred way of making 1,2-disubstituted and 1,5-disubstituted imidazole derivatives is shown in Scheme 13. Imidazole can be heated with 3-fluorobenzonitrile in the presence of a base. The coupled product can then be treated with an alkyl lithium base and quenched with $ClCO_2Me$ to give the 1,2-disubstituted compound. Further treatment with a solution prepared of $H_2N$—A—B in trimethylaluminum can give the amide, which can be further modified via the Pinner reaction to form the desired compound. The 1,5-disubstituted compounds can be made using the same procedure, except that the initial anion is protected and a second anion is formed which is then quenched as noted above. Further modifications can follow the same procedures as the 1,2-disubstituted compounds.

Scheme 13

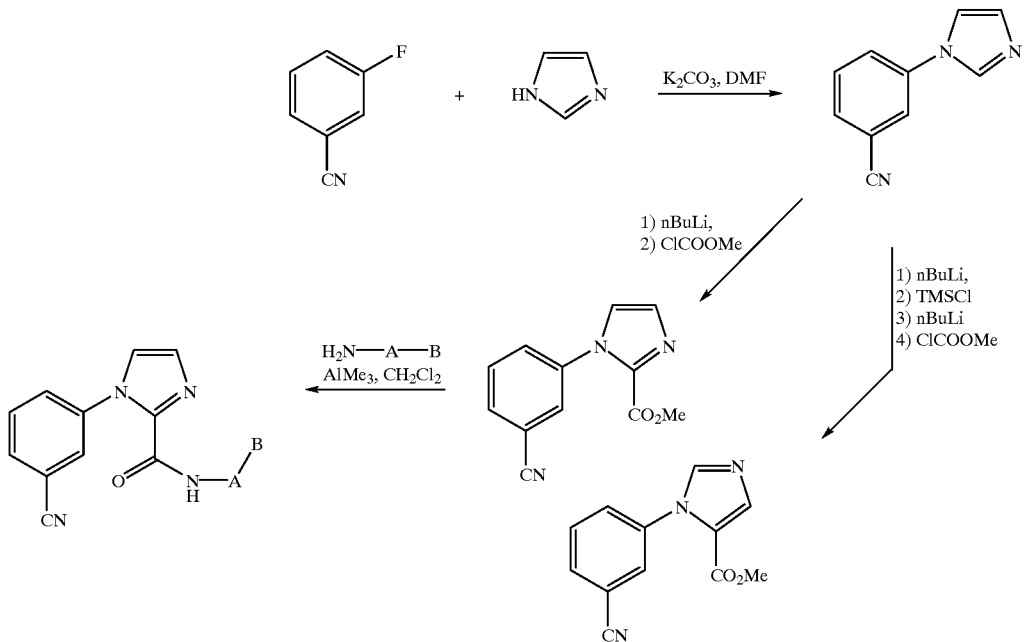

Another way of making 1,2-disubstituted imidazole derivatives is described in Scheme 14. By reacting an N-substituted imidazole with a cyanate, the amide can be obtained. This amide can then be coupled with group B as will be described later.

Scheme 14

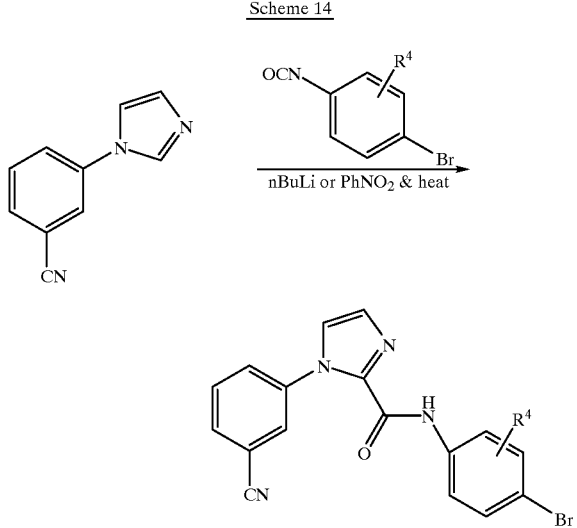

Another means of making 1,5-disubstituted imidazole derivatives is described in Scheme 15. Alkylation with 2-bromoethylacetate and subsequent reaction with Gold's reagent in the presence of a base, such as NaOMe, or LDA, can form ester substituted imidazoles which can be further modified as previously discribed.

Scheme 15

A general procedure to make 2,4,5-trisubstituted or 4,5-disubstituted imidazole derivatives is shown in Scheme 16. After metal halogen exchange of the Q—E—G fragment, it can be reacted with the amide shown, brominated with NBS and cyclized with excess $NH_3$ and $R^{1a}CO_2H$ to afford an imidazole. This can then be modified as before.

Scheme 16

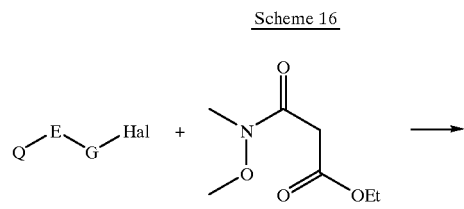

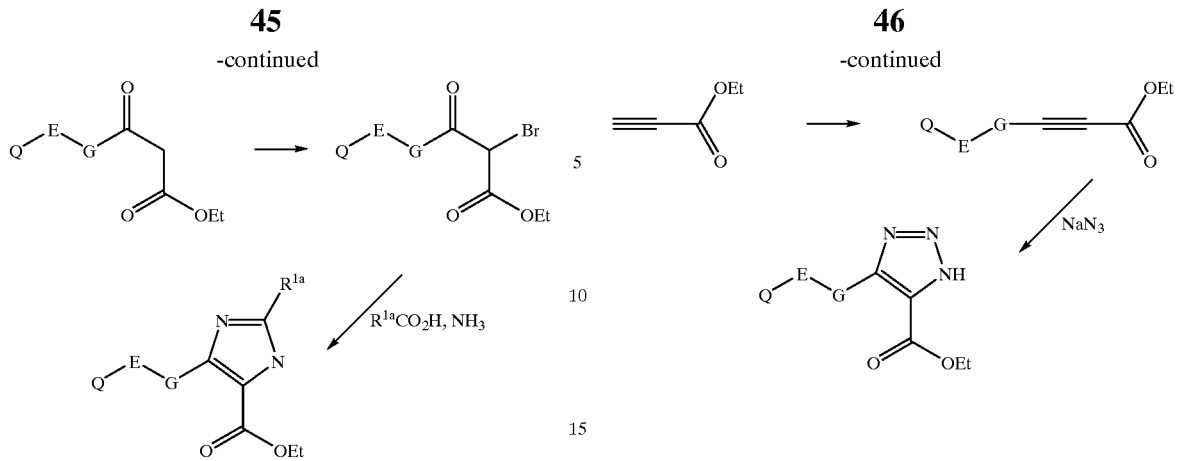

A general procedure to make 4,5-disubstituted triazole derivatives is described in Scheme 17. Ethyl propiolate can be substituted in the presence of CuI/Pd and then reacted with NaN₃ to form a triazole. The triazole can be converted as described previously.

Scheme 17

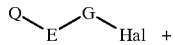

The tetrazole compounds of the present invention where Z is —CONH— can be prepared as exemplified in Scheme 18. An appropiately substituted amine can be acylated with ethyl oxalyl chloride. The resulting amide can be converted to the tetrazole either by the methods described by Duncia (*J. Org. Chem.* 1991, 2395–2400) or Thomas (*Synthesis* 1993, 767–768). The amide can be converted to the iminoyl chloride first and the reacted with NaN₃ to form the 5-carboethoxytetrazole (*J. Org. Chem.* 1993, 58, 32–35 and *Bioorg. & Med. Chem. Lett.* 1996, 6, 1015–1020). The 5-carboethoxytetrazole can then be further modified as described in Scheme 7.

The tetrazole compounds of the present invention where Z is —CO— can also be prepared via iminoyl chloride (*Chem. Ber.* 1961, 94, 1116 and *J. Org. Chem.* 1976, 41, 1073) using an appropriately substituted acyl chloride as starting material. The ketone-linker can be reduced to compounds wherein Z is alkyl.

Scheme 18

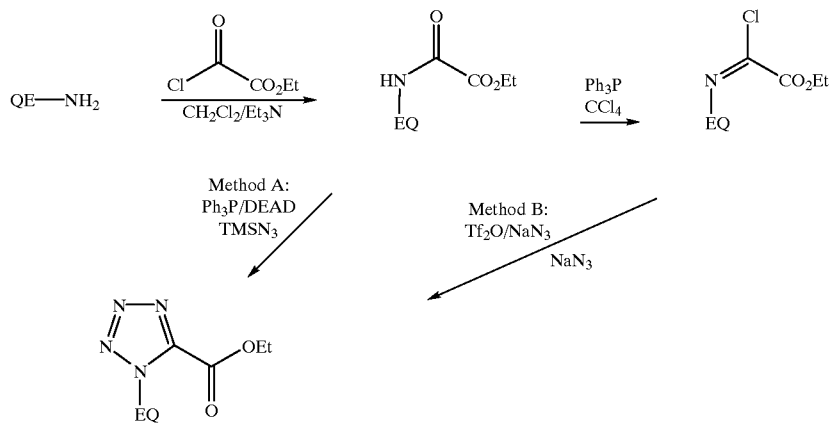

The methods described in Scheme 18 can also be used to synthesize compounds where the E—Q is linked to the carbon atom of the tetrazole as shown in Scheme 19. The 5-substituted tetrazole can then be alkylated or acylated to give the desired products.

Scheme 19

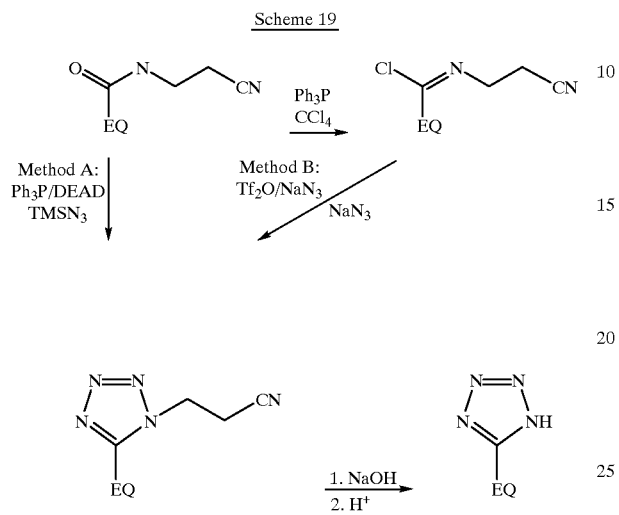

The tetrazole compounds of the present invention wherein Z is —SO$_2$NH—, —S—, —S(O)—, SO$_2$— can be prepared from the thiol prepared as shown in Scheme 20. Appropiately substituted thioisocyanate can be reacted with sodium azide to give the 5-thiotetrazole (*J. Org. Chem.* 1967, 32, 3580–3592). The thio-compound can be modified as described in Scheme 9.

The tetrazole compounds of the present invention wherein Z is —O— can be prepared via the same method described in Scheme 20 by using appropiately substituted isocyanate as the starting material. The hydroxy compound can be modified similarity to the thiols described in Scheme 9.

Scheme 20

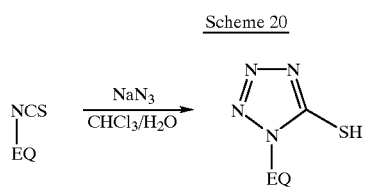

The tetrazole compounds of the present invention wherein Z is —NH—, —NHCO—, —NHSO$_2$— can be prepared from 5-aminotetrazole, which can be prepared by Smiles Rearrangement as shown in Scheme 21. The thio-compound prepared as described in Scheme 20 can be alkylated with 2-chloroacetamide. The resulting compound can then be refluxed in ethanolic sodium hydroxide to give the corresponding 5-amino-tetrazole (*Chem. Pharm. Bull.* 1991, 39, 3331–3334). The resulting 5-amino-tetrazole can then be alkylated or acylated to form the desired products.

Scheme 21

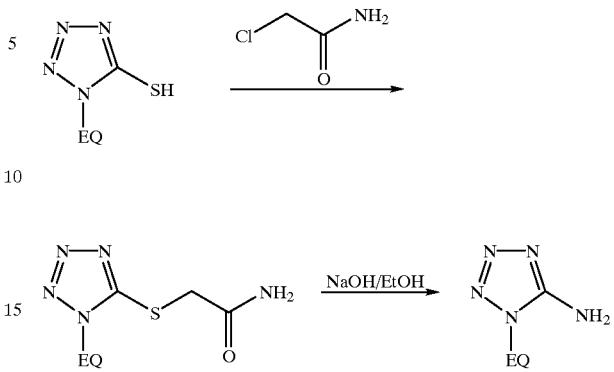

Pyrazoles of Formula I (such as those described in Scheme can be prepared by the condensation of an appropriately substituted hydrazine with a variety of diketo esters. Condensations of this type typically afford a mixture of pyrazole regioisomers which can be effectively separated via silica gel column chromatography. The esters can be converted to Z—A—B as previously described.

Alternatively, if in Scheme 22, the starting diketone contains CH$_3$ in place of CO$_2$Et, then the resulting methyl pyrazole can be separated and oxidized as in Route b1 in Scheme 12 to form the pyrazole carboxylic acid.

Scheme 22

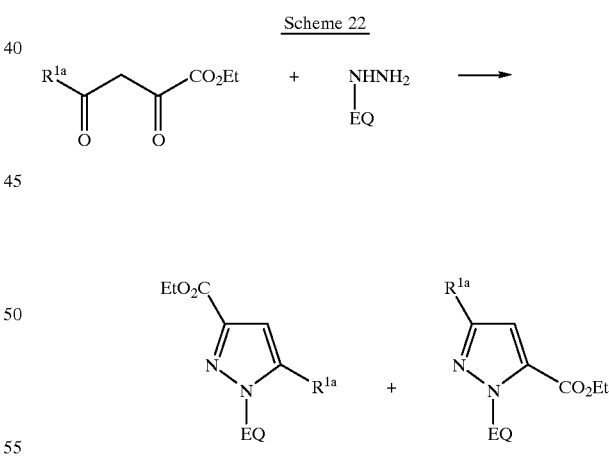

When ketoimidates are used for condensations with hydrazines the corresponding pyrazole amino esters are obtained (Scheme 23). Conversion of these intermediates to the final compounds of formula I can then be accomplished by the protection of the amino functionality with a suitable protecting group or by derivatization (e.g. sulfonamide) and then modifying the ester as previously noted.

Scheme 23

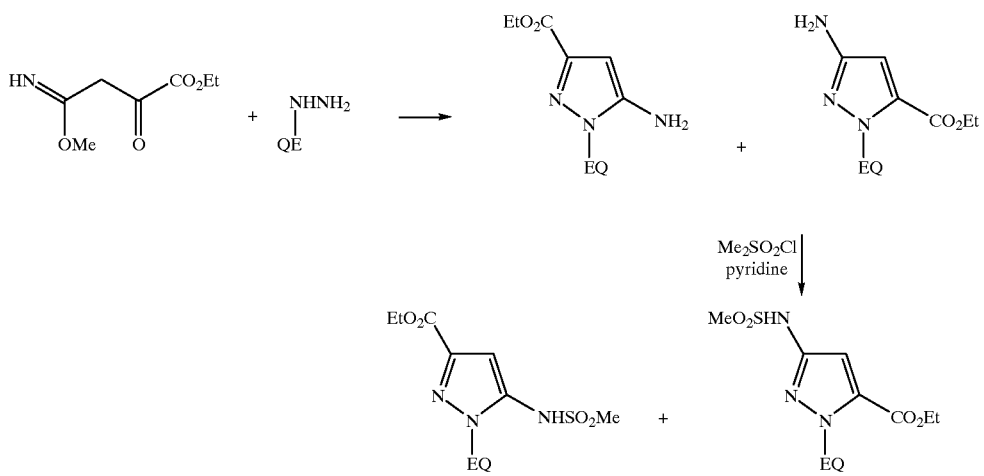

As shown in Scheme 24, pyrazoles wherein the 4-position is substituted can be prepared by bromination (bromine or NBS in either dichloromethane or acetic acid) of the initial pyrazole. Conversion of 4-bromo-pyrazole to 4-carboxylic acid pyrazole can be accomplished by a number of methods commonly known to those in the art of organic synthesis. Further manipulations as previously described can afford pyrazoles of the present invention.

Pyrazoles can also be prepared according to method described in Scheme 25. The bromo-pyrazoles are formed as in Scheme 24. QE can then be coupled using palladium catalysed Suzuki cross-coupling methodology. Further modification is achieved as previously described.

Scheme 24

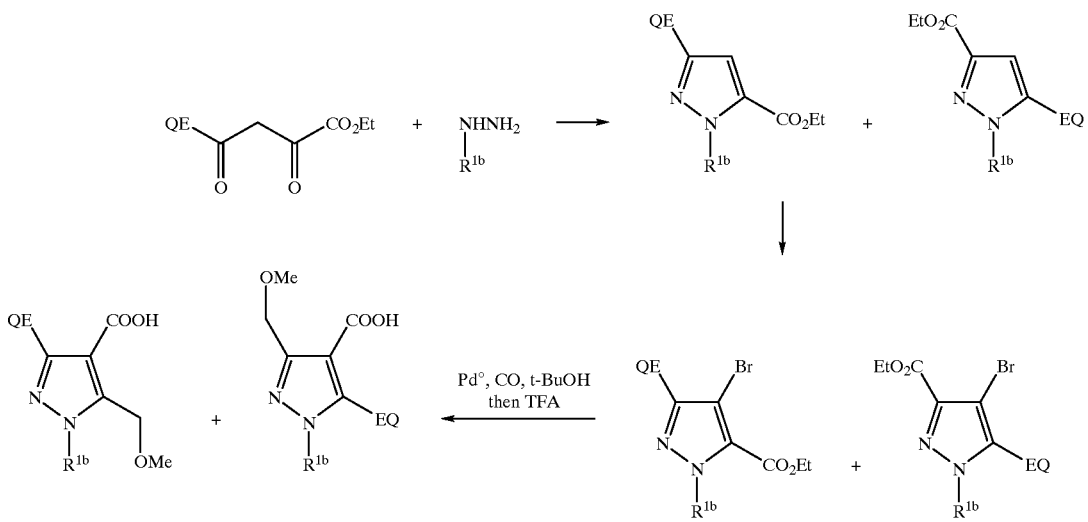

Scheme 25

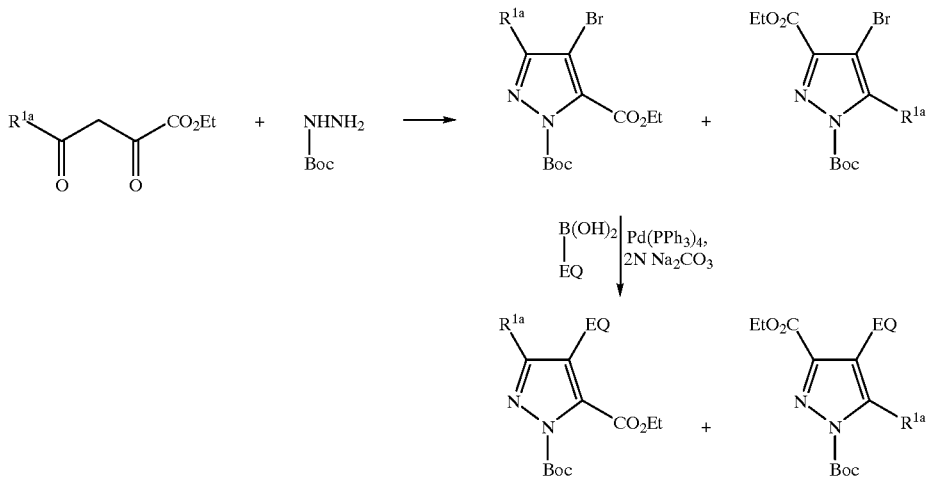

5-substituted phenylpyrazoles can be prepared by the method shown in Scheme 26. Conversion of the 5-hydroxy pyrazole to its triflate (triflic anhydride, lutidine in dichloromethane) or bromide (POBr₃) followed by palladium Suzuki cross-coupling with an apppropriately substituted phenylboronic acid should then afford 5-substituted pyrazoles. Conversion of this intermediate to the 4-bromo derivative followed by its carbonylation as described in Scheme 24 should then afford the appropriate ester which can be further afford the compounds of formula I.

1-Substituted-1,2,3-triazoles of the present invention can be prepared by the treatment of an appropriately substituted azide with a variety of dipolarophiles (*Tetrahedron* 1971, 27, 845 and *J. Amer. Chem. Soc.* 1951, 73, 1207) as shown in Scheme 27. Typically a mixture of regioisomers are obtained which can be easily separated and elaborated to the triazole carboxylic acids. Further transformations as previously described can then afford the compounds of the present invention.

Scheme 26

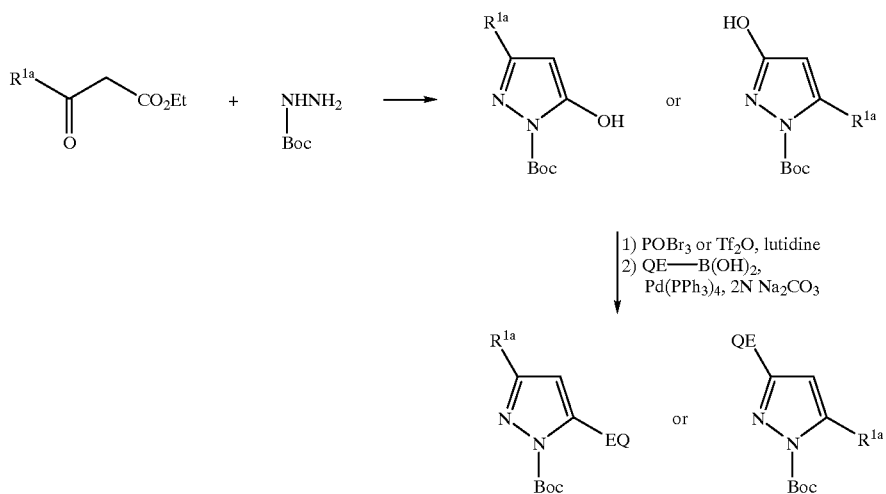

Scheme 27

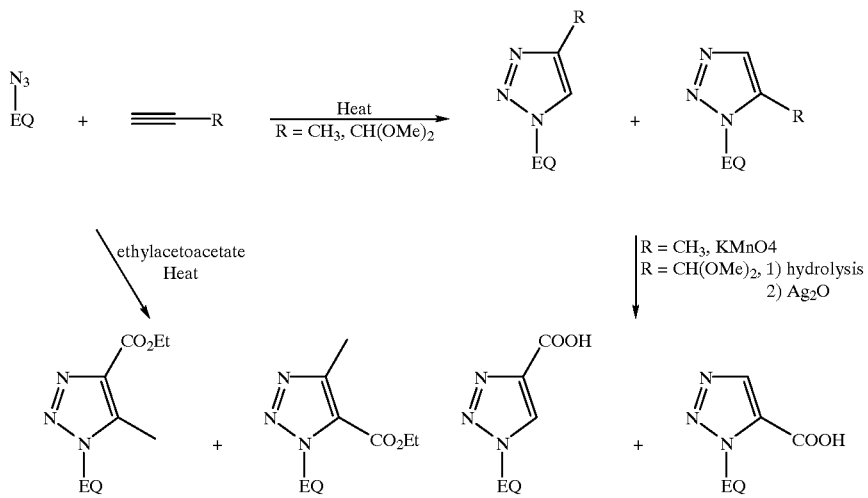

1,2,4-Triazoles of the present invention can be obtained by the methodology of Huisgen et al (*Liebigs Ann. Chem.* 1962, 653, 105) by the cycloaddition of nitriliminium species (derived from the treatment of triethylamine and chloro hydrazone) and an appropriate nitrile dipolarophile (Scheme 28). This methodology provides a wide variety of 1,2,4 triazoles with a varied substitution pattern at the 1, 3, and 5 positions.

Scheme 28

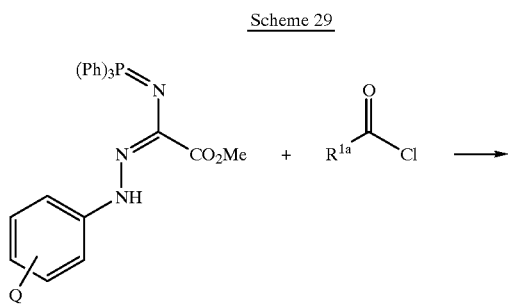

$R^{1b}$ = Ester, Alkyl, Aryl
$R^{1a}$ = phenyl or ester 1,2,4 Triazoles can also be prepared by the methodology of Zecchi et al (*Synthesis* 1986, 9, 772) by an aza Wittig condensation (Scheme 29).

Scheme 29

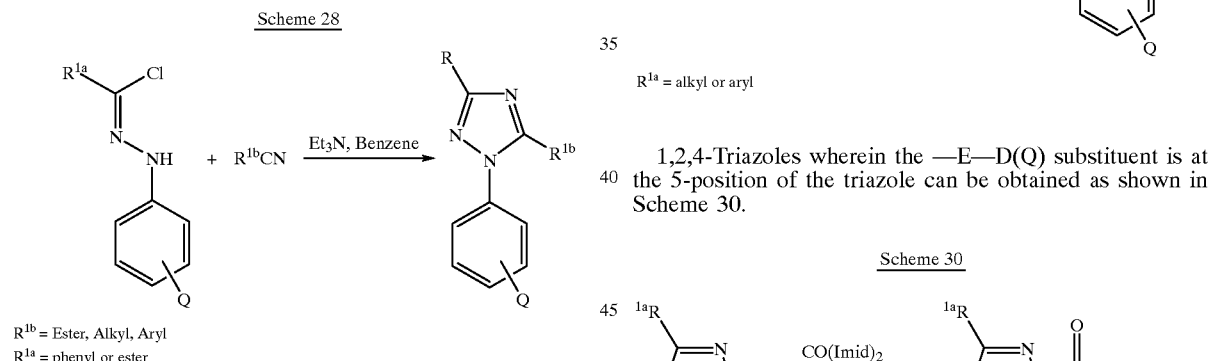

-continued

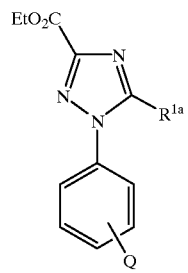

$R^{1a}$ = alkyl or aryl 1,2,4-Triazoles wherein the —E—D(Q) substituent is at the 5-position of the triazole can be obtained as shown in Scheme 30.

Scheme 30

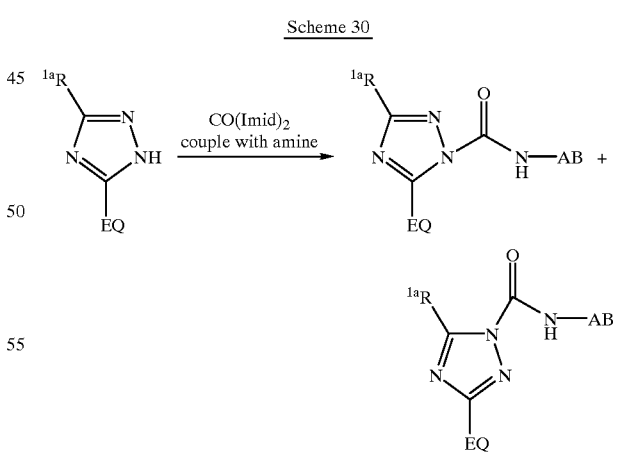

1,3,4-Triazoles of the present invention can be obtained via the methodology of Moderhack et al (*J. Prakt. Chem.* 1996, 338, 169). As shown in Scheme 31, this reaction involves the condensation of a carbazide with an appropriately substituted commercially available thioisocyanate to form the cyclic thiourea derivative. Alkylation or nucleophilic displacement reactions on the thiono-urea intermediate can then afford a thio-alkyl or aryl intermediate which can be hydrolysed, oxidized and decarboxylated to the 5-H 2-thio-triazole intermediate which can be converted to the compounds of the present invention. Alternatively the thiono-urea intermediate can be oxidized directly to the 2-H triazole which can then be converted to the ester and modified as previously described. The thiono-urea intermediate can also be oxidized to the sulfonyl chloride by methods shown previously.

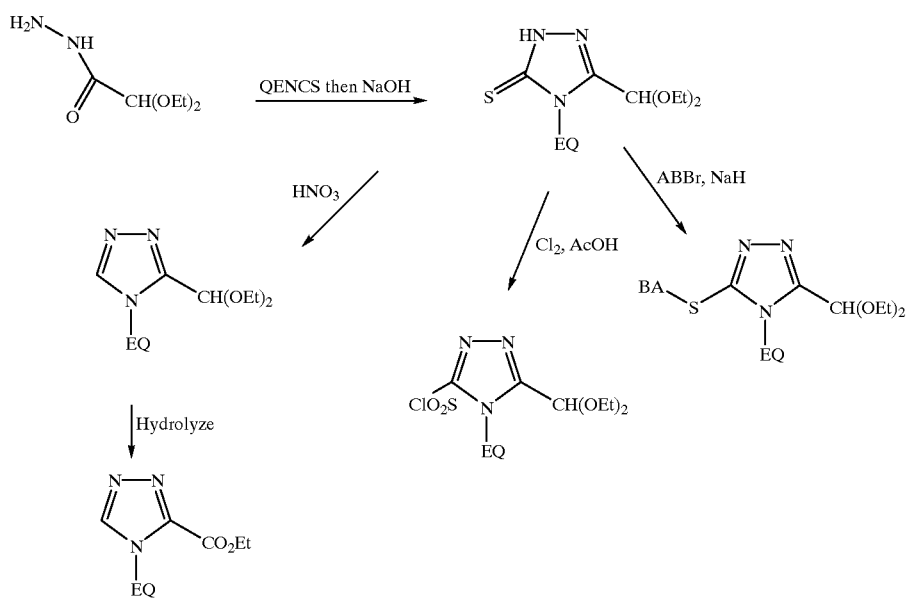

Scheme 31

The imidazole core shown in Scheme 32 can be prepared by the condensation of 3-cyanoaniline with n-butylglyoxylate to afford the imine which can then be treated with TosylMIC in basic methanol to afford the desired imidazole compound. Coupling of the ester under standard conitions then affords a variety of analogs which then can be further manipulated to afford e.g. the benzylamine or the benzamidines.

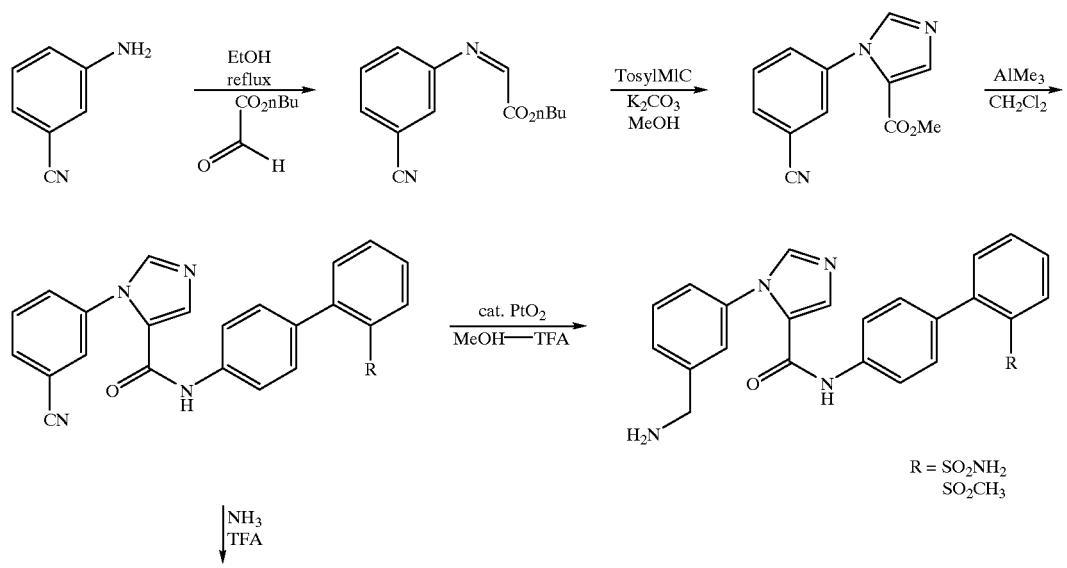

Scheme 32

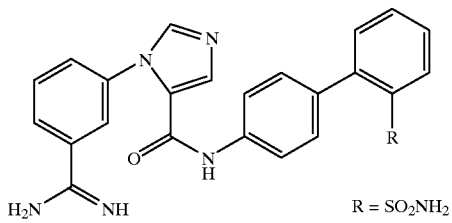

R = SO₂NH₂

Compounds of the present invention wherein AB is a biphenylamine or similar amine may be prepared as shown in Scheme 33. 4-Bromoaniline can be protected as Boc-derivative and coupled to a phenylboronic acid under Suzuki conditions (*Bioorg. Med. Chem. Lett.* 1994, 189). Deprotection with TFA provides the aminobiphenyl compound. Other similar amines wherein A and/or B are heterocycles can be prepared by the same method using appropiately substituted boronic acids and arylbromide. The bromoaniline can also be linked to the core ring structures first as described above, and then undergo a Suzuki reaction to give the desired product.

Scheme 33

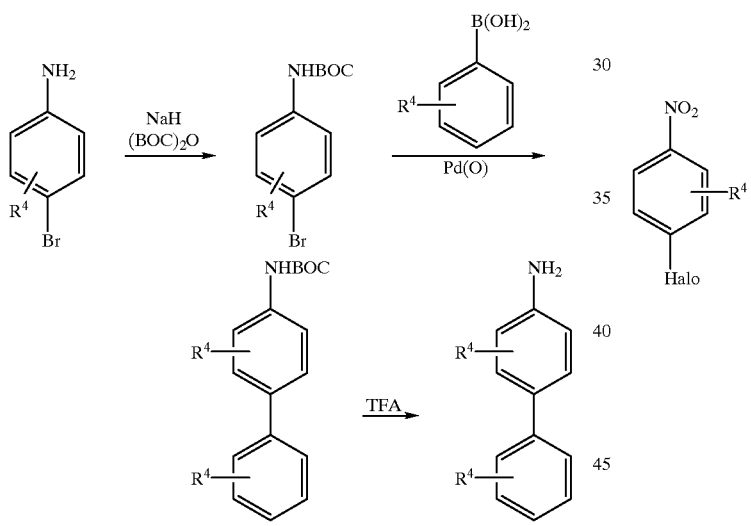

Compounds of the present invention wherein A—B is A—X—Y can be prepared like the piperazine derivative shown in Scheme 34.

Scheme 34

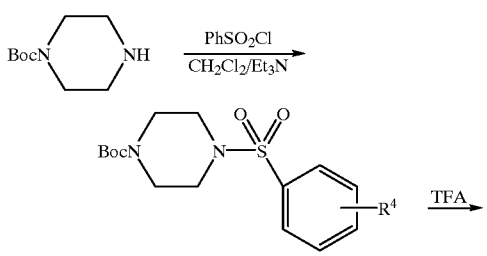

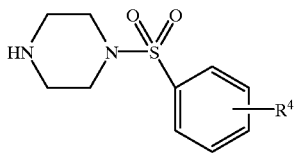

Scheme 35 shows how one can couple cyclic groups wherein X=NH, O, or S.

Scheme 35

[Scheme 35 diagram]

X = NH, O, S

When B is defined as X—Y, the following description applies. Groups A and B are available either through commercial sources, known in the literature or readily synthesized by the adaptation of standard procedures known to practioners skilled in the art of organic synthesis. The required reactive functional groups appended to analogs of A and B are also available either through commercial sources, known in the literature or readily synthesized by the adaptation of standard procedures known to practioners skilled in the art of organic synthesis. In the tables that follow the chemistry required to effect the coupling of A to B is outlined.

TABLE A

Preparation of Amide, Ester, Urea, Sulfonamide and Sulfamide linkages between A and B.

| Rxn. No. | if A contains: | then the reactive substituent of Y is: | to give the following product A-X-Y: |
|---|---|---|---|
| 1 | A-NHR$^2$ as a substituent | ClC(O)-Y | A-NR$^2$-C(O)-Y |
| 2 | a secondary NH as part of a ring or chain | ClC(O)-Y | A-C(O)-Y |
| 3 | A-OH as a substituent | ClC(O)-Y | A-O-C(O)-Y |
| 4 | A-NHR$^2$ as a substituent | ClC(O)-CR$^2$R$^{2a}$-Y | A-NR$^2$-C(O)-CR$^2$R$^{2a}$-Y |
| 5 | a secondary NH as part of a ring or chain | ClC(O)-CR$^2$R$^{2a}$-Y | A-C(O)-CR$^2$R$^{2a}$-Y |
| 6 | A-OH as a substituent | ClC(O)-CR$^2$R$^{2a}$-Y | A-O-C(O)-CR$^2$R$^{2a}$-Y |
| 7 | A-NHR$^3$ as a substituent | ClC(O)NR$^2$-Y | A-NR$^2$-C(O)NR$^2$-Y |
| 8 | a secondary NH as part of a ring or chain | ClC(O)NR$^2$-Y | A-C(O)NR$^2$-Y |
| 9 | A-OH as a substituent | ClC(O)NR$^2$-Y | A-O-C(O)NR$^2$-Y |
| 10 | A-NHR$^2$ as a substituent | ClSO$_2$-Y | A-NR$^2$-SO$^2$-Y |
| 11 | a secondary NH as part of a ring or chain | ClSO$_2$-Y | A-SO$^2$-Y |
| 12 | A-NHR$^2$ as a substituent | ClSO$_2$-CR$^2$R$^{2a}$-Y | A-NR$^2$-SO$_2$-CR$^2$R$^{2a}$-Y |
| 13 | a secondary NH as part of a ring or chain | ClSO$_2$-CR$^2$R$^{2a}$-Y | A-SO$_2$-CR$^2$R$^{2a}$-Y |
| 14 | A-NHR$^2$ as a substituent | ClSO$_2$-NR$^2$-Y | A-NR$^2$-SO$^2$-NR$^2$-Y |
| 15 | a secondary NH as part of a ring or chain | ClSO$_2$-NR$^2$-Y | A-SO$_2$-NR$^2$-Y |
| 16 | A-C(O)Cl | HO-Y as a substituent | A-C(O)-O-Y |
| 17 | A-C(O)Cl | NHR$^2$-Y as a substituent | A-C(O)-NR$^2$-Y |
| 18 | A-C(O)Cl | a secondary NH as part of a ring or chain | A-C(O)-Y |
| 19 | A-CR$^2$R$^{2a}$C(O)Cl | HO-Y as a substituent | A-CR$^2$R$^{2a}$C(O)-O-Y |
| 20 | A-CR$^2$R$^{2a}$C(O)Cl | NHR$^2$-Y as a substituent | A-CR$^2$R$^{2a}$C(O)-NR$^2$-Y |
| 21 | A-CR$^2$R$^{2a}$C(O)Cl | a secondary NH as part of a ring or chain | A-CR$^2$R$^{2a}$C(O)-Y |
| 22 | A-SO$_2$Cl | NHR$^2$-Y as a substituent | A-SO$_2$-NR$^2$-Y |
| 23 | A-SO$_2$Cl | a secondary NH as part of a ring or chain | A-SO$_2$-Y |
| 24 | A-CR$^2$R$^{2a}$SO$_2$Cl | NHR$^2$-Y as a substituent | A-CR$^2$R$^{2a}$SO$_2$-NR$^2$-Y |
| 25 | A-CR$^2$R$^{2a}$SO$_2$Cl | a secondary NH as part of a ring or chain | A-CR$^2$R$^{2a}$SO$_2$-Y |

The chemistry of Table A can be carried out in aprotic solvents such as a chlorocarbon, pyridine, benzene or toluene, at temperatures ranging from −20° C. to the reflux point of the solvent and with or without a trialkylamine base.

TABLE B

Preparation of ketone linkages between A and B.

| Rxn. No. | if A contains: | then the reactive substituent of Y is: | to give the following product A-X-Y: |
|---|---|---|---|
| 1 | A-C(O)Cl | BrMg-Y | A-C(O)-Y |
| 2 | A-CR$^2$R$^{2a}$C(O)Cl | BrMg-Y | A-CR$^2$R$^{2a}{}_2$C(O)-Y |
| 3 | A-C(O)Cl | BrMgCR$^2$R$^{2a}$-Y | A-C(O)CR$^2$R$^{2a}$-Y |
| 4 | A-CR$^2$R$^{2a}$C(O)Cl | BrMgCR$^2$R$^{2a}$-Y | A-CR$^2$R$^{2a}$C(O)CR$^2$R$^{2a}$-Y |

The coupling chemistry of Table B can be carried out by a variety of methods. The Grignard reagent required for Y is prepared from a halogen analog of Y in dry ether, dimethoxyethane or tetrahydrofuran at 0° C. to the reflux point of the solvent. This Grignard reagent can be reacted directly under very controlled conditions, that is low temeprature (−20° C. or lower) and with a large excess of acid chloride or with catalytic or stoichiometric copper bromide.dimethyl sulfide complex in dimethyl sulfide as a solvent or with a variant thereof. Other methods available include transforming the Grignard reagent to the cadmium reagent and coupling according to the procedure of Carson and Prout (Org. Syn. Col. Vol. 3 (1955) 601) or a coupling mediated by Fe(acac)$_3$ according to Fiandanese et al.(Tetrahedron Lett., (1984) 4805), or a coupling mediated by manganese (II) catalysis (Cahiez and Laboue, Tetrahedron Lett., 33(31), (1992) 4437).

TABLE C

Preparation of ether and thioether linkages between A and B

| Rxn. No. | if A contains: | then the reactive substituent of Y is: | to give the following product A-X-Y: |
|---|---|---|---|
| 1 | A-OH | Br-Y | A-O-Y |
| 2 | A-CR$^2$R$^{2a}$-OH | Br-Y | A-CR$^2$R$^{2a}$O-Y |
| 3 | A-OH | Br-CR$^2$R$^{2a}$-Y | A-OCR$^2$R$^{2a}$-Y |
| 4 | A-SH | Br-Y | A-S-Y |
| 5 | A-CR$^2$R$^{2a}$-SH | Br-Y | A-CR$^2$R$^{2a}$S-Y |
| 6 | A-SH | Br-CR$^2$R$^{2a}$-Y | A-SCR$^2$R$^{2a}$-Y |

The ether and thioether linkages of Table C can be prepared by reacting the two components in a polar aprotic solvent such as acetone, dimethylformamide or dimethylsulfoxide in the presence of a base such as potassium carbonate, sodium hydride or potassium t-butoxide at temperature ranging from ambient temperature to the reflux point of the solvent used.

TABLE D

Preparation of -SO- and -SO2- linkages from thioethers of Table C.

| Rxn. No. | if the starting material is: | and it is oxidized with Alumina (wet)/ Oxone (Greenhalgh, Synlett, (1992) 235) the product is: | and it is oxidized with m-chloroperbenzoic acid (Satoh et al., Chem. Lett. (1992) 381), the product is: |
|---|---|---|---|
| 1 | A-S-Y | A-S(O)-Y | A-SO$_2$-Y |
| 2 | A-CR$^2$R$^{2a}$S-Y | A-CR$^2$R$^{2a}$S(O)-Y | A-CR$^2$R$^{2a}$SO$_2$-Y |
| 3 | A-SCR$^2$R$^{2a}$-Y | A-S(O)CR$^2$R$^{2a}$-Y | A-SO$_2$CR$^2$R$^{2a}$-Y |

The thioethers of Table C serve as a convenient starting material for the preparation of the sulfoxide and sulfone analogs of Table D. A combination of wet alumina and oxone can provide a reliable reagent for the oxidation of the thioether to the sulfoxide while m-chloroperbenzoic acid oxidation will give the sulfone.

TABLE E

Methods of Preparing Group E

| Rxn | Q | D is to be | then a transformation that may be used is: |
|---|---|---|---|
| 1 | —CN | —C(=NH)NH2 | E—C≡N  i) HCl MeOH  ii) NH$_3$OAc, MeOH  →  E—C(NH$_2$)=NH |
| 2 | —CN | —CH2NH2 | E—C≡N  LiAlH$_4$ / Et$_2$O  →  E—CH$_2$NH$_2$ |
| 3 | —CO2H | —CH2NH2 | E—C(=O)OH  i) iBuOC(O)Cl, NMM, THF then NaBH$_4$, H$_2$O/THF;  ii) MsCl, Et$_3$N, CH$_2$Cl$_2$;  iii) NaN$_3$, DMF;  iv) SnCl$_2$, MeOH  →  E—CH$_2$NH$_2$ |
| 4 | —CO2H | —NH2 | E—C(=O)OH  i) iBuOC(O)Cl, NMM, THF then NaN$_3$ and heat;  ii) tBuOH, reflux;  iii) HCl, Et$_2$O  →  E—NH$_2$ |

In Table E several methods of transforming a functional group Q into group D of Formula 1 are shown. While not all possible functional groups for Q and D are listed and the synthetic methods suggested are not comprehensive, Table E is meant to illustrate strategies and transformations available to a practitioner skilled in the art of organic synthesis for preparing compounds of Formula 1. In reaction 1 of Table E the transformation of a nitrile into an amidine by the Pinner methodology is shown; in reaction 2 the direct reduction of a nitrile by a hydride reducing agent to a methylene amine is illustrated. In reaction 3, the utility of a carboxylic acid, which may be readily derived from its ester or a nitrile if necessary, in the preparation of a methylene amine is shown. This synthetic route is exceptionally flexible because of the several stable intermediates prepared en route to the final product. As outlined, formation of an activated analog, such as the mixed anhydride, allows for the mild reduction of the acid to the methylene alcohol, this may in turn be transformed into a leaving group by sulfonylation or halogenation or protected with a suitable protecting group to be transformed later in the synthesis as the chemistry demands. Once the methylene alcohol is so activated, displacement by an efficient nitrogen nucleophile, such as azide anion, can again provide another suitably stable analog, -the methylene azide- which may be used as a protected form of the methylene amine or transformed directly into the methylene amine group by reduction. Reaction 4 addresses the problem of appending the amine functionality directly through a bond to group E of Formula 1. Once again, the carboxylic acid provides a convenient entre into this selection for group D. The well-know Curtius rearrangement is illustrated here; an activated acid analog can be used to form an acyl azide which upon thermal decomposition is rearranged to the corresponding isocyanate. The isocyanate intermediate may then be captured as a stable carbamate by the addition of a suitable alcohol and further heating. This carbamate can be used as a stable protecting group for the amine or cleaved directly to the desired D. Alternatively, it may be convenient to quench the isocyanate intermediate with water to give the amine directly.

Other features of the invention will become apparent in the course of the following descriptions of exemplary embodiments which are given for illustration of the invention and are not intended to be limiting thereof.

EXAMPLES

Example 1

3-Methyl-1-(2-aminomethyl-4-methoxyphenyl)-1H-pyrazole-5-(N-(2'-sulfamido-[1,1']-biphen-4-yl))carboxyamide, trifluoroacetic acid salt Part A: 2-Carboxy-4-methoxyphenylhydrazine: 2-Nitro-5-methoxybenzoic acid (5.0 g) in methanol (150 mL) was shaken under an atmosphere of hydrogen (50 psi) in the presence of 10% palladium on carbon catalyst (0.5 g) until hydrogen uptake ceased (ca. 3 h). The methanol solution was purge with nitrogen, filtered through a pad of Celite® and evaporated. There was obtained 4.2 g (25.1 mmol) of the aniline; ESI mass spectrum analysis m/z (relative intensity) 168 (M+H, 100).

The aniline prepared above (4.2 g, 25.1 mmol) in concentrated hydrochloric acid (50 mL) was cooled to 0° C. and sodium nitrite (2.08 g, 30.2 mmol) in cold water (20 mL) was added dropwise. This mixture was stirred at 0° C. for 30 min −1 h then tin(II)chloride dihydrate (17.0 g, 75.4 mmol) in cold concentrated hydrochloric acid (25 mL) was added dropwise. This mixture was allowed to thaw to ambient temperature over 3–5 h then filtered and air dried for several more. The filter cake was broken up and dried further in a vacuum oven at 60° C. overnight. There was obtained 8.76 g of 2-carboxy-4-methoxyphenylhydrazine tin salt.

Part B: Ethyl 2-N-(methoxy)imino-4-oxopentanoate: A mixture of ethyl pentanoate-2,4-dione (24.5 g, 154.9 mmol) and methoxyamine hydrogen chloride (13.58 g, 162.6 mmol) in ethanol (100 mL) was allowed to stand over activated 3 Å molecular sieves (75 g) at ambient temperature for 18 h. Following removal of the molecular sieves by filtration, dichloromethane (100 mL) was added and the reaction filtered. The resulting solution was evaporated and the residue applied to a silica gel column. The title compound was isolated in a homogenous form by elution with 5:1 hexane:ethyl acetate to give 9.09 g of product.

Part C: Ethyl 3-methyl-1-(2-carboxy-4-methoxyphenyl)-1H-pyrazole-5-carboxylate and ethyl 5-methyl-1-(2-carboxy-4-methoxyphenyl)-1H-pyrazole-3-carboxylate: Ethyl 2-N-(methoxy)imino-4-oxopentanoate (1.0 g, 5.35 mmol) and crude 2-carboxy-4-methoxyphenylhydrazine (5.83 g) in acetonitrile (40 mL) and acetic acid (5 mL) was stirred at ambient temperature for 3 h then heated at reflux for an additional 3 h. The reaction was cooled to ambient tem[]perature, diluted with methylene chloride (150 mL) and filtered. The filtrate was evaporated and the product isolated by flash chromatography by elution with 10% methanol in chloroform. This material (1.28 g) co-eluted as a mixture of regiosiomers as evident by proton NMR. ESI mass spectrum analysis m/z (relative intensity) 306 (M+H, 100).

Part D: Ethyl 3-methyl-1-(2-hydroxymethyl-4-methoxyphenyl)-1H-pyrazole-5-carboxylate and ethyl 5-methyl-1-(2-hydroxymethyl-4-methoxyphenyl)-1H-pyrazole-3-carboxylate: The mixture of regioisomers prepared in part C (1.28 g, 4.2 mmol) was dissolved in tetrahydrofuran (60 mL) and cooled to 0° C. To the cold solution was added N-methylmorpholine (0.42 g, 4.2 mmol) and isobutylchloroformate (0.57 g, 4.2 mmol). The reaction was stirred for 30 min at 0° C., the precipitate removed by filtration and the cold solution poured immediately into a cold (5° C.) solution of sodium borohydride (0.48 g, 12.6 mmol) in water (20 mL) and tetrahydrofuran (20 mL). The reaction was allowed to thaw to room temperature over 18 h. The reaction mixture was evaporated, partitioned between ethyl acetate (100 mL) and 1N hydrochloric acid (50 mL), then washed with 5% sodium bicarbonate (50 mL) and brine (50 mL). The organic layer was dried and evaporated; three products were isolated by elution of the crude mixture from a silica gel column with 2:1 hexane:ethyl acetate. The first product to elute was a ring closed lactone (0.14 g); ESI mass spectrum analysis m/z (relative intensity) 245 (M+H, 100). The second product isolated was ethyl 3-methyl-1-(2-hydroxymethyl-4-methoxyphenyl)-1H-pyrazole-5-carboxylate (0.18 g) as determined by proton NMR nOe experiments; ESI mass spectrum analysis m/z (relative intensity) 291(M+H, 100). The third product to elute was the regioisomer ethyl 5-methyl-1-(2-hydroxymethyl-4-methoxyphenyl)-1H-pyrazole-3-carboxylate (0.14 g); ESI mass spectrum analysis m/z (relative intensity) 291(M+H, 100).

Part E: Ethyl 3-methyl-1-(2-azidomethyl-4-methoxyphenyl)-1H-pyrazole-5-carboxylate: Ethyl 3-methyl-1-(2-hydroxymethyl-4-methoxyphenyl)-1H-pyrazole-5-carboxylate (0.18 g, 0.62 mmol) was dissolved in chloroform (20 mL) then methanesulfonyl chloride (0.3 g, 2.6 mmol) and triethylamine (0.26 g, 2.6 mmol) added. The reaction was complete in 6 h; it was evaporated, dissolved in ethyl acetate (100 mL), washed with 1N hydrochloric acid (50 mL) and brine (50 mL), dried and evaporated to give 0.22 g of product.

The mesylate prepared above (0.22 g, 0.6 mmol) and sodium azide (0.12 g, 1.79 mmol) were dissolved in dimethylformamide (15 mL) and heated for 1.5 h at 60° C., then diluted with brine (50 mL), extracted with ethyl acetate (100 mL), dried and evaporated. There was obtained 0.11 g of ethyl 3-methyl-1-(2-azidomethyl-4-methoxyphenyl)-1H-pyrazole-5-carboxylate; ESI mass spectrum analysis m/z (relative intensity) 316 (M+H, 100).

Part F: 3-Methyl-1-(2-azidomethyl-4-methoxyphenyl)-1H-pyrazole-5-carboxylic acid: Ethyl 3-methyl-1-(2-azidomethyl-4-methoxyphenyl)-1H-pyrazole-5-carboxylate (0.11 g, 0.35 mmol) in ethanol (2 mL) and water (2 mL) was stirred with 50% sodium hydroxide (3 drops) at 45° C. and followed by TLC (1:1 hexane:ethyl acetate). When all of the ester was consumed the reaction was cooled, diluted with brine and washed with ethyl ether (25 mL). The aqueous layer was acidified with 1N hydrochloric acid (pH=1), extracted with ethyl acetate (2×30 mL), dried and evaporated. There was obtained 3-methyl-1-(2-azidomethyl-4-methoxyphenyl)-1H-pyrazole-5-carboxylic acid (0.06 g); ESI mass spectrum analysis m/z (relative intensity) 285 (M+H, 100).

Part G: 3-Methyl-1-(2-azidomethyl-4-methoxyphenyl)-1H-pyrazole-5-(N-(4-(2-N-t-butylsulfamido)phenyl)phenyl) carboxyamide: 3-Methyl-1-(2-azidomethyl-4-methoxyphenyl)-1H-pyrazole-5-carboxylic acid (0.60 g, 0.21 mmol) in dichloromethane (5 mL) was cooled to 0° C. and oxalyl chloride (0.21 mL of a 2M solution in dichloromethane) and dimethyl formamide (1 drop) were added. The reaction was complete inside of 1 h; it was evaporated and pumped on to remove residual HCl. There was obtained 0.17 g of the acid chloride.

To the acid chloride prepared above (0.17 g, 0.50 mmol) in dichloromethane (3 mL) was added dropwise to an ice-cold solution of 4-(2-N-tertbutylsulfonamido)phenyl aniline (0.15 g, 0.51 mmol), pyridine (0.39 g, 4.4 mmol) and 4,4-dimethylaminopyridine (0.09 g, 0.7 mmol) in dichloromethane (15 mL). The reaction was allowed to warm to ambient temperature over 18 h, then evaporated, dissolved in ethyl acetate (30 mL), washed with 1N hydrochloric acid (20 mL) and dried. Silica gel flash chromatography, eluting with a gradient of 2:1 to 1:1 hexane:ethyl acetate, gave 0.09 g of 3-methyl-1-(2-azidomethyl-4-methoxyphenyl)-1H-pyrazole-5-(N-(4-(2-N-t-butylsulfamido)phenyl)phenyl) carboxyamide; ESI mass spectrum analysis m/z (relative intensity) 572 (M+H, 100).

Part H: 3-Methyl-1-(2-aminomethyl-4-methoxyphenyl)-1H-pyrazole-5-(N-(2'-sulfamido-[1,1']-biphen-4-yl)) carboxyamide.TFA: 3-Methyl-1-(2-azidomethyl-4-methoxyphenyl)-1H-pyrazole-5-(N-(2'-N-t-butylsulfamido-[1,1']-biphen-4-yl))carboxyamide (0.09 g, 0.16 mmol) was stirred with tin(II) chloride dihydrate (0.11 g, 0.47 mmol) in methanol (10 mL). When the reaction was complete by TLC (1:1 hexane:ethyl acetate) it was evaporated to give a crude mixture of the aminomethyl product and tin salts weighing 0.39 g. The material was heated at reflux in trifluoroacetic acid (10 mL) for 45 min then evaporated. The residue was partitioned between 1N sodium hydroxide (30 mL) and ethyl acetate (30 mL). The ethyl acetate solution was dried and evaporated to give 0.04 g of crude product. This material was purified further by hplc utilizing gradient elution with a mixture of water:acetonitrile with 0.05% trifluoroacetic acid on a reverse phase C18 (60 Å) column to give 0.010 g of the title compound; mp 184.3° C.; HRMS (M+H)$^+$ calc. m/z: 492.170551, obs m/z: 492.171712.

Example 2

5-Methyl-1-(2-aminomethyl-4-methoxyphenyl)-1H-pyrazole-3-(N-(2'-sulfamido-[1,1']-biphen-4-yl)) carboxyamide, trifluoroacetic acid salt The regioisomeric acid prepared in Example 1, ethyl 5-methyl-1-(2-hydroxymethyl-4-methoxyphenyl)-1H-pyrazole-3-carboxylate (0.14 g, 0.48 mmol), was transformed into the azidomethyl analog, coupled with 4-(2-N-tertbutylsulfonamido)phenyl aniline and transformed into 5-methyl-1-(2-aminomethyl-4-methoxyphenyl)-1H-pyrazole-3-(N-(4-(2-sulfamido)phenyl)phenyl)

carboxyamide by the same procedures described in Example 1. The final product was purified further by hplc utilizing gradient elution with a mixture of water:acetonitrile with 0.05% trifluoroacetic acid on a reverse phase C18 (60 Å) column; HRMS (M+H)$^+$ calc. m/z: 492.170551, obs m/z: 492.169327.

Example 3

3-methyl-1-(2-N,N-dimethylaminomethyl-4-methoxyphenyl)-1H-pyrazole-5-(N-(2'-N-methylsulfamido-[1,1']-biphen-4-yl))carboxyamide, trifluoroacetic acid salt 3-Methyl-1-(2-azidomethyl-4-methoxyphenyl)-1H-pyrazole-5-(N-(2'-N-t-butylsulfamido-[1,1']-biphen-4-yl)) carboxyamide (0.09 g, 0.16 mmol), prepared in Example 1, was stirred with tin(II) chloride dihydrate (0.11 g, 0.47 mmol) in methanol (10 mL). When the reaction was complete by TLC (1:1 hexane:ethyl acetate) it was evaporated to give a crude mixture of the aminomethyl product and tin salts weighing 0.39 g. A portion of the crude reduction product (0.1 g, 0.20 mmol) prepared above was stirred at ambient temperature with methyl iodide (0.2 mL), and potassium hydrogen carbonate (solid, 0.2 g) in methanol (4 mL) at ambient temperature. After 18 h the reaction was evaporated and stirred with chloroform (30 mL), filtered and evaporated again to give 0.28 g of crude product.

The material from above was heated at reflux in trifluoroacetic acid (10 mL) for 45 min then evaporated. The residue was partitioned between 1N sodium hydroxide (30 mL) and ethyl acetate (30 mL). The ethyl acetate solution was dried and evaporated to give crude product. This material was purified further by hplc utilizing gradient elution with a mixture of water:acetonitrile with 0.05% trifluoroacetic acid on a reverse phase C18 (60 Å) column to give the title compound; mp 114.5° C.; HRMS (M+H)$^+$ calc. m/z: 534.217502, obs m/z: 534.218000.

Example 4

3-Trifluoromethyl-1-(2-aminomethyl-4-methoxyphenyl)-1H-pyrazole-5-(N-(3-fluoro-2'-sulfamido-[1,1]-biphen-4-yl))carboxyamide, trifluoroacetic acid salt Part A: 3-Trifluoromethyl-1-(2-carboxy-4-methoxyphenyl)-5-(furan-2-yl)-1H-pyrazole: Crude 2-carboxy-4-methoxyphenylhydrazine (8.88 g), prepared in Example 1, and 4,4,4-trifluoro-1-(2-furyl)-1,3-butanedione (7.4 g, 135.9 mmol) in acetic acid (150 mL) was heated at 100° C. for 4 h. The hot reaction mixture was evaporated and the residue stirred in a biphasic mixture of water (150 mL) and chloroform (150 mL). The layers were filtered and separated, the solid percipitate washed several times with additional chloroform (3×50 mL) and the chloroform layer and washings combined, dried and evaporated. There was obtained 3.55 g of 3-trifluoromethyl-1-(2-carboxy-4-methoxyphenyl)-5-(furan-2-yl)-1H-pyrazole; ESI (-ve) mass spectrum analysis m/z (relative intensity) 351 (M–H, 100).

Part B: 3-Trifluoromethyl-1-(2-hydroxymethyl-4-methoxyphenyl)-5-(furan-2-yl)-1H-pyrazole: 3-Trifluoromethyl-1-(2-carboxy-4-methoxyphenyl)-5-(furan-2-yl)-1H-pyrazole (3.55 g, 10.1 mmol) in tetrahydrofuran (100 mL) was cooled to 0° C. then N-methylmorpholine (1.02 g, 10.1 mmol) and isobutyl chloroformate (1.38 g, 10.1 mmol) were added. The reaction mixture was stirred for 30 min at 0° C., filtered and added immediately to a cold solution of sodium borohydride (1.15 g, 30.2 mmol) in water (50 mL) and tetrahydrofuran (50 mL). The reaction mixture was evaporated, partitioned between ethyl acetate (100 mL) and 1N hydrochloric acid (50 mL), then washed with 5% sodium bicarbonate (50 mL) and brine (50 mL). The organic layer was dried and evaporated then purified further by flash chromatography using 4:1 hexane:ethyl acetate as the eluent. There was obtained 1.5 g of 3-trifluoromethyl-1-(2-hydroxymethyl-4-methoxyphenyl)-5-(furan-2-yl)-1H-pyrazole; ESI mass spectrum analysis m/z (relative intensity) 339 (M+H, 100).

Part C: 3-Trifluoromethyl-1-(2-azidomethyl-4-methoxyphenyl)-5-(furan-2-yl)-1H-pyrazole: To a cooled chloroform (50 mL) solution of 3-trifluoromethyl-1-(2-hydroxymethyl-4-methoxyphenyl)-5-(furan-2-yl)-1H-pyrazole (1.5 g, 4.44 mmol) and triethylamine (1.79 g, 17.7 mmol) was added a chloroform solution (10 mL) of methanesulfonyl chloride (2.03 g, 17.7 mmol). The reaction was complete in 4 h. It was evaporated, dissolved in ethyl acetate (100 mL) and the ethyl acetate solution washed with cold 5% NaHSO$_4$ (50 mL) and cold saturated NaHCO$_3$ (50 mL). The organic layer was dried and evaporated to give 2.1 g of the mesylate which was used immediately in the next reaction; ESI mass spectrum analysis m/z (relative intensity) 417(M+H, 100).

A mixture of the mesylate prepared above (2.1 g, 5.05 mmol) and sodium azide (0.98 g, 15.1 mmol) in dimethylformamide (40 mL) was heated at 60° C. for 2 h. The reaction mixture was cooled, diluted with brine (100 mL) and extracted with ethyl acetate (100 mL). The ethyl acetate extract was washed with water (5×50 mL) then dried and evaporated. There was obtained 1.43 g of 3-trifluoromethyl-1-(2-azidomethyl-4-methoxyphenyl)-5-(furan-2-yl)-1H-pyrazole; ESI mass spectrum analysis m/z (relative intensity) 364 (M+H, 100).

Part D: 3-Trifluoromethyl-1-(2-azidomethyl-4-methoxyphenyl)-1H-pyrazole-5-carboxylic acid: To 1.43 g of 3-trifluoromethyl-1-(2-azidomethyl-4-methoxyphenyl)-5-(furan-2-yl)-1H-pyrazole (3.9 mmol) in acetone (60 mL) was added potassium permaganate (5.0 g, 27.5 m mol) in water (60 mL).

The reaction was heated at 60° C. for 3 h, then cooled to ambient temperature and isopropyl alcohol (60 mL) added. This mixture was stirred for 18 h then filtered through a Celite® pad and washed with copious amounts of isopropyl alcohol. The combined filtrates were evaporated, the residue dissolved in 1N NaOH (50 mL) and washed with ethyl ether (2×50 mL). The basic layer was acidified with 1N HCl (75 mL) and solid NaCl added. The suspension was extracted with EtOAc (3×100 mL); the extracts were dried and evaporated. There was obtained 0.91 g of 3-trifluoromethyl-1-(2-azidomethyl-4-methoxyphenyl)-1H-pyrazole-5-carboxylic acid; ESI (-ve) mass spectrum analysis m/z (relative intensity) 340 (M–H, 100).

Part E: 3-Trifluoromethyl-1-(2-azidomethyl-4-methoxyphenyl)-1H-pyrazole-5-carboxylic acid chloride: 3-Trifluoromethyl-1-(2-azidomethyl-4-methoxyphenyl)-1H-pyrazole-5-carboxylic acid (1.09 g, 3.2 mmol) in dichloromethane (50 mL) was stirred at 0° C. with oxalyl chloride from 3.2 mL of a 2M dichloromethane solution of the reagent and a catalytic amount of DMF (3 drops). The reaction was complete in 3 h, then evaporated and pumped on to remove residual reagent. There was obtained 1.04 g (2.9 rmol) of 3-trifluoromethyl-1-(2-azidomethyl-4-methoxyphenyl)-1H-pyrazole-5-carboxylic acid chloride.

Part F: 3-Trifluoromethyl-1-(2-azidomethyl-4-methoxyphenyl)-1H-pyrazole-5-(N-(2-fluoro-4-(2-N-tertbutylsulfamido-[1,1]-biphen-4-yl))carboxyamide: 3-Trifluoromethyl-1-(2-azidomethyl-4-methoxyphenyl)-1H-pyrazole-5-carboxylic acid chloride prepared above (0.52 g, 1.45 nmol) in dichloromethane (10 mL) was added dropwise to an ice-cold solution of 2-fluoro-4-(2-N- tertbutylsulfonamido)phenyl aniline (0.56 g, 1.74 mmol), pyridine (1.14 g, 14.5 imol) and 4,4-dimethylaminopyridine (0.21 g, 1.74 mmol) in dichloromethane (30 mL). The reaction was allowed to warm to ambient temperature over 18 h, then evaporated, dissolved in ethyl acetate (100 mL), washed with 1N hydrochloric acid (50 mL) and dried. Silica gel flash chromatography, eluting with 4:1 hexane:ethyl acetate, gave 0.28 g of 3-trifluoromethyl-1-(2-azidomethyl-4-methoxyphenyl)-1H-pyrazole-5-(N-(2-fluoro-4-(2-N-tertbutylsulfamidophenyl)phenyl)carboxyamide; ESI (-ve) mass spectrum analysis m/z (relative intensity) 644 (M−H, 100).

Part G: 3-Trifluoromethyl-1-(2-aminomethyl-4-methoxyphen-1-yl)-1H-pyrazole-5-(N-(2-fluoro-4-(2-sulfamido-[1,1]-biphen-4-yl))carboxyamide.TFA: 3-Trifluoromethyl-1-(2-azidomethyl-4-methoxyphenyl)-1H-pyrazole-5-(N-(2-fluoro-4-(2-N-tertbutylsulfamidophenyl)phenyl)carboxyamide (0.28 g, 0.43 mmol) and tin(II)chloride dihydrate (0.29 g, 1.3 mmol) was stirred in methanol (30 mL) for 18 h. The reaction was evaporated and the reduction product (0.60 g) was carried on to the next step without further processing.

The product prepared above was refluxed in trifluoroacetic acid (20 mL) for 30 min, then evaporated. The residue was suspened in 1N NaOH (30 mL), extracted with EtOAc (3×50 mL), dried and evaporated. This material was purified further by hplc utilizing gradient elution with a mixture of water:acetonitrile with 0.05% trifluoroacetic acid on a reverse phase C18 (60 Å) column to give the title compound; mp 103.2° C.; ESI ESI mass spectrum analysis m/z (relative intensity) 564.2 (M+H, 100).

Example 5

3-Trifluoromethyl-1-(2-aminomethyl-4-methoxyphenyl)-1H-pyrazole-5-(N-(3-fluoro-2'-methylsulfonyl-[1,1]-biphen-4-yl))carboxyamide, trifluoroacetic acid salt Part A: 3-Trifluoromethyl-1-(2-azidomethyl-4-methoxyphenyl)-1H-pyrazole-5-(N-(2-fluoro-4-(2-methylsulfonylphenyl)phenyl)carboxyamide: 3-Trifluoromethyl-1-(2-azidomethyl-4-methoxyphenyl)-1H-pyrazole-5-carboxylic acid chloride prepared in Example 4 (0.52 g, 1.45 mmol) in dichloromethane (10 mL) was added dropwise to an ice-cold solution of 2-fluoro-4-(2-methylsulfonylphenyl)aniline (0.52 g, 1.74 mmol), pyridine (1.14 g, 14.5 mmol) and 4,4-dimethylaminopyridine (0.21 g, 1.74 mmol) in dichloromethane (30 mL). The reaction was allowed to warm to ambient temperature over 18 h, then evaporated, dissolved in ethyl acetate (100 mL), washed with 1N hydrochloric acid (50 mL) and dried. Silica gel flash chromatography, eluting with a gradient of 5:1 to 1:1 hexane:ethyl acetate, gave 0.46 g of 3-trifluoromethyl-1-(2-azidomethyl-4-methoxyphenyl)-1H-pyrazole-5-(N-(2-fluoro-4-(2-methylsulfonylphenyl)phenyl)carboxyamide; ESI mass spectrum analysis m/z (relative intensity) 587(M+H, 100).

Part B: 3-Trifluoromethyl-1-(2-aminomethyl-4-methoxyphenyl)-1H-pyrazole-5-(N-(3-fluoro-2'-methylsulfonyl-[1,1]-biphen-4-yl))carboxyamide.TFA: 3-Trifluoromethyl-1-(2-azidomethyl-4-methoxyphenyl)-1H-pyrazole-5-(N-(3-fluoro-2'-methylsulfonyl-[1,1]-biphen-4-yl))carboxyamide (0.46 g, 0.78 mmol) and tin(II) chloride dihydrate (0.53 g, 2.35 mmol) was stirred in methanol (25 mL) for 18 h. The reaction was evaporated and the residue was suspended in 1N NaOH (50 mL), extracted with EtOAc (3×100 mL), dried and evaporated to give 0.29 g of crude product. This material was purified further by hplc utilizing gradient elution with a mixture of water:acetonitrile with 0.05% trifluoroacetic acid on a reverse phase C18 (60 Å) column to give the title compound; mp 101.5° C.; ESI mass spectrum analysis m/z (relative intensity) 563(M+H, 100).

Example 6

3-Trifluoromethyl-1-(2-aminomethyl-4-methoxyphenyl)-1H-pyrazole-5-(N-(2'-methylsulfonyl-[1,1]-biphen-4-yl))carboxyuide, trifluoroacetic acid salt Part A: 3-Trifluoromethyl-1-(2-azidomethyl-4-methoxyphenyl)-1H-pyrazole-5-(N-(2'-methylsulfonyl-[1,1]-biphen-4-yl))carboxyamide: 3-Trifluoromethyl-1-(2-azidomethyl-4-methoxyphenyl)-1H-pyrazole-5-carboxylic acid chloride and 4-(2-methylsulfonylphenyl)aniline were treated in the manner described for Example 5, Part A to give 3-trifluoromethyl-1-(2-azidomethyl-4-methoxyphenyl)-1H-pyrazole-5-(N-(4-(2-methylsulfonylphenyl)phenyl)carboxyamide.

Part B: 3-Trifluoromethyl-1-(2-aminomethyl-4-methoxyphenyl)-1H-pyrazole-5-(N-(2'-methylsulfonyl-[1,1]-biphen-4-yl))carboxyamide.TFA: 3-Trifluoromethyl-1-(2-azidomethyl-4-methoxyphenyl)-1H-pyrazole-5-(N-(4-(2-methylsulfonylphenyl)phenyl)carboxyamide was treated in the same manner as Example 5, Part B to give the title compound; HRMS (M+H)$^+$ calc. m/z: 545.147037, obs m/z: 545.145700.

Example 7

3-Trifluoromethyl-1-(2-aminomethyl-4-methoxyphenyl)-1H-pyrazole-5-(N-(2'-sulfamido-[1,1]-biphen-4-yl))carboxyamide, trifluoroacetic acid salt Part A: 3-Trifluoromethyl-1-(2-azidomethyl-4-methoxyphenyl)-1H-pyrazole-5-(N-(2'-N-tertbutylsulfamido-[1,1]-biphen-4-yl))carboxyamide: 3-Trifluoromethyl-1-(2-azidomethyl-4-methoxyphenyl)-1H-pyrazole-5-carboxylic acid chloride and 4-(2-N-tertbutylsulfonamido)phenyl aniline were treated as described in Example 4, Part F to give 3-trifluoromethyl-1-(2-azidomethyl-4-methoxyphenyl)-1H-pyrazole-5-(N-(4-(2-N-tertbutylsulfamidophenyl)phenyl)carboxyamide.

Part B: 3-Trifluoromethyl-1-(2-aminomethyl-4-methoxyphen-1-yl)-1H-pyrazole-5-(N-(2'-sulfamido-[1,1]-biphen-4-yl))carboxyamide.TFA: 3-Trifluoromethyl-1-(2-azidomethyl-4-methoxyphenyl)-1H-pyrazole-5-(N-(4-(2-N-tertbutylsulfamidophenyl)phenyl)carboxyamide was treated as described in Example 4, Part G to give the title compound; LRMS (M+H)$^+$: m/z 546.2.

Example 8

3-Trifluoromethyl-1-(2-aminomethyl-4-methoxyphenyl)-1H-pyrazole-5-(N-(4-N-pyrrolidinocarbonyl)phenyl)carboxyamide.TFA Part A: 5-(Furan-2-yl)-3-trifluoromethyl-1-(2-carboxyl-4-methoxyphenyl)-1H-pyrazole: 3-Methoxy-6-aminobenzoic acid (23 g, 138 mmol) in conc. HCl (300 mL) was cooled to 0° C. and NaNO$_2$ (11.4 g, 165 imnol) in H$_2$O (50 mL) was added dropwise while the temperature of the reaction was maintained below 10° C. The reaction was stirred at or below 10° C. for 1 h, then SnCl$_2$.H$_2$O (92.3 g, 413 mmol) in conc. HCl (125 mL) was added dropwise. The reaction was allowed to thaw to ambient temperature and stirred for 3 h. The precipitate was filtered and air-dried then heated in a vacuum oven for 18 h. There was obtained 71.4 g of 3-methoxy-6-hydrazinobenzoic acid entrained with tin (II) salts.

The hydrazine prepared above (71.4 g) in acetic acid (800 mL) was heated at 45° C. until dissolved, then 4,4,4-trifluoromethyl-1-(2-furyl)-1,3-butanedione (28.42 g, 138 mmol) was added and the mixture heated at reflux for 2.5 h. The reaction was cooled and evaporated to dryness. The residue was partitioned between $H_2O$ (400 mL) and $CHCl_3$ (400 mL) and stirred for 30 min. The biphasic mixture was filtered, the layers separated and the organic layer dried ($Na_2SO_4$) and evaporated to give 49.4 g of 5-(furan-2-yl)-3-trifluoromethyl-1-(2-carboxyl-4-methoxyphenyl)-1H-pyrazole; LRMS (ES$^-$) M$^-$: 351 m/z.

Part B: 3-Trifluoromethyl-1-(2-azidomethyl-4-methoxyphenyl)-1H-pyrazole-5-carboxylic acid: To a solution of 5-(furan-2-yl)-3-trifluoromethyl-1-(2-carboxyl-4-methoxyphenyl)-1H-pyrazole (49.4 g, 140.3 mmol) in THF (600 mL) at 0° C. was added N-methylmorpholine (14.9 g, 147 mmol) and isobutylchloroformate (20.1 g, 147.3 mmol). After 3 h at 0° C., the reaction mixture was filtered into a $H_2O$: THF (200 mL: 200 mL) solution of $NaBH_4$ (10.6 g, 280 mmol) at 0° C. After 18 h, the reaction was quenched with 1N HCl (500 mL) then the THF was removed in vaccuo. The remaining aqueous suspension was saturated with solid NaCl and extracted with EtOAc, dried ($Na_2SO_4$) and evaporated. The crude product was recrystallized from 1-chlorobutane to give 16.8 g of benzyl alcohol product. The mother liquors were applied to a column of flash $SiO_2$ (500 g) and eluted with 2:1 hexane: EtOAc to give 8.7 g of benzyl alcohol product; LRMS ES$^+$ (M+H)$^+$: 339 m/z.

The benzyl alcohol product (8.7 g, 25.1 rmnol) prepared above and $Et_3N$ (3.1 g, 30.9 mmol) in $CH_2Cl_2$ (200 mL) was cooled to 0° C. Methanesulfonyl chloride (3.5 g, 30.9 mmol) in $CH_2Cl_2$ (10 mL) was added dropwise. The cooling bath was removed and the reaction stirred for 3 h. A 5% solution of $NaHSO_4$ (200 mL) was added, the organic layer was separated, dried and evaporated to give 10.25 g of mesylate.

The mesylate (10.25 g, 24.6 mmol) from above and $NaN_3$ (4.8 g, 73.8 mmol) in DMF (100 mL) was stirred at ambient temperature for 18 h. The reaction was diluted with brine (500 mL), extracted with EtOAc and the extracts washed with $H_2O$ (5×150 mL). The EtOAc layer was dried ($Na_2SO_4$) and evaporated to give 8.16 of the azidomethyl compound; LRMS ES$^+$ (M+H)$^+$: 364 m/z.

The azidomethyl coumpound (23 g, 63.4 mmol) in acetone (400 mL) was heated at 60° C., then $KMnO_4$ (50 g, 317 mmol) in $H_2O$ (300 mL) was added. After addition was complete, the reaction was heated for 1.5 h. The cooled reaction was filtered through a pad of Celite® and evaporated. The water layer was made basic with 1N NaOH (200 mL) and washed with $Et_2O$ (3×), then acidified with conc. HCl, saturated with solid NaCl and extracted with EtOAc (3×). The EtOAc layer was dried and evaporated to give 15.1 g of 3-trifluoromethyl-1-(2-azidomethyl-4-methoxyphenyl)-1H-pyrazole-5-carboxylic acid; LRMS ES$^-$ (M–H)$^-$: 340 m/z.

Part C: 3-Trifluoromethyl-1-(2-azidomethyl-4-methoxyphenyl)-1H-pyrazole-5-(N-(4-N-carboxylpyrrolidino)phenyl)carboxyamide: To 3-trifluoromethyl-1-(2-azidomethyl-4-methoxyphenyl)-1H-pyrazole-5-carboxylic acid (0.44 g, 1.29 mmol) prepared above in $CH_2Cl_2$ at 0° C. was added a 2M solution of oxalyl chloride in $CH_2Cl_2$ (2 equivalents, 1.29 mL) followed by a drop of DMF. The ice bath was removed and the reaction stirred for 3 h then evaporated. The resulting acid chloride was combined with N-(4-aminobenzoyl)pyrrolidine (0.32 g, 1.68 mmol) and DMAP (0.47 g, 3.87 mmol) and dissolved in $CH_2Cl_2$ (20 mL). The reaction was stirred for 18 h, then evaporated and dissolved in EtOAc. The EtOAc layer was washed with 1N HCl and brine, dried ($Na_2SO_4$) and evaporated. The product was purified further by a column of flash $SiO_2$ (50 g) eluting with 5–10% MeOH in $CHCl_3$ to give 0.24 g of 3-trifluoromethyl-1-(2-azidomethyl-4-methoxyphenyl)-1H-pyrazole-5-(N-(4-N-carboxylpyrrolidino)phenyl)carboxyamide; LRMS ES$^+$ (M+H)$^+$: 514 m/z.

Part D: 3-Trifluoromethyl-1-(2-aminomethyl-4-methoxyphenyl)-1H-pyrazole-5-(N-(4-N-carboxylpyrrolidino)phenyl)carboxyamide.TFA: A mixture of 3-trifluoromethyl-1-(2-azidomethyl-4-methoxyphenyl)-1H-pyrazole-5-(N-(4-N-carboxylpyrrolidino)phenyl) carboxyamide (0.24 g, 0.27 mmol) and $SnCl_2.2H_2O$ (0.24 g, 0.95 mmol) in MeOH (20 mL) was stirred for 18 h. The reaction was evaporated and dissolved in 1N NaOH. The basic layer was extracted with EtOAc dried and evaporated. The crude product was purified further by HPLC utilizing gradient elution with a mixture of water:acetonitrile with 0.05% trifluoroacetic acid on a reverse phase C18 (60 Å) column to give 31.2 mg of title compound; mp 117.52° C.; HRMS (M+H)$^+$ calc. m/z: 488.190950, obs: 488.191005.

Example 9

N-Benzylsulfonyl-4-(3-trifluoromethyl-1-(2-aminomethyl-4-metboxyphenyl)-1H-pyrazole-5-carboxyamido)piperidine.TFA 3-Trifluoromethyl-1-(2-azidomethyl-4-methoxyphenyl)-1H-pyrazole-5-carboxylic acid prepared in Part B of Example 8 was coupled with N-Benzylsulfonyl-4-aminopiperidine according to the procedure in Part C of Example 8. The title compound was prepared and purified by the method outlined in Part D of Example 8; mp 98.3° C.; HRMS (M+H)$^+$ calc. m/z: 552.189236 obs: 552.188800.

Example 10

3-Trifluoromethyl-1-(2-aminomethyl-4-methoxyphenyl)-1H-pyrazole-5-(N-(5-(2'-sulfonamido)phenyl)pyrid-2-yl) carboxyamide.TFA 3-Trifluoromethyl-1-(2-azidomethyl-4-methoxyphenyl)-1H-pyrazole-5-carboxylic acid prepared in Part B of Example 8 was coupled with 2-amino-5-((2-N-t-butylsulfonamido)phenyl)pyridine according to the procedure in Part C of Example 8. The azidomethyl group was reduced to the aminomethyl group with $SnCl_2.2H_2O$ by the method outlined in Part D of Example 8. The crude reduction product was then refluxed in trifluoroacetic acid (10 mL) for 1 h to remove the t-butyl protecting group. The title compound was isolated by . HPLC utilizing gradient elution with a mixture of water:acetonitrile with 0.05% trifluoroacetic acid on a reverse phase C18 (60 Å) column; mp 86.6° C.; HRMS (M+H)$^+$ calc. m/z: 547.137535, obs: 547.138200.

Example 11

3-Trifluoromethyl-1-(2-aminomethyl-4-methoxyphenyl)-1H-pyrazole-5-(N-(5-(pyrid-2-yl)) pyrid-2-yl) carboxyamide.TFA 3-Trifluoromethyl-1-(2-azidomethyl-4-methoxyphenyl)-1H-pyrazole-5-carboxylic acid prepared in Part B of Example 8 was coupled with 2-amino-5-(pyrid-2-yl) pyridine according to the procedure in Part C of Example 8. The title compound was prepared and purified by the method outlined in Part D of Example 8; mp 48.2° C.; HRMS (M+H)$^+$: 469.1602 m/z.

Example 12

N-Benzyl-4-(3-trifluoromethyl-1-(2-aminomethyl-4-methoxyphenyl)-1H-pyrazole-5-carboxyamido) piperidine.TFA 3-Trifluoromethyl-1-(2-azidomethyl-4-methoxyphenyl)-1H-pyrazole-5-carboxylic acid prepared in Part B of Example 8 was coupled with N-Benzyl-4-aminopiperidine according to the procedure in Part C of Example 8. The title compound was prepared and purified by the method outlined in Part D of Example 8; mp 116.1° C.; HRMS (M+H)+: 488.2266 m/z.

Example 13

N-Phenylsulfonyl-4-(3-trifluoromethyl-1-(2-aminomethyl-4-methoxyphenyl)-1H-pyrazole-5-carboxyamido)piperidine.TFA 3-Trifluoromethyl-1-(2-azidomethyl-4-methoxyphenyl)-1H-pyrazole-5-carboxylic acid prepared in Part B of Example 8 was coupled with N-phenylsulfonyl-4-aminopiperidine according to the procedure in Part C of Example 8. The title compound was prepared and purified by the method outlined in Part D of Example 8; mp 103° C.; HRMS (M+H)+: 538.1729 m/z.

Example 14

3-Trifluoromethyl-1-(2-aminomethyl-4-chlorophenyl)-1H-pyrazole-5-(N-(3-fluoro-2'-methylsulfonyl-[1,1']-biphen-4-yl))carboxyamide.TFA 3-Trifluoromethyl-1-(2-azidomethyl-4-chlorophenyl)-1H-pyrazole-5-carboxylic acid was prepared from 3-chloro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 2-fluoro-4-((2-methansulfonyl)phenyl)aniline according to the procedure in Part C of Example 8. The title compound was prepared and purified by the method outlined in Part D of Example 8; mp 97.5° C.; HRMS (M+H)+: 567.0891 m/z.

Example 15

3-Trifluoromethyl-1-(2-aminomethyl-4-chlorophenyl)-1H-pyrazole-5-(N-(3-fluoro-2'-sulfamido-[1,1']-biphen-4-yl))carboxyamide.TFA 3-Trifluoromethyl-1-(2-azidomethyl-4-chlorophenyl)-1H-pyrazole-5-carboxylic acid was prepared from 3-chloro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 2-fluoro-4-((2-N-t-butylsulfonamido)phenyl)aniline according to the procedure in Part C of Example 8. The azidomethyl group was reduced to the aminomethyl group with $SnCl_2 \cdot 2H_2O$ by the method outlined in Part D of Example 8. The crude reduction product was then refluxed in trifluoroacetic acid (10 mL) for 1 h to remove the Gil t-butyl protecting group. The title compound was isolated by HPLC utilizing gradient elution with a mixture of water:acetonitrile with 0.05% trifluoroacetic acid on a reverse phase C18 (60 Å) column; mp 128° C.; HRMS (M+H)+: 568.0832 m/z.

Example 16

3-Trifluoromethyl-1-(2-aminomethyl-5-chlorophenyl)-1H-pyrazole-5-(N-(3-fluoro-2'-methylsulfonyl-[1,1']-biphen-4-yl))carboxyamide.TFA 3-Trifluoromethyl-1-(2-azidomethyl-5-chlorophenyl)-1H-pyrazole-5-carboxylic acid was prepared from 4-chloro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 2-fluoro-4-((2-methansulfonyl)phenyl)aniline according to the procedure in Part C of Example 8. The title compound was prepared and purified by the method outlined in Part D of Example 8; mp 99.7° C.; HRMS (M+H)+: 567.0859 m/z.

Example 17

3-Trifluoromethyl-1-(2-aminomethyl-4-chlorophenyl)-1H-pyrazole-5-(N-(3-fluoro-2'-sulfamido-[1,1']-biphen-4-yl))carboxyamide.TFA 3-Trifluoromethyl-1-(2-azidomethyl-5-chlorophenyl)-1H-pyrazole-5-carboxylic acid was prepared from 4-chloro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 2-fluoro-4-((2-N-t-butylsulfonamido)phenyl)aniline according to the procedure in Part C of Example 8. The azidomethyl group was reduced to the aminomethyl group with $SnCl_2 \cdot 2H_2O$ by the method outlined in Part D of Example 8. The crude reduction product was then refluxed in trifluoroacetic acid (10 mL) for 1 h to remove the t-butyl protecting group. The title compound was isolated by HPLC utilizing gradient elution with a mixture of water:acetonitrile with 0.05% trifluoroacetic acid on a reverse phase C18 (60 Å) column; mp 127.4° C.; HRMS (M+H)+: 568.0837 m/z.

Example 18

3-Trifluoromethyl-1-(2-aminomethyl-4-fluorophenyl)-1H-pyrazole-5-(N-(3-fluoro-2'-methylsulfonyl-[1,1']-biphen-4-yl))carboxyamide.TFA 3-Trifluoromethyl-1-(2-azidomethyl-4-fluorophenyl)-1H-pyrazole-5-carboxylic acid was prepared from 3-fluoro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 2-fluoro-4-((2-methansulfonyl)phenyl)aniline according to the procedure in Part C of Example 8. The title compound was prepared and purified by the method outlined in Part D of Example 8; mp 125° C.; HRMS (M+H)+: 551.1177 m/z.

Example 19

3-Trifluoromethyl-1-(2-aminomethyl-4-fluorophenyl)-1H-pyrazole-5-(N-(3-fluoro-2'-sulfamido-[1,1']-biphen-4-yl))carboxyamide.TFA 3-Trifluoromethyl-1-(2-azidomethyl-4-fluorophenyl)-1H-pyrazole-5-carboxylic acid was prepared from 3-fluoro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 2-fluoro-4-((2-N-t-butylsulfonamido)phenyl)aniline according to the procedure in Part C of Example 8. The azidomethyl group was reduced to the aminomethyl group with $SnCl_2 \cdot H_2O$ by the method outlined in Part D of Example 8. The crude reduction product was then refluxed in trifluoroacetic acid (10 mL) for 1 h to remove the t-butyl protecting group. The title compound was isolated by HPLC utilizing gradient elution with a mixture of water:acetonitrile with 0.05% trifluoroacetic acid on a reverse phase C18 (60 Å) column; mp 113.1° C.; HRMS (M+H)+: 552.1112 m/z.

Example 20

3-Trifluoromethyl-1-(2-aminomethyl-5-fluorophenyl)-1H-pyrazole-5-(N-(3-fluoro-2'-methylsulfonyl-[1,1']-biphen-4-yl))carboxyamide.TFA 3-Trifluoromethyl-1-(2-azidomethyl-5-fluorophenyl)-1H-pyrazole-5-carboxylic acid was prepared from 4-fluoro- 6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 2-fluoro-4-((2-methansulfonyl)phenyl)aniline according to the procedure in Part C of Example 8. The title compound was prepared and purified by the method outlined in Part D of Example 8; mp 97.2° C.; HRMS (M+H)$^+$: 551.1179 m/z.

Example 21

3-Trifluoronothyl-1-(2-aminomethyl-5-fluorophonyl)-1H-pyrazole-5-(N-(3-fluoro-2'-sulfamido-[1,1']-biphen-4-yl))carboxyamide.TFA 3-Trifluoromethyl-1-(2-azidomethyl-5-fluorophenyl)-1H-pyrazole-5-carboxylic acid was prepared from 4-fluoro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 2-fluoro-4-((2-N-t-butylsulfonamido)phenyl)aniline according to the procedure in Part C of Example 8. The azidomethyl group was reduced to the aminomethyl group with $SnCl_2.2H_2O$ by the method outlined in Part D of Example 8. The crude reduction product was then refluxed in trifluoroacetic acid (10 mL) for 1 h to remove the t-butyl protecting group. The title compound was isolated by HPLC utilizing gradient elution with a mixture of water:acetonitrile with 0.05% trifluoroacetic acid on a reverse phase C18 (60 Å) column; mp 101° C.; HRMS (M+H)$^+$: 552.1120 m/z.

Example 22

3-Trifluoromethyl-1-(2-aminomethyl-4,5-difluorophenyl)-1H-pyrazole-5-(N-(3-fluoro-2'-methylsulfonyl-[1,1']-biphen-4-yl)) carboxyamide.TFA 3-Trifluoromethyl-1-(2-azidomethyl-4,5-difluorophenyl)-1H-pyrazole-5-carboxylic acid was prepared from 3,4-difluoro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 2-fluoro-4-((2-methansulfonyl)phenyl)aniline according to the procedure in Part C of Example 8. The title compound was prepared and purified by the method outlined in Part D of Example 8; HRMS (M+H)$^+$: 569.1082 m/z.

Example 23

3-Trifluoromethyl-1-(2-aminomethyl-4,5-difluorophenyl)-1H-pyrazole-5-(N-(3-fluoro-2'-sulfamido-[1,1']-biphen-4-yl))carboxyamide.TFA 3-Trifluoromethyl-1-(2-azidomethyl-4,5-difluorophenyl)-1H-pyrazole-5-carboxylic acid was prepared from 3,4-difluoro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 2-fluoro-4-((2-N-t-butylsulfonamido)phenyl) aniline according to the procedure in Part C of Example 8. The azidomethyl group was reduced to the aminomethyl group with $SnCl_2.2H_2O$ by the method outlined in Part D of Example 8. The crude reduction product was then refluxed in trifluoroacetic acid (10 mL) for 1 h to remove the t-butyl protecting group. The title compound was isolated by HPLC utilizing gradient elution with a mixture of water:acetonitrile with 0.05% trifluoroacetic acid on a reverse phase C18 (60 Å) column; mp 118.7° C.; HRMS (M+H)$^+$: 570.1038 m/z.

Example 24

3-Trifluoromethyl-1-(2-aminomethyl-3-fluorophenyl)-1H-pyrazole-5-(N-(3-fluoro-2'-methylsulfonyl-[1,1']-biphen-4-yl)) carboxyamide.TFA 3-Trifluoromethyl-1-(2-azidomethyl-3-fluorophenyl)-1H-pyrazole-5-carboxylic acid was prepared from 2-fluoro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 2-fluoro-4-((2-methansulfonyl)phenyl)aniline according to the procedure in Part C of Example 8. The title compound was prepared and purified by the method outlined in Part D of Example 8; mp 105.1° C.; HRMS (M+H)$^+$: 551.1180 m/z.

Example 25

3-Trifluoromethyl-1-(2-aminomethyl-3-fluorophenyl)-1H-pyrazole-5-(N-(3-fluoro-2'-sulfamido-[1,1']-biphen-4-yl))carboxyamide.TFA 3-Trifluoromethyl-1-(2-azidomethyl-3-fluorophenyl)-1H-pyrazole-5-carboxylic acid was prepared from 2-fluoro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 2-fluoro-4-((2-N-t-butylsulfonamido)phenyl)aniline according to the procedure in Part C of Example 8. The azidomethyl group was reduced to the aminomethyl group with $SnCl_2.2H_2O$ by the method outlined in Part D of Example 8. The crude reduction product was then refluxed in trifluoroacetic acid (10 mL) for 1 h to remove the t-butyl protecting group. The title compound was isolated by HPLC utilizing gradient elution with a mixture of water:acetonitrile with 0.05% trifluoroacetic acid on a reverse phase C18 (60 Å) column; mp 115.8° C.; HRMS (M+H)$^+$: 552.1111 m/z.

Example 26

3-Trifluoromethyl-1-(2-aminomethyl-4-fluorophenyl)-1H-pyrazole-5-(N-(4-(2-methylsulfonyl-[1,1']-biphen-4-yl)) carboxyamide.TFA 3-Trifluoromethyl-1-(2-azidomethyl-4-fluorophenyl)-1H-pyrazole-5-carboxylic acid was prepared from 3-fluoro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 4-((2-methansulfonyl) phenyl)aniline according to the procedure in Part C of Example 8. The title compound was prepared and purified by the method outlined in Part D of Example 8; mp 110.3° C.; HRMS (M+H)$^+$: 533.1265 m/z.

Example 27

3-Trifluoromethyl-1-(2-aminomethyl-4-fluorophenyl)-1H-pyrazole-5-(N-(4-(2-sulfamido-[1, 1']-biphen-4-yl)) carboxyamide.TFA 3-Trifluoromethyl-1 (2-azidomethyl-4-fluorophenyl)-1H-pyrazole-5-carboxylic acid was prepared from 3-fluoro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 4-((2-N-t-butylsulfonamido)phenyl)aniline according to the procedure in Part C of Example 8. The azidomethyl group was reduced to the aminomethyl group with SnCl$_2$.2H$_2$O by the method outlined in Part D of Example 8. The crude reduction product was then refluxed in trifluoroacetic acid (10 mL) for 1 h to remove the t-butyl protecting group. The title compfound was isolated by HPLC utilizing gradient elution with a mixture of water:acetonitrile with 0.05% trifluoroacetic acid on a reverse phase C18 (60 Å) column; mp 136.8° C.; HRMS (M+H)$^+$: 534.1227 m/z.

Example 28

3-Trifluoromethyl-1-(2-aminomethyl-4-fluorophenyl)-1H-pyrazole-5-(N-(4- (N-((N'-methylsulfonyl)iminoly)pyrrolidino))phenyl) carboxyamide.TFA Part A: 4-Amino-N-((N'-methylsulfonyl)iminoyl) pyrrolidine: 4-Nitrobenzonitrile (5.4 g, 36.5 mmol) in anhydrous methyl acetate (200 mL) and MeOH (20 mL) was cooled to 0° C. and treated with a stream of dry HCl gas for 1 h. The reaction was securely stoppered and left to stand at 5° C. in a refrigerator for 24 h. The solvent was removed and the reaction was evaporated repeatedly (5×) with Et$_2$O to remove the last traces of free HCl. There was obtained 28.6 g of the imidate as an HCl salt . This material was dissolved in anhydrous MeOH (100 mL) and pyrrolidine (40.1 mmol, 2.85 g) added. The reaction was stirred for 18 h, then evaporated and stirred in 1N HCl (150 mL); the insoluable material was removed by filtration then the HCl solution evaporated. The residue was dried by the azeotropic removal of H$_2$O with EtOH and there was obtained 7.44 g of the amidine product; LRMS ES$^+$ (M+H)$^+$: 220.1 m/z.

The free base of the amidine prepared above was formed by suspending the product in 1N NaOH (250 mL) and extracting this suspension with CHCl$_3$ (3×). The material was dried and evaporated to give 4.49 g of product.

To 3.1 g of the free base of the amidine prepared above (14.2 mmol) in CH$_2$Cl$_2$ (100 mL) at 0° C. was added DMAP (2.1 g, 17 mmol) followed by methanesulfonyl chloride (1.95 g, 17 mmol) in CH$_2$Cl$_2$ (25 mL). After 18 h at ambient temperature, the reaction was washed with 1N HCl (2×), 1N NaOH and brine, dried and evaporated. There was obtained 3.6 g of the mesylation product; LRMS ES$^+$ (M+H)$^+$: 298.1.

The mesyltion product (3.6 g, 12 mmol) and SnCl2.2H2O (8.12 g, 36 mmol) in EtOH (100 mL) was heated at reflux for 2 h. The solvent was removed and the residue partioned between 1N NaOH (150 mL) and CH$_2$Cl$_2$ (100 mL). The aqueous layer was extracted with CH$_2$Cl$_2$ (2×100 mL), dried (Na$_2$SO$_4$) and evaporated to give 2.7 g of 4-amino-N-((N'-methylsulfonyl)iminoyl)pyrrolidine; LRMS ES$^+$ (M+H)$^+$: 268.1 m/z.

Part B: 3-Trifluoromethyl-1-(2-aminomethyl-4-fluorophenyl)-1H-pyrazole-5-(N-(4-(N-((N'-methylsulfonyl)iminoly)pyrrolidino))phenyl) carboxamide.TFA: 3-Trifluoromethyl-1-(2-azidomethyl-4-fluorophenyl)-1H-pyrazole-5-carboxylic acid was prepared from 3-fluoro-6-aminobenzoic acid by essentially the same method used for 3-trifluoromethyl-1-(2-azidomethyl-4-methoxyphenyl)-1H-pyrazole-5-carboxylic acid in Parts A and B of Example 8. This compound was coupled with 4-amino-N-((N'-methylsulfonyl)iminoyl)pyrrolidine, prepared in Part A of Example 28, according to the procedure in Part C of Example 8.

The title compound was prepared and purified by the method outlined in Part D of Example 8; mp 138.4° C.; HRMS (M+H)$^+$: 553.1640 m/z.

Example 29

3-Trifluoromethyl-1-(2-(N-glycyl)aminomethyl-4-methoxyphenyl)-1H-pyrazole-5-(N-(3-fluoro-2'-methylsulfonyl-[1,1']-biphen-4-yl)) carboxyamide.TFA 3-Trifluoromethyl-1-(2-(N-glycyl)aminomethyl-4-methoxyphenyl)-1H-pyrazole-5-(N-(3-fluoro-2'-methylsulfonyl-[1,1']-biphen-4-yl))carboxyamide.TFA: A mixture of 3-Trifluoromethyl-1-(2-aminomethyl-4-methoxyphenyl)-1H-pyrazole-5-(N-(3-fluoro-2'-methylsulfonyl-[1,1']-biphen-4-yl))carboxyamide.TFA (prepared in Example 5, 0.15 g, 0.22 mmol),N-Boc glycine (0.039 g, 0.22 mmol) and HBTU (0.084 g, 0.22 mmol) in DMF (3 mL) were cooled to 0° C. and NMM (0.075 g, 0.75 mmol) added. After 6 h, the reaction was diluted with brine and extracted with EtOAc. The EtOAc layer was washed with 5% NaHSO$_4$ and brine (5×) then dried (MgSO$_4$) and evaporated to give 0.14 g of product; LRMS ES$^+$ (M+H)$^+$: 720.4 m/z.

The product from above was stirred in 5% TFA in CH$_2$Cl$_2$ (20 mL) for 18 h. The reaction was evaporated and the product purified by HPLC utilizing gradient elution with a mixture of water:acetonitrile with 0.05% trifluoroacetic acid on a reverse phase C18 (60 Å) column to give 0.087 g of the title compound; mp 92.5° C.; HRMS (M+H)$^+$: 620.160000 m/z.

Example 30

3-Trifluoromethyl-1-(2-(N-phenylacetyl) aminomethyl-4-methoxyphenyl)-1H-pyrazole-5-(N-(3-fluoro-2'-methylsulfonyl-[1,1']-biphen-4-yl)) carboxyamide 3-Trifluoromethyl-1-(2-(N-phenylacetyl)aminomethyl-4-methoxyphenyl)-1H-pyrazole-5-(N-(3-fluoro-2'-methylsulfonyl-[1,1']-biphen-4-yl))carboxyamide: A mixture of 3-Trifluoromethyl-1-(2-aminomethyl-4-methoxyphenyl)-1H-pyrazole- 5-(N-(3-fluoro-2'-methylsulfonyl-[1,1'-biphen-4-yl))carboxyamide.TFA (prepared in Example 5, 0.15 g, 0.22 mmol) and Et$_3$N (0.068 g, 0.66 mmol) in CH$_2$Cl$_2$ (10 mL) was cooled to 0° C. and phenylacetyl chloride (0.22 mol in 1 mL of CH$_2$Cl$_2$) was added dropwise. The reaction was complete in 3 h. It was diluted with more CH$_2$Cl$_2$ then washed with 1N HCl, dried and evaporated. The residue was purified further by MPLC on a 200 g column of flash SiO$_2$ by elution with 1:1 Hexane:EtOAc. Fractions (25 mL) were collected and the product isolated in tubes 44–75. There was obtained 0.086 g of the desired product; mp 179–181° C.; HRMS (M+H)$^+$: 681.1786 m/z.

Example 31

3-(Trifluoromethyl)-1-(2-(aminomethyl)phenyl)-1H-pyrazole-5-(N-(2'-methylsulfonyl-1,1']-biphen-4-yl) )carboxyamide.TFA 2-[5-(2-Furyl)-3-(trifluoromethyl)-1H-pyrazol-1-yl] benzoic acid: 4,4,4-Trifluoro-1-(2-furyl)-1,3-butanedione (2.4 mL, 16 mmol) was added to 2-hydrazinobenzoic acid (3.01 g, 16 mmol) in acetic acid (20 mL) and heated at reflux for 25 h. The reaction was cooled, diluted with EtOAc, and extracted twice with water. The organic layer was dried over Na$_2$SO$_4$, filtered, and evaporated to yield a thick red paste (5.71 g, >100%). $^1$H NMR (CDCl$_3$) δ8.18 (dd, 1H, J=7.7, J'=1.8), 7.74 (td, 1H, J=7.7, J'=1.4), 7.65 (td, 1H, J=7.7, J'=1.5), 7.50 (dd, 1H, J=7.3, J'=1.1), 7.35 (m, 1H), 6.89 (s, 1H), 6.28 (m, 1H), 5.76 (d, 1H, J=3.3).

2-[5-(2-Furyl)-3-(trifluoromethyl)-1H-pyrazol-1-yl] benzamide: 2-[5-(2-Furyl)-3-(trifluoromethyl)-1H-pyrazol-1-yl]benzoic acid (5.13 g, 16 nmmol) was dissolved in thionyl chloride (25 mL) and heated at reflux for 2 h. The excess thionyl chloride was evaporated, and the resulting acid chloride was placed under high vacuum. The acid chloride was then redissolved in CH$_2$Cl$_2$ (25 mL) and cooled to 0° C. Conc. aqueous NH$_3$ (6 mL) was added portionwise over 30 min. The resulting mixture was stirred at 0° C. for 30 min, then at room temperature for 1 h.

The reaction was diluted with water and extracted with CH$_2$Cl$_2$ (3×). The organic layers were combined and extracted with 2M Na$_2$CO$_3$. The organic layer was dried over MgSO$_4$, filtered, and evaporated to yield the desired product (4.76 g, 93%). $^1$H NMR (CDCl$_3$) δ7.98 (dd, 1H, J=7.3, J'=2.2), 7.67 (m, 2H), 7.41 (m, 2H), 6.96 (s, 1H), 6.28 (m, 1H), 5.89 (bs, 1H), 5.67 (d, 1H, J=2.9).

2-[5-(2-Furyl)-3-(trifluoromethyl)-1H-pyrazol-1-yl] benzonitrile: 2-[5-(2-Furyl)-3-(trifluoromethyl)-1H-pyrazol-1-yl]benzamide (6.73 g, 21 mmol) and triethylamine (5.8 mL, 42 mmol) were combined in dry CH$_2$Cl$_2$ (55 mL) under argon and cooled to 0° C. Trichloroacetyl chloride (2.7 mL, 24 mmol) in CH$_2$Cl$_2$ (15 mL) was added dropwise over 30 min. The resulting solution was stirred at 0° C. for 20 min, then at room temperature for 65 min. The reaction was quenched with a small amount of water, then partitioned between 1M HCl and CH$_2$Cl$_2$. The organic layer was removed and extracted with sat. NaHCO$_3$, then dried over Na$_2$SO$_4$, filtered, and evaporated to yield crude product (6.66 g). The crude product was chromatographed on silica gel (30–40% EtOAc/hexanes) to yield a yellow solid (6.51 g, >100%). $^1$H NMR (CDCl$_3$) δ7.79 (m, 2H), 7.64 (m, 2H), 7.39 (d, 1H, J=1.8), 6.96 (s, 1H), 6.37 (m, 1H), 6.04 (d, 1H, J=3.7).

2-[5-(2-Furyl)-3-(trifluoromethyl)-1H-pyrazol-1-yl] benzylamine: Cobalt chloride (1.76 g, 13.6 mmol) was added to 2-[5-(2-furyl)-3-(trifluoromethyl)-1H-pyrazol-1-yl]benzonitrile (4.12 g, 13.6 mmol) and sodium borohydride (1.03 g, 27.2 mmol) in DMF (40 mL). The reaction turned black and became warm. An ice bath was added and the reaction was stirred at 0° C. for 45 min, then at room temperature for 23 h. Additional sodium borohydride (0.25 g, 6.6 mmol) was added and the resulting mixture was stirred at room temperature for 6 h. A room temperature water bath was added, and the reaction was quenched with water (10 mL) over 10 min, then MeOH (20 mL), then 6M HCl (20 mL) over 15 min. The quenched reaction was stirred at room temperature for 16 h, diluted with EtOAc, and extracted with water and 0.1M HCl. The resulting emulsion was filtered through celite, and the organic layer was removed, dried over Na$_2$SO$_4$, filtered, and evaporated to yield crude product (857 mg). The aqueous layers were combined and neutralized (pH 8) with solid Na$_2$CO$_3$ (6.9 g). Addition of EtOAc yielded another emulsion, which was filtered through celite. The organic layer was removed, and the aqueous layer was extracted again with EtOAc. The organic layers were combined, dried over Na$_2$SO$_4$, filtered, and evaporated to yield a second batch of crude product (3.55 g). The two batches of crude product were combined and chromatographed on silica gel (0–10% MeOH/CHCl$_3$) to yield the desired product (3.77 g, 90%). $^1$H NMR (CDCl$_3$) δ7.59 (m, 2H), 7.38 (m, 2H), 7.33 (d, 1H, J=7.3), 6.96 (s, 1H), 6.27 (m, 1H), 5.59 (d, 1H, J=3.6), 3.51 (s, 2H).

t-Butyl 2-[5-(2-furyl)-3-(trifluoromethyl)-1H-pyrazol-1-yl]benzylcarbamate: Triethylamine (2.6 mL, 18.7 mmol) and di-t-butyl dicarbonate (4.0 g, 18.4 mmol) were added to 2-[5-(2-furyl)-3-(trifluoromethyl)-1H-pyrazol-1-yl] benzylamine (3.77 g, 12.3 mmol) in THF (60 mL) and stirred at room temperature for 17 h. The reaction was concentrated, diluted with Et$_2$O, and extracted with water (2×). The aqueous layers were combined and extracted with Et$_2$O. The organic layers were combined, dried over MgSO$_4$, filtered, and evaporated to yield crude product (5.58 g). The crude product was chromatographed on silica gel (10–20% EtOAc/hexanes) to yield a waxy solid (3.82 g, 76%). $^1$H NMR (CDCl$_3$) δ7.57 (m, 2H), 7.43 (m, 2H), 7.32 (d, 1H, J=7.7), 6.95 (s, 1H), 6.28 (m, 1H), 5.66 (d, 1H, J=3.3), 4.82 (bs, 1H), 4.01 (bd, 2H, J=6.2), 1.39 (s, 9H).

1-(2-([(t-Butoxycarbonyl)amino]methyl)phenyl)-3-(trifluoromethyl)-1H-pyrazol-1-yl-5-carboxylic acid: t-Butyl 2-[5-(2-furyl)-3-(trifluoromethyl)-1H-pyrazol-1-yl] benzylcarbamate (3.77 g, 9.2 nmol) was dissolved in t-BuOH (60 mL). A 5% aqueous solution of NaH$_2$PO$_4$ (40 mL) was added, followed by portionwise addition of solid KMnO$_4$ (5.86 g, 37 mmol) over 25 min. The resulting mixture was heated at 65° C. for 40 min. Additional KMnO$_4$ (1.39 g, 8.8 mmol) was added, and the reaction continued heating at 65° C. for 35 min. The reaction mixture was cooled and filtered through celite, using EtOH and acetone to rinse the celite. The filtrate was concentrated to approx. half its original volume and treated with aq. sodium bisulfite to remove residual KMnO$_4$. The resulting mixture was extracted with EtOAc, and the organic layer was removed, dried over Na$_2$SO$_4$, filtered, and evaporated to yield crude product (1.50 g). The aqueous layer was cooled in ice, acidified with 1M HCl (6 mL) and extracted with EtOAc (containing a small amount of EtOH). Before separating, both layers were filtered through celite and treated with sat NaHCO$_3$ (1.5 mL). The aqueous layer was removed and extracted twice with EtOAc/EtOH. Solid NaCl was added both times to aid separation of the emulsion. The aqueous layer was extracted with CHCl$_3$, adjusted to pH 5 with 1M HCl, and extracted twice with CHCl$_3$/EtOH. The final 6 organic layers were combined, dried over Na$_2$SO$_4$, filtered, and evaporated to yield a second batch of product (2.43 g, 68%). The first batch of product was chromatographed on silica gel (0–30% MeOH/CHCl$_3$) to yield clean product (0.95 g, 27%). 1H NMR (DMSO) δ7.34 (m, 4H), 7.16 (d, 1H), 6.81 (bs, 1H), 3.79 (bd, 2H), 1.32 (s, 9H).

1-[2-(([(t-Butoxycarbonyl)amino]methyl)phenyl)-5-(2'-methylsufonyl-[1,1']-biphen-4-yl))aminocarbonyl]-3-(trifluoromethyl)pyrazole: Oxalyl chloride (90 μl, 1.0 mmol) and DMF (2 drops) were added to 1-(2-([(t-butoxycarbonyl) amino]methyl)phenyl)-3-(trifluoromethyl)-1H-pyrazol-1-yl-5-carboxylic acid (200 mg, 0.52 mmol) in CH$_2$Cl$_2$ (5 mL) and the resulting solution was stirred for 90 min at room temperature. The solvents were evaporated and the resulting compound was placed briefly under high vacuum before redissolving in CH$_2$Cl$_2$ (5 mL). Triethylamine (220 μl, 1.6 mmol), 4-amino-2'-methylsulfonyl-[1,1']-biphenyl hydrochloride (177 mg, 0.62 mmol), and 4-dimethylaminopyridine (20 mg, 0.16 mmol) were added, and the resulting solution was stirred for 23 h at room temperature. The reaction was extracted with ice-cooled 1M HCl, then sat. NaHCO$_3$. The organic layer was ried over MgSO$_4$, filtered, and evaporated to yield crude roduct (241 mg). The crude product was chromatographed on silica gel (30–40% EtOAc/hexanes) to yield the desired product (64 mg, 20%). $^1$H NMR (CDCl$_3$) δ8.21 (d, 1H, J=8.1), 7.58 (m, 5H), 7.35 (m, 8H), 7.18 (s, 1H), 4.16 (d, 2H, J=5.8), 2.59 (s, 3H), 1.33 (s, 9H).

3-(Trifluoromethyl)-1-(2-(aminomethyl)phenyl)-1H-pyrazole-5-(N-(2'-methylsulfonyl-[1,1']-biphen-4-yl)) carboxyamide trifluoroacetic acid salt: TFA (1 mL) was added to 1-[2-(([(t-butoxycarbonyl)aminolmethyl)phenyl)-5-(2'-methylsufonyl-[1,1']-biphen-4-yl))aminocarbonyl]-3-(trifluoromethyl)pyrazole (64 mg, 0.10 mmol) in CH$_2$Cl$_2$ (1 mL) and stirred at room temperature for 21 h. The reaction was evaporated and purified by reverse phase prep. HPLC (15–70% MeCN/H$_2$O/0.5% TFA) to yield the desired product (30 mg, 46%). $^1$H NMR (DMSO) d 10.79 (s, 1H), 8.16 (bs, 2H), 8.04 (d, 1H, J=7.7), 7.77 (s, 1H), 7.71 (td, 1H, J=5.8), 7.64 (m, 6H), 7.51 (m, 1H), 7.45 (d, 1H, J=7.6), 7.34 (m, 3H), 3.79 (bm, 2H), 2.78 (s, 3H). $^{19}$F NMR (DMSO) d −61.22, −73.97. HRMS calc. C$_{25}$H$_{22}$N$_4$O$_3$F$_3$S: 515.1365; found, 515.1359.

Example 32

3-Trifluoromethyl-1-(2-(aminomethyl)phenyl)-1H-pyrazole-5-(N-(2'-aminosulfonyl-[1,1']-biphen-4-yl)) carboxyamide.TFA 1-[2-(([(t-Butoxycarbonyl)amino]methyl)phenyl)-5-(2'-(t-butylamino)sulfonyl-[1,1']-biphen-4-yl))aminocarbonyl]-

3-(trifluoromethyl)pyrazole: Oxalyl chloride (90 μl, 1.0 mmol) and DMF (2 drops) were added to 1-(2-([(t-butoxycarbonyl)amino]methyl)phenyl)-3-(trifluoromethyl)-1H-pyrazol-1-yl-5-carboxylic acid (Example 31 Part A, 200 mg, 0.52 mmnol) in $CH_2Cl_2$ (5 mL) and the resulting solution was stirred for 95 min at room temperature. The solvents were evaporated and the resulting compound was placed briefly under high vacuum before redissolving in $CH_2Cl_2$ (5 mL).

Triethylamine (150 μl, 1.1 mmol), 4-amino-2'-(t-butylamino)sulfonyl-[1,1']-biphenyl (190 mg, 0.62 mmol), and 4-dimethylaminopyridine (20 mg, 0.16 mmol) were added, and the resulting solution was stirred for 23 h at room temperature. The reaction was extracted with dilute brine solution, ice-cooled 1M HCl, and sat. $NaHCO_3$. The organic layer was dried over $MgSO_4$, filtered, and evaporated to yield crude product (371 mg). The crude product was chromatographed on silica gel (30% EtOAc/hexanes) to yield the desired product (74 mg, 21%). $^1H$ NMR ($CDCl_3$) δ8.64 (bs, 1H), 8.15 (dd, 1H, J=7.7, J'=1.5), 7.45 (m, 10H), 7.25 (d, 1H, J=6.9), 7.20 (s, 1H), 5.33 (bs, 1H), 4.15 (d, 2H, J=5.8), 3.49 (bs, 1H), 1.34 (s, 9H), 0.97 (s, 9H).

3-Trifluoromethyl-1-(2-(aminomethyl)phenyl)-1H-pyrazole-5-(N-(2'-aminosulfonyl-[1,1']-biphen-4-yl))carboxyamide trifluoroacetic acid salt: TFA (2 mL) was added to 1-[2-(([(t-butoxycarbonyl)amino]methyl)phenyl)-5-(2'-(t-butylamino)sulfonyl-[1,1']-biphen-4-yl))aminocarbonyl]-3-(trifluoromethyl)pyrazole (74 mg, 0.11 mmol) in $CH_2Cl_2$ (1 mL) and stirred at room temperature for 19 h. Additional TFA (2 mL) was added, and the reaction continued stirring for 3 h. The reaction was evaporated and purified by reverse phase prep. HPLC (15–70% MeCN/$H_2O$/0.5% TFA) to yield the desired product (41 mg, 59%). $^1H$ NMR (DMSO) δ10.75 (s, 1H), 8.17 (bs, 3H), 7.98 (dd, 1H, J=7.3), 7.76 (s, 1H), 7.57 (m, 7H), 7.44 (d, 1H, J=6.7), 7.32 (d, 2H, J=8.8), 7.25 (m, 3H) 3.79 (bd, 2H, J=5.1). $^{19}F$ NMR (DMSO) δ−61.22, −73.99. HRMS calc. $C_{24}H_{21}N_5O_3F_3S$: 516.1317; found, 516.1319.

Example 33

3-Trifluoromethyl-1-(2-(aminomethyl)phenyl)-1H-pyrazole-5-(N-(3-fluoro-2'-aminosulfonyl-[1,1']-biphen-4-yl) ) carboxyamide.TFA 1-[2-((([(t-Butoxycarbonyl)amino]methyl)phenyl)-5-(3-fluoro-2'-(t-butylamino)sulfonyl-[1,1']-biphen-4-yl))aminocarbonyl]-3-(trifluoromethyl)pyrazole: Oxalyl chloride (300 μl, 3.4 mmol) and DMF (3 drops) were added to 1-(2-[(t-butoxycarbonyl)amino]methylphenyl)-3-(trifluoromethyl)-1H-pyrazol-1-yl-5-carboxylic acid (Example 31 Part A, 888 mg, 2.3 mmol) in $CH_2Cl_2$ (30 mL) and the resulting solution was stirred for 65 min at room temperature. The solvents were evaporated and the resulting compound was placed briefly under high vacuum before redissolving in $CH_2Cl_2$ (30 mL). 4-Amino-3-fluoro-2'-(t-butylamino)sulfonyl-[1,1']-biphenyl (890 mg, 2.8 mmol), and 4-dimethylaminopyridine (420 mg, 3.4 mmol) were added, and the resulting solution was stirred for 22 h at room temperature. The reaction was concentrated and chromatographed on silica gel (20–30% EtOAc/hexanes). The fractions containing product were combined and concentrated to half the original volume, then extracted 3× with ice-cooled 1M HCl, 2× with room temperature 1M HCl, sat. $NaHCO_3$, 2M HCl, and sat. $NaHCO_3$. The organic layer was dried over $Na_2SO_4$, filtered, and evaporated to yield the desired product (600 mg, 38%).

3-Trifluoromethyl-1-(2-(aminomethyl)phenyl)-1H-pyrazole-5-(N-(3-fluoro-2'-aminosulfonyl-[1,1']-biphen-4-yl))carboxyamide trifluoroacetic acid salt: TFA (9 mL) was added to 1-[2-((([(t-butoxycarbonyl)amino]methyl)phenyl)-5-(3-fluoro-2'-(t-butylamino)sulfonyl-[1,1']-biphen-4-yl))aminocarbonyl]-3-(trifluoromethyl)pyrazole (600 mg, 0.87 mmol) in $CH_2Cl_2$ (3 mL) and stirred at room temperature for 18 h. The reaction was evaporated and purified by reverse phase prep. HPLC (10–70% MeCN/$H_2O$/0.5% TFA) to yield impure product (349 mg). This material was again purified by reverse phase HPLC (5–70% MeCN/$H_2O$/0.5% TFA) to yield clean product (162 mg, 35%). Any impure fractions containing product were combined and purified by reverse phase HPLC (20–60% MeCN/$H_2O$/0.5% TFA) to yield additional product (119 mg, 26%) $^1H$ NMR (DMSO) δ10.62 (s, 1H), 8.16 (bs, 2H), 7.98 (dd, 1H, J=7.0, J'=2.2), 7.79 (s, 1H), 7.54 (m, 7H), 7.39 (s, 2H), 7.28 (m, 2H), 7.15 (d, 1H, J=8.4), 3.78 (bm, 2H). $^{19}F$ NMR (DMSO) δ−61.26, −74.29, −122.79. HRMS calc. $C_{24}H_{20}N_5O_3F_4S$: 534.1223; found, 534.1216.

Example 34

3-Trifluoromethyl-1-(2-(aminomethyl)phenyl)-1H-pyrazole-5-(N-(3-fluoro-2'-methylsulfonyl-[1,1']-biphen-4-yl))carboxyamide.TFA 1-[2-((([(t-Butoxycarbonyl)amino]methyl)phenyl)-5-(3-fluoro-2'-methylsulfonyl-[1,1']-biphen-4-yl))aminocarbonyl]-3-(trifluoromethyl)pyrazole: Oxalyl chloride (320 μl, 3.7 mmol) and DMF (4 drops) were added to 1-(2-([(t-butoxy carbonyl)amino]methyl)phenyl)-3-(trifluoromethyl)-1H-pyrazol-1-yl-5-carboxylic acid (Example 31 Part A, 940 mg, 2.4 mmol) in $CH_2Cl_2$ (35 mL) and the resulting solution was stirred for 55 min at room temperature. The solvents were evaporated and the resulting compound was placed briefly under high vacuum before redissolving in $CH_2Cl_2$ (20 mL). 4-Amino-3-fluoro-2'-methylsulfonyl-[1,1']-biphenyl (750 mg, 2.8 rmnmol) in $CH_2Cl_2$ (15 mL), and 4-dimethylaminopyridine (447 mg, 3.7 mmol) were added, and the resulting solution was stirred for 20 h at room temperature. The reaction was concentrated and chromatographed on silica gel (30–40% EtOAc/hexanes) to yield impure product (802 mg), which was purified on reverse phase prep. HPLC (10–70% MeCN/$H_2O$/0.5% TFA) to yield clean product (645 mg, 42%).

3-Trifluoromethyl-1-(2-(aminomethyl)phenyl)-1H-pyrazole-5-(N-(3-fluoro-2'-methylsulfonyl-[1,1']-biphen-4-yl))carboxyamide trifluoroacetic acid salt: TFA (2 mL) was added to 1-[2-((([(t-butoxycarbonyl)amino]methyl)phenyl)-5-(3-fluoro-2'-methylsulfonyl-[1,1'-biphen-4-yl))aminocarbonyl]-3-(trifluoromethyl)pyrazole (132 mg, 0.21 mmol) in $CH_2Cl_2$ (2 mL) and stirred at room temperature for 5 h. The reaction was evaporated and purified by reverse phase prep. HPLC (10–70% MeCN/$H_2O$/0.5% TFA) to yield the desired product (80 mg, 59%). $^1H$ NMR (DMSO) δ10.65, (s, 1H), 8.16 (bs, 3H), 8.05 (d, 1H, J=6.6), 7.79 (s, 1H), 7.73 (td, 1H, J=6.2, J'=1.5), 7.67 (dd, 1H, J=7.7, J'=1.5), 7.54 (m, 5H), 7.35 (m, 2H), 7.19 (d, 1H, J=8.0), 3.78 (bd, 2H, J=5.5), 2.88 (s, 3H). $^{19}F$ NMR (DMSO) δ−61.26, −74.11, −122.19. HRMS calc. $C_{25}H_{21}N_4O_3F_4S$: 533.1217; found, 533.1258.

Example 35

3-Trifluoromethyl-1-(2-(N-(glycyl)aminomethyl)phenyl)-1H-pyrazole-5-(N-(3-fluoro-2'-methylsulfonyl-[1,1']-biphen-4-yl))carboxyamide.TFA The title compound was prepared from 1-[2-((aminomethyl)phenyl)-5-(3-fluoro-2'-methylsulfonyl-[1,1']-biphen-4-yl))aminocarbonyl]-3-(trifluoromethyl)pyrazole trifluoroacetic acid salt (prepared in Example 34) and N-Boc glycine according to the procedure in Example 29; HRMS (M+H)$^+$: 590.1495 m/z.

Example 36

3-Trifluoromethyl-1-(2-((N-(N-methylglycyl) aminomethyl)phenyl)-1H-pyrazole-5-(N-(3-fluoro-2'-methyloulfonyl-[1,1']-biphen-4-yl)) carboxyamide.TFA The title compound was prepared from 1-[2-((aminomethyl)phenyl)-5-(3-fluoro-2'-methylsulfonyl-[1,1']-biphen-4-yl)aminocarbonyl]-3-(trifluoromethyl) pyrazole trifluoroacetic acid salt (prepared in Example 34) and N-Boc-N-methyl glycine according to the procedure in Example 29; HRMS (M+H)$^+$: 604.1655 m/z.

Example 37

3-Trifluoromethyl-1-(2-carboxamidophenyl)-1H-pyrazole-5-(N-(3-fluoro-2'-methylsulfonyl-1,1']-biphen-4-yl))carboxyamide Methyl 2-[5-(2-furyl)-3-(trifluoromethyl)-1H-pyrazol-1-yl]benzoate: 2-[5-(2-furyl)-3-(trifluoromethyl)-1H-pyrazol-1-yl]benzoic acid (Example 31 Part A, 26.5 g, 82 mmol) was dissolved in SOCl$_2$ (130 mL) and heated at reflux for 2.5 h. Excess SOCl$_2$ was evaporated, and the residual acid chloride was placed under high vacuum. The acid chloride was cooled to 0° C., and dry MeOH (130 mL) was added. The resulting solution was allowed to warm slowly to room temperature, then stirred at room temperature for 22 h. The solvent was evaporated, and the crude product was chromatographed on silica gel (0–30% EtOAc/hexanes) to yield the desired product (22.6 g, 82%). $^1$H NMR (CDCl$_3$) δ8.10 (dd, 1H, J=7.3, J'=1.9), 7.67 (m, 2H), 7.50 (dd, 1H, J=7.7, J'=1.4), 7.37 (s, 1H), 6.92 (s, 1H), 6.29 (m, 1H), 5.77 (d, 1H, J=3.3), 3.62 (s, 3H).

1-(2-Carbomethoxyphenyl)-3-(trifluoromethyl)-1H-pyrazol-1-yl]-5-carboxylic acid: A 5% aq. solution of NaH$_2$PO$_4$ (320 mL) and water (200 mL) were added to methyl 2-[5-(2-furyl)-3-(trifluoromethyl)-1H-pyrazol-1-yl]benzoate (23.7 g, 71 mmol) in t-BuOH (470 mL). The reaction was immersed in a room temperature water bath, and solid KMnO$_4$ (55.8 g, 353 nmol) was added portionwise over 1 h. The reaction was heated at 70° C. for 90 min, cooled, and filtered through celite. The celite was rinsed with acetone and EtOAc. The filtrate was concentrated to remove most of the organics, then extracted with EtOAc. The organic layer was extracted with sat. Na$_2$SO$_3$, dried over Na$_2$SO$_4$, filtered, evaporated, and set aside. The aqueous layers were combined and neutralized to pH 6.5 with 2M HCl (100 mL), and then extracted with EtOAc (3×). The organic layers were combined, dried over Na$_2$SO$_4$, and evaporated to yield clean product (14.8 g, 67%). $^1$H NMR (CDCl$_3$) δ8.10 (dd, 1H, J=7.3, J=1.5), 7.64 (m, 2H), 7.42 (dd, 1H, J=7.3, J'=1.1), 7.31 (s, 1H), 3.69 (s, 3H).

1-[2-Carbomethoxyphenyl-5-(3-fluoro-2'-methylsulfonyl-[1,1']-biphen-4-yl))aminocarbonyl]-3-(trifluoromethyl)pyrazole: Oxalyl chloride (2.9 mL, 33 mmol) and DMF (10 drops) were added to 1-(2-carbomethoxyphenyl)-3-(trifluoromethyl)-1H-pyrazol-1-yl]-5-carboxylic acid (7.0 g, 22 mmol) in dry CH$_2$Cl$_2$ (240 mL), and the resulting solution was stirred at room temperature for 80 min. The solvents were evaporated, and the resulting compound was placed briefly under high vacuum before redissolving in CH$_2$Cl$_2$ (240 mL). 4-Amino-3-fluoro-2'-methylsulfonyl-[1,1']-biphenyl hydrochloride (7.4 g, 25 mmol) and 4-dimethylaminopyridine (7.1 g, 58 mmol) were added, and the resulting solution was stirred at room temperature for 67 h. The reaction was extracted with 1M HCl (2×), then sat. NaHCO$_3$. The organic layer was dried over MgSO$_4$, filtered, and evaporated to yield crude product. The crude product was chromatographed on silica gel (30–50% EtOAc/hexanes) to yield the desired product (12.4 g, 99%). $^1$H NMR (CDCl$_3$) δ8.29 (t, 1H, J=8.1), 8.21 (m, 2H), 8.11 (dd, 1H, J=7.7, J'=1.5), 7.62 (m, 5H), 7.30 (m, 2H), 7.14 (m, 2H), 3.77 (s, 3H), 2.69 (s, 3H).

1-[2-Carboxyphenyl-5-(3-fluoro-2'-methylsulfonyl-[1,1']-biphen-4-yl))aminocarbonyl]-3-(trifluoromethyl) pyrazole: 1M LiOH (34 mL)was added to 1-[2-carbomethoxyphenyl-5-(3-fluoro-2'-methylsulfonyl-[1,1']-biphen-4-yl))aminocarbonyl]-3-(trifluoromethyl)pyrazole (12.0 g, 21 mmol) in THF (285 mL) and stirred at room temperature for 26 h. Additional 1M LiOH (15 mL) was added, and the reaction continued stirring for 18 h. The resulting solution was heated at 35° C. for 2.5 h, then at 50° C. for 18 h. The reaction was cooled, concentrated, and partitioned between Et$_2$O and water. The organic layer was extracted again with water (2×). A small amount of white solid was assumed to be product, and was added to the aqueous layer. The aqueous layers were combined, neutralized to pH 7 with 2M HCl (23 mL), and extracted with EtOAc. Additional 2M HCl (2 mL) was added to the aqueous, which was extracted twice with EtOAc. The EtOAc layers were combined, dried over Na$_2$SO$_4$, filtered, and evaporated to yield the desired product (10.3 g, 88%). $^1$H NMR (CDCl$_3$) δ8.21 (m, 4H), 7.75 (m, 1H), 7.60 (m, 4H), 7.29 (m, 3H), 7.13 (m, 2H), 2.70 (s, 3H).

3-Trifluoromethyl-1-(2-carboxamidophenyl)-1H-pyrazole-5-(N-(3-fluoro-2'-methylsulfonyl-[1,1']-biphen-4-yl))carboxyamide: 1-[2-Carboxyphenyl-5-(3-fluoro-2'-methylsulfonyl-[1,1']-biphen-4-yl))aminocarbonyl]-3-(trifluoromethyl)pyrazole (3.0 g, 5.5 mmol) was dissolved in SOCl$_2$ (10 mL) and heated at reflux for 2 h. Excess SOCl$_2$ was evaporated, and the residual acid chloride was placed under high vacuum. The acid chloride was dissolved in dry CH$_2$Cl$_2$ and cooled to 0° C., and conc. aq. NH$_3$ (2.0 mL) was added over 20 min. The resulting mixture was stirred at room temperature for 18 h. The reaction was diluted with CH$_2$Cl$_2$ and extracted with water. The aqueous layer was extracted with CHCl$_3$, MeOH/CH$_2$Cl$_2$, and CH$_2$Cl$_2$. All of the organics were combined and extracted with sat. NaHCO$_3$ (2×), 1M HCl, and sat. NaCl. The organic layer was dried over MgSO$_4$, filtered, evaporated, and chromatographed on silica gel (30–75% EtOAc/hexanes) to yield the desired product (794 mg, 27%). $^1$H NMR (CDCl$_3$, 400 MHz) δ9.53 (bs, 1H), 8.25 (t, 1H, J=8.3), 8.20 (dd, 1H, J=7.8, J'=1.2), 7.75 (m, 1H), 7.60 (m, 4H), 7.45 (m, 1H), 7.29 (dd, 1H, J=7.6, J'=1.2), 7.20 (dd, 1H, J=11.2, J'=1.9), 7.12 (m, 2H), 6.13 (bs, 1H), 5.68 (bs, 1H), 2.67 (s, 3H).

Example 38

3-Trifluoromethyl-1-(2-cyanophenyl)-1H-pyrazole-5-(N-(3-fluoro-2'-methylsulfonyl-[1,1']-biphen-4-yl)) carboxyamide 1-[2-Cyanophenyl-5-(3-fluoro-2'-methylsulfonyl-[1,1']-biphen-4-yl))aminocarbonyl]-3-(trifluoromethyl)pyrazole: 1-[2-Carboxamidophenyl-5-(3-fluoro-2'-methylsulfonyl-[1,1']-biphen-4-yl))aminocarbonyl]-3-(trifluoromethyl) pyrazole (Example 36, 715 mg, 1.3 mmol) and triethylamine (360 μL, 2.6 mmol) were combined in dry CH$_2$Cl$_2$ (10 mL) and cooled to 0° C. Trichloroacetyl chloride (160 μl, 1.4 mmol) was added over 5 min. The resulting solution was stirred at 0° C. for 30 min, then at room temperature for 2 h. Additional triethylamine (200 μL, 1.4 mmol) was added, and the reaction continued stirring at room temperature for 68 h. Additional trichloroacetyl chloride (20 μL, 0.2 mmol) was added. After stirring 2 h, the reaction was quenched with water. The organic layer was removed and extracted with 1 HCl and sat. NaHCO$_3$. A small amount of sat. NaCl was added to break up the emulsion. The organic layer was dried over Na$_2$SO$_4$, filtered, evaporated, and chromatographed on silica gel (20–75% EtOAc/hexanes) to yield the desired product (114 mg, 17%). 1H NMR (CDCl$_3$) δ8.25 (m, 2H), 8.09 (bs, 1H), 7.82 (m, 2H), 7.65 (m, 4H), 7.35 (m, 2H), 7.20 (m, 2H), 2.72 (s, 3H).

Example 39

1-(2'-Aminomethylphenyl)-5- [[(2'-methylsulfonyl)-3-fluoro-[1,1']-biphen-4-yl]aminocarbonyl]-tetrazole TFA salt Ethyl 1-(2-cyanophenyl)-5-tetrazole carboxylate: To a solution of anthranilonitrile (10.00 g) and Et$_3$N (13.21 mL) in CH$_2$Cl$_2$ (250 mL) was added ethyloxalyl chloride (9.92 mL) in a dropwise fashion over 30 minutes. The reaction was stirred at RT under N$_2$ for 3 h. The reaction mixture was filtered. The filtrate was washed with water (2×150 mL) and brine (1×150 mL), filtered through phase separatory paper and evaporated. The residue was dissolved in 60 mL of CH$_2$Cl$_2$ and 300 mL of hexane was added. The solution was allowed to stand at RT for the weekend. The precipitate was filtered, rinsed with hexane, and dried under vacuum to give 17.74 g of 1-(2-cyanophenyl)-oxoacetic acid ethyl ester.

A solution of triphenylphosphine (16.83 g) in CCl$_4$ (100 mL) was stirred at 0° C. for 30 minutes. 1-(2-Cyanophenyl)-oxoacetic acid ethyl ester (7.00 g) in CCl$_4$ (100 mL) was added and the reaction was stirred at reflux under N$_2$ for 16 h. The reaction was cooled to RT and the precipitate filtered off. The filtrate was evaporated and dissolved in CH$_3$CN (300 mL). Sodium azide (2.29 g) was added and the reaction stirred at RT under N$_2$ for 16 h. The solvent was evaporated and the residue taken up in EtOAc (100 mL). The organic solution was washed with water (2×100 mL) and brine (1×100 mL), dried over MgSO$_4$, and evaporated. The crude material was purified by silica gel chromatography eluting with CH$_2$Cl$_2$ to give 3.80 g of the title compound; LRMS (ES$^+$) M$^+$: 244 m/z 1-(2'-Aminomethylphenyl)-5-[[(2'-methylsulfonyl)-3-fluoro-[1,1']-biphen-4-yl]aminocarbonyl]-tetrazole: To a solution of [(2'-methylaminosulfonyl)-3-fluoro-[1,1']-biphen-4-yl]amine (0.32 g) in anhydrous CH$_2$Cl$_2$ (10 mL) was added trimethylaluminum (2.12 mL, 2M in heptane). The reaction was stirred at RT under N$_2$ for 30 minutes. A solution of ethyl 1-(2-cyanophenyl)-5-tetrazole carboxylate (0.28 g) in anhydrous CH$_2$Cl$_2$ (10 mL) was added and the reaction was stirred at RT under N$_2$ for 64 h. The reaction was quenched with 5 drops of 1N HCl and diluted with CH$_2$Cl$_2$ (30 mL). The organic solution was washed with water (2×25 mL) and brine (1×25 mL), filtered through phase separatory paper, and evaporated. The crude material was purified by silica gel chromatography eluting with 10% EtOH/CH$_2$Cl$_2$ to give 0.35 g of 1-(2'-cyanophenyl)-5-[[(2'-methylsulfonyl)-3-fluoro-[1,1']-biphen-4-yl]aminocarbonyl]-tetrazole; LMRS (ES$^-$) M$^-$: 461 m/z.

Cobalt chloride (0.098 g ) was added to 1-(2'-cyanophenyl)-5-[[(2'-methylsulfonyl)-3-fluoro-[1,1']-biphen-4-yl]aminocarbonyl]-tetrazole (0.35 g) and sodium borohydride (0.072 g) in DMF (5 mL). The reaction was stirred at room temperature for 16 h. The resulting mixture was stirred at room temperature for 16 h. 6M HCl (5 mL) was added over 5 min. The quenched reaction was stirred at room temperature for 3.5 h, diluted with EtOAc and water. The resulting emulsion was filtered through celite, and the organic layer was washed with 1N HCl, dried over Na$_2$SO$_4$, filtered, and evaporated to yield crude product (100 mg). The aqueous layers were combined and neutralized (pH 7) with saturate NaHCO$_3$, extracted with EtOAc. The organic layers were combined, dried over Na$_2$SO$_4$, filtered, and evaporated to yield a second batch of crude product. The two batches of crude product were combined and purified by reverse phase HPLC (10–90% MeCN/H$_2$O/0.5% TFA) to yield 102 mg of the title compound as its TFA salt. LMRS (ES$^+$) M$^+$: 467 m/z.

Example 40

1-(2'-Aminomethylphenyl)-5-[(2'-aminosulfonyl-[1,1']-biphen-4-yl)aminocarbonyl]-tetrazole.TFA The title compound was prepared in an analogous fashion as its TFA salt. LRMS (ES$^+$) M$^+$: 468 m/z.

Example 41

1-[2-(Aminomethyl)phenyl]3-thiomethoxy-5-[(2-fluoro)-(2'-methylsulfonyl-[1,1']-biphen-4-yl)aminocarbonyl]pyrazole.TFA Methyl 3-(thiomethoxy)pyrazole-5-carboxylate: A mixture of methyl 4,4-bis(thiomethoxy)-2-oxo-3-butenoate (9.9 g, 48 mmol) and hydrazine monohydrate (2.6 mL, 53 mmol) in 200 mL of glacial acetic acid was stirred at 100° C. for 18 h. The reaction was cooled and concentrated. The residue was taken up in ethyl acetate, washed with sat'd aq NaHCO$_3$ and brine, dried (MgSO$_4$) and concentrated. The solid residue was recrystallized from hexanes/ethyl acetate to afford 6.0 g (73%) of the title compound. $^1$H NMR (CDCl$_3$) δ11.0 (broad s, 1H), 6.74 (s, 1H), 3.88 (s, 3H), 2.48 (s, 3H).

Methyl 1-[2-formylphenyl]-3-(thiomethoxy)pyrazole-5-carboxylate: To a solution of methyl 3-(thiomethoxy)pyrazole-5-carboxylate (0.87 g, 5.05 mmol) in 20 mL of 1,4-dioxane was added 2-formylphenyl boronic acid (1.13 g, 7.58 mmol), pyridine (0.82 mL, 10.1 mmol), crushed 4 A molecular sieves and cupric acetate (1.38 g, 7.58 mmol). The flask was equipped with a drying tube and the mixture was allowed to stir at ambient temperature under an air atmosphere for 18 h. The mixture was filtered through a pad of Celite and concentrated. The residue was purified by flash chromatography to afford 0.22 g (16%) of the title compound. $^1$H NMR (CDCl$_3$) δ9.66 (s, 1H), 8.02 (dd, 1H), 7.69 (td, 1H), 7.63 (t, 1H), 7.42 (d, 1H), 6.96 (s, 1H), 3.75 (s, 3H), 2.55 (s, 3H).

1-[(2-(Hydroxymethyl)phenyl]-3-thiomethoxy-5-[(2-fluoro)-(2'-methylsulfonyl-[1,1']-biphen-4-yl) aminocarbonyl]pyrazole: To a solution of methyl 1-[2-formylphenyl]-3-(thiomethoxy)pyrazole-5-carboxylate (0.48 g, 1.74 mmol) in 15 mL of methanol at 0° C. was added sodium borohydride (33 mg, 0.87 mmol). The cooling bath was removed and the reaction was stirred for 10 min and then quenched by dilution with water. The reaction mixture was extracted with ethyl acetate and the organics were washed with brine, dried (MgSO$_4$) and concentrated to afford 0.41 g (85%) of about a 2:1 mixture of a hydroxy ester and a seven-membered ring lactone. This mixture was used without purification. To a solution of (2-fluoro-2'-methylsulfonyl-[1,1']-biphen-4-yl)amine hydrochloride (0.89 g, 2.94 mmol) in methylene chloride was added trimethylaluminum (2.95 mL of a 2.0 M solution in hexanes, 5.89 mmol) dropwise. This solution was stirred until gas evolution ceased (15–20 min) and then there was added the hydroxy ester/lactone mixture from above (0.41 g, 1.47 mmol) in methylene chloride. The resulting solution was allowed to stir at reflux for 4 h and then it was cooled and quenched by dropwise addition of sat'd aq ammonium chloride. The mixture was diluted with ethyl acetate, the layers were separated, the organic layer was washed with water and brine, dried (MgSO$_4$) and concentrated. The solid residue was purified by flash chromatography (elution with 1:1 hexanes/ethyl acetate) to afford 0.68 g (91%) of the title compound. LRMS (ES+): 534.1 (M+Na)$^+$.

1-[(2-(Bromomethyl)phenyl]-3-thiomethoxy-5-[(2-fluoro)-(2'-methylsulfonyl-[1,1']-biphen-4-yl) aminocarbonyl]pyrazole: To a solution of 1-[(2-(hydroxymethyl)phenyl]-3-thiomethoxy-5-[(2-fluoro)-(2'-methylsulfonyl-[1,1']-biphen-4-yl)aminocarbonyl]pyrazole (0.68 g, 1.3 mmol) in 20 mL of methylene chloride was added carbon tetrabromide (1.06 g, 3.2 mmol) and triphenylphosphine (0.84 g, 3.2 mmol). The resulting solution was stirred at ambient temperature for 4 h. The reaction was diluted with ethyl acetate, washed with water and brine, dried (MgSO$_4$) and concentrated. The residue was purified by flash chromatography (elution with 3:1 hexanes/ethyl acetate) to afford 0.60 g (81%) of the title compound.

1-[(2-(Azidomethyl)phenyl]-3-thiomethoxy-5-[(2-fluoro)-(2'-methylsulfonyl-[1,1']-biphen-4-yl) aminocarbonyl]pyrazole: To a solution of 1-[(2-(bromomethyl)phenyl]-3-thiomethoxy-5-[(2- fluoro)-(2'-methylsulfonyl-[1,1']-biphen-4-yl)aminocarbonyl]pyrazole (0.42 g, 0.73 nmol) in 5 mL of N,N-dimethylformamide was added sodium azide (0.38 g, 5.85 mmol). This mixture was stirred at ambient temperature for 1 h and then was diluted with ethyl acetate. The organics were washed with water and brine, dried (MgSO$_4$) and concentrated to afford 0.38 g (97%) of the title compound which was used directly without purification. LRMS (ES$^+$): 559.1 (M+Na)$^+$.

1-[2-(Aminomethyl)phenyl)-3-thiomethoxy-5-[(2-fluoro)-(2'-methylsulfonyl-[1,1']-biphen-4-yl) aminocarbonyl]pyrazole, trifluoroacetic acid salt: To a solution of 1-[(2-(azidomethyl)phenyl]-3-thiomethoxy-5-[(2-fluoro)-(2'-methylsulfonyl-[1,1']-biphen-4-yl) aminocarbonyl]pyrazole (0.38 g, 0.71 mmol) in 10 mL of methanol was added tin (II) chloride (0.80 g, 4.24 mmol). The reaction mixture was stirred at reflux for 1 h and then was cooled to room temperature and diluted with ethyl acetate. The organics were washed with 5% aq sodium hydroxide and brine, dried (MgSO$_4$) and concentrated. The residue was purified by preparative HPLC (C18 reverse phase column, elution with a H$_2$O/CH$_3$CN gradient with 0.5% TFA) and lyophilized to afford 230 mg (52%) of the title compound as a white powder. LRMS (ES+): 511.1 (M+H)$^+$.

Example 42

1-[2-(aminomethyl)phenyl]-3-methysulfonyl-5-[(2-fluoro)-(2'-methylsulfonyl-[1,1']-biphen-4-yl) aminocarbonyl]pyrazole.TFA 1-[(2-(Bromomethyl)phenyl]-3-methylsulfonyl-5-[(2-fluoro)- (2'-methylsulfonyl-[1,1']-biphen-4-yl) aminocarbonyl]pyrazole: To a solution of 1-[(2-(bromomethyl)phenyl]-3-thiomethoxy-5-[(2-fluoro)-(2'-methylsulfonyl-[1,1']-biphen-4-yl)aminocarbonyl]pyrazole (85 mg, 0.15 mmol) in 10 mL of methylene chloride was added m-chloroperoxybenzoic acid (130 mg of 57–86% pure material, ~0.5 mmol). The resulting solution was stirred at ambient temperature for 3 h. The reaction was diluted with ethyl acetate, washed with sat'd aq NaHCO$_3$ and brine, dried (MgSO$_4$) and concentrated to afford 80 mg (88%) of the title compound which was sufficiently pure to be used without purification.

1-[(2-(Azidomethyl)phenyl]-3-methylsulfonyl-5-[(2-fluoro)-(2'-methylsulfonyl-[1,1']-biphen-4-yl) aminocarbonyl]pyrazole: To a solution of 1-[(2-(bromomethyl)phenyl]-3-methylsulfonyl-5-[(2-fluoro)-(2'-methylsulfonyl-[1,1']-biphen-4-yl)aminocarbonyl]pyrazole (55 mg, 0.09 mmol) in 1 mL of dimethylsulfoxide was added sodium azide (30 mg, 0.45 mmol). This mixture was stirred at ambient temperature for 1 h and then was diluted with ethyl acetate. The organics were washed with water and brine, dried (MgSO$_4$) and concentrated to afford 50 mg (97%) of the title compound which was used directly without purification. LRMS (ES+): 591.1 (M+Na)$^+$.

1-[2-(Aminomethyl)phenyl]-3-methylsulfonyl-5-[(2-fluoro)-(2'-methylsulfonyl-[1,1']-biphen-4-yl) aminocarbonyl]pyrazole, trifluoroacetic acid salt: To a solution of 1-[(2-(azidomethyl)phenyl]-3-methylsulfonyl-5-[(2-fluoro)-(2'-methylsulfonyl-[1,1']-biphen-4-yl) aminocarbonyl]pyrazole (90 mg, 0.16 mmol) in 4 mL of methanol was added tin (II) chloride (0.30 g, 1.6 mmol). The reaction mixture was stirred at reflux for 1 h and then was cooled to room temperature and diluted with ethyl acetate. The organics were washed with 5% aq sodium hydroxide and brine, dried (MgSO$_4$) and concentrated. The residue was purified by preparative HPLC (C18 reverse phase column, elution with a H$_2$O/CH$_3$CN gradient with 0.5% TFA) and lyophilized to afford 18 mg (17%) of the title compound as a white powder. LRMS (ES+): 543.2 (M+H)$^+$.

Example 43

1-[2-(aminomethyl)phenyl]-5-[(2-fluoro)-(2'-methylsulfonyl-1,1']-biphen-4-yl)aminocarbonyl] triazole.TFA 2-Azidobenzyl alcohol: To a solution of 2-aminobenzyl alcohol (12.0 g, 97.4 mmol) in 50 mL of trifluoroacetic acid at 0° C. was added sodium nitrite (7.39 g, 107.2 mmol). This solution was stirred for 45 min and then there was added sodium azide (6.33 g, 97.4 inmol) dropwise as a solution in water. The resulting mixture was stirred at 0° C. for 45 min and then was carefully quenched by slow addition of potassium carbonate. The reaction mixture was diluted with ethyl acetate, washed with brine, dried (MgSO$_4$), filtered through a pad of silica gel and concentrated to afford 10.5 g (72%) of the title compound which was used without further purification. $^1$H NMR (CDCl$_3$) δ7.33 (m, 2H), 7.14 (m, 2H), 4.59 (s, 2H), 2.69 (broad s, 1H).

(2-Azidophenyl)methyl propiolate: To a solution of 2-azidobenzyl alcohol (15.66 g, 105.1 mol) in 200 mL of methylene chloride was added propiolic acid (7.1 mL, 115.6 immol), dicyclohexylcarbodiimide (20.0 g, 110.3 mnmol) and 4-dimethylaminopyridine (1.93 g, 15.8 mmol). The resulting mixture was allowed to stir at ambient temperature for 18 h. The mixture was filtered, concentrated and the residue was purified by flash chromatography (elution with 1:1 hexanes/ethyl acetate) to afford 10.7 g (51%) of the title compound. $^1$H NMR (CDCl$_3$) δ7.40 (m, 2H), 7.17 (m, 2H), 5.20 (s, 2H), 2.92 (s, 1H).

Triazololactone: A solution of (2-azidophenyl)methyl propiolate (10.7 g, 53.2 mmol) in 100 mL of toluene was stirred at 100° C. for 18 h. The reaction was cooled and concentrated and the residue was purified by flash chromatography (elution with 1:1 hexanes/ethyl acetate) to afford 1.4 g (13%) of the title compound. $^1$H NMR (CDCl$_3$) δ8.38 (s, 1H), 8.04 (d, 1H), 7.63 (m, 1H), 7.54 (m, 2H), 5.16 (s, 2H).

1-[(2-(Hydroxymethyl)phenyl]-5-[(2-fluoro)-(2'-methylsulfonyl-[1,1']-biphen-4-yl)aminocarbonyl]triazole: To a solution of (2-fluoro-2'-methylsulfonyl-[1,1']-biphen-4-yl)amine hydrochloride (2.10 g, 6.96 mmol) in methylene chloride was added trimethylaluminum (20.8 mL of a 2.0 M solution in hexanes, 41.8 mmol) dropwise. This solution was stirred until gas evolution ceased (about 30 min) and then there was added the triazololactone from above (1.40 g, 6.96 mmol) as a solution in methylene chloride. The resulting solution was allowed to stir at reflux for 18 h and then it was cooled and quenched by dropwise addition of sat'd aq ammonium chloride. The mixture was diluted with ethyl acetate, the layers were separated, the organic layer was washed with water and brine, dried (MgSO$_4$) and concentrated. The solid residue was purified by flash chromatography (elution with 3:1 ethyl acetate/hexanes) to afford 1.0 g (31%) of the title compound. LRMS (ES+): 467.2 (M+H)$^+$.

1-[(2-(Bromomethyl)phenyl]-5-[(2-fluoro)-(2'-methylsulfonyl-[1,1']-biphen-4-yl)aminocarbonyl]triazole:

To a solution of 1-[(2-(hydroxymethyl)phenyl]-5-[(2-fluoro)-(2'-methylsulfonyl-[1,1']-biphen-4-yl)aminocarbonyl]triazole (0.80 g, 1.71 mmol) in 20 mL of methylene chloride was added carbon tetrabromide (2.83 g, 8.55 mmol) and triphenylphosphine (2.24 g, 8.55 mmol). The resulting solution was stirred at ambient temperature for 18 h. The reaction was diluted with ethyl acetate, washed with water and brine, dried (MgSO$_4$) and concentrated. The residue was purified by flash chromatography (elution with 1:1 hexanes/ethyl acetate) to afford 0.80 g (89%) of the title compound. LRMS (ES+): 529.1/531.1 (M+H)$^+$.

1-[(2-(Azidomethyl)phenyl]-5-[(2-fluoro)-(2'-methylsulfonyl-[1,1']-biphen-4-yl)aminocarbonyl]triazole: To a solution of 1-[(2-(bromomethyl)phenyl]-5-[(2-fluoro)-(2'-methylsulfonyl-[1,1']-biphen-4-yl)aminocarbonyl]triazole (0.25 g, 0.47 mmol) in 10 mL of N,N-dimethylformamide was added sodium azide (0.37 g, 5.6 imol). This mixture was stirred at 65° C. for 18 h and then was cooled and diluted with ethyl acetate. The organics were washed with water and brine, dried (MgSO$_4$) and concentrated to afford 0.22 g (96%) of the title compound which was used directly without purification. LRMS (ES+): 514.2 (M+Na)$^+$.

1-[2-(Aminomethyl)phenyl]-5-[(2-fluoro)-(2'-methylsulfonyl-[1,1']-biphen-4-yl)aminocarbonyl]triazole, trifluoroacetic acid salt: To a solution of 1-[(2-(azidomethyl)phenyl]-5-[(2-fluoro)-(2'-methylsulfonyl-[1,1']-biphen-4-yl)aminocarbonyl]triazole (0.22 g, 0.45 mmol) in 10 mL of absolute ethanol was added 10% palladium on carbon catalyst (25 mg) and concentrated HCl (0.04 mL, 0.45 mmol). The reaction mixture was stirred at ambient temperature under 1 atm of hydrogen for 2 h and then was filtered through a pad of Celite and concentrated. The residue was purified by preparative HPLC (C18 reverse phase column, elution with a H$_2$O/CH$_3$CN gradient with 0.5% TFA) and lyophilized to afford 26 mg (10%) of the title compound as a white powder. LRMS (ES+): 466.2 (M+H)$^+$.

Example 44

1-[2-(Aminomethyl)phenyl]-5-[(2-fluoro)-(2'-methylsulfonyl)-[1,1']-biphen-4-yl)aminocarbonyl]pyrazole.TFA Methyl 1-[2-methylphenyl]pyrazole-5-carboxylate: A neat mixture of methyl pyruvate (11.37 mL, 125.9 mmol) and dimethylformamide dimethylacetal (16.72 mL, 125.9 mmol) was stirred at 80° C. for 24 h. The mixture was cooled and concentrated. A portion of the residue (4.00 g, 25.45 mmol) was dissolved in 50 mL of glacial acetic acid and then there was added o-tolylhydrazine hydrochloride (4.44 g, 27.99 mmol). This mixture was stirred at 100° C. for 18 h and then was cooled and concentrated. The residue was dissolved in ethyl acetate, washed with sat'd aq sodium carbonate and brine, dried (MgSO$_4$) and concentrated. The residue was purified by flash chromatography (elution with 2:1 hexanes/ethyl acetate) to afford 3.0 g (55%) of the title compound. $^1$H NMR (CDCl$_3$) δ7.70 (d, 1H), 7.4–7.2 (m, 4H), 7.00 (d, 1H), 3.71 (s, 3H), 2.00 (s, 3H).

Methyl 1-[2-(bromomethyl)phenyl]pyrazole-5-carboxylate: To a solution of methyl 1-[2-methylphenyl]pyrazole-5-carboxylate (1.00 g, 4.62 mmol) in 20 mL of carbon tetrachloride was added N-bromosuccinimide (0.823 g, 4.62 mmol) and AIBN (76 mg, 0.46 mmol). This mixture was stirred at 80° C. for 18 h. The volatiles were removed and the residue was taken up in ether, filtered through a pad of silica gel and concentrated to afford 1.3 g (95%) of the title compound which was used without further purification. LRMS (ES+): 295.0/297.0 (M+H)$^+$.

Methyl 1-[2-(azidomethyl)phenyl]pyrazole-5-carboxylate: To a solution of methyl 1-[2-(bromomethyl) phenyl]pyrazole-5-carboxylate (1.30 g, 4.40 mmol) in 10 mL of N,N-dimethylformamide was added sodium azide (2.86 g, 44.0 mmol). This mixture was stirred at ambient temperature for 48 h and then was diluted with ethyl acetate. The organics were washed with water and brine, dried (MgSO$_4$) and concentrated to afford 0.80 g (71%) of the title compound which was used directly without purification. LRMS (ES+): 280.1 (M+Na)$^+$.

1-[(2-(Azidomethyl)phenyl]-5-[(2-fluoro)-(2'-methylsulfonyl-[1,1']-biphen-4-yl)aminocarbonyl]pyrazole: To a solution of (2-fluoro-2'-methylsulfonyl-[1,1']-biphen-4-yl)amine hydrochloride (0.94 g, 3.11 mmol) in 20 mL of methylene chloride was added trimethylaluminum (4.67 mL of a 2.0 M solution in hexanes, 9.33 mmol) dropwise. This solution was stirred until gas evolution ceased (about 30 min) and then there was methyl 1-[2-(azidomethyl)phenyl]pyrazole-5-carboxylate (0.80 g, 3.11 mmol) as a solution in methylene chloride. The resulting solution was allowed to stir at reflux for 18 h and then it was cooled and quenched by dropwise addition of sat'd aq ammonium chloride. The mixture was diluted with ethyl acetate, the layers were separated, the organic layer was washed with water and brine, dried (MgSO$_4$), filtered through a pad of silica gel and concentrated to afford 1.0 g (67%) of the title compound. LRMS (ES+): 513.0 (M+Na)$^+$.

1-[2-(Aminomethyl)phenyl]-5-[(2-fluoro)-(2'-methylsulfonyl-[1,1']-biphen-4-yl)aminocarbonyl]pyrazole, trifluoroacetic acid salt: To a solution of 1-[(2-(azidomethyl)phenyl]-5-[(2-fluoro)-(2'-methylsulfonyl-[1,1']-biphen-4-yl)aminocarbonyl]pyrazole (0.50 g, 1.0 mmol) in 20 mL of absolute ethanol was added 10% palladium on carbon catalyst (50 mg) and concentrated HCl (0.085 mL, 1.0 mmol). The reaction mixture was stirred at ambient temperature under 1 atm of hydrogen for 2 h and then was filtered through a pad of Celite and concentrated. The residue was purified by preparative HPLC (C18 reverse phase column, elution with a H$_2$O/CH$_3$CN gradient with 0.5% TFA) and lyophilized to afford 60 mg (10%) of the title compound as a white powder. LRMS (ES+): 465.2 (M+H)$^+$.

Example 45

1-[2-(Aminomethyl)phenyl]-3-trifluoromethyl-5-[((2-fluoro)-(2'-pyrrolidinomethyl)-[1,1']-biphen-4-yl) aminocarbonyl]pyrazole.TFA Part A: 2-Fluoro-4-((2'-tert-butyldimethylsilyloxymethyl)phenyl)aniline: A solution of 2-formylphenylboronic acid (5 g, 33.3 mmol) and 4-bromo-2-fluoroaniline (4.2 g, 22.2 mmol) in THF (80 mL) and aqueous Na$_2$CO$_3$ solution (2M, 80 mL) was bubbled with nitrogen for 10 minutes. After Pd(PPh$_3$)$_4$ (1.54 g, 1.33 mmol) was added, the resulting mixture was refluxed under nitrogen for 4 hours. The THF layer was separated and filtered through a pad of silica gel. The silica gel was washed with THF. To the combined filtrates containing 2-fluoro-4-(2'-formylphenyl)aniline (65 mL) was portion by portion added NaBH$_4$ (2.2 g, 29.1 mmoL). The resulting mixture was stirred at room temperature for 1 hour, quenched with 1N HCl (10 mL), and washed with 1N HCl (100 mL×3). The combined HCl layers were neutralized with 50% NaOH to pH 12 and extracted with EtOAc (100 mL×3). The EtOAc layers were dried over Na$_2$SO$_4$, concentrated, and purified by column chromatography with a graduate solvent (hexane to EtOAc) to give 2-fluoro-4-(2'-hydroxymethylphenyl)aniline (3.83 g, 97.6%). $^1$H NMR (CDCl$_3$) δ7.53 (dd, J=6.6 Hz, J=2.2 Hz, 1H), 7.36–7.33 (m, 2H), 7.25 (dd, J=6.6 Hz, J=2.2 Hz, 1H), 7.06 (dd, J=12.1 Hz, J=1.8 Hz, 1H), 6.97 (dd, J=8.0 Hz, J=1.8 Hz, 1H), 6.82 (t, J=8.8 Hz, 1H), 4.63 (s, 2H), 3.79 (bs, 2H); $^{19}$F NMR (CDCl$_3$): δ−135.66 (dd, J=12.21 Hz, J=9.2 Hz); CIMS(CI) m/z 218 (M+H, 100%).

To a solution of 2-fluoro-4-(2'-hydroxymethyl-phenyl) aniline (5 g, 23 mmol) in THF (150 mL) was added imidazole (2.35 g, 34.5 mmol) and 2'-tert-butyldimethylsilylchloride (5.18 g, 34.5 mmol), and the resulting mixture was stirred at room temperature for 24 hours. The mixture was diluted with hexane (150 mL) and washed with water (150 mL). The organic layer was washed with brine, dried over MgSO$_4$, purified by column chromatography with hexane and methylenechloride (1 to 1) to give 2-fluoro-4-((2'-tert-butyldimethylsilyloxymethyl)phenyl) aniline (7.1 g, 92.8%) as a colorless oil. $^1$H NMR (CDCl$_3$) δ7.55 (dd, J=7.7 Hz, J=1.1 Hz, 1H), 7.35 (dd, J=7.4 Hz, J=1.9 Hz, 1H), 7.30 (dd, J=9.1 Hz, J=1.4 Hz, 1H), 7.20 (dd, J=7.3 Hz, J=1.5 Hz, 1H), 7.05 (dd, J=12.1 Hz, J=1.8 Hz, 1H), 6.93 (dd, J=8.0 Hz, J=1.4 Hz, 1H), 6.80 (dd, J=9.1 Hz, J=8.0 Hz, 1H), 4.60 (s 2H), 3.77 (bs, 2H), 0.91 (s, 9H), 0.04 (s, 6H); $^{19}$F NMR (CDCl$_3$): δ−136.04; CIMS: 332 (M+H, 100).

Part B: 1-(2-cyanophenyl)-5-furyl-3-trifluoromethylpyrazole: To a solution of 4,4,4-trifluoro-1-(2-furyl)-1,3-butanedione (2.06 g, 10 mmol) in ethanol (mL) was added hydrazine monohydrate (0.46 g, 10 mmol). The resulting mixture was refluxed for 16 hours and dried under vacuum to give 5-furyl-3-trifluoromethyl-3-hydroxypyrazoline in almost quantitative yield. $^1$H NMR (CDCl$_3$) δ7.48 (d, J=1.9 Hz, 1H), 6.63 (d, J=3.7 Hz, 1H), 6.47 (dd, J=3.7 Hz, J=1.9 Hz, 1H), 6.16 (s, 1H), 3.48 (d, J=17.9 Hz, 1H), 3.18 (d, J=17.9 Hz, 1H); $^{19}$F NMR (CDCl$_3$): δ−81.47; ESMS(+): 221 (M+H, 100).

To a solution of 2-fluorobenzonitrile (0.605 g, 5 mmol) and 5-furyl-3-trifluoromethyl-3-hydroxypyrazoline (1.1 g, 5 mmol) in DMF (10 mL) was added Cs$_2$CO$_3$ (1.63 g, 5 mmol), and the resulting mixture was stirred at 110° C. for 16 hours. The mixture was diluted with EtOAc, washed with brine (×5), dried over MgSO$_4$, and purified by column chromatography with a gradient solvent (hexane to ethyl acetate) to give 1-(2-cyanophenyl)-5-furyl-3-trifluoromethylpyrazole and 1-(2-cyanophenyl)-3-furyl-5-trifluoromethylpyrazole (1.27 g, 83.8%) in a ratio of 95 to 5. $^1$H NMR (CDCl$_3$) δ7.82 (dd, J=7.7 Hz, J=1.5 Hz, 1H), 7.77 (dd, J=7.7 Hz, J=1.5 Hz, 1H), 7.66 (td, J=7.7 Hz, J=1.1 Hz, 1H), 7.61 (d, J=7.7 Hz, 1H), 7.39 (d, J=1.4 Hz, 1H), 6.96 (s, 1H), 6.37 (dd, J=3.3 Hz, J=1.4 Hz, 1H), 6.04 (d, J=3.3 Hz, 1H); $^{19}$F NMR (CDCl$_3$): δ−62.98; ESMS(+): 304 (M+H, 100).

Part C: 1-(2-(N-Boc-aminomethyl)phenyl)-3-trifluoromethylpyrazol-5-yl-carboxylic acid: To a solution of 1-(2-cyanophenyl)-5-furyl-3-trifluoromethylpyrazole (1.5 g, 4.67 mmol) in DMF (20 mL) was portion by portion added NaBH$_4$ (0.71 g, 18.7 mmol) and then CoCl$_2$ (0.61 g, 4,67 mmol) at 0° C. After the resulting mixture was stirred at room temperature for 18 hours, a black suspension was cooled to 0° C. and carefully acidified with 6N HCl (20 mL). The resulting mixture was stirred at room temperature for 3 hours, and neutralized with 1N NaOH to pH 14. The mixture was diluted with EtOAc (100 mL), and filtered through a pad of sand (top layer) and Celite (bottom layer). The filtrate was separated and the organic layer was washed with brine (5×10 mL), dried over Na$_2$SO$_4$, and concentrated to give 1-(2-(aminomethyl)phenyl)-5-furyl-3-trifluoromethylpyrazole (1.4 g, 91.5%). $^1$H NMR (CD$_3$OD) δ7.69–7.61 (m, 2H), 7.52 (d, J=1.5 Hz, 1H), 7 47 (td, J=7.7 Hz, J=1.1 Hz, 1H), 7.34 (d, J=8.0 Hz, 1H), 7.07 (s, 1H), 6.34 (dd, J=1.8 Hz, J=3.6 Hz, 1H), 5.75 (d, J=3.3 Hz, 1H), 3.40 (s, 2H); ESMS(+): 308 (M+H, 100);

To a solution of 1-(2-(aminomethyl)phenyl)-5-furyl-3-trifluoromethylpyrazole (1.4 g, 4.27 mmol) in THF (10 mL) was added a solution of (Boc)$_2$O (1.4 g, 6.4 mmol) in THF (10 mL), and the resulting mixture was stirred at room temperature for 1 hour. The mixture was diluted with EtOAc (100 mL), washed with water and brine, dried over Na$_2$SO$_4$, and concentrated to provide crude 1-(2-(N-Boc-aminomethyl)phenyl)-5-furyl-3-trifluoromethylpyrazole. $^1$H NMR (CDCl$_3$) δ7.60–7.55 (m, 2H), 7.42 (d, J=6.2 Hz, 1H), 7 40 (s, 1H), 7.32 (d, J=7.7 Hz, 1H), 6.95 (s, 1H), 6.28 (dd, J=1.8 Hz, J=3.3 Hz, 1H), 5.65 (d, J=3.3 Hz, 1H), 4.01 (d, J=6.8 Hz, 2H), 3.40 (s, 2H), 1.41 (s, 9H); $^{19}$F NMR (CDCl$_3$): δ−62.76.

To a solution of crude product in acetone (20 mL) and water (20 mL) was portion by portion added KMnO$_4$ (3.95 g, 25 mmol), and the resulting mixture was stirred at 60° C. for 20 minutes and then filtered through Celite. The filtrate was concentrated, acidified with 1N HCl to pH 4, and extracted with EtOAc (3×50 mL). The organic layer was washed with brine, dried over Na$_2$SO$_4$, concentrated, and purified by column chromatography with 20% MeOH in dichloromethane to provide 1-(2-(N-Boc-aminomethyl) phenyl)-3-trifluoromethylpyrazol-5-yl-carboxylic acid (1.05 g, 56% for the two steps). ESMS(−): 384.2 (M−H, 100).

Part D: 1-(2-(N-Boc-aminomethyl)phenyl)-3-trifluoromethyl-5-[((2-fluoro)-(2'-hydroxymethylsilyloxymethyl)-[1,1']-biphen-4-yl) aminocarbonyl]pyrazole: To a solution of 1-(2-(N-Boc-aminomethyl)phenyl)-3-trifluoromethylpyrazol-5-yl-carboxylic acid (0.768 g, 2 mmol) in CH$_2$Cl$_2$ (50 mL) was added DMF (1 drop) and oxalyl chloride (0.381 g, 3 mmol), and the resulting mixture was stirred at room temperature for 1.5 hours. The mixture was concentrated and the residue was dissolved in THF (10 mL). To the solution was added a solution of 2-fluoro-4-(2'-(tert-butyldimethylsilyloxymethyl)phenyl)aniline (0.6 g, 1.8 mmoL) in THF (10 mL) and Et$_3$N (1.5 mL), and the resulting mixture was stirred at room temperature for 24 hours. The mixture was diluted with EtOAc (100 mL), washed with water and brine, dried over MgSO$_4$, and purified on thin layer chromatography with CH$_2$Cl$_2$/hexane (3:2) to give 1-(2-(N-Boc-aminomethyl)phenyl)-3-trifluoromethyl-5-[((2-fluoro)-(2'-tert-butyldimethylsilyloxymethyl)-[1,1']-biphen-4-yl) aminocarbonyl]pyrazole (0.49 g, 80%).

To a solution of 1-(2'-N-Boc-aminomethylphenyl)-3-trifluoromethyl-5-[((2-fluoro)-(2'-tert-butyldimethylsilyloxymethyl]-[1,1']-biphen-4-yl) aminocarbonyl]pyrazole (0.57 g, 0.93 mmol) in THF (10 mL) was added Bu$_4$NF (1M in THF, 3 mL), and the resulting solution was stirred at room temperature for 2 hours. The mixture was diluted with EtOAc (150 mL), washed with water (20 mL), dried over Na$_2$SO$_4$, and purified by column chromatography with a gradient solvent (hexane to EtOAc) to give 1-(2-(N-Boc-aminomethyl)phenyl)-3-trifluoromethyl-5-[((2-fluoro)-(2'-hydroxymethyl)-[1,1']-biphen-4-yl)aminocarbonyl]pyrazole (484 mg, ~100%). $^1$H NMR (CD$_3$OD) δ7.69 (t, J=8.0 Hz, 1H), 7.55–7.27 (m, 9H), 7.21 (dd, J=7.4 Hz, J=1.8 Hz, 1H), 7.13 (dd, J=8.4 Hz, J=1.1 Hz, 1H), 4.46 (s, 2H), 4.05 (s, 2H), 1.34 (s, 9H); $^{19}$F NMR (CD$_3$OD): δ−64.08, −125.53; ESMS(+): 606.3 (M+Na, 100).

Part E: 1-(2-(aminomethyl)phenyl)-3-trifluoromethyl-5-[((2-fluoro)-(2'-pyrrolidinomethyl)-[1,1']-biphen-4-yl) aminocarbonyl]pyrazole, TFA salt: To a solution of 1-(2-(N-Boc-aminomethyl)phenyl)-3-trifluoromethyl-5-[((2-fluoro)-(2'-hydroxymethyl)-[1,1']-biphen-4-yl)aminocarbonyl] pyrazole (150 mg, 0.26 mmol) in THF (5 mL) was added Cs$_2$CO$_3$ (167 mg, 0.51 mmol) and MsCl (4 mg, 0.39 mmol). After the resulting mixture was stirred at room temperature for 18 hours and concentrated, the residue was dissolved in THF (10 mL) and treated with pyrrolidine (0.5 mL) at room temperature 8 hours. ESMS(+): 638.4 (M+H, 100). The mixture was treated with TFA/CH$_2$Cl$_2$ (1 to 1, 10 mL) at room temperature for 5 hours, and concentrated. The residue was purified on HPLC with a gradient solvent (H$_2$O—CH$_3$CN-0.05% TFA) on C18 give the title compound (50 mg, 36% for the two steps) $^1$H NMR (CD$_3$OD) δ7.80 (T, J=8.1 HZ, 1H), 7.71–7.30 (m. 9H), 7.27 (dd, J=11.3 Hz, J=1.8 Hz, 1H), 7.15 (d, J=8.4 Hz, 1H), 4.40 (s, 2H), 3.99 (s, 2H), 3.42–3.34 (m, 2H), 2.93–2.87 (m, 2H), 2.00–1.94 (m, 4H); $^{19}$F NMR (CD$_3$OD): δ−64.22, −77.57 (TFA), −123.82; HRMS: 538.2243 for C$_{29}$H$_{28}$O$_1$F$_4$N$_5$.

Example 46

1-[2-(Aminomethyl)phenyl]-3-trifluoromethyl-5-[((2-fluoro)-(2'-hydroxymethyl)-[1,1']-biphen-4-yl)aminocarbonyl]pyrazole.TFA A solution of 1-(2-(N-Boc-aminomethyl)phenyl)-3-trifluoromethyl-5-[((2-fluoro)-(2'-hydroxymethylsilyloxymethyl)-[1,1']-biphen-4-yl)aminocarbonyl]pyrazole (10 mg) was treated with TFA/CH$_2$Cl$_2$ (1 to 1, 1 mL) at room temperature for 3 hours and concentrated. The residue was purified by HPLC with a gradient solvent (H$_2$O—CH$_3$CN-0.05% TFA) on C18 to give the title compound (2 mg). $^1$H NMR (CD$_3$OD): δ7.66–7.45 (m, 6H), 7.38–7.21 (m, 4H), 7.15 (d, J=9.5 Hz, 1H), 7,10 (d, J=6.6 Hz, 1H), 4.39 (s, 2H), 3.91 (s, 2H); $^{19}$F NMR (CD$_3$OD): δ−64.23, −77.38, −125.40; ESMS(−): 483.2 (M−H, 100).

TABLE 1

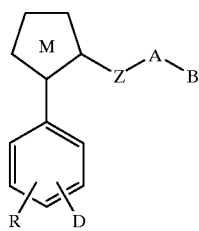

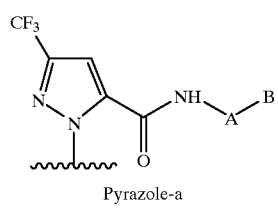

Pyrazole-a

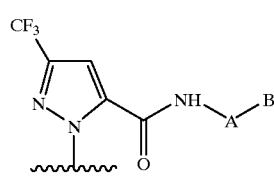

Pyrazole-b

TABLE 1-continued

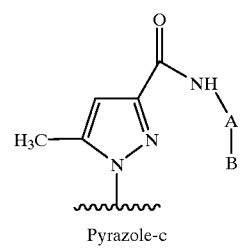

Pyrazole-c

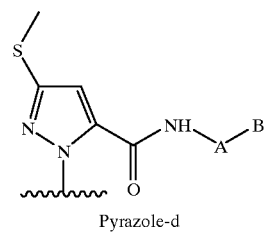

Pyrazole-d

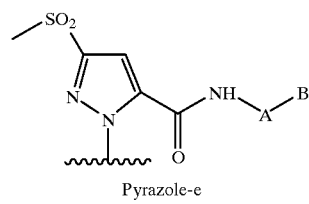

Pyrazole-e

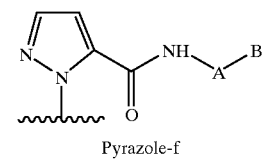

Pyrazole-f

TABLE 1-continued

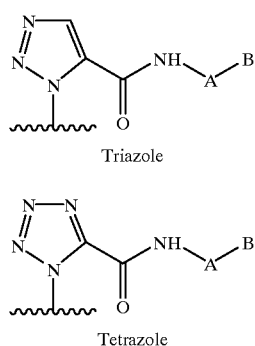

Triazole

Tetrazole

Unless otherwise indicated, D is at the 2-position and is CH$_2$NH$_2$.

| Ex | M | A-B | MS |
|---|---|---|---|
| 1 | pyrazole-b (R = 4-OCH$_3$) | 2'-H$_2$NSO$_2$-biphenyl | 492.2 |
| 2 | pyrazole-c (R = 4-OCH$_3$) | 2'-H$_2$NSO$_2$-biphenyl | 492.2 |
| 3 | pyrazole-b (D = CH$_2$N (Me)$_2$) (R = 4-OCH$_3$) | 2'-(CH$_3$)HNSO$_2$-biphenyl | 512 |
| 4 | pyrazole-a (R = 4-OCH$_3$) | 3-F-2'-H$_2$NSO$_2$-biphenyl | 528.1 |
| 5 | pyrazole-a (R = 4-OCH$_3$) | 3-F-2'-CH$_3$SO$_2$-biphenyl | 378.2 |
| 6 | pyrazole-a (R = 4-OCH$_3$) | 2'-CH$_3$SO$_2$-biphenyl | 545.1 |
| 7 | pyrazole-a (R = 4-OCH$_3$) | 2'-H$_2$NSO$_2$-biphenyl | 546.2 |
| 8 | pyrazole-a (R = 4-OCH$_3$) | 4-(N-pyrrolidino-carbonyl)phenyl | 488.2 |
| 9 | pyrazole-a (R = 4-OCH$_3$) | phenylmethylsulfonyl-piperidin-4-yl | 552.2 |
| 10 | pyrazole-a (R = 4-OCH$_3$) | 5-(2-H$_2$NSO$_2$-phenyl)pyrid-2-yl | 547.1 |
| 11 | pyrazole-a (R = 4-OCH$_3$) | 5-(2-pyridyl)pyrid-2-yl | 469.2 |
| 12 | pyrazole-a (R = 4-OCH$_3$) | benzylpiperidin-4-yl | 488.2 |
| 13 | pyrazole-a (R = 4-OCH$_3$) | phenylsulfonylpiperidin-4-yl | 538.2 |
| 14 | pyrazole-a (R = 4-Cl) | 3-F-2'-CH$_3$SO$_2$-biphenyl | 567.1 |
| 15 | pyrazole-a (R = 4-Cl) | 3-F-2'-H$_2$NSO$_2$-biphenyl | 568.1 |
| 16 | pyrazole-a (R = 5-Cl) | 3-F-2'-CH$_3$SO$_2$-biphenyl | 567.1 |
| 17 | pyrazole-a (R = 5-Cl) | 3-F-2'-H$_2$NSO$_2$-biphenyl | 568.1 |
| 18 | pyrazole-a (R = 4-F) | 3-F-2'-CH$_3$SO$_2$-biphenyl | 551.1 |
| 19 | pyrazole-a (R = 4-F) | 3-F-2'-H$_2$NSO$_2$-biphenyl | 552.1 |
| 20 | pyrazole-a (R= 5-F) | 3-F-2'-CH$_3$SO$_2$-biphenyl | 551.1 |
| 21 | pyrazole-a (R = 5-F) | 3-F-2'-H$_2$NSO$_2$-biphenyl | 552.1 |
| 22 | pyrazole-a (R = 4,5-F) | 3-F-2'-CH$_3$SO$_2$-biphenyl | 569.1 |
| 23 | pyrazole-a (R = 4,5-F) | 3-F-2'-H$_2$NSO$_2$-biphenyl | 570.1 |
| 24 | pyrazole-a (R = 3-F) | 3-F-2'-CH$_3$SO$_2$-biphenyl | 551.1 |
| 25 | pyrazole-a (R = 3-F) | 3-F-2'-H$_2$NSO$_2$-biphenyl | 552.1 |
| 26 | pyrazole-a (R = 4-F) | 2'-CH$_3$SO$_2$-biphenyl | 533.1 |
| 27 | pyrazole-a (R = 4-F) | 2'-H$_2$NSO$_2$-biphenyl | 534.1 |
| 28 | pyrazole-a (R = 4-F) | 4-(N-pyrrolidino-CH$_3$SO$_2$-iminolyl)phenyl | 553.2 |
| 29 | pyrazole-a (D = N-glycyl-NH$_2$CH$_2$) (R = 4-OCH$_3$) | 3-F-2'-CH$_3$SO$_2$-biphenyl | 620.2 |
| 30 | pyrazole-a (D = C$_6$H$_5$CH$_2$C(O)—NH$_2$CH$_2$) (R = 4-OCH$_3$) | 3-F-2'-CH$_3$SO$_2$-biphenyl | 681.2 |
| 31 | pyrazole-a | 2'-CH$_3$SO$_2$-biphenyl | 515.1 |
| 32 | pyrazole-a | 2'-H$_2$NSO$_2$-biphenyl | 516.1 |
| 33 | pyrazole-a | 3-F-2'-H$_2$NSO$_2$-biphenyl | 534.1 |
| 34 | pyrazole-a | 3-F-2'-CH$_3$SO$_2$-biphenyl | 533.1 |
| 35 | pyrazole-a (D = glycyl-NH$_2$CH$_2$) | 3-F-2'-CH$_3$SO$_2$-biphenyl | 590.1 |
| 36 | pyrazole-a (D = N-CH$_3$-glycyl-NH$_2$CH$_2$) | 3-F-2'-CH$_3$SO$_2$-biphenyl | 604.2 |
| 37 | pyrazole-a (D = CONH$_2$) | 3-F-2'-CH$_3$SO$_2$-biphenyl E | |
| 38 | pyrazole-a (D = CN) | 3-F-2'-CH$_3$SO$_2$-biphenyl | |
| 39 | tetrazole | 3-F-2'-CH$_3$SO$_2$-biphenyl | 467 |
| 40 | tetrazole | 3-F-2'-H$_2$NSO$_2$-biphenyl | 468 |
| 41 | pyrazole-d | 3-F-2'-CH$_3$SO$_2$-biphenyl | 511.1 |
| 42 | pyrazole-e | 3-F-2'-CH$_3$SO$_2$-biphenyl | 543.2 |
| 43 | triazole | 3-F-2'-CH$_3$SO$_2$-biphenyl | 466.2 |
| 44 | pyrazole-f | 3-F-2'-CH$_3$SO$_2$-biphenyl | 465.2 |

The following tables contain representative examples of the present invention. Each entry in each table is intended to be paired with each formulae at the start of the table. For example, in Table 2, example 1 is intended to be paired with each of formulae a-bbbb and in Table 3, example 1 is intended to be paired with each of formulae a-bbbb.

The following groups are intended for group A in the following tables.

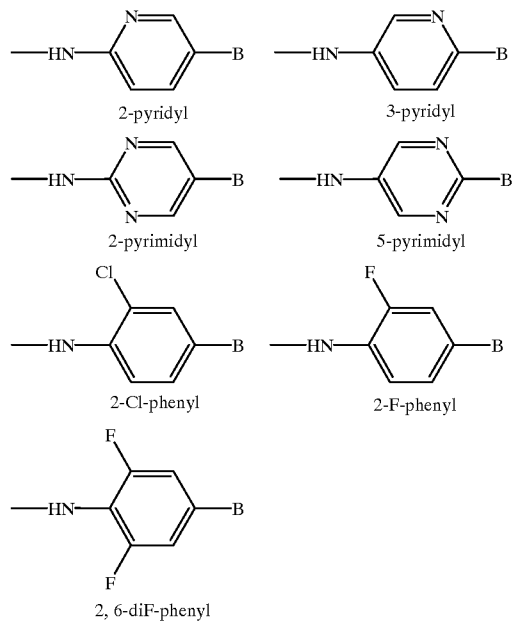

TABLE 2
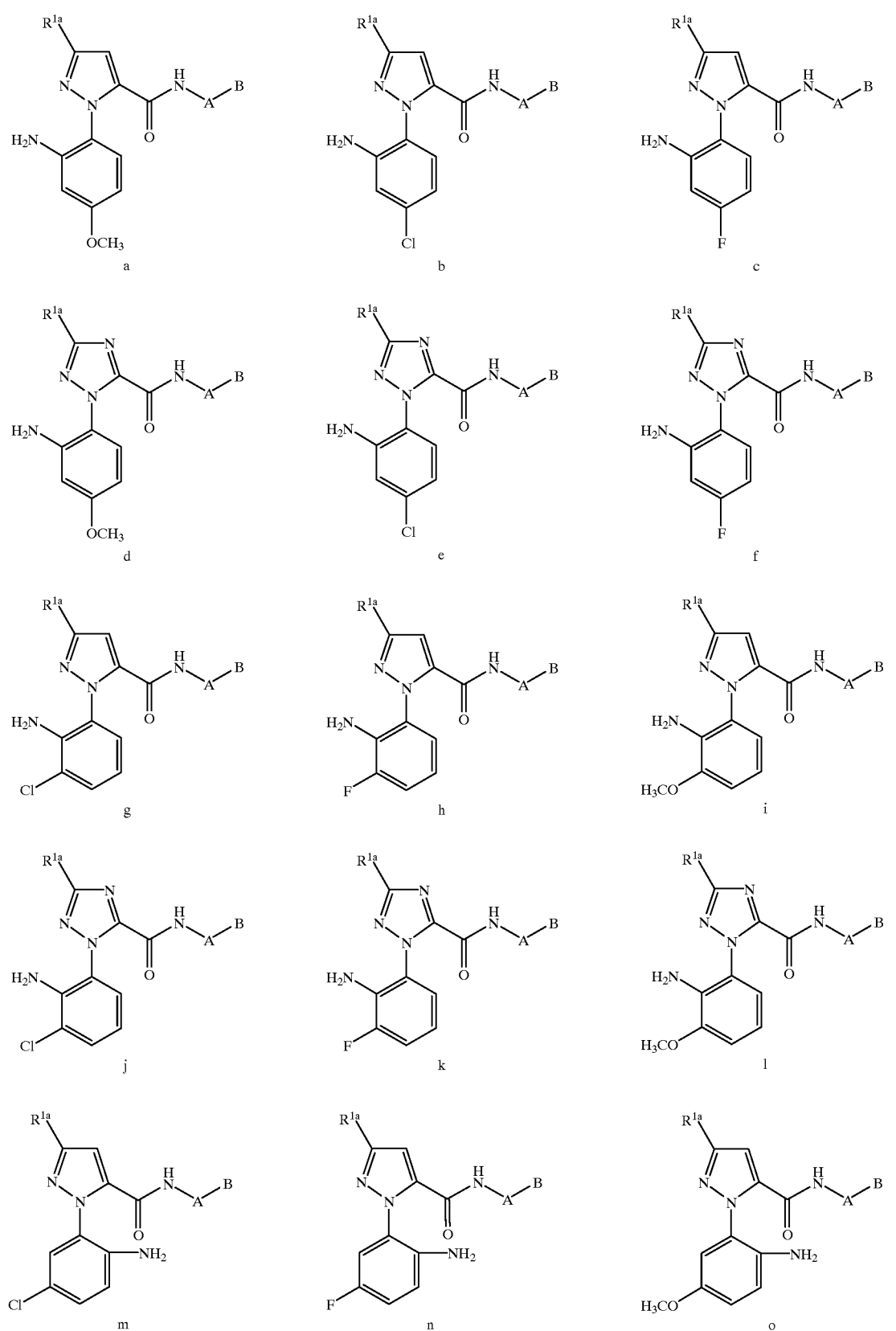

TABLE 2-continued
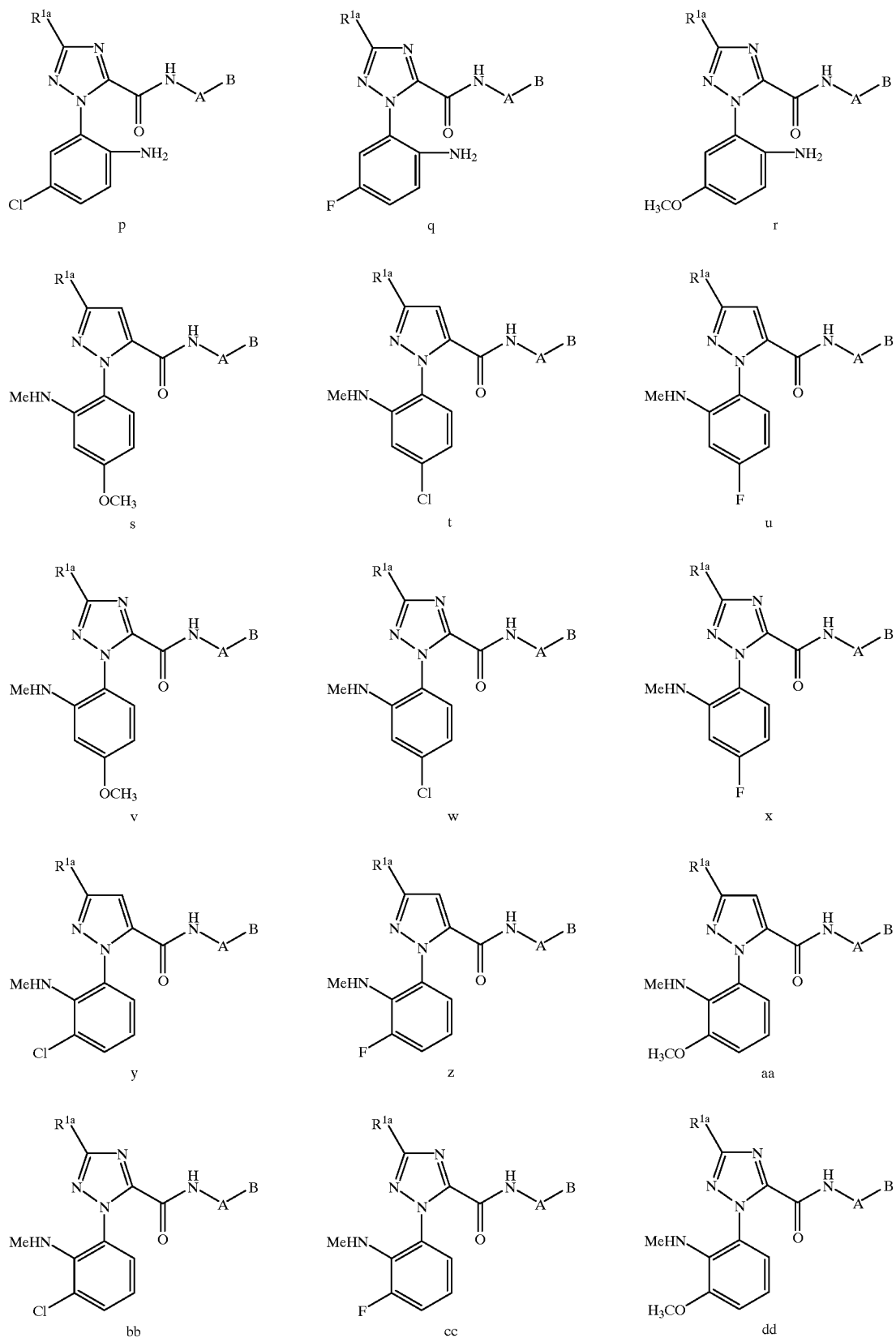

TABLE 2-continued
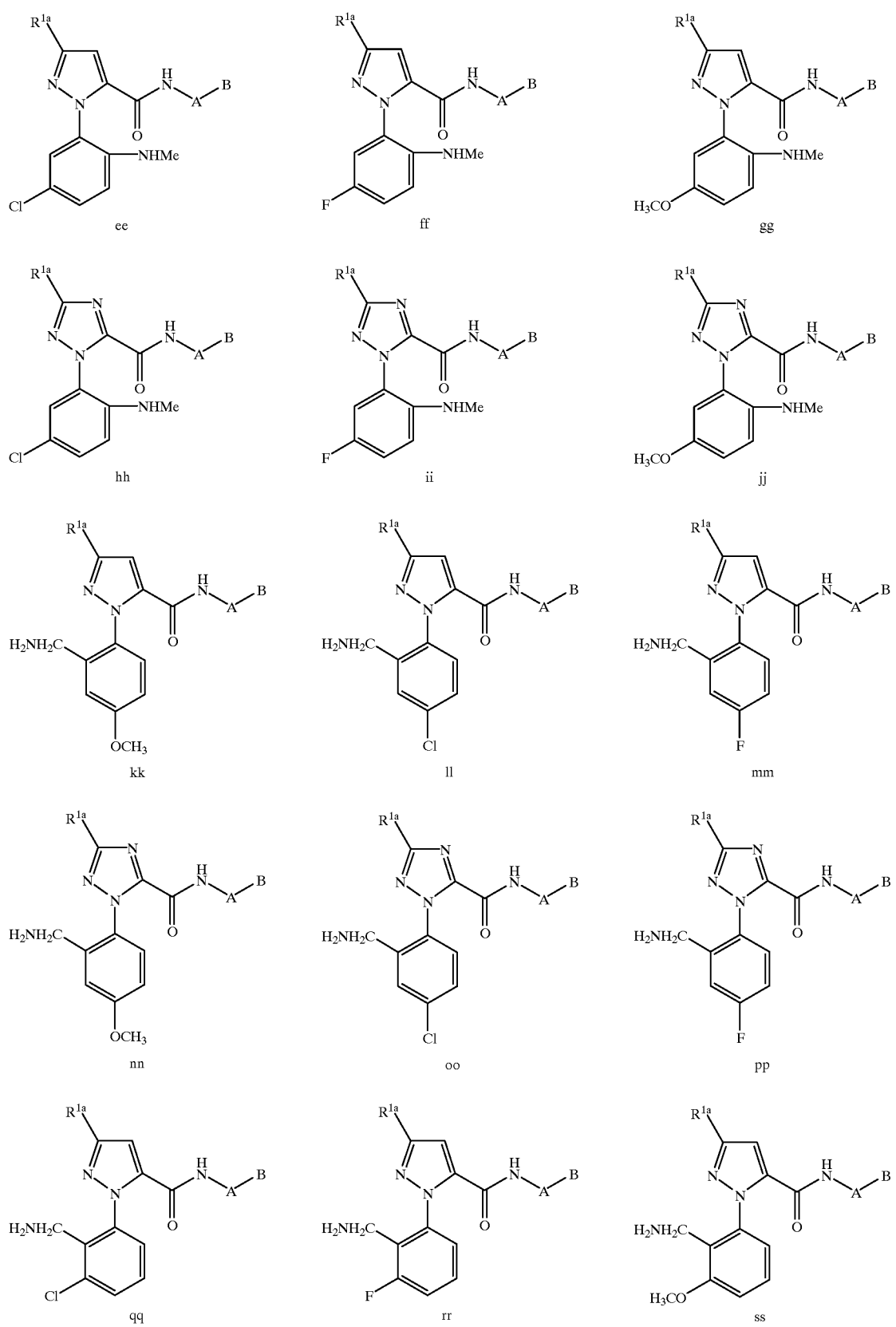

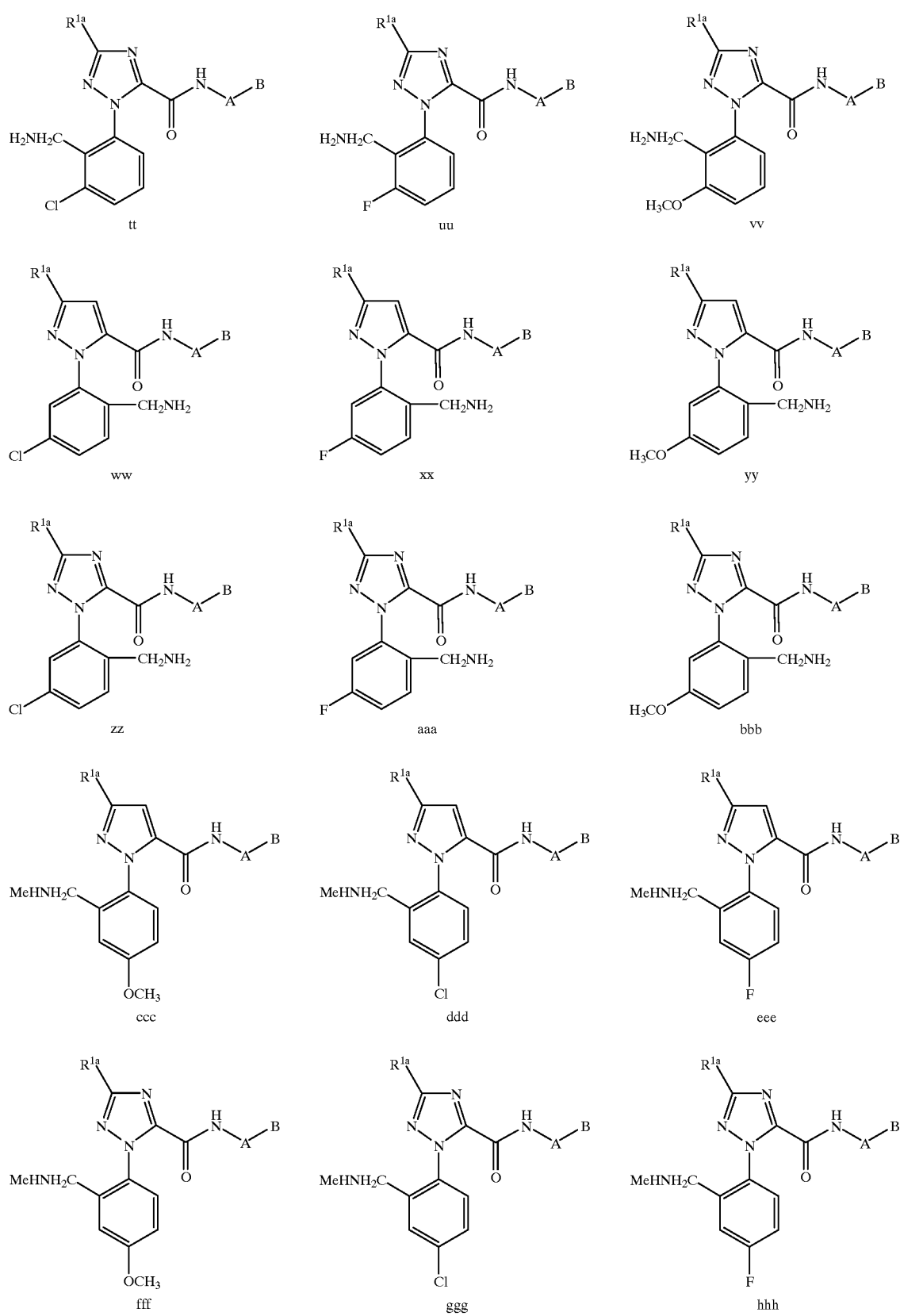

TABLE 2-continued
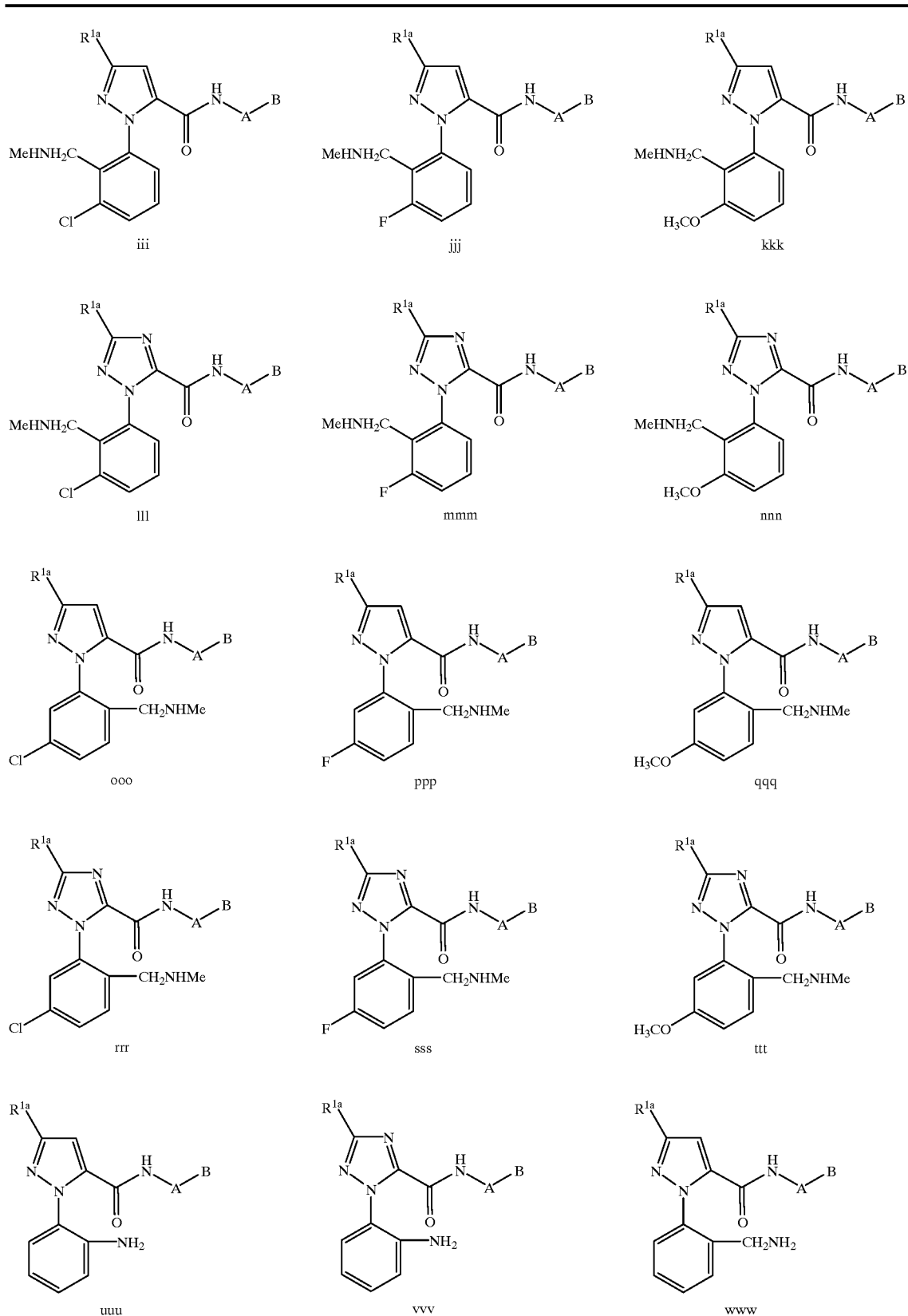

TABLE 2-continued

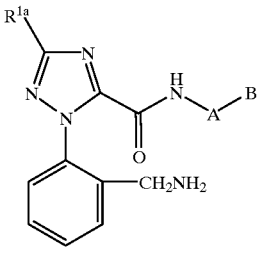
xxx

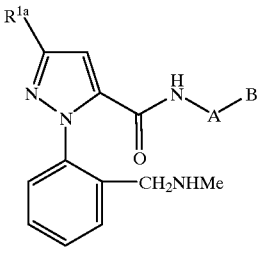
yyy

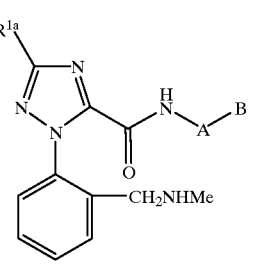
zzz

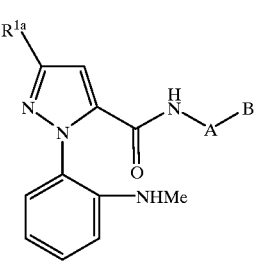
aaaa

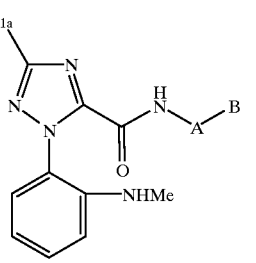
bbbb

| Ex. # | R$^{1a}$ | A | B |
| --- | --- | --- | --- |
| 1 | CH$_3$ | phenyl | 2-(aminosulfonyl)phenyl |
| 2 | CH$_3$ | phenyl | 2-(methylaminosulfonyl)phenyl |
| 3 | CH$_3$ | phenyl | 1-pyrrolidinocarbonyl |
| 4 | CH$_3$ | phenyl | 2-(methylsulfonyl)phenyl |
| 5 | CH$_3$ | phenyl | 4-morpholino |
| 6 | CH$_3$ | phenyl | 2-(1'-CF$_3$-tetrazol-2-yl)phenyl |
| 7 | CH$_3$ | phenyl | 4-morpholinocarbonyl |
| 8 | CH$_3$ | phenyl | 2-methyl-1-imidazolyl |
| 9 | CH$_3$ | phenyl | 5-methyl-1-imidazolyl |
| 10 | CH$_3$ | phenyl | 2-methylsulfonyl-1-imidazolyl |
| 11 | CH$_3$ | 2-pyridyl | 2-(aminosulfonyl)phenyl |
| 12 | CH$_3$ | 2-pyridyl | 2-(methylaminosulfonyl)phenyl |
| 13 | CH$_3$ | 2-pyridyl | 1-pyrrolidinocarbonyl |
| 14 | CH$_3$ | 2-pyridyl | 2-(methylsulfonyl)phenyl |
| 15 | CH$_3$ | 2-pyridyl | 4-morpholino |
| 16 | CH$_3$ | 2-pyridyl | 2-(1'-CF$_3$-tetrazol-2-yl)phenyl |
| 17 | CH$_3$ | 2-pyridyl | 4-morpholinocarbonyl |
| 18 | CH$_3$ | 2-pyridyl | 2-methyl-1-imidazolyl |
| 19 | CH$_3$ | 2-pyridyl | 5-methyl-1-imidazolyl |
| 20 | CH$_3$ | 2-pyridyl | 2-methylsulfonyl-1-imidazolyl |
| 21 | CH$_3$ | 3-pyridyl | 2-(aminosulfonyl)phenyl |
| 22 | CH$_3$ | 3-pyridyl | 2-(methylaminosulfonyl)phenyl |
| 23 | CH$_3$ | 3-pyridyl | 1-pyrrolidinocarbonyl |
| 24 | CH$_3$ | 3-pyridyl | 2-(methylsulfonyl)phenyl |
| 25 | CH$_3$ | 3-pyridyl | 4-morpholino |
| 26 | CH$_3$ | 3-pyridyl | 2-(1'-CF$_3$-tetrazol-2-yl)phenyl |
| 27 | CH$_3$ | 3-pyridyl | 4-morpholinocarbonyl |
| 28 | CH$_3$ | 3-pyridyl | 2-methyl-1-imidazolyl |
| 29 | CH$_3$ | 3-pyridyl | 5-methyl-1-imidazolyl |
| 30 | CH$_3$ | 3-pyridyl | 2-methylsulfonyl-1-imidazolyl |
| 31 | CH$_3$ | 2-pyrimidyl | 2-(aminosulfonyl)phenyl |
| 32 | CH$_3$ | 2-pyrimidyl | 2-(methylaminosulfonyl)phenyl |
| 33 | CH$_3$ | 2-pyrimidyl | 1-pyrrolidinocarbonyl |
| 34 | CH$_3$ | 2-pyrimidyl | 2-(methylsulfonyl)phenyl |
| 35 | CH$_3$ | 2-pyrimidyl | 4-morpholino |
| 36 | CH$_3$ | 2-pyrimidyl | 2-(1'-CF$_3$-tetrazol-2-yl)phenyl |
| 37 | CH$_3$ | 2-pyrimidyl | 4-morpholinocarbonyl |
| 38 | CH$_3$ | 2-pyrimidyl | 2-methyl-1-imidazolyl |
| 39 | CH$_3$ | 2-pyrimidyl | 5-methyl-1-imidazolyl |
| 40 | CH$_3$ | 2-pyrimidyl | 2-methylsulfonyl-1-imidazolyl |
| 41 | CH$_3$ | 5-pyrimidyl | 2-(aminosulfonyl)phenyl |
| 42 | CH$_3$ | 5-pyrimidyl | 2-(methylaminosulfonyl)phenyl |
| 43 | CH$_3$ | 5-pyrimidyl | 1-pyrrolidinocarbonyl |
| 44 | CH$_3$ | 5-pyrimidyl | 2-(methylsulfonyl)phenyl |
| 45 | CH$_3$ | 5-pyrimidyl | 4-morpholino |
| 46 | CH$_3$ | 5-pyrimidyl | 2-(1'-CF$_3$-tetrazol-2-yl)phenyl |
| 47 | CH$_3$ | 5-pyrimidyl | 4-morpholinocarbonyl |
| 48 | CH$_3$ | 5-pyrimidyl | 2-methyl-1-imidazolyl |
| 49 | CH$_3$ | 5-pyrimidyl | 5-methyl-1-imidazolyl |

TABLE 2-continued

| | | | |
|---|---|---|---|
| 50 | CH$_3$ | 5-pyrimidyl | 2-methylsulfonyl-1-imidazolyl |
| 51 | CH$_3$ | 2-Cl-phenyl | 2-(aminosulfonyl)phenyl |
| 52 | CH$_3$ | 2-Cl-phenyl | 2-(methylaminosulfonyl)phenyl |
| 53 | CH$_3$ | 2-Cl-phenyl | 1-pyrrolidinocarbonyl |
| 54 | CH$_3$ | 2-Cl-phenyl | 2-(methylsulfonyl)phenyl |
| 55 | CH$_3$ | 2-Cl-phenyl | 4-morpholino |
| 56 | CH$_3$ | 2-Cl-phenyl | 2-(1'-CF$_3$-tetrazol-2-yl)phenyl |
| 57 | CH$_3$ | 2-Cl-phenyl | 4-morpholinocarbonyl |
| 58 | CH$_3$ | 2-Cl-phenyl | 2-methyl-1-imidazolyl |
| 59 | CH$_3$ | 2-Cl-phenyl | 5-methyl-1-imidazolyl |
| 60 | CH$_3$ | 2-Cl-phenyl | 2-methylsulfonyl-1-imidazolyl |
| 61 | CH$_3$ | 2-F-phenyl | 2-(aminosulfonyl)phenyl |
| 62 | CH$_3$ | 2-F-phenyl | 2-(methylaminosulfonyl)phenyl |
| 63 | CH$_3$ | 2-F-phenyl | 1-pyrrolidinocarbonyl |
| 64 | CH$_3$ | 2-F-phenyl | 2-(methylsulfonyl)phenyl |
| 65 | CH$_3$ | 2-F-phenyl | 4-morpholino |
| 66 | CH$_3$ | 2-F-phenyl | 2-(1'-CF$_3$-tetrazol-2-yl)phenyl |
| 67 | CH$_3$ | 2-F-phenyl | 4-morpholinocarbonyl |
| 68 | CH$_3$ | 2-F-phenyl | 2-methyl-1-imidazolyl |
| 69 | CH$_3$ | 2-F-phenyl | 5-methyl-1-imidazolyl |
| 70 | CH$_3$ | 2-F-phenyl | 2-methylsulfonyl-1-imidazolyl |
| 71 | CH$_3$ | 2,6-diF-phenyl | 2-(aminosulfonyl)phenyl |
| 72 | CH$_3$ | 2,6-diF-phenyl | 2-(methylaminosulfonyl)phenyl |
| 73 | CH$_3$ | 2,6-diF-phenyl | 1-pyrrolidinocarbonyl |
| 74 | CH$_3$ | 2,6-diF-phenyl | 2-(methylsulfonyl)phenyl |
| 75 | CH$_3$ | 2,6-diF-phenyl | 4-morpholino |
| 76 | CH$_3$ | 2,6-diF-phenyl | 2-(1'-CF$_3$-tetrazol-2-yl)phenyl |
| 77 | CH$_3$ | 2,6-diF-phenyl | 4-morpholinocarbonyl |
| 78 | CH$_3$ | 2,6-diF-phenyl | 2-methyl-1-imidazolyl |
| 79 | CH$_3$ | 2,6-diF-phenyl | 5-methyl-1-imidazolyl |
| 80 | CH$_3$ | 2,6-diF-phenyl | 2-methylsulfonyl-1-imidazolyl |
| 81 | CH$_2$CH$_3$ | phenyl | 2-(aminosulfonyl)phenyl |
| 82 | CH$_2$CH$_3$ | phenyl | 2-(methylaminosulfonyl)phenyl |
| 83 | CH$_2$CH$_3$ | phenyl | 1-pyrrolidinocarbonyl |
| 84 | CH$_2$CH$_3$ | phenyl | 2-(methylsulfonyl)phenyl |
| 85 | CH$_2$CH$_3$ | phenyl | 4-morpholino |
| 86 | CH$_2$CH$_3$ | phenyl | 2-(1'-CF$_3$-tetrazol-2-yl)phenyl |
| 87 | CH$_2$CH$_3$ | phenyl | 4-morpholinocarbonyl |
| 88 | CH$_2$CH$_3$ | phenyl | 2-methyl-1-imidazolyl |
| 89 | CH$_2$CH$_3$ | phenyl | 5-methyl-1-imidazolyl |
| 90 | CH$_2$CH$_3$ | phenyl | 2-methylsulfonyl-1-imidazolyl |
| 91 | CH$_2$CH$_3$ | 2-pyridyl | 2-(aminosulfonyl)phenyl |
| 92 | CH$_2$CH$_3$ | 2-pyridyl | 2-(methylaminosulfonyl)phenyl |
| 93 | CH$_2$CH$_3$ | 2-pyridyl | 1-pyrrolidinocarbonyl |
| 94 | CH$_2$CH$_3$ | 2-pyridyl | 2-(methylsulfonyl)phenyl |
| 95 | CH$_2$CH$_3$ | 2-pyridyl | 4-morpholino |
| 96 | CH$_2$CH$_3$ | 2-pyridyl | 2-(1'-CF$_3$-tetrazol-2-yl)phenyl |
| 97 | CH$_2$CH$_3$ | 2-pyridyl | 4-morpholinocarbonyl |
| 98 | CH$_2$CH$_3$ | 2-pyridyl | 2-methyl-1-imidazolyl |
| 99 | CH$_2$CH$_3$ | 2-pyridyl | 5-methyl-1-imidazolyl |
| 100 | CH$_2$CH$_3$ | 2-pyridyl | 2-methylsulfonyl-1-imidazolyl |
| 101 | CH$_2$CH$_3$ | 3-pyridyl | 2-(aminosulfonyl)phenyl |
| 102 | CH$_2$CH$_3$ | 3-pyridyl | 2-(methylaminosulfonyl)phenyl |
| 103 | CH$_2$CH$_3$ | 3-pyridyl | 1-pyrrolidinocarbonyl |
| 104 | CH$_2$CH$_3$ | 3-pyridyl | 2-(methylsulfonyl)phenyl |
| 105 | CH$_2$CH$_3$ | 3-pyridyl | 4-morpholino |
| 106 | CH$_2$CH$_3$ | 3-pyridyl | 2-(1'-CF$_3$-tetrazol-2-yl)phenyl |
| 107 | CH$_2$CH$_3$ | 3-pyridyl | 4-morpholinocarbonyl |
| 108 | CH$_2$CH$_3$ | 3-pyridyl | 2-methyl-1-imidazolyl |
| 109 | CH$_2$CH$_3$ | 3-pyridyl | 5-methyl-1-imidazolyl |
| 110 | CH$_2$CH$_3$ | 3-pyridyl | 2-methylsulfonyl-1-imidazolyl |
| 111 | CH$_2$CH$_3$ | 2-pyrimidyl | 2-(aminosulfonyl)phenyl |
| 112 | CH$_2$CH$_3$ | 2-pyrimidyl | 2-(methylaminosulfonyl)phenyl |
| 113 | CH$_2$CH$_3$ | 2-pyrimidyl | 1-pyrrolidinocarbonyl |
| 114 | CH$_2$CH$_3$ | 2-pyrimidyl | 2-(methylsulfonyl)phenyl |
| 115 | CH$_2$CH$_3$ | 2-pyrimidyl | 4-morpholino |
| 116 | CH$_2$CH$_3$ | 2-pyrimidyl | 2-(1'-CF$_3$-tetrazol-2-yl)phenyl |
| 117 | CH$_2$CH$_3$ | 2-pyrimidyl | 4-morpholinocarbonyl |
| 118 | CH$_2$CH$_3$ | 2-pyrimidyl | 2-methyl-1-imidazolyl |
| 119 | CH$_2$CH$_3$ | 2-pyrimidyl | 5-methyl-1-imidazolyl |
| 120 | CH$_2$CH$_3$ | 2-pyrimidyl | 2-methylsulfonyl-1-imidazolyl |
| 121 | CH$_2$CH$_3$ | 5-pyrimidyl | 2-(aminosulfonyl)phenyl |
| 122 | CH$_2$CH$_3$ | 5-pyrimidyl | 2-(methylaminosulfonyl)phenyl |
| 123 | CH$_2$CH$_3$ | 5-pyrimidyl | 1-pyrrolidinocarbonyl |
| 124 | CH$_2$CH$_3$ | 5-pyrimidyl | 2-(methylsulfonyl)phenyl |
| 125 | CH$_2$CH$_3$ | 5-pyrimidyl | 4-morpholino |
| 126 | CH$_2$CH$_3$ | 5-pyrimidyl | 2-(1'-CF$_3$-tetrazol-2-yl)phenyl |
| 127 | CH$_2$CH$_3$ | 5-pyrimidyl | 4-morpholinocarbonyl |
| 128 | CH$_2$CH$_3$ | 5-pyrimidyl | 2-methyl-1-imidazolyl |

TABLE 2-continued

| | | | |
|---|---|---|---|
| 129 | $CH_2CH_3$ | 5-pyrimidyl | 5-methyl-1-imidazolyl |
| 130 | $CH_2CH_3$ | 5-pyrimidyl | 2-methylsulfonyl-1-imidazolyl |
| 131 | $CH_2CH_3$ | 2-Cl-phenyl | 2-(aminosulfonyl)phenyl |
| 132 | $CH_2CH_3$ | 2-Cl-phenyl | 2-(methylaminosulfonyl)phenyl |
| 133 | $CH_2CH_3$ | 2-Cl-phenyl | 1-pyrrolidinocarbonyl |
| 134 | $CH_2CH_3$ | 2-Cl-phenyl | 2-(methylsulfonyl)phenyl |
| 135 | $CH_2CH_3$ | 2-Cl-phenyl | 4-morpholino |
| 136 | $CH_2CH_3$ | 2-Cl-phenyl | 2-(1'-$CF_3$-tetrazol-2-yl)phenyl |
| 137 | $CH_2CH_3$ | 2-Cl-phenyl | 4-morpholinocarbonyl |
| 138 | $CH_2CH_3$ | 2-Cl-phenyl | 2-methyl-1-imidazolyl |
| 139 | $CH_2CH_3$ | 2-Cl-phenyl | 5-methyl-1-imidazolyl |
| 140 | $CH_2CH_3$ | 2-Cl-phenyl | 2-methylsulfonyl-1-imidazolyl |
| 141 | $CH_2CH_3$ | 2-F-phenyl | 2-(aminosulfonyl)phenyl |
| 142 | $CH_2CH_3$ | 2-F-phenyl | 2-(methylaminosulfonyl)phenyl |
| 143 | $CH_2CH_3$ | 2-F-phenyl | 1-pyrrolidinocarbonyl |
| 144 | $CH_2CH_3$ | 2-F-phenyl | 2-(methylsulfonyl)phenyl |
| 145 | $CH_2CH_3$ | 2-F-phenyl | 4-morpholino |
| 146 | $CH_2CH_3$ | 2-F-phenyl | 2-(1'-$CF_3$-tetrazol-2-yl)phenyl |
| 147 | $CH_2CH_3$ | 2-F-phenyl | 4-morpholinocarbonyl |
| 148 | $CH_2CH_3$ | 2-F-phenyl | 2-methyl-1-imidazolyl |
| 149 | $CH_2CH_3$ | 2-F-phenyl | 5-methyl-1-imidazolyl |
| 150 | $CH_2CH_3$ | 2-F-phenyl | 2-methylsulfonyl-1-imidazolyl |
| 151 | $CH_2CH_3$ | 2,6-diF-phenyl | 2-(aminosulfonyl)phenyl |
| 152 | $CH_2CH_3$ | 2,6-diF-phenyl | 2-(methylaminosulfonyl)phenyl |
| 153 | $CH_2CH_3$ | 2,6-diF-phenyl | 1-pyrrolidinocarbonyl |
| 154 | $CH_2CH_3$ | 2,6-diF-phenyl | 2-(methylsulfonyl)phenyl |
| 155 | $CH_2CH_3$ | 2,6-diF-phenyl | 4-morpholino |
| 156 | $CH_2CH_3$ | 2,6-diF-phenyl | 2-(1'-$CF_3$-tetrazol-2-yl)phenyl |
| 157 | $CH_2CH_3$ | 2,6-diF-phenyl | 4-morpholinocarbonyl |
| 158 | $CH_2CH_3$ | 2,6-diF-phenyl | 2-methyl-1-imidazolyl |
| 159 | $CH_2CH_3$ | 2,6-diF-phenyl | 5-methyl-1-imidazolyl |
| 160 | $CH_2CH_3$ | 2,6-diF-phenyl | 2-methylsulfonyl-1-imidazolyl |
| 161 | $CF_3$ | phenyl | 2-(aminosulfonyl)phenyl |
| 162 | $CF_3$ | phenyl | 2-(methylaminosulfonyl)phenyl |
| 163 | $CF_3$ | phenyl | 1-pyrrolidinocarbonyl |
| 164 | $CF_3$ | phenyl | 2-(methylsulfonyl)phenyl |
| 165 | $CF_3$ | phenyl | 4-morpholino |
| 166 | $CF_3$ | phenyl | 2-(1'-$CF_3$-tetrazol-2-yl)phenyl |
| 167 | $CF_3$ | phenyl | 4-morpholinocarbonyl |
| 168 | $CF_3$ | phenyl | 2-methyl-1-imidazolyl |
| 169 | $CF_3$ | phenyl | 5-methyl-1-imidazolyl |
| 170 | $CF_3$ | phenyl | 2-methylsulfonyl-1-imidazolyl |
| 171 | $CF_3$ | 2-pyridyl | 2-(aminosulfonyl)phenyl |
| 172 | $CF_3$ | 2-pyridyl | 2-(methylaminosulfonyl)phenyl |
| 173 | $CF_3$ | 2-pyridyl | 1-pyrrolidinocarbonyl |
| 174 | $CF_3$ | 2-pyridyl | 2-(methylsulfonyl)phenyl |
| 175 | $CF_3$ | 2-pyridyl | 4-morpholino |
| 176 | $CF_3$ | 2-pyridyl | 2-(1'-$CF_3$-tetrazol-2-yl)phenyl |
| 177 | $CF_3$ | 2-pyridyl | 4-morpholinocarbonyl |
| 178 | $CF_3$ | 2-pyridyl | 2-methyl-1-imidazolyl |
| 179 | $CF_3$ | 2-pyridyl | 5-methyl-1-imidazolyl |
| 180 | $CF_3$ | 2-pyridyl | 2-methylsulfonyl-1-imidazolyl |
| 181 | $CF_3$ | 3-pyridyl | 2-(aminosulfonyl)phenyl |
| 182 | $CF_3$ | 3-pyridyl | 2-(methylaminosulfonyl)phenyl |
| 183 | $CF_3$ | 3-pyridyl | 1-pyrrolidinocarbonyl |
| 184 | $CF_3$ | 3-pyridyl | 2-(methylsulfonyl)phenyl |
| 185 | $CF_3$ | 3-pyridyl | 4-morpholino |
| 186 | $CF_3$ | 3-pyridyl | 2-(1'-$CF_3$-tetrazol-2-yl)phenyl |
| 187 | $CF_3$ | 3-pyridyl | 4-morpholinocarbonyl |
| 188 | $CF_3$ | 3-pyridyl | 2-methyl-1-imidazolyl |
| 189 | $CF_3$ | 3-pyridyl | 5-methyl-1-imidazolyl |
| 190 | $CF_3$ | 3-pyridyl | 2-methylsulfonyl-1-imidazolyl |
| 191 | $CF_3$ | 2-pyrimidyl | 2-(aminosulfonyl)phenyl |
| 192 | $CF_3$ | 2-pyrimidyl | 2-(methylaminosulfonyl)phenyl |
| 193 | $CF_3$ | 2-pyrimidyl | 1-pyrrolidinocarbonyl |
| 194 | $CF_3$ | 2-pyrimidyl | 2-(methylsulfonyl)phenyl |
| 195 | $CF_3$ | 2-pyrimidyl | 4-morpholino |
| 196 | $CF_3$ | 2-pyrimidyl | 2-(1'-$CF_3$-tetrazol-2-yl)phenyl |
| 197 | $CF_3$ | 2-pyrimidyl | 4-morpholinocarbonyl |
| 198 | $CF_3$ | 2-pyrimidyl | 2-methyl-1-imidazolyl |
| 199 | $CF_3$ | 2-pyrimidyl | 5-methyl-1-imidazolyl |
| 200 | $CF_3$ | 2-pyrimidyl | 2-methylsulfonyl-1-imidazolyl |
| 201 | $CF_3$ | 5-pyrimidyl | 2-(aminosulfonyl)phenyl |
| 202 | $CF_3$ | 5-pyrimidyl | 2-(methylaminosulfonyl)phenyl |
| 203 | $CF_3$ | 5-pyrimidyl | 1-pyrrolidinocarbonyl |
| 204 | $CF_3$ | 5-pyrimidyl | 2-(methylsulfonyl)phenyl |
| 205 | $CF_3$ | 5-pyrimidyl | 4-morpholino |
| 206 | $CF_3$ | 5-pyrimidyl | 2-(1'-$CF_3$-tetrazol-2-yl)phenyl |
| 207 | $CF_3$ | 5-pyrimidyl | 4-morpholinocarbonyl |

TABLE 2-continued

| | | | |
|---|---|---|---|
| 208 | $CF_3$ | 5-pyrimidyl | 2-methyl-1-imidazolyl |
| 209 | $CF_3$ | 5-pyrimidyl | 5-methyl-1-imidazolyl |
| 210 | $CF_3$ | 5-pyrimidyl | 2-methylsulfonyl-1-imidazolyl |
| 211 | $CF_3$ | 2-Cl-phenyl | 2-(aminosulfonyl)phenyl |
| 212 | $CF_3$ | 2-Cl-phenyl | 2-(methylaminosulfonyl)phenyl |
| 213 | $CF_3$ | 2-Cl-phenyl | 1-pyrrolidinocarbonyl |
| 214 | $CF_3$ | 2-Cl-phenyl | 2-(methylsulfonyl)phenyl |
| 215 | $CF_3$ | 2-Cl-phenyl | 4-morpholino |
| 216 | $CF_3$ | 2-Cl-phenyl | 2-(1'-$CF_3$-tetrazol-2-yl)phenyl |
| 217 | $CF_3$ | 2-Cl-phenyl | 4-morpholinocarbonyl |
| 218 | $CF_3$ | 2-Cl-phenyl | 2-methyl-1-imidazolyl |
| 219 | $CF_3$ | 2-Cl-phenyl | 5-methyl-1-imidazolyl |
| 220 | $CF_3$ | 2-Cl-phenyl | 2-methylsulfonyl-1-imidazolyl |
| 221 | $CF_3$ | 2-F-phenyl | 2-(aminosulfonyl)phenyl |
| 222 | $CF_3$ | 2-F-phenyl | 2-(methylaminosulfonyl)phenyl |
| 223 | $CF_3$ | 2-F-phenyl | 1-pyrrolidinocarbonyl |
| 224 | $CF_3$ | 2-F-phenyl | 2-(methylsulfonyl)phenyl |
| 225 | $CF_3$ | 2-F-phenyl | 4-morpholino |
| 226 | $CF_3$ | 2-F-phenyl | 2-(1'-$CF_3$-tetrazol-2-yl)phenyl |
| 227 | $CF_3$ | 2-F-phenyl | 4-morpholinocarbonyl |
| 228 | $CF_3$ | 2-F-phenyl | 2-methyl-1-imidazolyl |
| 229 | $CF_3$ | 2-F-phenyl | 5-methyl-1-imidazolyl |
| 230 | $CF_3$ | 2-F-phenyl | 2-methylsulfonyl-1-imidazolyl |
| 231 | $CF_3$ | 2,6-diF-phenyl | 2-(aminosulfonyl)phenyl |
| 232 | $CF_3$ | 2,6-diF-phenyl | 2-(methylaminosulfonyl)phenyl |
| 233 | $CF_3$ | 2,6-diF-phenyl | 1-pyrrolidinocarbonyl |
| 234 | $CF_3$ | 2,6-diF-phenyl | 2-(methylsulfonyl)phenyl |
| 235 | $CF_3$ | 2,6-diF-phenyl | 4-morpholino |
| 236 | $CF_3$ | 2,6-diF-phenyl | 2-(1'-$CF_3$-tetrazol-2-yl)phenyl |
| 237 | $CF_3$ | 2,6-diF-phenyl | 4-morpholinocarbonyl |
| 238 | $CF_3$ | 2,6-diF-phenyl | 2-methyl-1-imidazolyl |
| 239 | $CF_3$ | 2,6-diF-phenyl | 5-methyl-1-imidazolyl |
| 240 | $CF_3$ | 2,6-diF-phenyl | 2-methylsulfonyl-1-imidazolyl |
| 241 | $SCH_3$ | phenyl | 2-(aminosulfonyl)phenyl |
| 242 | $SCH_3$ | phenyl | 2-(methylaminosulfonyl)phenyl |
| 243 | $SCH_3$ | phenyl | 1-pyrrolidinocarbonyl |
| 244 | $SCH_3$ | phenyl | 2-(methylsulfonyl)phenyl |
| 245 | $SCH_3$ | phenyl | 4-morpholino |
| 246 | $SCH_3$ | phenyl | 2-(1'-$CF_3$-tetrazol-2-yl)phenyl |
| 247 | $SCH_3$ | phenyl | 4-morpholinocarbonyl |
| 248 | $SCH_3$ | phenyl | 2-methyl-1-imidazolyl |
| 249 | $SCH_3$ | phenyl | 5-methyl-1-imidazolyl |
| 250 | $SCH_3$ | phenyl | 2-methylsulfonyl-1-imidazolyl |
| 251 | $SCH_3$ | 2-pyridyl | 2-(aminosulfonyl)phenyl |
| 252 | $SCH_3$ | 2-pyridyl | 2-(methylaminosulfonyl)phenyl |
| 253 | $SCH_3$ | 2-pyridyl | 1-pyrrolidinocarbonyl |
| 254 | $SCH_3$ | 2-pyridyl | 2-(methylsulfonyl)phenyl |
| 255 | $SCH_3$ | 2-pyridyl | 4-morpholino |
| 256 | $SCH_3$ | 2-pyridyl | 2-(1'-$CF_3$-tetrazol-2-yl)phenyl |
| 257 | $SCH_3$ | 2-pyridyl | 4-morpholinocarbonyl |
| 258 | $SCH_3$ | 2-pyridyl | 2-methyl-1-imidazolyl |
| 259 | $SCH_3$ | 2-pyridyl | 5-methyl-1-imidazolyl |
| 260 | $SCH_3$ | 2-pyridyl | 2-methylsulfonyl-1-imidazolyl |
| 261 | $SCH_3$ | 3-pyridyl | 2-(aminosulfonyl)phenyl |
| 262 | $SCH_3$ | 3-pyridyl | 2-(methylaminosulfonyl)phenyl |
| 263 | $SCH_3$ | 3-pyridyl | 1-pyrrolidinocarbonyl |
| 264 | $SCH_3$ | 3-pyridyl | 2-(methylsulfonyl)phenyl |
| 265 | $SCH_3$ | 3-pyridyl | 4-morpholino |
| 266 | $SCH_3$ | 3-pyridyl | 2-(1'-$CF_3$-tetrazol-2-yl)phenyl |
| 267 | $SCH_3$ | 3-pyridyl | 4-morpholinocarbonyl |
| 268 | $SCH_3$ | 3-pyridyl | 2-methyl-1-imidazolyl |
| 269 | $SCH_3$ | 3-pyridyl | 5-methyl-1-imidazolyl |
| 270 | $SCH_3$ | 3-pyridyl | 2-methylsulfonyl-1-imidazolyl |
| 271 | $SCH_3$ | 2-pyrimidyl | 2-(aminosulfonyl)phenyl |
| 272 | $SCH_3$ | 2-pyrimidyl | 2-(methylaminosulfonyl)phenyl |
| 273 | $SCH_3$ | 2-pyrimidyl | 1-pyrrolidinocarbonyl |
| 274 | $SCH_3$ | 2-pyrimidyl | 2-(methylsulfonyl)phenyl |
| 275 | $SCH_3$ | 2-pyrimidyl | 4-morpholino |
| 276 | $SCH_3$ | 2-pyrimidyl | 2-(1'-$CF_3$-tetrazol-2-yl)phenyl |
| 277 | $SCH_3$ | 2-pyrimidyl | 4-morpholinocarbonyl |
| 278 | $SCH_3$ | 2-pyrimidyl | 2-methyl-1-imidazolyl |
| 279 | $SCH_3$ | 2-pyrimidyl | 5-methyl-1-imidazolyl |
| 280 | $SCH_3$ | 2-pyrimidyl | 2-methylsulfonyl-1-imidazolyl |
| 281 | $SCH_3$ | 5-pyrimidyl | 2-(aminosulfonyl)phenyl |
| 282 | $SCH_3$ | 5-pyrimidyl | 2-(methylaminosulfonyl)phenyl |
| 283 | $SCH_3$ | 5-pyrimidyl | 1-pyrrolidinocarbonyl |
| 284 | $SCH_3$ | 5-pyrimidyl | 2-(methylsulfonyl)phenyl |
| 285 | $SCH_3$ | 5-pyrimidyl | 4-morpholino |
| 286 | $SCH_3$ | 5-pyrimidyl | 2-(1'-$CF_3$-tetrazol-2-yl)phenyl |

TABLE 2-continued

| | | | |
|---|---|---|---|
| 287 | SCH$_3$ | 5-pyrimidyl | 4-morpholinocarbonyl |
| 288 | SCH$_3$ | 5-pyrimidyl | 2-methyl-1-imidazolyl |
| 289 | SCH$_3$ | 5-pyrimidyl | 5-methyl-1-imidazolyl |
| 290 | SCH$_3$ | 5-pyrimidyl | 2-methylsulfonyl-1-imidazolyl |
| 291 | SCH$_3$ | 2-Cl-phenyl | 2-(aminosulfonyl)phenyl |
| 292 | SCH$_3$ | 2-Cl-phenyl | 2-(methylaminosulfonyl)phenyl |
| 293 | SCH$_3$ | 2-Cl-phenyl | 1-pyrrolidinocarbonyl |
| 294 | SCH$_3$ | 2-Cl-phenyl | 2-(methylsulfonyl)phenyl |
| 295 | SCH$_3$ | 2-Cl-phenyl | 4-morpholino |
| 296 | SCH$_3$ | 2-Cl-phenyl | 2-(1'-CF$_3$-tetrazol-2-yl)phenyl |
| 297 | SCH$_3$ | 2-Cl-phenyl | 4-morpholinocarbonyl |
| 298 | SCH$_3$ | 2-Cl-phenyl | 2-methyl-1-imidazolyl |
| 299 | SCH$_3$ | 2-Cl-phenyl | 5-methyl-1-imidazolyl |
| 300 | SCH$_3$ | 2-Cl-phenyl | 2-methylsulfonyl-1-imidazolyl |
| 301 | SCH$_3$ | 2-F-phenyl | 2-(aminosulfonyl)phenyl |
| 302 | SCH$_3$ | 2-F-phenyl | 2-(methylaminosulfonyl)phenyl |
| 303 | SCH$_3$ | 2-F-phenyl | 1-pyrrolidinocarbonyl |
| 304 | SCH$_3$ | 2-F-phenyl | 2-(methylsulfonyl)phenyl |
| 305 | SCH$_3$ | 2-F-phenyl | 4-morpholino |
| 306 | SCH$_3$ | 2-F-phenyl | 2-(1'-CF$_3$-tetrazol-2-yl)phenyl |
| 307 | SCH$_3$ | 2-F-phenyl | 4-morpholinocarbonyl |
| 308 | SCH$_3$ | 2-F-phenyl | 2-methyl-1-imidazolyl |
| 309 | SCH$_3$ | 2-F-phenyl | 5-methyl-1-imidazolyl |
| 310 | SCH$_3$ | 2-F-phenyl | 2-methylsulfonyl-1-imidazolyl |
| 311 | SCH$_3$ | 2,6-diF-phenyl | 2-(aminosulfonyl)phenyl |
| 312 | SCH$_3$ | 2,6-diF-phenyl | 2-(methylaminosulfonyl)phenyl |
| 313 | SCH$_3$ | 2,6-diF-phenyl | 1-pyrrolidinocarbonyl |
| 314 | SCH$_3$ | 2,6-diF-phenyl | 2-(methylsulfonyl)phenyl |
| 315 | SCH$_3$ | 2,6-diF-phenyl | 4-morpholino |
| 316 | SCH$_3$ | 2,6-diF-phenyl | 2-(1'-CF$_3$-tetrazol-2-yl)phenyl |
| 317 | SCH$_3$ | 2,6-diF-phenyl | 4-morpholinocarbonyl |
| 318 | SCH$_3$ | 2,6-diF-phenyl | 2-methyl-1-imidazolyl |
| 319 | SCH$_3$ | 2,6-diF-phenyl | 5-methyl-1-imidazolyl |
| 320 | SCH$_3$ | 2,6-diF-phenyl | 2-methylsulfonyl-1-imidazolyl |
| 321 | SOCH$_3$ | phenyl | 2-(aminosulfonyl)phenyl |
| 322 | SOCH$_3$ | phenyl | 2-(methylaminosulfonyl)phenyl |
| 323 | SOCH$_3$ | phenyl | 1-pyrrolidinocarbonyl |
| 324 | SOCH$_3$ | phenyl | 2-(methylsulfonyl)phenyl |
| 325 | SOCH$_3$ | phenyl | 4-morpholino |
| 326 | SOCH$_3$ | phenyl | 2-(1'-CF$_3$-tetrazol-2-yl)phenyl |
| 327 | SOCH$_3$ | phenyl | 4-morpholinocarbonyl |
| 328 | SOCH$_3$ | phenyl | 2-methyl-1-imidazolyl |
| 329 | SOCH$_3$ | phenyl | 5-methyl-1-imidazolyl |
| 330 | SOCH$_3$ | phenyl | 2-methylsulfonyl-1-imidazolyl |
| 331 | SOCH$_3$ | 2-pyridyl | 2-(aminosulfonyl)phenyl |
| 332 | SOCH$_3$ | 2-pyridyl | 2-(methylaminosulfonyl)phenyl |
| 333 | SOCH$_3$ | 2-pyridyl | 1-pyrrolidinocarbonyl |
| 334 | SOCH$_3$ | 2-pyridyl | 2-(methylsulfonyl)phenyl |
| 335 | SOCH$_3$ | 2-pyridyl | 4-morpholino |
| 336 | SOCH$_3$ | 2-pyridyl | 2-(1'-CF$_3$-tetrazol-2-yl)phenyl |
| 337 | SOCH$_3$ | 2-pyridyl | 4-morpholinocarbonyl |
| 338 | SOCH$_3$ | 2-pyridyl | 2-methyl-1-imidazolyl |
| 339 | SOCH$_3$ | 2-pyridyl | 5-methyl-1-imidazolyl |
| 340 | SOCH$_3$ | 2-pyridyl | 2-methylsulfonyl-1-imidazolyl |
| 341 | SOCH$_3$ | 3-pyridyl | 2-(aminosulfonyl)phenyl |
| 342 | SOCH$_3$ | 3-pyridyl | 2-(methylaminosulfonyl)phenyl |
| 343 | SOCH$_3$ | 3-pyridyl | 1-pyrrolidinocarbonyl |
| 344 | SOCH$_3$ | 3-pyridyl | 2-(methylsulfonyl)phenyl |
| 345 | SOCH$_3$ | 3-pyridyl | 4-morpholino |
| 346 | SOCH$_3$ | 3-pyridyl | 2-(1'-CF$_3$-tetrazol-2-yl)phenyl |
| 347 | SOCH$_3$ | 3-pyridyl | 4-morpholinocarbonyl |
| 348 | SOCH$_3$ | 3-pyridyl | 2-methyl-1-imidazolyl |
| 349 | SOCH$_3$ | 3-pyridyl | 5-methyl-1-imidazolyl |
| 350 | SOCH$_3$ | 3-pyridyl | 2-methylsulfonyl-1-imidazolyl |
| 351 | SOCH$_3$ | 2-pyrimidyl | 2-(aminosulfonyl)phenyl |
| 352 | SOCH$_3$ | 2-pyrimidyl | 2-(methylaminosulfonyl)phenyl |
| 353 | SOCH$_3$ | 2-pyrimidyl | 1-pyrrolidinocarbonyl |
| 354 | SOCH$_3$ | 2-pyrimidyl | 2-(methylsulfonyl)phenyl |
| 355 | SOCH$_3$ | 2-pyrimidyl | 4-morpholino |
| 356 | SOCH$_3$ | 2-pyrimidyl | 2-(1'-CF$_3$-tetrazol-2-yl)phenyl |
| 357 | SOCH$_3$ | 2-pyrimidyl | 4-morpholinocarbonyl |
| 358 | SOCH$_3$ | 2-pyrimidyl | 2-methyl-1-imidazolyl |
| 359 | SOCH$_3$ | 2-pyrimidyl | 5-methyl-1-imidazolyl |
| 360 | SOCH$_3$ | 2-pyrimidyl | 2-methylsulfonyl-1-imidazolyl |
| 361 | SOCH$_3$ | 5-pyrimidyl | 2-(aminosulfonyl)phenyl |
| 362 | SOCH$_3$ | 5-pyrimidyl | 2-(methylaminosulfonyl)phenyl |
| 363 | SOCH$_3$ | 5-pyrimidyl | 1-pyrrolidinocarbonyl |
| 364 | SOCH$_3$ | 5-pyrimidyl | 2-(methylsulfonyl)phenyl |
| 365 | SOCH$_3$ | 5-pyrimidyl | 4-morpholino |

TABLE 2-continued

| | | | |
|---|---|---|---|
| 366 | SOCH₃ | 5-pyrimidyl | 2-(1'-CF₃-tetrazol-2-yl)phenyl |
| 367 | SOCH₃ | 5-pyrimidyl | 4-morpholinocarbonyl |
| 368 | SOCH₃ | 5-pyrimidyl | 2-methyl-1-imidazolyl |
| 369 | SOCH₃ | 5-pyrimidyl | 5-methyl-1-imidazolyl |
| 370 | SOCH₃ | 5-pyrimidyl | 2-methylsulfonyl-1-imidazolyl |
| 371 | SOCH₃ | 2-Cl-phenyl | 2-(aminosulfonyl)phenyl |
| 372 | SOCH₃ | 2-Cl-phenyl | 2-(methylaminosulfonyl)phenyl |
| 373 | SOCH₃ | 2-Cl-phenyl | 1-pyrrolidinocarbonyl |
| 374 | SOCH₃ | 2-Cl-phenyl | 2-(methylsulfonyl)phenyl |
| 375 | SOCH₃ | 2-Cl-phenyl | 4-morpholino |
| 376 | SOCH₃ | 2-Cl-phenyl | 2-(1'-CF₃-tetrazol-2-yl)phenyl |
| 377 | SOCH₃ | 2-Cl-phenyl | 4-morpholinocarbonyl |
| 378 | SOCH₃ | 2-Cl-phenyl | 2-methyl-1-imidazolyl |
| 379 | SOCH₃ | 2-Cl-phenyl | 5-methyl-1-imidazolyl |
| 380 | SOCH₃ | 2-Cl-phenyl | 2-methylsulfonyl-1-imidazolyl |
| 381 | SOCH₃ | 2-F-phenyl | 2-(aminosulfonyl)phenyl |
| 382 | SOCH₃ | 2-F-phenyl | 2-(methylaminosulfonyl)phenyl |
| 383 | SOCH₃ | 2-F-phenyl | 1-pyrrolidinocarbonyl |
| 384 | SOCH₃ | 2-F-phenyl | 2-(methylsulfonyl)phenyl |
| 385 | SOCH₃ | 2-F-phenyl | 4-morpholino |
| 386 | SOCH₃ | 2-F-phenyl | 2-(1'-CF₃-tetrazol-2-yl)phenyl |
| 387 | SOCH₃ | 2-F-phenyl | 4-morpholinocarbonyl |
| 388 | SOCH₃ | 2-F-phenyl | 2-methyl-1-imidazolyl |
| 389 | SOCH₃ | 2-F-phenyl | 5-methyl-1-imidazolyl |
| 390 | SOCH₃ | 2-F-phenyl | 2-methylsulfonyl-1-imidazolyl |
| 391 | SOCH₃ | 2,6-diF-phenyl | 2-(aminosulfonyl)phenyl |
| 392 | SOCH₃ | 2,6-diF-phenyl | 2-(methylaminosulfonyl)phenyl |
| 393 | SOCH₃ | 2,6-diF-phenyl | 1-pyrrolidinocarbonyl |
| 394 | SOCH₃ | 2,6-diF-phenyl | 2-(methylsulfonyl)phenyl |
| 395 | SOCH₃ | 2,6-diF-phenyl | 4-morpholino |
| 396 | SOCH₃ | 2,6-diF-phenyl | 2-(1'-CF₃-tetrazol-2-yl)phenyl |
| 397 | SOCH₃ | 2,6-diF-phenyl | 4-morpholinocarbonyl |
| 398 | SOCH₃ | 2,6-diF-phenyl | 2-methyl-1-imidazolyl |
| 399 | SOCH₃ | 2,6-diF-phenyl | 5-methyl-1-imidazolyl |
| 400 | SOCH₃ | 2,6-diF-phenyl | 2-methylsulfonyl-1-imidazolyl |
| 401 | SO₂CH₃ | phenyl | 2-(aminosulfonyl)phenyl |
| 402 | SO₂CH₃ | phenyl | 2-(methylaminosulfonyl)phenyl |
| 403 | SO₂CH₃ | phenyl | 1-pyrrolidinocarbonyl |
| 404 | SO₂CH₃ | phenyl | 2-(methylsulfonyl)phenyl |
| 405 | SO₂CH₃ | phenyl | 4-morpholino |
| 406 | SO₂CH₃ | phenyl | 2-(1'-CF₃-tetrazol-2-yl)phenyl |
| 407 | SO₂CH₃ | phenyl | 4-morpholinocarbonyl |
| 408 | SO₂CH₃ | phenyl | 2-methyl-1-imidazolyl |
| 409 | SO₂CH₃ | phenyl | 5-methyl-1-imidazolyl |
| 410 | SO₂CH₃ | phenyl | 2-methylsulfonyl-1-imidazolyl |
| 411 | SO₂CH₃ | 2-pyridyl | 2-(aminosulfonyl)phenyl |
| 412 | SO₂CH₃ | 2-pyridyl | 2-(methylaminosulfonyl)phenyl |
| 413 | SO₂CH₃ | 2-pyridyl | 1-pyrrolidinocarbonyl |
| 414 | SO₂CH₃ | 2-pyridyl | 2-(methylsulfonyl)phenyl |
| 415 | SO₂CH₃ | 2-pyridyl | 4-morpholino |
| 416 | SO₂CH₃ | 2-pyridyl | 2-(1'-CF₃-tetrazol-2-yl)phenyl |
| 417 | SO₂CH₃ | 2-pyridyl | 4-morpholinocarbonyl |
| 418 | SO₂CH₃ | 2-pyridyl | 2-methyl-1-imidazolyl |
| 419 | SO₂CH₃ | 2-pyridyl | 5-methyl-1-imidazolyl |
| 420 | SO₂CH₃ | 2-pyridyl | 2-methylsulfonyl-1-imidazolyl |
| 421 | SO₂CH₃ | 3-pyridyl | 2-(aminosulfonyl)phenyl |
| 422 | SO₂CH₃ | 3-pyridyl | 2-(methylaminosulfonyl)phenyl |
| 423 | SO₂CH₃ | 3-pyridyl | 1-pyrrolidinocarbonyl |
| 424 | SO₂CH₃ | 3-pyridyl | 2-(methylsulfonyl)phenyl |
| 425 | SO₂CH₃ | 3-pyridyl | 4-morpholino |
| 426 | SO₂CH₃ | 3-pyridyl | 2-(1'-CF₃-tetrazol-2-yl)phenyl |
| 427 | SO₂CH₃ | 3-pyridyl | 4-morpholinocarbonyl |
| 428 | SO₂CH₃ | 3-pyridyl | 2-methyl-1-imidazolyl |
| 429 | SO₂CH₃ | 3-pyridyl | 5-methyl-1-imidazolyl |
| 430 | SO₂CH₃ | 3-pyridyl | 2-methylsulfonyl-1-imidazolyl |
| 431 | SO₂CH₃ | 2-pyrimidyl | 2-(aminosulfonyl)phenyl |
| 432 | SO₂CH₃ | 2-pyrimidyl | 2-(methylaminosulfonyl)phenyl |
| 433 | SO₂CH₃ | 2-pyrimidyl | 1-pyrrolidinocarbonyl |
| 434 | SO₂CH₃ | 2-pyrimidyl | 2-(methylsulfonyl)phenyl |
| 435 | SO₂CH₃ | 2-pyrimidyl | 4-morpholino |
| 436 | SO₂CH₃ | 2-pyrimidyl | 2-(1'-CF₃-tetrazol-2-yl)phenyl |
| 437 | SO₂CH₃ | 2-pyrimidyl | 4-morpholinocarbonyl |
| 438 | SO₂CH₃ | 2-pyrimidyl | 2-methyl-1-imidazolyl |
| 439 | SO₂CH₃ | 2-pyrimidyl | 5-methyl-1-imidazolyl |
| 440 | SO₂CH₃ | 2-pyrimidyl | 2-methylsulfonyl-1-imidazolyl |
| 441 | SO₂CH₃ | 5-pyrimidyl | 2-(aminosulfonyl)phenyl |
| 442 | SO₂CH₃ | 5-pyrimidyl | 2-(methylaminosulfonyl)phenyl |
| 443 | SO₂CH₃ | 5-pyrimidyl | 1-pyrrolidinocarbonyl |
| 444 | SO₂CH₃ | 5-pyrimidyl | 2-(methylsulfonyl)phenyl |

TABLE 2-continued

| | | | |
|---|---|---|---|
| 445 | SO$_2$CH$_3$ | 5-pyrimidyl | 4-morpholino |
| 446 | SO$_2$CH$_3$ | 5-pyrimidyl | 2-(1'-CF$_3$-tetrazol-2-yl)phenyl |
| 447 | SO$_2$CH$_3$ | 5-pyrimidyl | 4-morpholinocarbonyl |
| 448 | SO$_2$CH$_3$ | 5-pyrimidyl | 2-methyl-1-imidazolyl |
| 449 | SO$_2$CH$_3$ | 5-pyrimidyl | 5-methyl-1-imidazolyl |
| 450 | SO$_2$CH$_3$ | 5-pyrimidyl | 2-methylsulfonyl-1-imidazolyl |
| 451 | SO$_2$CH$_3$ | 2-Cl-phenyl | 2-(aminosulfonyl)phenyl |
| 452 | SO$_2$CH$_3$ | 2-Cl-phenyl | 2-(methylaminosulfonyl)phenyl |
| 453 | SO$_2$CH$_3$ | 2-Cl-phenyl | 1-pyrrolidinocarbonyl |
| 454 | SO$_2$CH$_3$ | 2-Cl-phenyl | 2-(methylsulfonyl)phenyl |
| 455 | SO$_2$CH$_3$ | 2-Cl-phenyl | 4-morpholino |
| 456 | SO$_2$CH$_3$ | 2-Cl-phenyl | 2-(1'-CF$_3$-tetrazol-2-yl)phenyl |
| 457 | SO$_2$CH$_3$ | 2-Cl-phenyl | 4-morpholinocarbonyl |
| 458 | SO$_2$CH$_3$ | 2-Cl-phenyl | 2-methyl-1-imidazolyl |
| 459 | SO$_2$CH$_3$ | 2-Cl-phenyl | 5-methyl-1-imidazolyl |
| 460 | SO$_2$CH$_3$ | 2-Cl-phenyl | 2-methylsulfonyl-1-imidazolyl |
| 461 | SO$_2$CH$_3$ | 2-F-phenyl | 2-(aminosulfonyl)phenyl |
| 462 | SO$_2$CH$_3$ | 2-F-phenyl | 2-(methylaminosulfonyl)phenyl |
| 463 | SO$_2$CH$_3$ | 2-F-phenyl | 1-pyrrolidinocarbonyl |
| 464 | SO$_2$CH$_3$ | 2-F-phenyl | 2-(methylsulfonyl)phenyl |
| 465 | SO$_2$CH$_3$ | 2-F-phenyl | 4-morpholino |
| 466 | SO$_2$CH$_3$ | 2-F-phenyl | 2-(1'-CF$_3$-tetrazol-2-yl)phenyl |
| 467 | SO$_2$CH$_3$ | 2-F-phenyl | 4-morpholinocarbonyl |
| 468 | SO$_2$CH$_3$ | 2-F-phenyl | 2-methyl-1-imidazolyl |
| 469 | SO$_2$CH$_3$ | 2-F-phenyl | 5-methyl-1-imidazolyl |
| 470 | SO$_2$CH$_3$ | 2-F-phenyl | 2-methylsulfonyl-1-imidazolyl |
| 471 | SO$_2$CH$_3$ | 2,6-diF-phenyl | 2-(aminosulfonyl)phenyl |
| 472 | SO$_2$CH$_3$ | 2,6-diF-phenyl | 2-(methylaminosulfonyl)phenyl |
| 473 | SO$_2$CH$_3$ | 2,6-diF-phenyl | 1-pyrrolidinocarbonyl |
| 474 | SO$_2$CH$_3$ | 2,6-diF-phenyl | 2-(methylsulfonyl)phenyl |
| 475 | SO$_2$CH$_3$ | 2,6-diF-phenyl | 4-morpholino |
| 476 | SO$_2$CH$_3$ | 2,6-diF-phenyl | 2-(1'-CF$_3$-tetrazol-2-yl)phenyl |
| 477 | SO$_2$CH$_3$ | 2,6-diF-phenyl | 4-morpholinocarbonyl |
| 478 | SO$_2$CH$_3$ | 2,6-diF-phenyl | 2-methyl-1-imidazolyl |
| 479 | SO$_2$CH$_3$ | 2,6-diF-phenyl | 5-methyl-1-imidazolyl |
| 480 | SO$_2$CH$_3$ | 2,6-diF-phenyl | 2-methylsulfonyl-1-imidazolyl |
| 481 | CH$_2$NH—SO$_2$CH$_3$ | phenyl | 2-(aminosulfonyl)phenyl |
| 482 | CH$_2$NH—SO$_2$CH$_3$ | phenyl | 2-(methylaminosulfonyl)phenyl |
| 483 | CH$_2$NH—SO$_2$CH$_3$ | phenyl | 1-pyrrolidinocarbonyl |
| 484 | CH$_2$NH—SO$_2$CH$_3$ | phenyl | 2-(methylsulfonyl)phenyl |
| 485 | CH$_2$NH—SO$_2$CH$_3$ | phenyl | 4-morpholino |
| 486 | CH$_2$NH—SO$_2$CH$_3$ | phenyl | 2-(1'-CF$_3$-tetrazol-2-yl)phenyl |
| 487 | CH$_2$NH—SO$_2$CH$_3$ | phenyl | 4-morpholinocarbonyl |
| 488 | CH$_2$NH—SO$_2$CH$_3$ | phenyl | 2-methyl-1-imidazolyl |
| 489 | CH$_2$NH—SO$_2$CH$_3$ | phenyl | 5-methyl-1-imidazolyl |
| 490 | CH$_2$NH—SO$_2$CH$_3$ | phenyl | 2-methylsulfonyl-1-imidazolyl |
| 491 | CH$_2$NH—SO$_2$CH$_3$ | 2-pyridyl | 2-(aminosulfonyl)phenyl |
| 492 | CH$_2$NH—SO$_2$CH$_3$ | 2-pyridyl | 2-(methylaminosulfonyl)phenyl |
| 493 | CH$_2$NH—SO$_2$CH$_3$ | 2-pyridyl | 1-pyrrolidinocarbonyl |
| 494 | CH$_2$NH—SO$_2$CH$_3$ | 2-pyridyl | 2-(methylsulfonyl)phenyl |
| 495 | CH$_2$NH—SO$_2$CH$_3$ | 2-pyridyl | 4-morpholino |
| 496 | CH$_2$NH—SO$_2$CH$_3$ | 2-pyridyl | 2-(1'-CF$_3$-tetrazol-2-yl)phenyl |
| 497 | CH$_2$NH—SO$_2$CH$_3$ | 2-pyridyl | 4-morpholinocarbonyl |
| 498 | CH$_2$NH—SO$_2$CH$_3$ | 2-pyridyl | 2-methyl-1-imidazolyl |
| 499 | CH$_2$NH—SO$_2$CH$_3$ | 2-pyridyl | 5-methyl-1-imidazolyl |
| 500 | CH$_2$NH—SO$_2$CH$_3$ | 2-pyridyl | 2-methylsulfonyl-1-imidazolyl |
| 501 | CH$_2$NH—SO$_2$CH$_3$ | 3-pyridyl | 2-(aminosulfonyl)phenyl |
| 502 | CH$_2$NH—SO$_2$CH$_3$ | 3-pyridyl | 2-(methylaminosulfonyl)phenyl |

TABLE 2-continued

| | | | |
|---|---|---|---|
| 503 | CH$_2$NH—SO$_2$CH$_3$ | 3-pyridyl | 1-pyrrolidinocarbonyl |
| 504 | CH$_2$NH—SO$_2$CH$_3$ | 3-pyridyl | 2-(methylsulfonyl)phenyl |
| 505 | CH$_2$NH—SO$_2$CH$_3$ | 3-pyridyl | 4-morpholino |
| 506 | CH$_2$NH—SO$_2$CH$_3$ | 3-pyridyl | 2-(1'-CF$_3$-tetrazol-2-yl)phenyl |
| 507 | CH$_2$NH—SO$_2$CH$_3$ | 3-pyridyl | 4-morpholinocarbonyl |
| 508 | CH$_2$NH—SO$_2$CH$_3$ | 3-pyridyl | 2-methyl-1-imidazolyl |
| 509 | CH$_2$NH—SO$_2$CH$_3$ | 3-pyridyl | 5-methyl-1-imidazolyl |
| 510 | CH$_2$NH—SO$_2$CH$_3$ | 3-pyridyl | 2-methylsulfonyl-1-imidazolyl |
| 511 | CH$_2$NH—SO$_2$CH$_3$ | 2-pyrimidyl | 2-(aminosulfonyl)phenyl |
| 512 | CH$_2$NH—SO$_2$CH$_3$ | 2-pyrimidyl | 2-(methylaminosulfonyl)phenyl |
| 513 | CH$_2$NH—SO$_2$CH$_3$ | 2-pyrimidyl | 1-pyrrolidinocarbonyl |
| 514 | CH$_2$NH—SO$_2$CH$_3$ | 2-pyrimidyl | 2-(methylsulfonyl)phenyl |
| 515 | CH$_2$NH—SO$_2$CH$_3$ | 2-pyrimidyl | 4-morpholino |
| 516 | CH$_2$NH—SO$_2$CH$_3$ | 2-pyrimidyl | 2-(1'-CF$_3$-tetrazol-2-yl)phenyl |
| 517 | CH$_2$NH—SO$_2$CH$_3$ | 2-pyrimidyl | 4-morpholinocarbonyl |
| 518 | CH$_2$NH—SO$_2$CH$_3$ | 2-pyrimidyl | 2-methyl-1-imidazolyl |
| 519 | CH$_2$NH—SO$_2$CH$_3$ | 2-pyrimidyl | 5-methyl-1-imidazolyl |
| 520 | CH$_2$NH—SO$_2$CH$_3$ | 2-pyrimidyl | 2-methylsulfonyl-1-imidazolyl |
| 521 | CH$_2$NH—SO$_2$CH$_3$ | 5-pyrimidyl | 2-(aminosulfonyl)phenyl |
| 522 | CH$_2$NH—SO$_2$CH$_3$ | 5-pyrimidyl | 2-(methylaminosulfonyl)phenyl |
| 523 | CH$_2$NH—SO$_2$CH$_3$ | 5-pyrimidyl | 1-pyrrolidinocarbonyl |
| 524 | CH$_2$NH—SO$_2$CH$_3$ | 5-pyrimidyl | 2-(methylsulfonyl)phenyl |
| 525 | CH$_2$NH—SO$_2$CH$_3$ | 5-pyrimidyl | 4-morpholino |
| 526 | CH$_2$NH—SO$_2$CH$_3$ | 5-pyrimidyl | 2-(1'-CF$_3$-tetrazol-2-yl)phenyl |
| 527 | CH$_2$NH—SO$_2$CH$_3$ | 5-pyrimidyl | 4-morpholinocarbonyl |
| 528 | CH$_2$NH—SO$_2$CH$_3$ | 5-pyrimidyl | 2-methyl-1-imidazolyl |
| 529 | CH$_2$NH—SO$_2$CH$_3$ | 5-pyrimidyl | 5-methyl-1-imidazolyl |
| 530 | CH$_2$NH—SO$_2$CH$_3$ | 5-pyrimidyl | 2-methylsulfonyl-1-imidazolyl |
| 531 | CH$_2$NH—SO$_2$CH$_3$ | 2-Cl-phenyl | 2-(aminosulfonyl)phenyl |
| 532 | CH$_2$NH—SO$_2$CH$_3$ | 2-Cl-phenyl | 2-(methylaminosulfonyl)phenyl |
| 533 | CH$_2$NH—SO$_2$CH$_3$ | 2-Cl-phenyl | 1-pyrrolidinocarbonyl |
| 534 | CH$_2$NH—SO$_2$CH$_3$ | 2-Cl-phenyl | 2-(methylsulfonyl)phenyl |
| 535 | CH$_2$NH—SO$_2$CH$_3$ | 2-Cl-phenyl | 4-morpholino |
| 536 | CH$_2$NH—SO$_2$CH$_3$ | 2-Cl-phenyl | 2-(1'-CF$_3$-tetrazol-2-yl)phenyl |
| 537 | CH$_2$NH—SO$_2$CH$_3$ | 2-Cl-phenyl | 4-morpholinocarbonyl |
| 538 | CH$_2$NH—SO$_2$CH$_3$ | 2-Cl-phenyl | 2-methyl-1-imidazolyl |
| 539 | CH$_2$NH—SO$_2$CH$_3$ | 2-Cl-phenyl | 5-methyl-1-imidazolyl |
| 540 | CH$_2$NH—SO$_2$CH$_3$ | 2-Cl-phenyl | 2-methylsulfonyl-1-imidazolyl |
| 541 | CH$_2$NH—SO$_2$CH$_3$ | 2-F-phenyl | 2-(aminosulfonyl)phenyl |
| 542 | CH$_2$NH | 2-F-phenyl | 2-(methylaminosulfonyl)phenyl |

TABLE 2-continued

| | | | |
|---|---|---|---|
| 543 | CH$_2$NH—SO$_2$CH$_3$ | 2-F-phenyl | 1-pyrrolidinocarbonyl |
| 544 | CH$_2$NH—SO$_2$CH$_3$ | 2-F-phenyl | 2-(methylsulfonyl)phenyl |
| 545 | CH$_2$NH—SO$_2$CH$_3$ | 2-F-phenyl | 4-morpholino |
| 546 | CH$_2$NH—SO$_2$CH$_3$ | 2-F-phenyl | 2-(1'-CF$_3$-tetrazol-2-yl)phenyl |
| 547 | CH$_2$NH—SO$_2$CH$_3$ | 2-F-phenyl | 4-morpholinocarbonyl |
| 548 | CH$_2$NH—SO$_2$CH$_3$ | 2-F-phenyl | 2-methyl-1-imidazolyl |
| 549 | CH$_2$NH—SO$_2$CH$_3$ | 2-F-phenyl | 5-methyl-1-imidazolyl |
| 550 | CH$_2$NH—SO$_2$CH$_3$ | 2-F-phenyl | 2-methylsulfonyl-1-imidazolyl |
| 551 | CH$_2$NH—SO$_2$CH$_3$ | 2,6-diF-phenyl | 2-(aminosulfonyl)phenyl |
| 552 | CH$_2$NH—SO$_2$CH$_3$ | 2,6-diF-phenyl | 2-(methylaminosulfonyl)phenyl |
| 553 | CH$_2$NH—SO$_2$CH$_3$ | 2,6-diF-phenyl | 1-pyrrolidinocarbonyl |
| 554 | CH$_2$NH—SO$_2$CH$_3$ | 2,6-diF-phenyl | 2-(methylsulfonyl)phenyl |
| 555 | CH$_2$NH—SO$_2$CH$_3$ | 2,6-diF-phenyl | 4-morpholino |
| 556 | CH$_2$NH—SO$_2$CH$_3$ | 2,6-diF-phenyl | 2-(1'-CF$_3$-tetrazol-2-yl)phenyl |
| 557 | CH$_2$NH—SO$_2$CH$_3$ | 2,6-diF-phenyl | 4-morpholinocarbonyl |
| 558 | CH$_2$NH—SO$_2$CH$_3$ | 2,6-diF-phenyl | 2-methyl-1-imidazolyl |
| 559 | CH$_2$NH—SO$_2$CH$_3$ | 2,6-diF-phenyl | 5-methyl-1-imidazolyl |
| 560 | CH$_2$NH—SO$_2$CH$_3$ | 2,6-diF-phenyl | 2-methylsulfonyl-1-imidazolyl |
| 561 | Cl | phenyl | 2-(aminosulfonyl)phenyl |
| 562 | Cl | phenyl | 2-(methylaminosulfonyl)phenyl |
| 563 | Cl | phenyl | 1-pyrrolidinocarbonyl |
| 564 | Cl | phenyl | 2-(methylsulfonyl)phenyl |
| 565 | Cl | phenyl | 4-morpholino |
| 566 | Cl | phenyl | 2-(1'-CF$_3$-tetrazol-2-yl)phenyl |
| 567 | Cl | phenyl | 4-morpholinocarbonyl |
| 568 | Cl | phenyl | 2-methyl-1-imidazolyl |
| 569 | Cl | phenyl | 5-methyl-1-imidazolyl |
| 570 | Cl | phenyl | 2-methylsulfonyl-1-imidazolyl |
| 571 | Cl | 2-pyridyl | 2-(aminosulfonyl)phenyl |
| 572 | Cl | 2-pyridyl | 2-(methylaminosulfonyl)phenyl |
| 573 | Cl | 2-pyridyl | 1-pyrrolidinocarbonyl |
| 574 | Cl | 2-pyridyl | 2-(methylsulfonyl)phenyl |
| 575 | Cl | 2-pyridyl | 4-morpholino |
| 576 | Cl | 2-pyridyl | 2-(1'-CF$_3$-tetrazol-2-yl)phenyl |
| 577 | Cl | 2-pyridyl | 4-morpholinocarbonyl |
| 578 | Cl | 2-pyridyl | 2-methyl-1-imidazolyl |
| 579 | Cl | 2-pyridyl | 5-methyl-1-imidazolyl |
| 580 | Cl | 2-pyridyl | 2-methylsulfonyl-1-imidazolyl |
| 581 | Cl | 3-pyridyl | 2-(aminosulfonyl)phenyl |
| 582 | Cl | 3-pyridyl | 2-(methylaminosulfonyl)phenyl |
| 583 | Cl | 3-pyridyl | 1-pyrrolidinocarbonyl |
| 584 | Cl | 3-pyridyl | 2-(methylsulfonyl)phenyl |
| 585 | Cl | 3-pyridyl | 4-morpholino |
| 586 | Cl | 3-pyridyl | 2-(1'-CF$_3$-tetrazol-2-yl)phenyl |
| 587 | Cl | 3-pyridyl | 4-morpholinocarbonyl |
| 588 | Cl | 3-pyridyl | 2-methyl-1-imidazolyl |
| 589 | Cl | 3-pyridyl | 5-methyl-1-imidazolyl |
| 590 | Cl | 3-pyridyl | 2-methylsulfonyl-1-imidazolyl |
| 591 | Cl | 2-pyrimidyl | 2-(aminosulfonyl)phenyl |
| 592 | Cl | 2-pyrimidyl | 2-(methylaminosulfonyl)phenyl |
| 593 | Cl | 2-pyrimidyl | 1-pyrrolidinocarbonyl |
| 594 | Cl | 2-pyrimidyl | 2-(methylsulfonyl)phenyl |
| 595 | Cl | 2-pyrimidyl | 4-morpholino |
| 596 | Cl | 2-pyrimidyl | 2-(1'-CF$_3$-tetrazol-2-yl)phenyl |
| 597 | Cl | 2-pyrimidyl | 4-morpholinocarbonyl |
| 598 | Cl | 2-pyrimidyl | 2-methyl-1-imidazolyl |
| 599 | Cl | 2-pyrimidyl | 5-methyl-1-imidazolyl |
| 600 | Cl | 2-pyrimidyl | 2-methylsulfonyl-1-imidazolyl |
| 601 | Cl | 5-pyrimidyl | 2-(aminosulfonyl)phenyl |
| 602 | Cl | 5-pyrimidyl | 2-(methylaminosulfonyl)phenyl |

TABLE 2-continued

| | | | |
|---|---|---|---|
| 603 | Cl | 5-pyrimidyl | 1-pyrrolidinocarbonyl |
| 604 | Cl | 5-pyrimidyl | 2-(methylsulfonyl)phenyl |
| 605 | Cl | 5-pyrimidyl | 4-morpholino |
| 606 | Cl | 5-pyrimidyl | 2-(1'-$CF_3$-tetrazol-2-yl)phenyl |
| 607 | Cl | 5-pyrimidyl | 4-morpholinocarbonyl |
| 608 | Cl | 5-pyrimidyl | 2-methyl-1-imidazolyl |
| 609 | Cl | 5-pyrimidyl | 5-methyl-1-imidazolyl |
| 610 | Cl | 5-pyrimidyl | 2-methylsulfonyl-1-imidazolyl |
| 611 | Cl | 2-Cl-phenyl | 2-(aminosulfonyl)phenyl |
| 612 | Cl | 2-Cl-phenyl | 2-(methylaminosulfonyl)phenyl |
| 613 | Cl | 2-Cl-phenyl | 1-pyrrolidinocarbonyl |
| 614 | Cl | 2-Cl-phenyl | 2-(methylsulfonyl)phenyl |
| 615 | Cl | 2-Cl-phenyl | 4-morpholino |
| 616 | Cl | 2-Cl-phenyl | 2-(1'-$CF_3$-tetrazol-2-yl)phenyl |
| 617 | Cl | 2-Cl-phenyl | 4-morpholinocarbonyl |
| 618 | Cl | 2-Cl-phenyl | 2-methyl-1-imidazolyl |
| 619 | Cl | 2-Cl-phenyl | 5-methyl-1-imidazolyl |
| 620 | Cl | 2-Cl-phenyl | 2-methylsulfonyl-1-imidazolyl |
| 621 | Cl | 2-F-phenyl | 2-(aminosulfonyl)phenyl |
| 622 | Cl | 2-F-phenyl | 2-(methylaminosulfonyl)phenyl |
| 623 | Cl | 2-F-phenyl | 1-pyrrolidinocarbonyl |
| 624 | Cl | 2-F-phenyl | 2-(methylsulfonyl)phenyl |
| 625 | Cl | 2-F-phenyl | 4-morpholino |
| 626 | Cl | 2-F-phenyl | 2-(1'-$CF_3$-tetrazol-2-yl)phenyl |
| 627 | Cl | 2-F-phenyl | 4-morpholinocarbonyl |
| 628 | Cl | 2-F-phenyl | 2-methyl-1-imidazolyl |
| 629 | Cl | 2-F-phenyl | 5-methyl-1-imidazolyl |
| 630 | Cl | 2-F-phenyl | 2-methylsulfonyl-1-imidazolyl |
| 631 | Cl | 2,6-diF-phenyl | 2-(aminosulfonyl)phenyl |
| 632 | Cl | 2,6-diF-phenyl | 2-(methylaminosulfonyl)phenyl |
| 633 | Cl | 2,6-diF-phenyl | 1-pyrrolidinocarbonyl |
| 634 | Cl | 2,6-diF-phenyl | 2-(methylsulfonyl)phenyl |
| 635 | Cl | 2,6-diF-phenyl | 4-morpholino |
| 636 | Cl | 2,6-diF-phenyl | 2-(1'-$CF_3$-tetrazol-2-yl)phenyl |
| 637 | Cl | 2,6-diF-phenyl | 4-morpholinocarbonyl |
| 638 | Cl | 2,6-diF-phenyl | 2-methyl-1-imidazolyl |
| 639 | Cl | 2,6-diF-phenyl | 5-methyl-1-imidazolyl |
| 640 | Cl | 2,6-diF-phenyl | 2-methylsulfonyl-1-imidazolyl |
| 641 | F | phenyl | 2-(aminosulfonyl)phenyl |
| 642 | F | phenyl | 2-(methylaminosulfonyl)phenyl |
| 643 | F | phenyl | 1-pyrrolidinocarbonyl |
| 644 | F | phenyl | 2-(methylsulfonyl)phenyl |
| 645 | F | phenyl | 4-morpholino |
| 646 | F | phenyl | 2-(1'-$CF_3$-tetrazol-2-yl)phenyl |
| 647 | F | phenyl | 4-morpholinocarbonyl |
| 648 | F | phenyl | 2-methyl-1-imidazolyl |
| 649 | F | phenyl | 5-methyl-1-imidazolyl |
| 650 | F | phenyl | 2-methylsulfonyl-1-imidazolyl |
| 651 | F | 2-pyridyl | 2-(aminosulfonyl)phenyl |
| 652 | F | 2-pyridyl | 2-(methylaminosulfonyl)phenyl |
| 653 | F | 2-pyridyl | 1-pyrrolidinocarbonyl |
| 654 | F | 2-pyridyl | 2-(methylsulfonyl)phenyl |
| 655 | F | 2-pyridyl | 4-morpholino |
| 656 | F | 2-pyridyl | 2-(1'-$CF_3$-tetrazol-2-yl)phenyl |
| 657 | F | 2-pyridyl | 4-morpholinocarbonyl |
| 658 | F | 2-pyridyl | 2-methyl-1-imidazolyl |
| 659 | F | 2-pyridyl | 5-methyl-1-imidazolyl |
| 660 | F | 2-pyridyl | 2-methylsulfonyl-1-imidazolyl |
| 661 | F | 3-pyridyl | 2-(aminosulfonyl)phenyl |
| 662 | F | 3-pyridyl | 2-(methylaminosulfonyl)phenyl |
| 663 | F | 3-pyridyl | 1-pyrrolidinocarbonyl |
| 664 | F | 3-pyridyl | 2-(methylsulfonyl)phenyl |
| 665 | F | 3-pyridyl | 4-morpholino |
| 666 | F | 3-pyridyl | 2-(1'-$CF_3$-tetrazol-2-yl)phenyl |
| 667 | F | 3-pyridyl | 4-morpholinocarbonyl |
| 668 | F | 3-pyridyl | 2-methyl-1-imidazolyl |
| 669 | F | 3-pyridyl | 5-methyl-1-imidazolyl |
| 670 | F | 3-pyridyl | 2-methylsulfonyl-1-imidazolyl |
| 671 | F | 2-pyrimidyl | 2-(aminosulfonyl)phenyl |
| 672 | F | 2-pyrimidyl | 2-(methylaminosulfonyl)phenyl |
| 673 | F | 2-pyrimidyl | 1-pyrrolidinocarbonyl |
| 674 | F | 2-pyrimidyl | 2-(methylsulfonyl)phenyl |
| 675 | F | 2-pyrimidyl | 4-morpholino |
| 676 | F | 2-pyrimidyl | 2-(1'-$CF_3$-tetrazol-2-yl)phenyl |
| 677 | F | 2-pyrimidyl | 4-morpholinocarbonyl |
| 678 | F | 2-pyrimidyl | 2-methyl-1-imidazolyl |
| 679 | F | 2-pyrimidyl | 5-methyl-1-imidazolyl |
| 680 | F | 2-pyrimidyl | 2-methylsulfonyl-1-imidazolyl |
| 681 | F | 5-pyrimidyl | 2-(aminosulfonyl)phenyl |

TABLE 2-continued

| | | | |
|---|---|---|---|
| 682 | F | 5-pyrimidyl | 2-(methylaminosulfonyl)phenyl |
| 683 | F | 5-pyrimidyl | 1-pyrrolidinocarbonyl |
| 684 | F | 5-pyrimidyl | 2-(methylsulfonyl)phenyl |
| 685 | F | 5-pyrimidyl | 4-morpholino |
| 686 | F | 5-pyrimidyl | 2-(1'-$CF_3$-tetrazol-2-yl)phenyl |
| 687 | F | 5-pyrimidyl | 4-morpholinocarbonyl |
| 688 | F | 5-pyrimidyl | 2-methyl-1-imidazolyl |
| 689 | F | 5-pyrimidyl | 5-methyl-1-imidazolyl |
| 690 | F | 5-pyrimidyl | 2-methylsulfonyl-1-imidazolyl |
| 691 | F | 2-Cl-phenyl | 2-(aminosulfonyl)phenyl |
| 692 | F | 2-Cl-phenyl | 2-(methylaminosulfonyl)phenyl |
| 693 | F | 2-Cl-phenyl | 1-pyrrolidinocarbonyl |
| 694 | F | 2-Cl-phenyl | 2-(methylsulfonyl)phenyl |
| 695 | F | 2-Cl-phenyl | 4-morpholino |
| 696 | F | 2-Cl-phenyl | 2-(1'-$CF_3$-tetrazol-2-yl)phenyl |
| 697 | F | 2-Cl-phenyl | 4-morpholinocarbonyl |
| 698 | F | 2-Cl-phenyl | 2-methyl-1-imidazolyl |
| 699 | F | 2-Cl-phenyl | 5-methyl-1-imidazolyl |
| 700 | F | 2-Cl-phenyl | 2-methylsulfonyl-1-imidazolyl |
| 701 | F | 2-F-phenyl | 2-(aminosulfonyl)phenyl |
| 702 | F | 2-F-phenyl | 2-(methylaminosulfonyl)phenyl |
| 703 | F | 2-F-phenyl | 1-pyrrolidinocarbonyl |
| 704 | F | 2-F-phenyl | 2-(methylsulfonyl)phenyl |
| 705 | F | 2-F-phenyl | 4-morpholino |
| 706 | F | 2-F-phenyl | 2-(1'-$CF_3$-tetrazol-2-yl)phenyl |
| 707 | F | 2-F-phenyl | 4-morpholinocarbonyl |
| 708 | F | 2-F-phenyl | 2-methyl-1-imidazolyl |
| 709 | F | 2-F-phenyl | 5-methyl-1-imidazolyl |
| 710 | F | 2-F-phenyl | 2-methylsulfonyl-1-imidazolyl |
| 711 | F | 2,6-diF-phenyl | 2-(aminosulfonyl)phenyl |
| 712 | F | 2,6-diF-phenyl | 2-(methylaminosulfonyl)phenyl |
| 713 | F | 2,6-diF-phenyl | 1-pyrrolidinocarbonyl |
| 714 | F | 2,6-diF-phenyl | 2-(methylsulfonyl)phenyl |
| 715 | F | 2,6-diF-phenyl | 4-morpholino |
| 716 | F | 2,6-diF-phenyl | 2-(1'-$CF_3$-tetrazol-2-yl)phenyl |
| 717 | F | 2,6-diF-phenyl | 4-morpholinocarbonyl |
| 718 | F | 2,6-diF-phenyl | 2-methyl-1-imidazolyl |
| 719 | F | 2,6-diF-phenyl | 5-methyl-1-imidazolyl |
| 720 | F | 2,6-diF-phenyl | 2-methylsulfonyl-1-imidazolyl |
| 721 | $CO_2CH_3$ | phenyl | 2-(aminosulfonyl)phenyl |
| 722 | $CO_2CH_3$ | phenyl | 2-(methylaminosulfonyl)phenyl |
| 723 | $CO_2CH_3$ | phenyl | 1-pyrrolidinocarbonyl |
| 724 | $CO_2CH_3$ | phenyl | 2-(methylsulfonyl)phenyl |
| 725 | $CO_2CH_3$ | phenyl | 4-morpholino |
| 726 | $CO_2CH_3$ | phenyl | 2-(1'-$CF_3$-tetrazol-2-yl)phenyl |
| 727 | $CO_2CH_3$ | phenyl | 4-morpholinocarbonyl |
| 728 | $CO_2CH_3$ | phenyl | 2-methyl-1-imidazolyl |
| 729 | $CO_2CH_3$ | phenyl | 5-methyl-1-imidazolyl |
| 730 | $CO_2CH_3$ | phenyl | 2-methylsulfonyl-1-imidazolyl |
| 731 | $CO_2CH_3$ | 2-pyridyl | 2-(aminosulfonyl)phenyl |
| 732 | $CO_2CH_3$ | 2-pyridyl | 2-(methylaminosulfonyl)phenyl |
| 733 | $CO_2CH_3$ | 2-pyridyl | 1-pyrrolidinocarbonyl |
| 734 | $CO_2CH_3$ | 2-pyridyl | 2-(methylsulfonyl)phenyl |
| 735 | $CO_2CH_3$ | 2-pyridyl | 4-morpholino |
| 736 | $CO_2CH_3$ | 2-pyridyl | 2-(1'-$CF_3$-tetrazol-2-yl)phenyl |
| 737 | $CO_2CH_3$ | 2-pyridyl | 4-morpholinocarbonyl |
| 738 | $CO_2CH_3$ | 2-pyridyl | 2-methyl-1-imidazolyl |
| 739 | $CO_2CH_3$ | 2-pyridyl | 5-methyl-1-imidazolyl |
| 740 | $CO_2CH_3$ | 2-pyridyl | 2-methylsulfonyl-1-imidazolyl |
| 741 | $CO_2CH_3$ | 3-pyridyl | 2-(aminosulfonyl)phenyl |
| 742 | $CO_2CH_3$ | 3-pyridyl | 2-(methylaminosulfonyl)phenyl |
| 743 | $CO_2CH_3$ | 3-pyridyl | 1-pyrrolidinocarbonyl |
| 744 | $CO_2CH_3$ | 3-pyridyl | 2-(methylsulfonyl)phenyl |
| 745 | $CO_2CH_3$ | 3-pyridyl | 4-morpholino |
| 746 | $CO_2CH_3$ | 3-pyridyl | 2-(1'-$CF_3$-tetrazol-2-yl)phenyl |
| 747 | $CO_2CH_3$ | 3-pyridyl | 4-morpholinocarbonyl |
| 748 | $CO_2CH_3$ | 3-pyridyl | 2-methyl-1-imidazolyl |
| 749 | $CO_2CH_3$ | 3-pyridyl | 5-methyl-1-imidazolyl |
| 750 | $CO_2CH_3$ | 3-pyridyl | 2-methylsulfonyl-1-imidazolyl |
| 751 | $CO_2CH_3$ | 2-pyrimidyl | 2-(aminosulfonyl)phenyl |
| 752 | $CO_2CH_3$ | 2-pyrimidyl | 2-(methylaminosulfonyl)phenyl |
| 753 | $CO_2CH_3$ | 2-pyrimidyl | 1-pyrrolidinocarbonyl |
| 754 | $CO_2CH_3$ | 2-pyrimidyl | 2-(methylsulfonyl)phenyl |
| 755 | $CO_2CH_3$ | 2-pyrimidyl | 4-morpholino |
| 756 | $CO_2CH_3$ | 2-pyrimidyl | 2-(1'-$CF_3$-tetrazol-2-yl)phenyl |
| 757 | $CO_2CH_3$ | 2-pyrimidyl | 4-morpholinocarbonyl |
| 758 | $CO_2CH_3$ | 2-pyrimidyl | 2-methyl-1-imidazolyl |
| 759 | $CO_2CH_3$ | 2-pyrimidyl | 5-methyl-1-imidazolyl |
| 760 | $CO_2CH_3$ | 2-pyrimidyl | 2-methylsulfonyl-1-imidazolyl |

TABLE 2-continued

| | | | |
|---|---|---|---|
| 761 | $CO_2CH_3$ | 5-pyrimidyl | 2-(aminosulfonyl)phenyl |
| 762 | $CO_2CH_3$ | 5-pyrimidyl | 2-(methylaminosulfonyl)phenyl |
| 763 | $CO_2CH_3$ | 5-pyrimidyl | 1-pyrrolidinocarbonyl |
| 764 | $CO_2CH_3$ | 5-pyrimidyl | 2-(methylsulfonyl)phenyl |
| 765 | $CO_2CH_3$ | 5-pyrimidyl | 4-morpholino |
| 766 | $CO_2CH_3$ | 5-pyrimidyl | 2-(1'-$CF_3$-tetrazol-2-yl)phenyl |
| 767 | $CO_2CH_3$ | 5-pyrimidyl | 4-morpholinocarbonyl |
| 768 | $CO_2CH_3$ | 5-pyrimidyl | 2-methyl-1-imidazolyl |
| 769 | $CO_2CH_3$ | 5-pyrimidyl | 5-methyl-1-imidazolyl |
| 770 | $CO_2CH_3$ | 5-pyrimidyl | 2-methylsulfonyl-1-imidazolyl |
| 771 | $CO_2CH_3$ | 2-Cl-phenyl | 2-(aminosulfonyl)phenyl |
| 772 | $CO_2CH_3$ | 2-Cl-phenyl | 2-(methylaminosulfonyl)phenyl |
| 773 | $CO_2CH_3$ | 2-Cl-phenyl | 1-pyrrolidinocarbonyl |
| 774 | $CO_2CH_3$ | 2-Cl-phenyl | 2-(methylsulfonyl)phenyl |
| 775 | $CO_2CH_3$ | 2-Cl-phenyl | 4-morpholino |
| 776 | $CO_2CH_3$ | 2-Cl-phenyl | 2-(1'-$CF_3$-tetrazol-2-yl)phenyl |
| 777 | $CO_2CH_3$ | 2-Cl-phenyl | 4-morpholinocarbonyl |
| 778 | $CO_2CH_3$ | 2-Cl-phenyl | 2-methyl-1-imidazolyl |
| 779 | $CO_2CH_3$ | 2-Cl-phenyl | 5-methyl-1-imidazolyl |
| 780 | $CO_2CH_3$ | 2-Cl-phenyl | 2-methylsulfonyl-1-imidazolyl |
| 781 | $CO_2CH_3$ | 2-F-phenyl | 2-(aminosulfonyl)phenyl |
| 782 | $CO_2CH_3$ | 2-F-phenyl | 2-(methylaminosulfonyl)phenyl |
| 783 | $CO_2CH_3$ | 2-F-phenyl | 1-pyrrolidinocarbonyl |
| 784 | $CO_2CH_3$ | 2-F-phenyl | 2-(methylsulfonyl)phenyl |
| 785 | $CO_2CH_3$ | 2-F-phenyl | 4-morpholino |
| 786 | $CO_2CH_3$ | 2-F-phenyl | 2-(1'-$CF_3$-tetrazol-2-yl)phenyl |
| 787 | $CO_2CH_3$ | 2-F-phenyl | 4-morpholinocarbonyl |
| 788 | $CO_2CH_3$ | 2-F-phenyl | 2-methyl-1-imidazolyl |
| 789 | $CO_2CH_3$ | 2-F-phenyl | 5-methyl-1-imidazolyl |
| 790 | $CO_2CH_3$ | 2-F-phenyl | 2-methylsulfonyl-1-imidazolyl |
| 791 | $CO_2CH_3$ | 2,6-diF-phenyl | 2-(aminosulfonyl)phenyl |
| 792 | $CO_2CH_3$ | 2,6-diF-phenyl | 2-(methylaminosulfonyl)phenyl |
| 793 | $CO_2CH_3$ | 2,6-diF-phenyl | 1-pyrrolidinocarbonyl |
| 794 | $CO_2CH_3$ | 2,6-diF-phenyl | 2-(methylsulfonyl)phenyl |
| 795 | $CO_2CH_3$ | 2,6-diF-phenyl | 4-morpholino |
| 796 | $CO_2CH_3$ | 2,6-diF-phenyl | 2-(1'-$CF_3$-tetrazol-2-yl)phenyl |
| 797 | $CO_2CH_3$ | 2,6-diF-phenyl | 4-morpholinocarbonyl |
| 798 | $CO_2CH_3$ | 2,6-diF-phenyl | 2-methyl-1-imidazolyl |
| 799 | $CO_2CH_3$ | 2,6-diF-phenyl | 5-methyl-1-imidazolyl |
| 800 | $CO_2CH_3$ | 2,6-diF-phenyl | 2-methylsulfonyl-1-imidazolyl |
| 801 | $CH_2OCH_3$ | phenyl | 2-(aminosulfonyl)phenyl |
| 802 | $CH_2OCH_3$ | phenyl | 2-(methylaminosulfonyl)phenyl |
| 803 | $CH_2OCH_3$ | phenyl | 1-pyrrolidinocarbonyl |
| 804 | $CH_2OCH_3$ | phenyl | 2-(methylsulfonyl)phenyl |
| 805 | $CH_2OCH_3$ | phenyl | 4-morpholino |
| 806 | $CH_2OCH_3$ | phenyl | 2-(1'-$CF_3$-tetrazol-2-yl)phenyl |
| 807 | $CH_2OCH_3$ | phenyl | 4-morpholinocarbonyl |
| 808 | $CH_2OCH_3$ | phenyl | 2-methyl-1-imidazolyl |
| 809 | $CH_2OCH_3$ | phenyl | 5-methyl-1-imidazolyl |
| 810 | $CH_2OCH_3$ | phenyl | 2-methylsulfonyl-1-imidazolyl |
| 811 | $CH_2OCH_3$ | 2-pyridyl | 2-(aminosulfonyl)phenyl |
| 812 | $CH_2OCH_3$ | 2-pyridyl | 2-(methylaminosulfonyl)phenyl |
| 813 | $CH_2OCH_3$ | 2-pyridyl | 1-pyrrolidinocarbonyl |
| 814 | $CH_2OCH_3$ | 2-pyridyl | 2-(methylsulfonyl)phenyl |
| 815 | $CH_2OCH_3$ | 2-pyridyl | 4-morpholino |
| 816 | $CH_2OCH_3$ | 2-pyridyl | 2-(1'-$CF_3$-tetrazol-2-yl)phenyl |
| 817 | $CH_2OCH_3$ | 2-pyridyl | 4-morpholinocarbonyl |
| 818 | $CH_2OCH_3$ | 2-pyridyl | 2-methyl-1-imidazolyl |
| 819 | $CH_2OCH_3$ | 2-pyridyl | 5-methyl-1-imidazolyl |
| 820 | $CH_2OCH_3$ | 2-pyridyl | 2-methylsulfonyl-1-imidazolyl |
| 821 | $CH_2OCH_3$ | 3-pyridyl | 2-(aminosulfonyl)phenyl |
| 822 | $CH_2OCH_3$ | 3-pyridyl | 2-(methylaminosulfonyl)phenyl |
| 823 | $CH_2OCH_3$ | 3-pyridyl | 1-pyrrolidinocarbonyl |
| 824 | $CH_2OCH_3$ | 3-pyridyl | 2-(methylsulfonyl)phenyl |
| 825 | $CH_2OCH_3$ | 3-pyridyl | 4-morpholino |
| 826 | $CH_2OCH_3$ | 3-pyridyl | 2-(1'-$CF_3$-tetrazol-2-yl)phenyl |
| 827 | $CH_2OCH_3$ | 3-pyridyl | 4-morpholinocarbonyl |
| 828 | $CH_2OCH_3$ | 3-pyridyl | 2-methyl-1-imidazolyl |
| 829 | $CH_2OCH_3$ | 3-pyridyl | 5-methyl-1-imidazolyl |
| 830 | $CH_2OCH_3$ | 3-pyridyl | 2-methylsulfonyl-1-imidazolyl |
| 831 | $CH_2OCH_3$ | 2-pyrimidyl | 2-(aminosulfonyl)phenyl |
| 832 | $CH_2OCH_3$ | 2-pyrimidyl | 2-(methylaminosulfonyl)phenyl |
| 833 | $CH_2OCH_3$ | 2-pyrimidyl | 1-pyrrolidinocarbonyl |
| 834 | $CH_2OCH_3$ | 2-pyrimidyl | 2-(methylsulfonyl)phenyl |
| 835 | $CH_2OCH_3$ | 2-pyrimidyl | 4-morpholino |
| 836 | $CH_2OCH_3$ | 2-pyrimidyl | 2-(1'-$CF_3$-tetrazol-2-yl)phenyl |
| 837 | $CH_2OCH_3$ | 2-pyrimidyl | 4-morpholinocarbonyl |
| 838 | $CH_2OCH_3$ | 2-pyrimidyl | 2-methyl-1-imidazolyl |
| 839 | $CH_2OCH_3$ | 2-pyrimidyl | 5-methyl-1-imidazolyl |

TABLE 2-continued

| | | | |
|---|---|---|---|
| 840 | $CH_2OCH_3$ | 2-pyrimidyl | 2-methylsulfonyl-1-imidazolyl |
| 841 | $CH_2OCH_3$ | 5-pyrimidyl | 2-(aminosulfonyl)phenyl |
| 842 | $CH_2OCH_3$ | 5-pyrimidyl | 2-(methylaminosulfonyl)phenyl |
| 843 | $CH_2OCH_3$ | 5-pyrimidyl | 1-pyrrolidinocarbonyl |
| 844 | $CH_2OCH_3$ | 5-pyrimidyl | 2-(methylsulfonyl)phenyl |
| 845 | $CH_2OCH_3$ | 5-pyrimidyl | 4-morpholino |
| 846 | $CH_2OCH_3$ | 5-pyrimidyl | 2-(1'-$CF_3$-tetrazol-2-yl)phenyl |
| 847 | $CH_2OCH_3$ | 5-pyrimidyl | 4-morpholinocarbonyl |
| 848 | $CH_2OCH_3$ | 5-pyrimidyl | 2-methyl-1-imidazolyl |
| 849 | $CH_2OCH_3$ | 5-pyrimidyl | 5-methyl-1-imidazolyl |
| 850 | $CH_2OCH_3$ | 5-pyrimidyl | 2-methylsulfonyl-1-imidazolyl |
| 851 | $CH_2OCH_3$ | 2-Cl-phenyl | 2-(aminosulfonyl)phenyl |
| 852 | $CH_2OCH_3$ | 2-Cl-phenyl | 2-(methylaminosulfonyl)phenyl |
| 853 | $CH_2OCH_3$ | 2-Cl-phenyl | 1-pyrrolidinocarbonyl |
| 854 | $CH_2OCH_3$ | 2-Cl-phenyl | 2-(methylsulfonyl)phenyl |
| 855 | $CH_2OCH_3$ | 2-Cl-phenyl | 4-morpholino |
| 856 | $CH_2OCH_3$ | 2-Cl-phenyl | 2-(1'-$CF_3$-tetrazol-2-yl)phenyl |
| 857 | $CH_2OCH_3$ | 2-Cl-phenyl | 4-morpholinocarbonyl |
| 858 | $CH_2OCH_3$ | 2-Cl-phenyl | 2-methyl-1-imidazolyl |
| 859 | $CH_2OCH_3$ | 2-Cl-phenyl | 5-methyl-1-imidazolyl |
| 860 | $CH_2OCH_3$ | 2-Cl-phenyl | 2-methylsulfonyl-1-imidazolyl |
| 861 | $CH_2OCH_3$ | 2-F-phenyl | 2-(aminosulfonyl)phenyl |
| 862 | $CH_2OCH_3$ | 2-F-phenyl | 2-(methylaminosulfonyl)phenyl |
| 863 | $CH_2OCH_3$ | 2-F-phenyl | 1-pyrrolidinocarbonyl |
| 864 | $CH_2OCH_3$ | 2-F-phenyl | 2-(methylsulfonyl)phenyl |
| 865 | $CH_2OCH_3$ | 2-F-phenyl | 4-morpholino |
| 866 | $CH_2OCH_3$ | 2-F-phenyl | 2-(1'-$CF_3$-tetrazol-2-yl)phenyl |
| 867 | $CH_2OCH_3$ | 2-F-phenyl | 4-morpholinocarbonyl |
| 868 | $CH_2OCH_3$ | 2-F-phenyl | 2-methyl-1-imidazolyl |
| 869 | $CH_2OCH_3$ | 2-F-phenyl | 5-methyl-1-imidazolyl |
| 870 | $CH_2OCH_3$ | 2-F-phenyl | 2-methylsulfonyl-1-imidazolyl |
| 871 | $CH_2OCH_3$ | 2,6-diF-phenyl | 2-(aminosulfonyl)phenyl |
| 872 | $CH_2OCH_3$ | 2,6-diF-phenyl | 2-(methylaminosulfonyl)phenyl |
| 873 | $CH_2OCH_3$ | 2,6-diF-phenyl | 1-pyrrolidinocarbonyl |
| 874 | $CH_2OCH_3$ | 2,6-diF-phenyl | 2-(methylsulfonyl)phenyl |
| 875 | $CH_2OCH_3$ | 2,6-diF-phenyl | 4-morpholino |
| 876 | $CH_2OCH_3$ | 2,6-diF-phenyl | 2-(1'-$CF_3$-tetrazol-2-yl)phenyl |
| 877 | $CH_2OCH_3$ | 2,6-diF-phenyl | 4-morpholinocarbonyl |
| 878 | $CH_2OCH_3$ | 2,6-diF-phenyl | 2-methyl-1-imidazolyl |
| 879 | $CH_2OCH_3$ | 2,6-diF-phenyl | 5-methyl-1-imidazolyl |
| 880 | $CH_2OCH_3$ | 2,6-diF-phenyl | 2-methylsulfonyl-1-imidazolyl |
| 881 | $CONH_2$ | phenyl | 2-(aminosulfonyl)phenyl |
| 882 | $CONH_2$ | phenyl | 2-(methylaminosulfonyl)phenyl |
| 883 | $CONH_2$ | phenyl | 1-pyrrolidinocarbonyl |
| 884 | $CONH_2$ | phenyl | 2-(methylsulfonyl)phenyl |
| 885 | $CONH_2$ | phenyl | 4-morpholino |
| 886 | $CONH_2$ | phenyl | 2-(1'-$CF_3$-tetrazol-2-yl)phenyl |
| 887 | $CONH_2$ | phenyl | 4-morpholinocarbonyl |
| 888 | $CONH_2$ | phenyl | 2-methyl-1-imidazolyl |
| 889 | $CONH_2$ | phenyl | 5-methyl-1-imidazolyl |
| 890 | $CONH_2$ | phenyl | 2-methylsulfonyl-1-imidazolyl |
| 891 | $CONH_2$ | 2-pyridyl | 2-(aminosulfonyl)phenyl |
| 892 | $CONH_2$ | 2-pyridyl | 2-(methylaminosulfonyl)phenyl |
| 893 | $CONH_2$ | 2-pyridyl | 1-pyrrolidinocarbonyl |
| 894 | $CONH_2$ | 2-pyridyl | 2-(methylsulfonyl)phenyl |
| 895 | $CONH_2$ | 2-pyridyl | 4-morpholino |
| 896 | $CONH_2$ | 2-pyridyl | 2-(1'-$CF_3$-tetrazol-2-yl)phenyl |
| 897 | $CONH_2$ | 2-pyridyl | 4-morpholinocarbonyl |
| 898 | $CONH_2$ | 2-pyridyl | 2-methyl-1-imidazolyl |
| 899 | $CONH_2$ | 2-pyridyl | 5-methyl-1-imidazolyl |
| 900 | $CONH_2$ | 2-pyridyl | 2-methylsulfonyl-1-imidazolyl |
| 901 | $CONH_2$ | 3-pyridyl | 2-(aminosulfonyl)phenyl |
| 902 | $CONH_2$ | 3-pyridyl | 2-(methylaminosulfonyl)phenyl |
| 903 | $CONH_2$ | 3-pyridyl | 1-pyrrolidinocarbonyl |
| 904 | $CONH_2$ | 3-pyridyl | 2-(methylsulfonyl)phenyl |
| 905 | $CONH_2$ | 3-pyridyl | 4-morpholino |
| 906 | $CONH_2$ | 3-pyridyl | 2-(1'-$CF_3$-tetrazol-2-yl)phenyl |
| 907 | $CONH_2$ | 3-pyridyl | 4-morpholinocarbonyl |
| 908 | $CONH_2$ | 3-pyridyl | 2-methyl-1-imidazolyl |
| 909 | $CONH_2$ | 3-pyridyl | 5-methyl-1-imidazolyl |
| 910 | $CONH_2$ | 3-pyridyl | 2-methylsulfonyl-1-imidazolyl |
| 911 | $CONH_2$ | 2-pyrimidyl | 2-(aminosulfonyl)phenyl |
| 912 | $CONH_2$ | 2-pyrimidyl | 2-(methylaminosulfonyl)phenyl |
| 913 | $CONH_2$ | 2-pyrimidyl | 1-pyrrolidinocarbonyl |
| 914 | $CONH_2$ | 2-pyrimidyl | 2-(methylsulfonyl)phenyl |
| 915 | $CONH_2$ | 2-pyrimidyl | 4-morpholino |
| 916 | $CONH_2$ | 2-pyrimidyl | 2-(1'-$CF_3$-tetrazol-2-yl)phenyl |
| 917 | $CONH_2$ | 2-pyrimidyl | 4-morpholinocarbonyl |
| 918 | $CONH_2$ | 2-pyrimidyl | 2-methyl-1-imidazolyl |

TABLE 2-continued

| | | | |
|---|---|---|---|
| 919 | CONH$_2$ | 2-pyrimidyl | 5-methyl-1-imidazolyl |
| 920 | CONH$_2$ | 2-pyrimidyl | 2-methylsulfonyl-1-imidazolyl |
| 921 | CONH$_2$ | 5-pyrimidyl | 2-(aminosulfonyl)phenyl |
| 922 | CONH$_2$ | 5-pyrimidyl | 2-(methylaminosulfonyl)phenyl |
| 923 | CONH$_2$ | 5-pyrimidyl | 1-pyrrolidinocarbonyl |
| 924 | CONH$_2$ | 5-pyrimidyl | 2-(methylsulfonyl)phenyl |
| 925 | CONH$_2$ | 5-pyrimidyl | 4-morpholino |
| 926 | CONH$_2$ | 5-pyrimidyl | 2-(1'-CF$_3$-tetrazol-2-yl)phenyl |
| 927 | CONH$_2$ | 5-pyrimidyl | 4-morpholinocarbonyl |
| 928 | CONH$_2$ | 5-pyrimidyl | 2-methyl-1-imidazolyl |
| 929 | CONH$_2$ | 5-pyrimidyl | 5-methyl-1-imidazolyl |
| 930 | CONH$_2$ | 5-pyrimidyl | 2-methylsulfonyl-1-imidazolyl |
| 931 | CONH$_2$ | 2-Cl-phenyl | 2-(aminosulfonyl)phenyl |
| 932 | CONH$_2$ | 2-Cl-phenyl | 2-(methylaminosulfonyl)phenyl |
| 933 | CONH$_2$ | 2-Cl-phenyl | 1-pyrrolidinocarbonyl |
| 934 | CONH$_2$ | 2-Cl-phenyl | 2-(methylsulfonyl)phenyl |
| 935 | CONH$_2$ | 2-Cl-phenyl | 4-morpholino |
| 936 | CONH$_2$ | 2-Cl-phenyl | 2-(1'-CF$_3$-tetrazol-2-yl)phenyl |
| 937 | CONH$_2$ | 2-Cl-phenyl | 4-morpholinocarbonyl |
| 938 | CONH$_2$ | 2-Cl-phenyl | 2-methyl-1-imidazolyl |
| 939 | CONH$_2$ | 2-Cl-phenyl | 5-methyl-1-imidazolyl |
| 940 | CONH$_2$ | 2-Cl-phenyl | 2-methylsulfonyl-1-imidazolyl |
| 941 | CONH$_2$ | 2-F-phenyl | 2-(aminosulfonyl)phenyl |
| 942 | CONH$_2$ | 2-F-phenyl | 2-(methylaminosulfonyl)phenyl |
| 943 | CONH$_2$ | 2-F-phenyl | 1-pyrrolidinocarbonyl |
| 944 | CONH$_2$ | 2-F-phenyl | 2-(methylsulfonyl)phenyl |
| 945 | CONH$_2$ | 2-F-phenyl | 4-morpholino |
| 946 | CONH$_2$ | 2-F-phenyl | 2-(1'-CF$_3$-tetrazol-2-yl)phenyl |
| 947 | CONH$_2$ | 2-F-phenyl | 4-morpholinocarbonyl |
| 948 | CONH$_2$ | 2-F-phenyl | 2-methyl-1-imidazolyl |
| 949 | CONH$_2$ | 2-F-phenyl | 5-methyl-1-imidazolyl |
| 950 | CONH$_2$ | 2-F-phenyl | 2-methylsulfonyl-1-imidazolyl |
| 951 | CONH$_2$ | 2,6-diF-phenyl | 2-(aminosulfonyl)phenyl |
| 952 | CONH$_2$ | 2,6-diF-phenyl | 2-(methylaminosulfonyl)phenyl |
| 953 | CONH$_2$ | 2,6-diF-phenyl | 1-pyrrolidinocarbonyl |
| 954 | CONH$_2$ | 2,6-diF-phenyl | 2-(methylsulfonyl)phenyl |
| 955 | CONH$_2$ | 2,6-diF-phenyl | 4-morpholino |
| 956 | CONH$_2$ | 2,6-diF-phenyl | 2-(1'-CF$_3$-tetrazol-2-yl)phenyl |
| 957 | CONH$_2$ | 2,6-diF-phenyl | 4-morpholinocarbonyl |
| 958 | CONH$_2$ | 2,6-diF-phenyl | 2-methyl-1-imidazolyl |
| 959 | CONH$_2$ | 2,6-diF-phenyl | 5-methyl-1-imidazolyl |
| 960 | CONH$_2$ | 2,6-diF-phenyl | 2-methylsulfonyl-1-imidazolyl |

TABLE 3

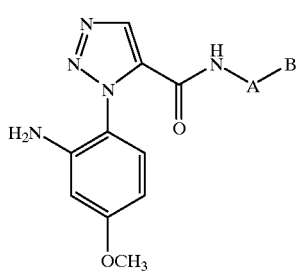

a

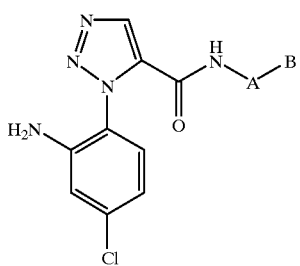

b

TABLE 3-continued

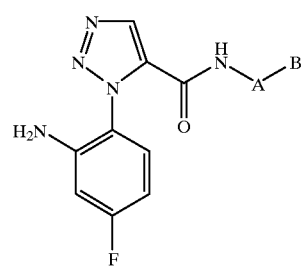

c

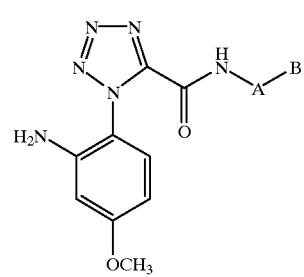

d e

TABLE 3-continued
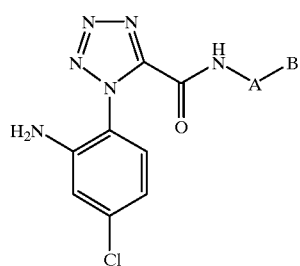 e
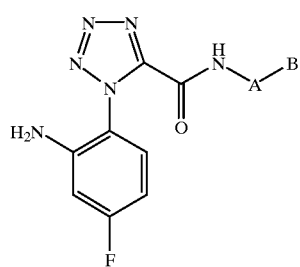 f
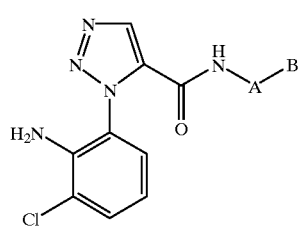 g
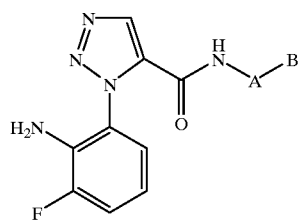 h
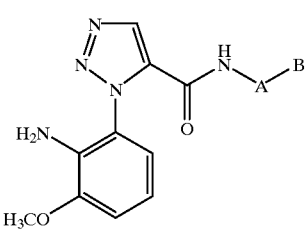 i
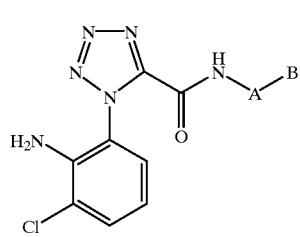 j
TABLE 3-continued
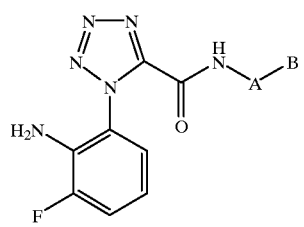 k
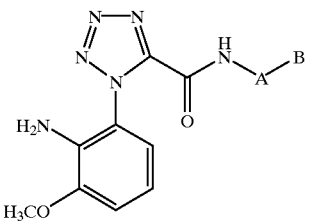 l
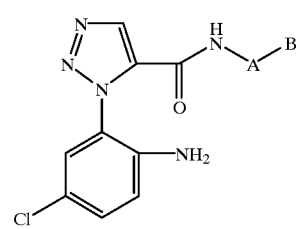 m
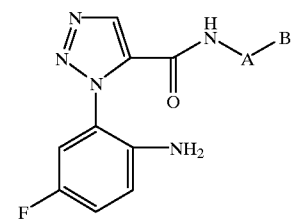 n
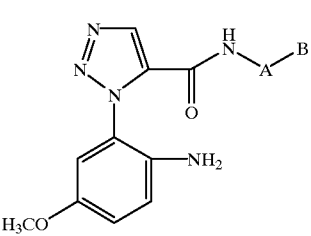 o
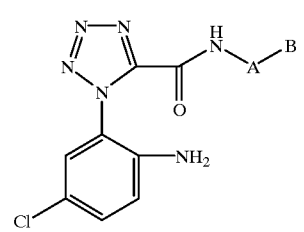 p
q TABLE 3-continued
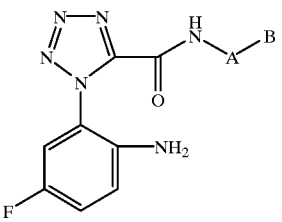
r
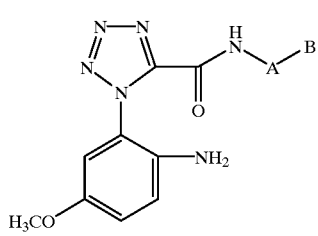
s
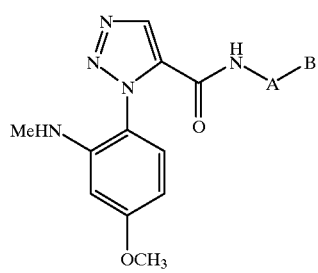
t
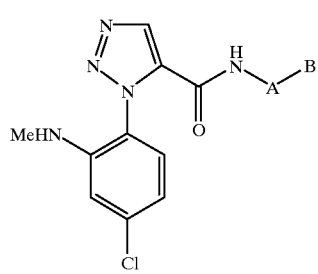
u
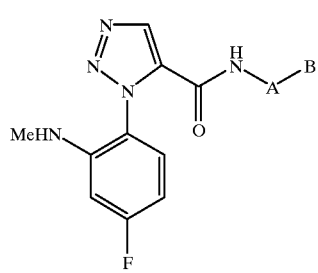
v
TABLE 3-continued
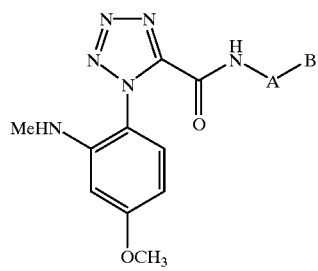
w
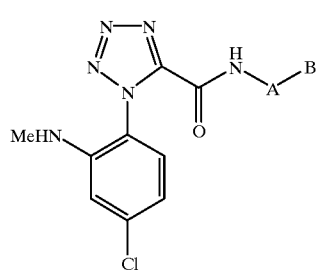
x
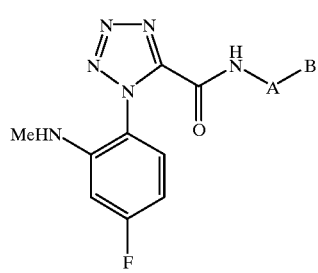
y
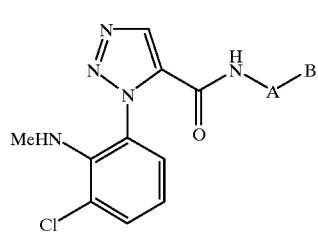
z
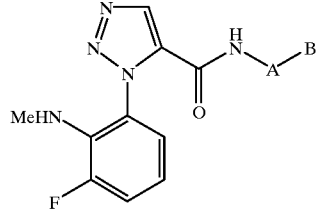
aa TABLE 3-continued
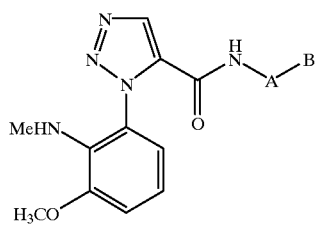
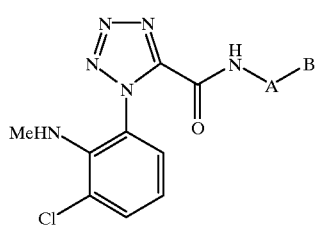
bb
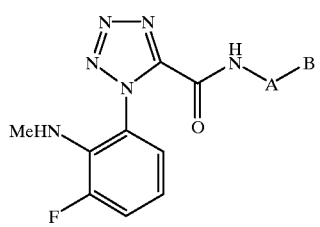
cc
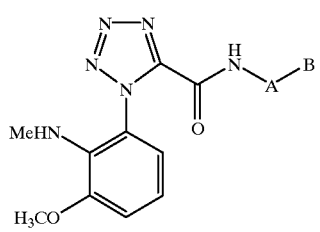
dd
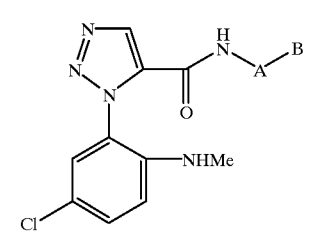
ee
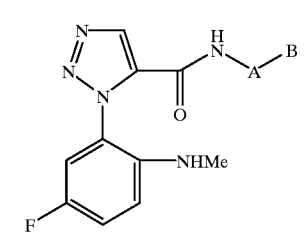
ff
gg
TABLE 3-continued
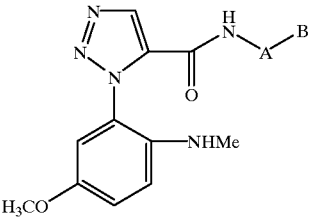
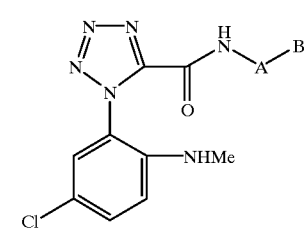
hh
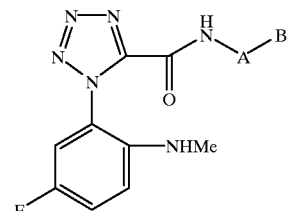
ii
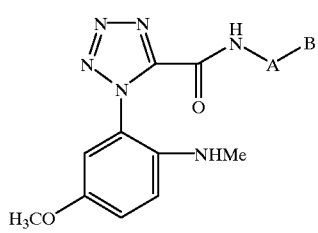
jj
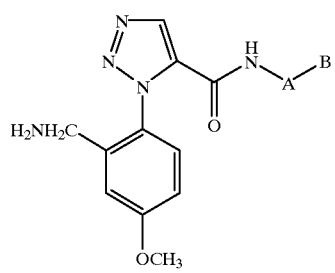
kk
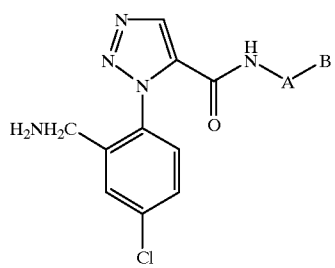
ll TABLE 3-continued
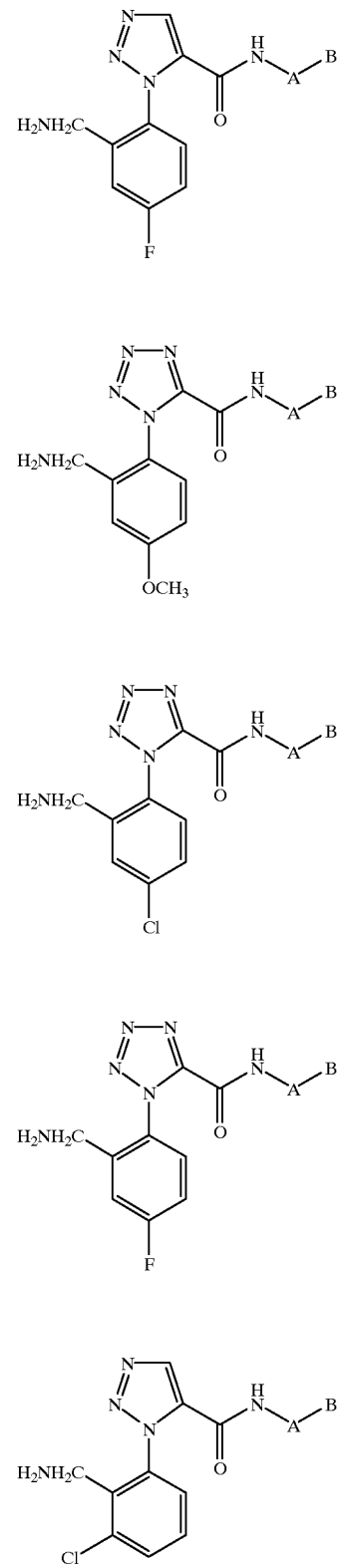
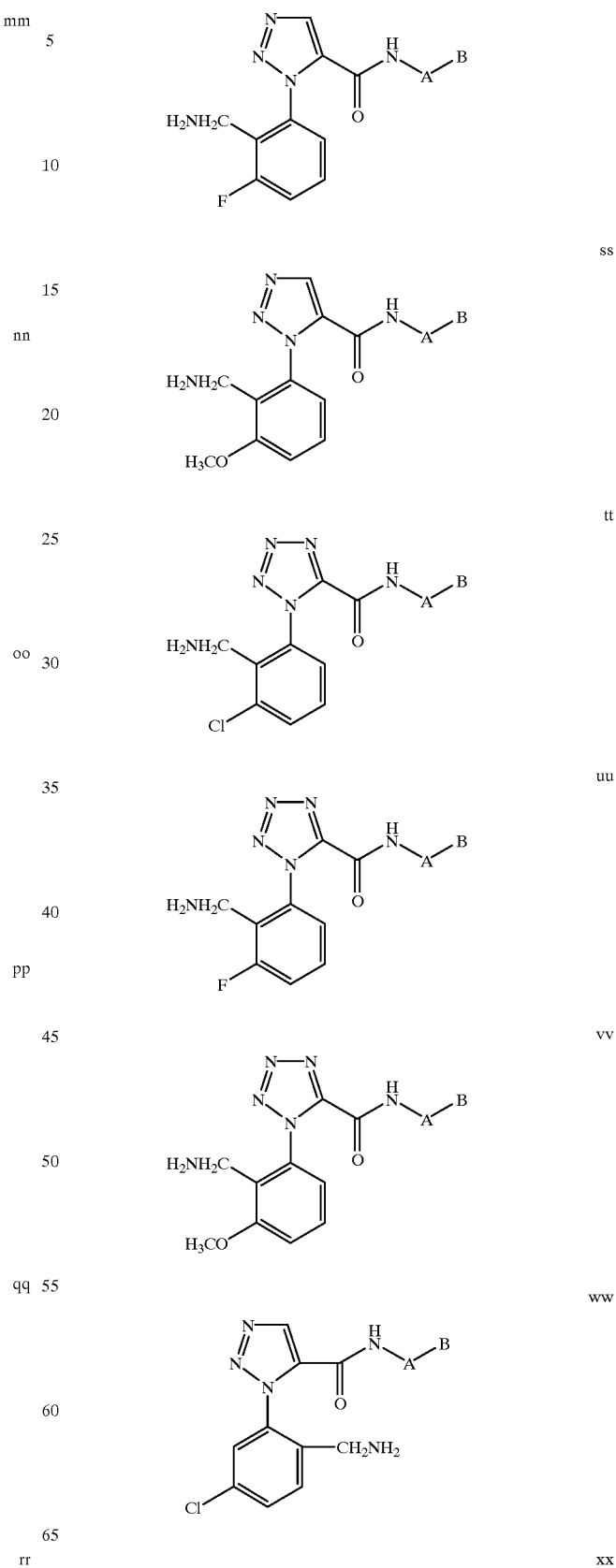

TABLE 3-continued
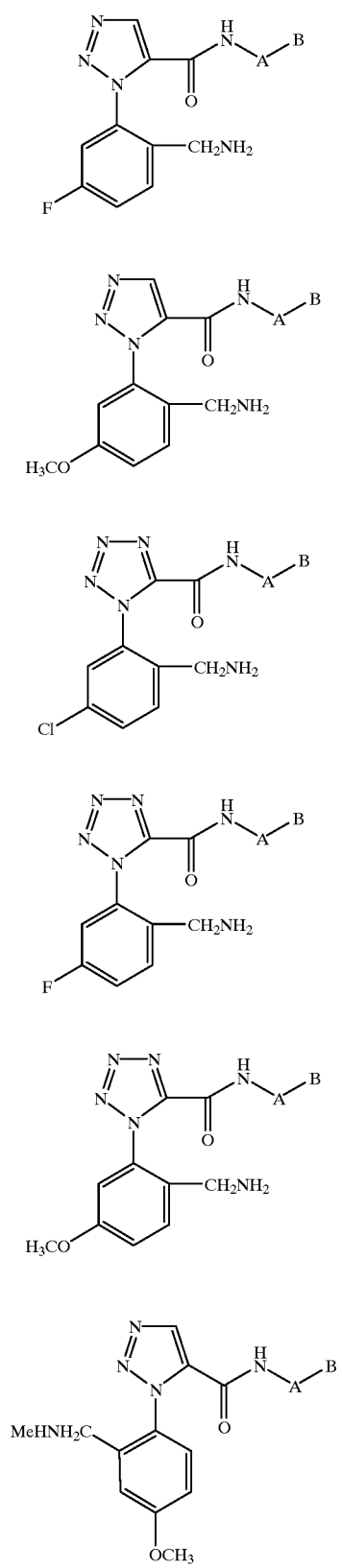
yy
zz
aaa
bbb
ccc
ddd
TABLE 3-continued
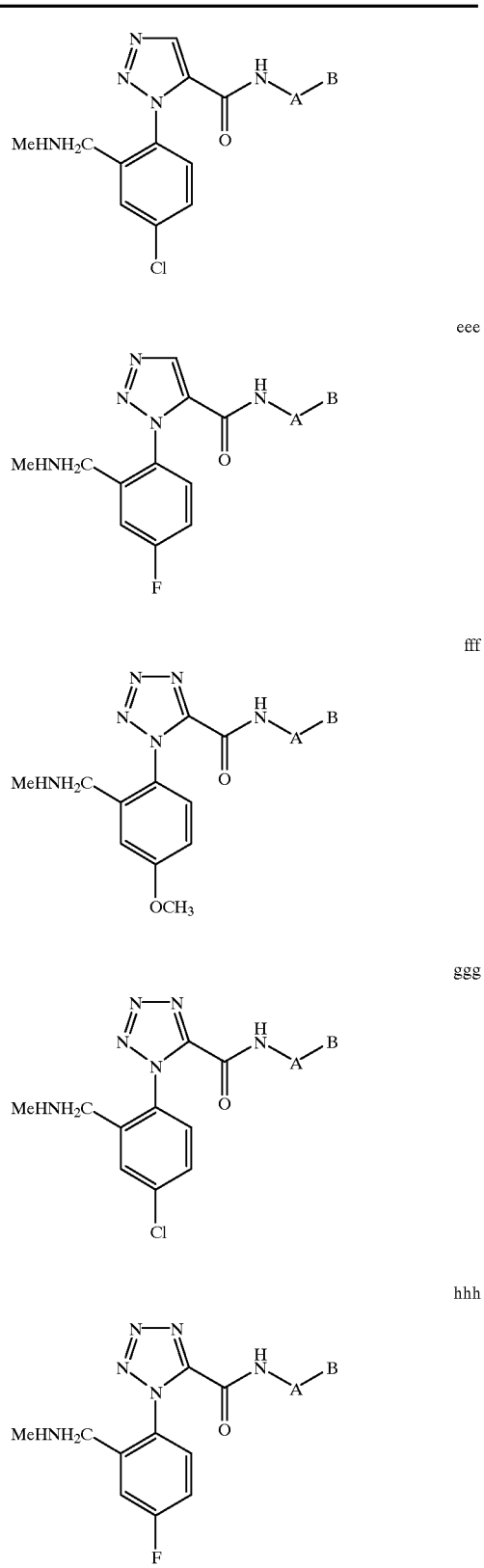
eee
fff
ggg
hhh
iii TABLE 3-continued
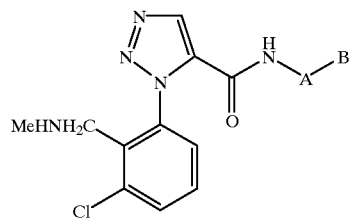
jjj
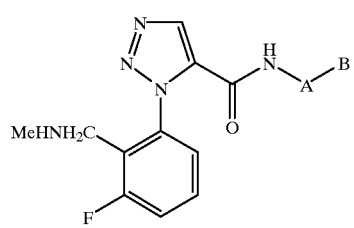
kkk
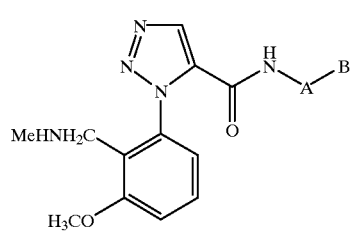
lll
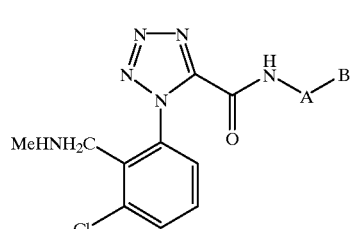
mmm
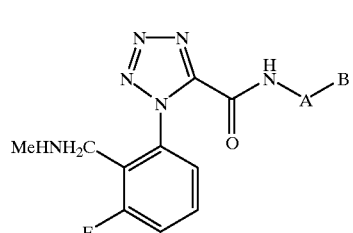
nnn
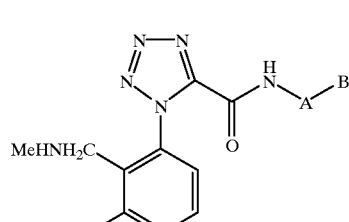
ooo
TABLE 3-continued
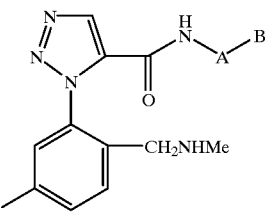
ppp
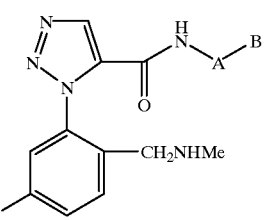
qqq
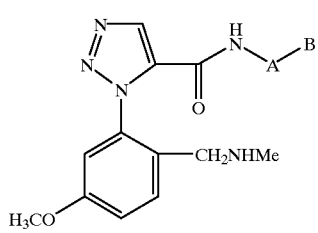
rrr
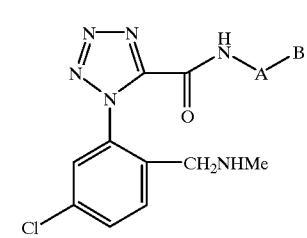
sss
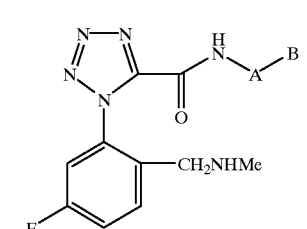
ttt
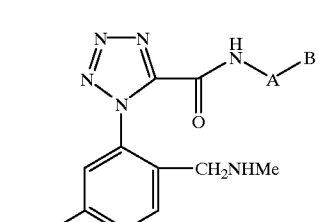
uuu TABLE 3-continued

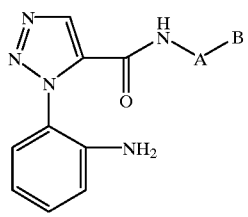
vvv

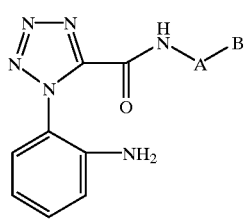
www

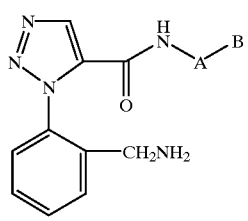
xxx

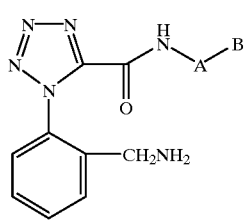
yyy

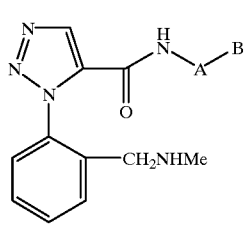
zzz

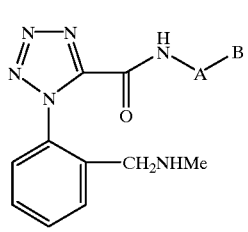
aaaa

TABLE 3-continued

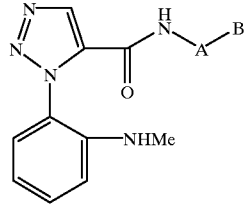

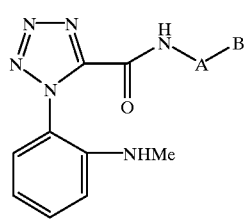
bbbb

| Ex # | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-CF$_3$-tetrazol-2-yl)phenyl |
| 7 | phenyl | 4-morpholinocarbonyl |
| 8 | phenyl | 2-methyl-1-imidazolyl |
| 9 | phenyl | 5-methyl-1-imidazolyl |
| 10 | phenyl | 2-methylsulfonyl-1-imidazolyl |
| 11 | 2-pyridyl | 2-(aminosulfonyl)phenyl |
| 12 | 2-pyridyl | 2-(methylaminosulfonyl)phenyl |
| 13 | 2-pyridyl | 1-pyrrolidinocarbonyl |
| 14 | 2-pyridyl | 2-(methylsulfonyl)phenyl |
| 15 | 2-pyridyl | 4-morpholino |
| 16 | 2-pyridyl | 2-(1'-CF$_3$-tetrazol-2-yl)phenyl |
| 17 | 2-pyridyl | 4-morpholinocarbonyl |
| 18 | 2-pyridyl | 2-methyl-1-imidazolyl |
| 19 | 2-pyridyl | 5-methyl-1-imidazolyl |
| 20 | 2-pyridyl | 2-methylsulfonyl-1-imidazolyl |
| 21 | 3-pyridyl | 2-(aminosulfonyl)phenyl |
| 22 | 3-pyridyl | 2-(methylaminosulfonyl)phenyl |
| 23 | 3-pyridyl | 1-pyrrolidinocarbonyl |
| 24 | 3-pyridyl | 2-(methylsulfonyl)phenyl |
| 25 | 3-pyridyl | 4-morpholino |
| 26 | 3-pyridyl | 2-(1'-CF$_3$-tetrazol-2-yl)phenyl |
| 27 | 3-pyridyl | 4-morpholinocarbonyl |
| 28 | 3-pyridyl | 2-methyl-1-imidazolyl |
| 29 | 3-pyridyl | 5-methyl-1-imidazolyl |
| 30 | 3-pyridyl | 2-methylsulfonyl-1-imidazolyl |
| 31 | 2-pyrimidyl | 2-(aminosulfonyl)phenyl |
| 32 | 2-pyrimidyl | 2-(methylaminosulfonyl)phenyl |
| 33 | 2-pyrimidyl | 1-pyrrolidinocarbonyl |
| 34 | 2-pyrimidyl | 2-(methylsulfonyl)phenyl |
| 35 | 2-pyrimidyl | 4-morpholino |
| 36 | 2-pyrimidyl | 2-(1'-CF$_3$-tetrazol-2-yl)phenyl |
| 37 | 2-pyrimidyl | 4-morpholinocarbonyl |
| 38 | 2-pyrimidyl | 2-methyl-1-imidazolyl |
| 39 | 2-pyrimidyl | 5-methyl-1-imidazolyl |
| 40 | 2-pyrimidyl | 2-methylsulfonyl-1-imidazolyl |
| 41 | 5-pyrimidyl | 2-(aminosulfonyl)phenyl |
| 42 | 5-pyrimidyl | 2-(methylaminosulfonyl)phenyl |
| 43 | 5-pyrimidyl | 1-pyrrolidinocarbonyl |
| 44 | 5-pyrimidyl | 2-(methylsulfonyl)phenyl |
| 45 | 5-pyrimidyl | 4-morpholino |
| 46 | 5-pyrimidyl | 2-(1'-CF$_3$-tetrazol-2-yl)phenyl |
| 47 | 5-pyrimidyl | 4-morpholinocarbonyl |
| 48 | 5-pyrimidyl | 2-methyl-1-imidazolyl |
| 49 | 5-pyrimidyl | 5-methyl-1-imidazolyl |
| 50 | 5-pyrimidyl | 2-methylsulfonyl-1-imidazolyl |
| 51 | 2-Cl-phenyl | 2-(aminosulfonyl)phenyl |
| 52 | 2-Cl-phenyl | 2-(methylaminosulfonyl)phenyl |
| 53 | 2-Cl-phenyl | 1-pyrrolidinocarbonyl |

TABLE 3-continued

| | | |
|---|---|---|
| 54 | 2-Cl-phenyl | 2-(methylsulfonyl)phenyl |
| 55 | 2-Cl-phenyl | 4-morpholino |
| 56 | 2-Cl-phenyl | 2-(1'-CF$_3$-tetrazol-2-yl)phenyl |
| 57 | 2-Cl-phenyl | 4-morpholinocarbonyl |
| 58 | 2-Cl-phenyl | 2-methyl-1-imidazolyl |
| 59 | 2-Cl-phenyl | 5-methyl-1-imidazolyl |
| 60 | 2-Cl-phenyl | 2-methylsulfonyl-1-imidazolyl |
| 61 | 2-F-phenyl | 2-(aminosulfonyl)phenyl |
| 62 | 2-F-phenyl | 2-(methylaminosulfonyl)phenyl |
| 63 | 2-F-phenyl | 1-pyrrolidinocarbonyl |
| 64 | 2-F-phenyl | 2-(methylsulfonyl)phenyl |
| 65 | 2-F-phenyl | 4-morpholino |
| 66 | 2-F-phenyl | 2-(1'-CF$_3$-tetrazol-2-yl)phenyl |
| 67 | 2-F-phenyl | 4-morpholinocarbonyl |
| 68 | 2-F-phenyl | 2-methyl-1-imidazolyl |
| 69 | 2-F-phenyl | 5-methyl-1-imidazolyl |
| 70 | 2-F-phenyl | 2-methylsulfonyl-1-imidazolyl |
| 71 | 2,6-diF-phenyl | 2-(aminosulfonyl)phenyl |
| 72 | 2,6-diF-phenyl | 2-(methylaminosulfonyl)phenyl |
| 73 | 2,6-diF-phenyl | 1-pyrrolidinocarbonyl |
| 74 | 2,6-diF-phenyl | 2-(methylsulfonyl)phenyl |
| 75 | 2,6-diF-phenyl | 4-morpholino |
| 76 | 2,6-diF-phenyl | 2-(1'-CF$_3$-tetrazol-2-yl)phenyl |
| 77 | 2,6-diF-phenyl | 4-morpholinocarbonyl |
| 78 | 2,6-diF-phenyl | 2-methyl-1-imidazolyl |
| 79 | 2,6-diF-phenyl | 5-methyl-1-imidazolyl |
| 80 | 2,6-diF-phenyl | 2-methylsulfonyl-1-imidazolyl |

TABLE 4

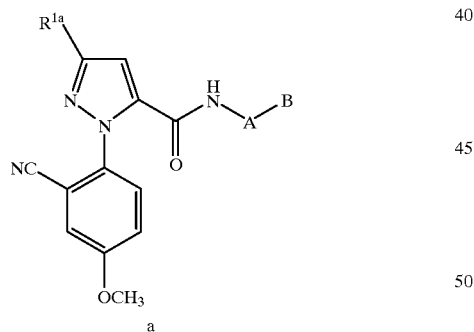

a

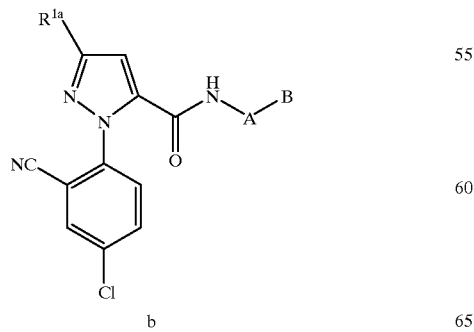

b

TABLE 4-continued

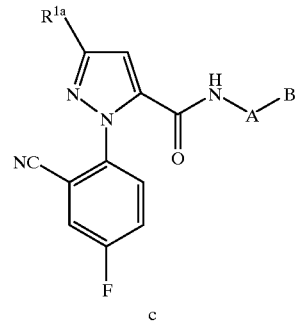

c

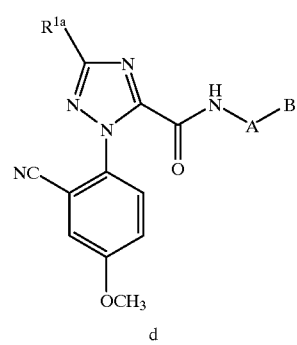

d

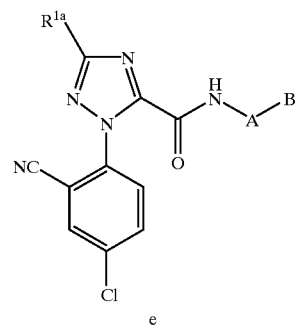

e

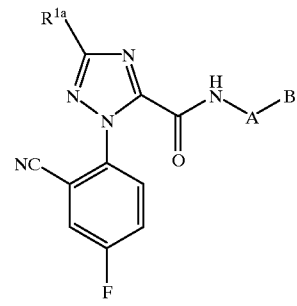

f

TABLE 4-continued
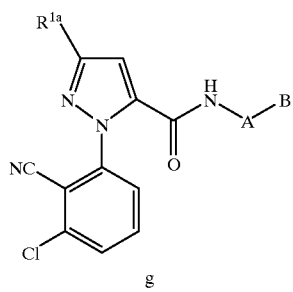
g
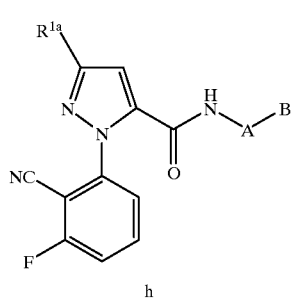
h
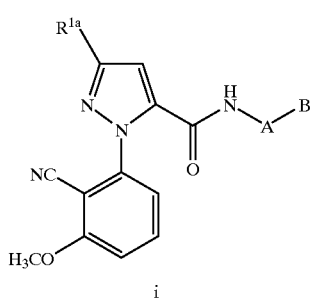
i
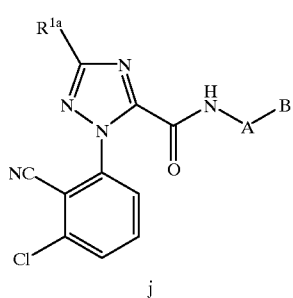
j
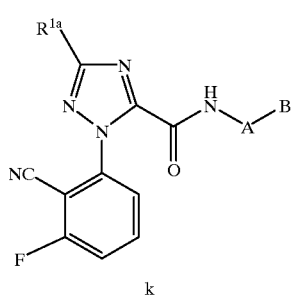
k
TABLE 4-continued
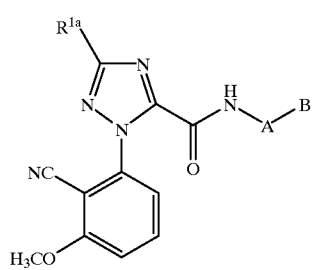
l
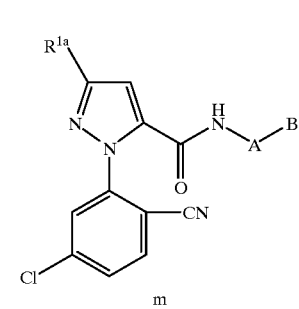
m
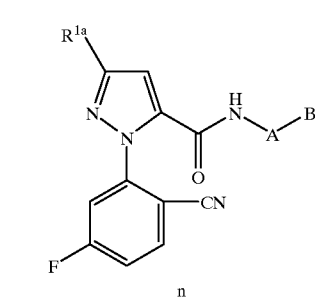
n
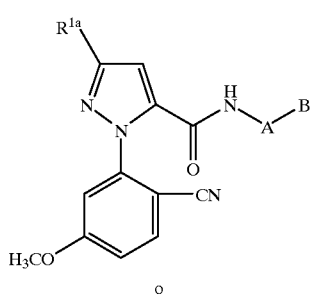
o
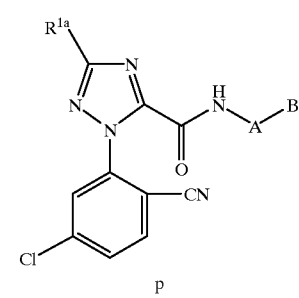
p TABLE 4-continued
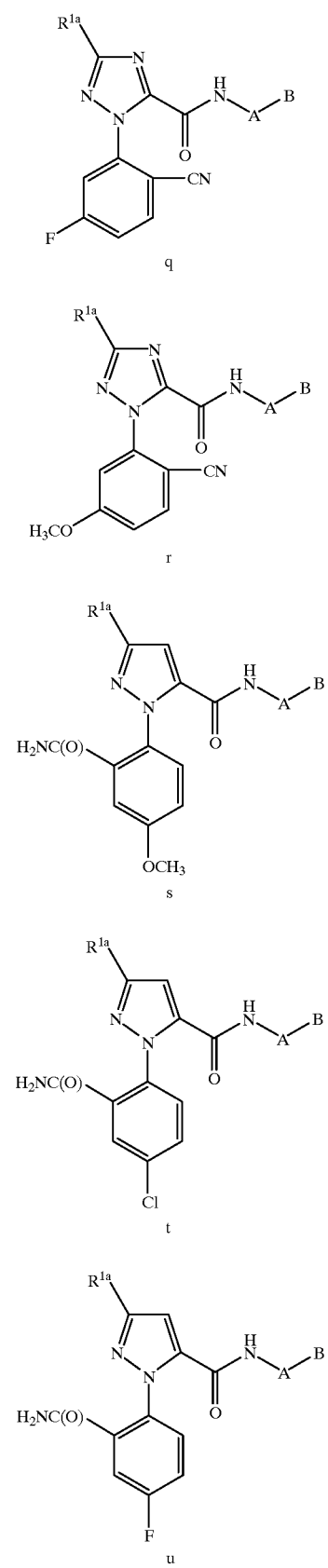
TABLE 4-continued
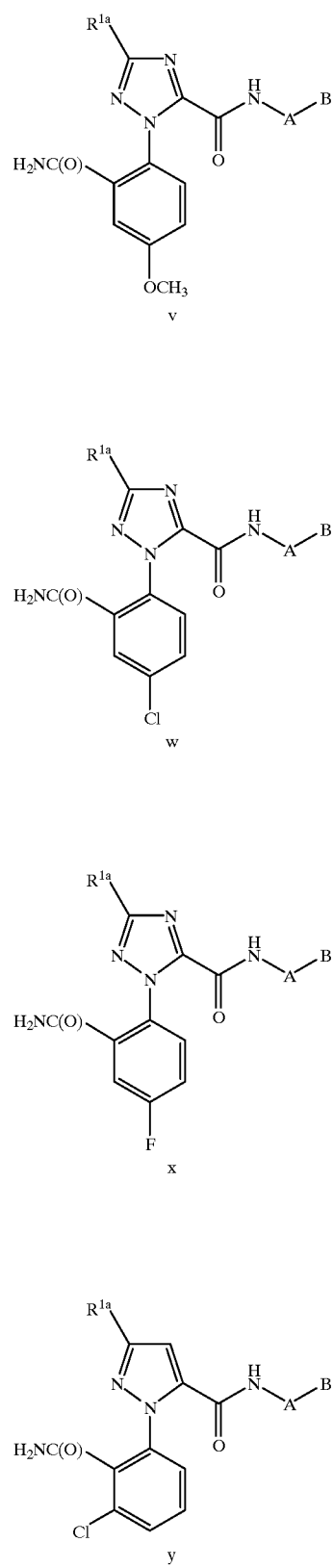

TABLE 4-continued
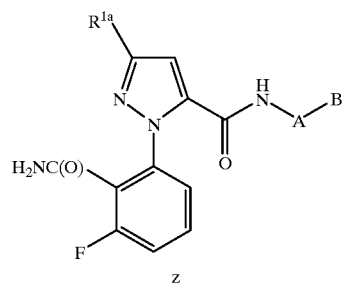
z
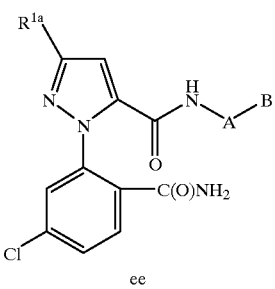
ee
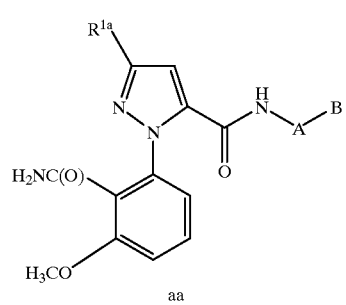
aa
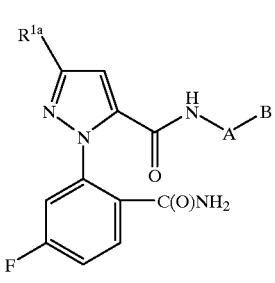
ff
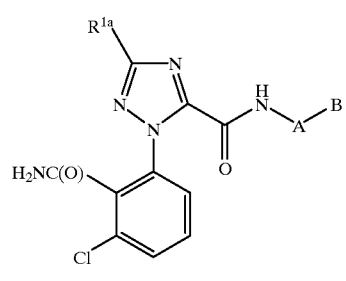
bb
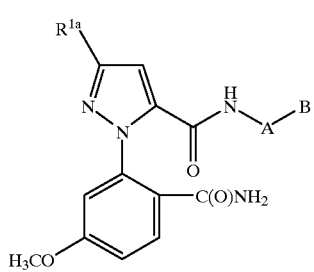
gg
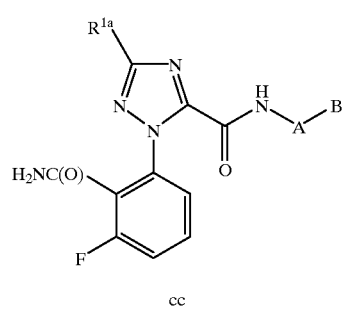
cc
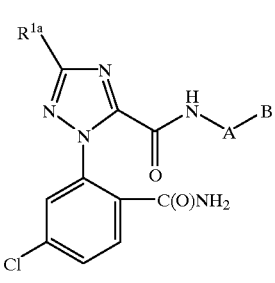
hh
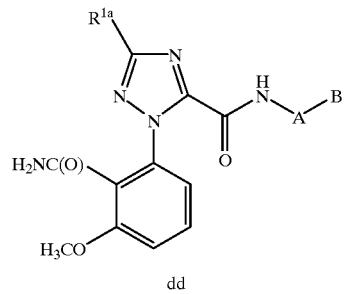
dd
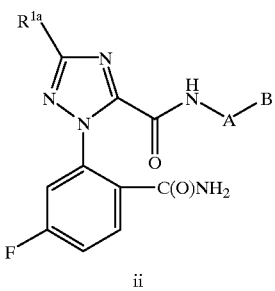
ii TABLE 4-continued
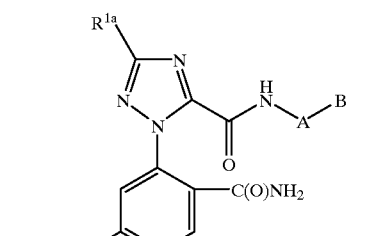
jj
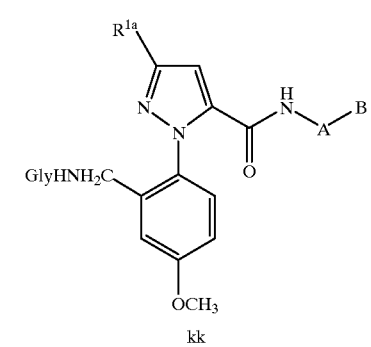
kk
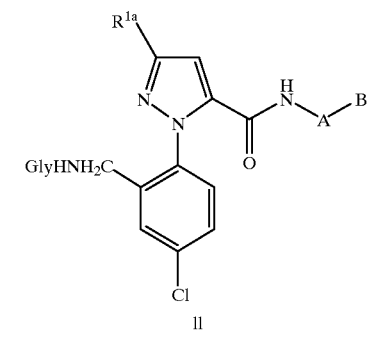
ll
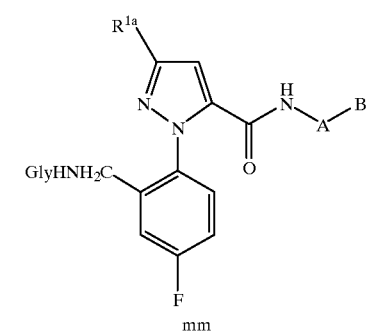
mm
TABLE 4-continued
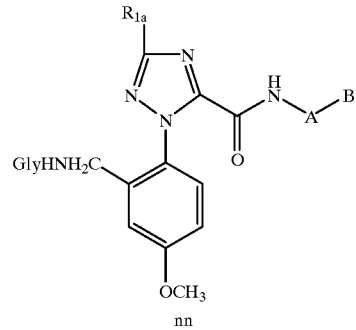
nn
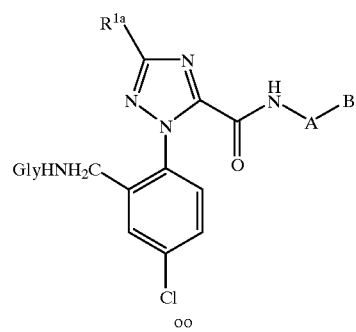
oo
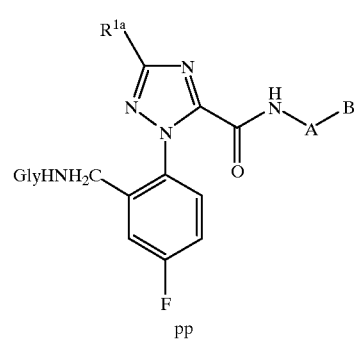
pp
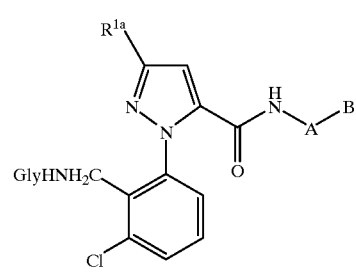
qq
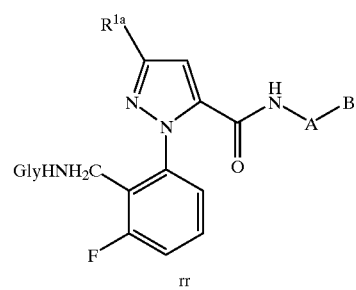
rr TABLE 4-continued
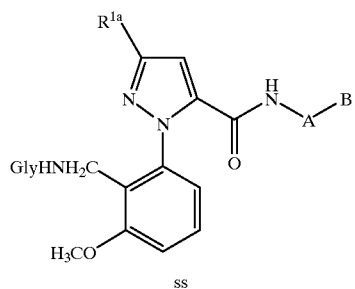
ss
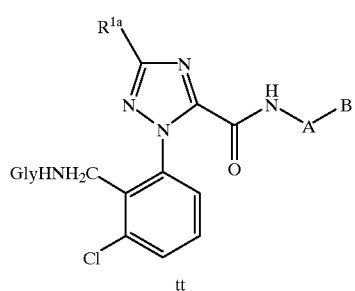
tt
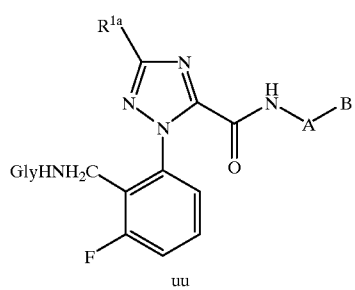
uu
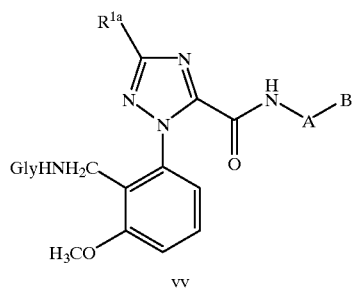
vv
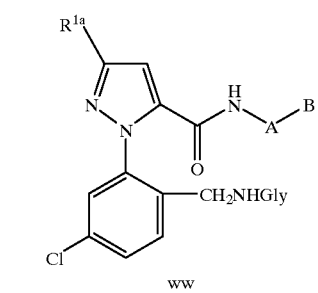
ww
TABLE 4-continued
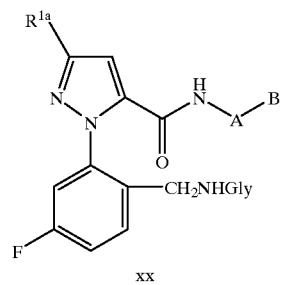
xx
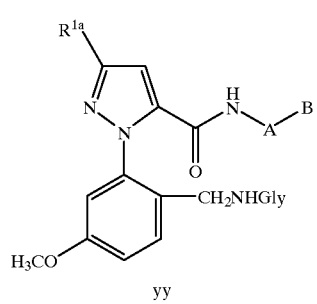
yy
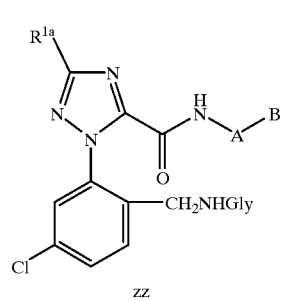
zz
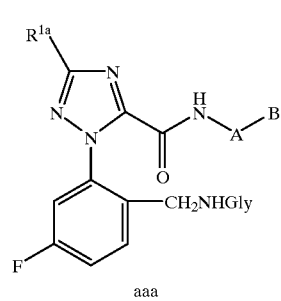
aaa
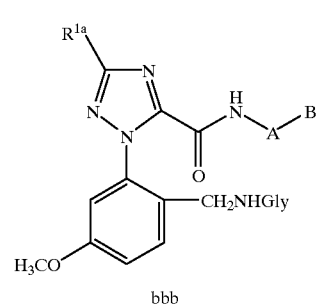
bbb

TABLE 4-continued

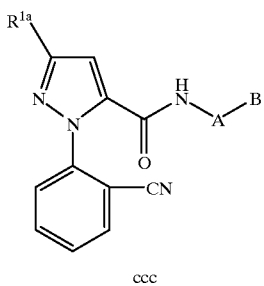

ccc

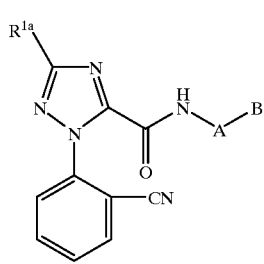

ddd

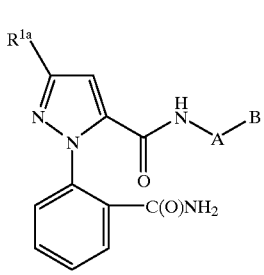

eee

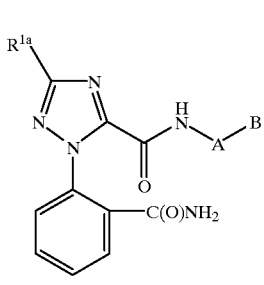

fff

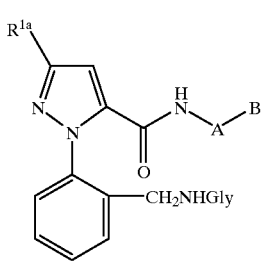

ggg

TABLE 4-continued

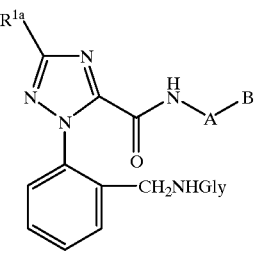

hhh

| Ex # | R$^{1a}$ | A | B |
|---|---|---|---|
| 1 | CH$_3$ | phenyl | 2-(aminosulfonyl)phenyl |
| 2 | CH$_3$ | phenyl | 2-(methylaminosulfonyl)phenyl |
| 3 | CH$_3$ | phenyl | 1-pyrrolidinocarbonyl |
| 4 | CH$_3$ | phenyl | 2-(methylsulfonyl)phenyl |
| 5 | CH$_3$ | phenyl | 4-morpholino |
| 6 | CH$_3$ | phenyl | 2-(1'-CF$_3$-tetrazol-2-yl)phenyl |
| 7 | CH$_3$ | phenyl | 4-morpholinocarbonyl |
| 8 | CH$_3$ | phenyl | 2-methyl-1-imidazolyl |
| 9 | CH$_3$ | phenyl | 5-methyl-1-imidazolyl |
| 10 | CH$_3$ | phenyl | 2-methylsulfonyl-1-imidazolyl |
| 11 | CH$_3$ | 2-pyridyl | 2-(aminosulfonyl)phenyl |
| 12 | CH$_3$ | 2-pyridyl | 2-(methylaminosulfonyl)phenyl |
| 13 | CH$_3$ | 2-pyridyl | 1-pyrrolidinocarbonyl |
| 14 | CH$_3$ | 2-pyridyl | 2-(methylsulfonyl)phenyl |
| 15 | CH$_3$ | 2-pyridyl | 4-morpholino |
| 16 | CH$_3$ | 2-pyridyl | 2-(1'-CF$_3$-tetrazol-2-yl)phenyl |
| 17 | CH$_3$ | 2-pyridyl | 4-morpholinocarbonyl |
| 18 | CH$_3$ | 2-pyridyl | 2-methyl-1-imidazolyl |
| 19 | CH$_3$ | 2-pyridyl | 5-methyl-1-imidazolyl |
| 20 | CH$_3$ | 2-pyridyl | 2-methylsulfonyl-1-imidazolyl |
| 21 | CH$_3$ | 3-pyridyl | 2-(aminosulfonyl)phenyl |
| 22 | CH$_3$ | 3-pyridyl | 2-(methylaminosulfonyl)phenyl |
| 23 | CH$_3$ | 3-pyridyl | 1-pyrrolidinocarbonyl |
| 24 | CH$_3$ | 3-pyridyl | 2-(methylsulfonyl)phenyl |
| 25 | CH$_3$ | 3-pyridyl | 4-morpholino |
| 26 | CH$_3$ | 3-pyridyl | 2-(1'-CF$_3$-tetrazol-2-yl)phenyl |
| 27 | CH$_3$ | 3-pyridyl | 4-morpholinocarbonyl |
| 28 | CH$_3$ | 3-pyridyl | 2-methyl-1-imidazolyl |
| 29 | CH$_3$ | 3-pyridyl | 5-methyl-1-imidazolyl |
| 30 | CH$_3$ | 3-pyridyl | 2-methylsulfonyl-1-imidazolyl |
| 31 | CH$_3$ | 2-pyrimidyl | 2-(aminosulfonyl)phenyl |
| 32 | CH$_3$ | 2-pyrimidyl | 2-(methylaminosulfonyl)phenyl |
| 33 | CH$_3$ | 2-pyrimidyl | 1-pyrrolidinocarbonyl |
| 34 | CH$_3$ | 2-pyrimidyl | 2-(methylsulfonyl)phenyl |
| 35 | CH$_3$ | 2-pyrimidyl | 4-morpholino |
| 36 | CH$_3$ | 2-pyrimidyl | 2-(1'-CF$_3$-tetrazol-2-yl)phenyl |
| 37 | CH$_3$ | 2-pyrimidyl | 4-morpholinocarbonyl |
| 38 | CH$_3$ | 2-pyrimidyl | 2-methyl-1-imidazolyl |
| 39 | CH$_3$ | 2-pyrimidyl | 5-methyl-1-imidazolyl |
| 40 | CH$_3$ | 2-pyrimidyl | 2-methylsulfonyl-1-imidazolyl |
| 41 | CH$_3$ | 5-pyrimidyl | 2-(aminosulfonyl)phenyl |
| 42 | CH$_3$ | 5-pyrimidyl | 2-(methylaminosulfonyl)phenyl |
| 43 | CH$_3$ | 5-pyrimidyl | i-pyrrolidinocarbonyl |
| 44 | CH$_3$ | 5-pyrimidyl | 2-(methylsulfonyl)phenyl |
| 45 | CH$_3$ | 5-pyrimidyl | 4-morpholino |
| 46 | CH$_3$ | 5-pyrimidyl | 2-(1'-CF$_3$-tetrazol-2-yl)phenyl |
| 47 | CH$_3$ | 5-pyrimidyl | 4-morpholinocarbonyl |
| 48 | CH$_3$ | 5-pyrimidyl | 2-methyl-1-imidazolyl |
| 49 | CH$_3$ | 5-pyrimidyl | 5-methyl-1-imidazolyl |
| 50 | CH$_3$ | 5-pyrimidyl | 2-methylsulfonyl-1-imidazolyl |
| 51 | CH$_3$ | 2-Cl-phenyl | 2-(aminosulfonyl)phenyl |
| 52 | CH$_3$ | 2-Cl-phenyl | 2-(methylaminosulfonyl)phenyl |
| 53 | CH$_3$ | 2-Cl-phenyl | 1-pyrrolidinocarbonyl |
| 54 | CH$_3$ | 2-Cl-phenyl | 2-(methylsulfonyl)phenyl |
| 55 | CH$_3$ | 2-Cl-phenyl | 4-morpholino |
| 56 | CH$_3$ | 2-Cl-phenyl | 2-(1'-CF$_3$-tetrazol-2-yl)phenyl |
| 57 | CH$_3$ | 2-Cl-phenyl | 4-morpholinocarbonyl |
| 58 | CH$_3$ | 2-Cl-phenyl | 2-methyl-1-imidazolyl |
| 59 | CH$_3$ | 2-Cl-phenyl | 5-methyl-1-imidazolyl |
| 60 | CH$_3$ | 2-Cl-phenyl | 2-methylsulfonyl-1-imidazolyl |
| 61 | CH$_3$ | 2-F-phenyl | 2-(aminosulfonyl)phenyl |
| 62 | CH$_3$ | 2-F-phenyl | 2-(methylaminosulfonyl)phenyl |

TABLE 4-continued

| # | | | |
|---|---|---|---|
| 63 | CH₃ | 2-F-phenyl | 1-pyrrolidinocarbonyl |
| 64 | CH₃ | 2-F-phenyl | 2-(methylsulfonyl)phenyl |
| 65 | CH₃ | 2-F-phenyl | 4-morpholino |
| 66 | CH₃ | 2-F-phenyl | 2-(1'-CF₃-tetrazol-2-yl)phenyl |
| 67 | CH₃ | 2-F-phenyl | 4-morpholinocarbonyl |
| 68 | CH₃ | 2-F-phenyl | 2-methyl-1-imidazolyl |
| 69 | CH₃ | 2-F-phenyl | 5-methyl-1-imidazolyl |
| 70 | CH₃ | 2-F-phenyl | 2-methylsulfonyl-1-imidazolyl |
| 71 | CH₃ | 2,6-diF-phenyl | 2-(aminosulfonyl)phenyl |
| 72 | CH₃ | 2,6-diF-phenyl | 2-(methylaminosulfonyl)phenyl |
| 73 | CH₃ | 2,6-diF-phenyl | i-pyrrolidinocarbonyl |
| 74 | CH₃ | 2,6-diF-phenyl | 2-(methylsulfonyl)phenyl |
| 75 | CH₃ | 2,6-diF-phenyl | 4-morpholino |
| 76 | CH₃ | 2,6-diF-phenyl | 2-(1'-CF₃-tetrazol-2-yl)phenyl |
| 77 | CH₃ | 2,6-diF-phenyl | 4-morpholinocarbonyl |
| 78 | CH₃ | 2,6-diF-phenyl | 2-methyl-1-imidazolyl |
| 79 | CH₃ | 2,6-diF-phenyl | 5-methyl-1-imidazolyl |
| 80 | CH₃ | 2,6-diF-phenyl | 2-methylsulfonyl-1-imidazolyl |
| 81 | CH₂CH₃ | phenyl | 2-(aminosulfonyl)phenyl |
| 82 | CH₂CH₃ | phenyl | 2-(methylaminosulfonyl)phenyl |
| 83 | CH₂CH₃ | phenyl | 1-pyrrolidinocarbonyl |
| 84 | CH₂CH₃ | phenyl | 2-(methylsulfonyl)phenyl |
| 85 | CH₂CH₃ | phenyl | 4-morpholino |
| 86 | CH₂CH₃ | phenyl | 2-(1'-CF₃-tetrazol-2-yl)phenyl |
| 87 | CH₂CH₃ | phenyl | 4-morpholinocarbonyl |
| 88 | CH₂CH₃ | phenyl | 2-methy1-1-imidazolyl |
| 89 | CH₂CH₃ | phenyl | 5-methyl-1-imidazolyl |
| 90 | CH₂CH₃ | phenyl | 2-methylsulfonyl-1-imidazolyl |
| 91 | CH₂CH₃ | 2-pyridyl | 2-(aminosulfonyl)phenyl |
| 92 | CH₂CH₃ | 2-pyridyl | 2-(methylaminosulfonyl)phenyl |
| 93 | CH₂CH₃ | 2-pyridyl | 1-pyrrolidinocarbonyl |
| 94 | CH₂CH₃ | 2-pyridyl | 2-(methylsulfonyl)phenyl |
| 95 | CH₂CH₃ | 2-pyridyl | 4-morpholino |
| 96 | CH₂CH₃ | 2-pyridyl | 2-(1'-CF₃-tetrazol-2-yl)phenyl |
| 97 | CH₂CH₃ | 2-pyridyl | 4-morpholinocarbonyl |
| 98 | CH₂CH₃ | 2-pyridyl | 2-methyl-1-imidazolyl |
| 99 | CH₂CH₃ | 2-pyridyl | 5-methyl-1-imidazolyl |
| 100 | CH₂CH₃ | 2-pyridyl | 2-methylsulfonyl-1-imidazolyl |
| 101 | CH₂CH₃ | 3-pyridyl | 2-(aminosulfonyl)phenyl |
| 102 | CH₂CH₃ | 3-pyridyl | 2-(methylaminosulfonyl)phenyl |
| 103 | CH₂CH₃ | 3-pyridyl | 1-pyrrolidinocarbonyl |
| 104 | CH₂CH₃ | 3-pyridyl | 2-(methylsulfonyl)phenyl |
| 105 | CH₂CH₃ | 3-pyridyl | 4-morpholino |
| 106 | CH₂CH₃ | 3-pyridyl | 2-(1'-CF₃-tetrazol-2-yl)phenyl |
| 107 | CH₂CH₃ | 3-pyridyl | 4-morpholinocarbonyl |
| 108 | CH₂CH₃ | 3-pyridyl | 2-methyl-1-imidazolyl |
| 109 | CH₂CH₃ | 3-pyridyl | 5-methyl-1-imidazolyl |
| 110 | CH₂CH₃ | 3-pyridyl | 2-methylsulfonyl-1-imidazolyl |
| 111 | CH₂CH₃ | 2-pyrimidyl | 2-(aminosulfonyl)phenyl |
| 112 | CH₂CH₃ | 2-pyrimidyl | 2-(methylaminosulfonyl)phenyl |
| 113 | CH₂CH₃ | 2-pyrimidyl | 1-pyrrolidinocarbonyl |
| 114 | CH₂CH₃ | 2-pyrimidyl | 2-(methylsulfonyl)phenyl |
| iis | CH₂CH₃ | 2-pyrimidyl | 4-morpholino |
| 116 | CH₂CH₃ | 2-pyrimidyl | 2-(1'-CF₃-tetrazol-2-yl)phenyl |
| 117 | CH₂CH₃ | 2-pyrimidyl | 4-morpholinocarbonyl |
| 118 | CH₂CH₃ | 2-pyrimidyl | 2-methyl-1-imidazolyl |
| 119 | CH₂CH₃ | 2-pyrimidyl | 5-methyl-1-imidazolyl |
| 120 | CH₂CH₃ | 2-pyrimidyl | 2-methylsulfonyl-1-imidazolyl |
| 121 | CH₂CH₃ | 5-pyrimidyl | 2-(aminosulfonyl)phenyl |
| 122 | CH₂CH₃ | 5-pyrimidyl | 2-(methylaminosulfonyl)phenyl |
| 123 | CH₂CH₃ | 5-pyrimidyl | 1-pyrrolidinocarbonyl |
| 124 | CH₂CH₃ | 5-pyrimidyl | 2-(methylsulfonyl)phenyl |
| 125 | CH₂CH₃ | 5-pyrimidyl | 4-morpholino |
| 126 | CH₂CH₃ | 5-pyrimidyl | 2-(1'-CF₃-tetrazol-2-yl)phenyl |
| 127 | CH₂CH₃ | 5-pyrimidyl | 4-morpholinocarbonyl |
| 128 | CH₂CH₃ | 5-pyrimidyl | 2-methyl-1-imidazolyl |
| 129 | CH₂CH₃ | 5-pyrimidyl | 5-methyl-1-imidazolyl |
| 130 | CH₂CH₃ | 5-pyrimidyl | 2-methylsulfonyl-1-imidazolyl |
| 131 | CH₂CH₃ | 2-Cl-phenyl | 2-(aminosulfonyl)phenyl |
| 132 | CH₂CH₃ | 2-Cl-phenyl | 2-(methylaminosulfonyl)phenyl |
| 133 | CH₂CH₃ | 2-Cl-phenyl | 1-pyrrolidinocarbonyl |
| 134 | CH₂CH₃ | 2-Cl-phenyl | 2-(methylsulfonyl)phenyl |
| 135 | CH₂CH₃ | 2-Cl-phenyl | 4-morpholino |
| 136 | CH₂CH₃ | 2-Cl-phenyl | 2-(1'-CF₃-tetrazol-2-yl)phenyl |
| 137 | CH₂CH₃ | 2-Cl-phenyl | 4-morpholinocarbonyl |
| 138 | CH₂CH₃ | 2-Cl-phenyl | 2-methyl-1-imidazolyl |
| 139 | CH₂CH₃ | 2-Cl-phenyl | 5-methyl-1-imidazolyl |
| 140 | CH₂CH₃ | 2-Cl-phenyl | 2-methylsulfonyl-1-imidazolyl |
| 141 | CH₂CH₃ | 2-F-phenyl | 2-(aminosulfonyl)phenyl |
| 142 | CH₂CH₃ | 2-F-phenyl | 2-(methylaminosulfonyl)phenyl |
| 143 | CH₂CH₃ | 2-F-phenyl | 1-pyrrolidinocarbonyl |
| 144 | CH₂CH₃ | 2-F-phenyl | 2-(methylsulfonyl)phenyl |
| 145 | CH₂CH₃ | 2-F-phenyl | 4-morpholino |
| 146 | CH₂CH₃ | 2-F-phenyl | 2-(1'-CF₃-tetrazol-2-yl)phenyl |
| 147 | CH₂CH₃ | 2-F-phenyl | 4-morpholinocarbonyl |
| 148 | CH₂CH₃ | 2-F-phenyl | 2-methyl-1-imidazolyl |
| 149 | CH₂CH₃ | 2-F-phenyl | 5-methyl-1-imidazolyl |
| 150 | CH₂CH₃ | 2-F-phenyl | 2-methylsulfonyl-1-imidazolyl |
| 151 | CH₂CH₃ | 2,6-diF-phenyl | 2-(aminosulfonyl)phenyl |
| 152 | CH₂CH₃ | 2,6-diF-phenyl | 2-(methylaminosulfonyl)phenyl |
| 153 | CH₂CH₃ | 2,6-diF-phenyl | 1-pyrrolidinocarbonyl |
| 154 | CH₂CH₃ | 2,6-diF-phenyl | 2-(methylsulfonyl)phenyl |
| 155 | CH₂CH₃ | 2,6-diF-phenyl | 4-morpholino |
| 156 | CH₂CH₃ | 2,6-diF-phenyl | 2-(1'-CF₃-tetrazol-2-yl)phenyl |
| 157 | CH₂CH₃ | 2,6-diF-phenyl | 4-morpholinocarbonyl |
| 158 | CH₂CH₃ | 2,6-diF-phenyl | 2-methyl-1-imidazolyl |
| 159 | CH₂CH₃ | 2,6-diF-phenyl | 5-methyl-1-imidazolyl |
| 160 | CH₂CH₃ | 2,6-diF-phenyl | 2-methylsulfonyl-1-imidazolyl |
| 161 | CF₃ | phenyl | 2-(aminosulfonyl)phenyl |
| 162 | CF₃ | phenyl | 2-(methylaminosulfonyl)phenyl |
| 163 | CF₃ | phenyl | 1-pyrrolidinocarbonyl |
| 164 | CF₃ | phenyl | 2-(methylsulfonyl)phenyl |
| 165 | CF₃ | phenyl | 4-morpholino |
| 166 | CF₃ | phenyl | 2-(1'-CF₃-tetrazol-2-yl)phenyl |
| 167 | CF₃ | phenyl | 4-morpholinocarbonyl |
| 168 | CF₃ | phenyl | 2-methyl-1-imidazolyl |
| 169 | CF₃ | phenyl | 5-methyl-1-imidazolyl |
| 170 | CF₃ | phenyl | 2-methylsulfonyl-1-imidazolyl |
| 171 | CF₃ | 2-pyridyl | 2-(aminosulfonyl)phenyl |
| 172 | CF₃ | 2-pyridyl | 2-(methylaminosulfonyl)phenyl |
| 173 | CF₃ | 2-pyridyl | 1-pyrrolidinocarbonyl |
| 174 | CF₃ | 2-pyridyl | 2-(methylsulfonyl)phenyl |
| 175 | CF₃ | 2-pyridyl | 4-morpholino |
| 176 | CF₃ | 2-pyridyl | 2-(1'-CF₃-tetrazol-2-yl)phenyl |
| 177 | CF₃ | 2-pyridyl | 4-morpholinocarbonyl |
| 178 | CF₃ | 2-pyridyl | 2-methyl-1-imidazolyl |
| 179 | CF₃ | 2-pyridyl | 5-methyl-1-imidazolyl |
| 180 | CF₃ | 2-pyridyl | 2-methylsulfonyl-1-imidazolyl |
| 181 | CF₃ | 3-pyridyl | 2-(aminosulfonyl)phenyl |
| 182 | CF₃ | 3-pyridyl | 2-(methylaminosulfonyl)phenyl |
| 183 | CF₃ | 3-pyridyl | 1-pyrrolidinocarbonyl |
| 184 | CF₃ | 3-pyridyl | 2-(methylsulfonyl)phenyl |
| 185 | CF₃ | 3-pyridyl | 4-morpholino |
| 186 | CF₃ | 3-pyridyl | 2-(1'-CF₃-tetrazol-2-yl)phenyl |
| 187 | CF₃ | 3-pyridyl | 4-morpholinocarbonyl |
| 188 | CF₃ | 3-pyridyl | 2-methyl-1-imidazolyl |
| 189 | CF₃ | 3-pyridyl | 5-methyl-1-imidazolyl |
| 190 | CF₃ | 3-pyridyl | 2-methylsulfonyl-1-imidazolyl |
| 191 | CF₃ | 2-pyrimidyl | 2-(aminosulfonyl)phenyl |
| 192 | CF₃ | 2-pyrimidyl | 2-(methylaminosulfonyl)phenyl |
| 193 | CF₃ | 2-pyrimidyl | 1-pyrrolidinocarbonyl |
| 194 | CF₃ | 2-pyrimidyl | 2-(methylsulfonyl)phenyl |
| 195 | CF₃ | 2-pyrimidyl | 4-morpholino |
| 196 | CF₃ | 2-pyrimidyl | 2-(1'-CF₃-tetrazol-2-yl)phenyl |
| 197 | CF₃ | 2-pyrimidyl | 4-morpholinocarbonyl |
| 198 | CF₃ | 2-pyrimidyl | 2-methyl-1-imidazolyl |
| 199 | CF₃ | 2-pyrimidyl | 5-methyl-1-imidazolyl |
| 200 | CF₃ | 2-pyrimidyl | 2-methylsulfonyl-1-imidazolyl |
| 201 | CF₃ | 5-pyrimidyl | 2-(aminosulfonyl)phenyl |
| 202 | CF₃ | 5-pyrimidyl | 2-(methylaminosulfonyl)phenyl |
| 203 | CF₃ | 5-pyrimidyl | 1-pyrrolidinocarbonyl |
| 204 | CF₃ | 5-pyrimidyl | 2-(methylsulfonyl)phenyl |
| 205 | CF₃ | 5-pyrimidyl | 4-morpholino |
| 206 | CF₃ | 5-pyrimidyl | 2-(1'-CF₃-tetrazol-2-yl)phenyl |
| 207 | CF₃ | 5-pyrimidyl | 4-morpholinocarbonyl |
| 208 | CF₃ | 5-pyrimidyl | 2-methyl-1-imidazolyl |
| 209 | CF₃ | 5-pyrimidyl | 5-methyl-1-imidazolyl |
| 210 | CF₃ | 5-pyrimidyl | 2-methylsulfonyl-1-imidazolyl |
| 211 | CF₃ | 2-Cl-phenyl | 2-(aminosulfonyl)phenyl |
| 212 | CF₃ | 2-Cl-phenyl | 2-(methylaminosulfonyl)phenyl |
| 213 | CF₃ | 2-Cl-phenyl | 1-pyrrolidinocarbonyl |
| 214 | CF₃ | 2-Cl-phenyl | 2-(methylsulfonyl)phenyl |
| 215 | CF₃ | 2-Cl-phenyl | 4-morpholino |
| 216 | CF₃ | 2-Cl-phenyl | 2-(1'-CF₃-tetrazol-2-yl)phenyl |
| 217 | CF₃ | 2-Cl-phenyl | 4-morpholinocarbonyl |
| 218 | CF₃ | 2-Cl-phenyl | 2-methyl-1-imidazolyl |
| 219 | CF₃ | 2-Cl-phenyl | 5-methyl-1-imidazolyl |
| 220 | CF₃ | 2-Cl-phenyl | 2-methylsulfonyl-1-imidazolyl |

TABLE 4-continued

| | | | |
|---|---|---|---|
| 221 | CF₃ | 2-F-phenyl | 2-(aminosulfonyl)phenyl |
| 222 | CF₃ | 2-F-phenyl | 2-(methylaminosulfonyl)phenyl |
| 223 | CF₃ | 2-F-phenyl | 1-pyrrolidinocarbonyl |
| 224 | CF₃ | 2-F-phenyl | 2-(methylsulfonyl)phenyl |
| 225 | CF₃ | 2-F-phenyl | 4-morpholino |
| 226 | CF₃ | 2-F-phenyl | 2-(1'-CF₃-tetrazol-2-yl)phenyl |
| 227 | CF₃ | 2-F-phenyl | 4-morpholinocarbonyl |
| 228 | CF₃ | 2-F-phenyl | 2-methyl-1-imidazolyl |
| 229 | CF₃ | 2-F-phenyl | 5-methyl-1-imidazolyl |
| 230 | CF₃ | 2-F-phenyl | 2-methylsulfonyl-1-imidazolyl |
| 231 | CF₃ | 2,6-diF-phenyl | 2-(aminosulfonyl)phenyl |
| 232 | CF₃ | 2,6-diF-phenyl | 2-(methylaminosulfonyl)phenyl |
| 233 | CF₃ | 2,6-diF-phenyl | 1-pyrrolidinocarbonyl |
| 234 | CF₃ | 2,6-diF-phenyl | 2-(methylsulfonyl)phenyl |
| 235 | CF₃ | 2,6-diF-phenyl | 4-morpholino |
| 236 | CF₃ | 2,6-diF-phenyl | 2-(1'-CF₃-tetrazol-2-yl)phenyl |
| 237 | CF₃ | 2,6-diF-phenyl | 4-morpholinocarbonyl |
| 238 | CF₃ | 2,6-diF-phenyl | 2-methyl-1-imidazolyl |
| 239 | CF₃ | 2,6-diF-phenyl | 5-methyl-1-imidazolyl |
| 240 | CF₃ | 2,6-diF-phenyl | 2-methylsulfonyl-1-imidazolyl |
| 241 | SCH₃ | phenyl | 2-(aminosulfonyl)phenyl |
| 242 | SCH₃ | phenyl | 2-(methylaminosulfonyl)phenyl |
| 243 | SCH₃ | phenyl | 1-pyrrolidinocarbonyl |
| 244 | SCH₃ | phenyl | 2-(methylsulfonyl)phenyl |
| 245 | SCH₃ | phenyl | 4-morpholino |
| 246 | SCH₃ | phenyl | 2-(1'-CF₃-tetrazol-2-yl)phenyl |
| 247 | SCH₃ | phenyl | 4-morpholinocarbonyl |
| 248 | SCH₃ | phenyl | 2-methyl-1-imidazolyl |
| 249 | SCH₃ | phenyl | 5-methyl-1-imidazolyl |
| 250 | SCH₃ | phenyl | 2-methylsulfonyl-1-imidazolyl |
| 251 | SCH₃ | 2-pyridyl | 2-(aminosulfonyl)phenyl |
| 252 | SCH₃ | 2-pyridyl | 2-(methylaminosulfonyl)phenyl |
| 253 | SCH₃ | 2-pyridyl | 1-pyrrolidinocarbonyl |
| 254 | SCH₃ | 2-pyridyl | 2-(methylsulfonyl)phenyl |
| 255 | SCH₃ | 2-pyridyl | 4-morpholino |
| 256 | SCH₃ | 2-pyridyl | 2-(1'-CF₃-tetrazol-2-yl)phenyl |
| 257 | SCH₃ | 2-pyridyl | 4-morpholinocarbonyl |
| 258 | SCH₃ | 2-pyridyl | 2-methyl-1-imidazolyl |
| 259 | SCH₃ | 2-pyridyl | 5-methyl-1-imidazolyl |
| 260 | SCH₃ | 2-pyridyl | 2-methylsulfonyl-1-imidazolyl |
| 261 | SCH₃ | 3-pyridyl | 2-(aminosulfonyl)phenyl |
| 262 | SCH₃ | 3-pyridyl | 2-(methylaminosulfonyl)phenyl |
| 263 | SCH₃ | 3-pyridyl | 1-pyrrolidinocarbonyl |
| 264 | SCH₃ | 3-pyridyl | 2-(methylsulfonyl)phenyl |
| 265 | SCH₃ | 3-pyridyl | 4-morpholino |
| 266 | SCH₃ | 3-pyridyl | 2-(1'-CF₃-tetrazol-2-yl)phenyl |
| 267 | SCH₃ | 3-pyridyl | 4-morpholinocarbonyl |
| 268 | SCH₃ | 3-pyridyl | 2-methyl-1-imidazolyl |
| 269 | SCH₃ | 3-pyridyl | 5-methyl-1-imidazolyl |
| 270 | SCH₃ | 3-pyridyl | 2-methylsulfonyl-1-imidazolyl |
| 271 | SCH₃ | 2-pyrimidyl | 2-(aminosulfonyl)phenyl |
| 272 | SCH₃ | 2-pyrimidyl | 2-(methylaminosulfonyl)phenyl |
| 273 | SCH₃ | 2-pyrimidyl | 1-pyrrolidinocarbonyl |
| 274 | SCH₃ | 2-pyrimidyl | 2-(methylsulfonyl)phenyl |
| 275 | SCH₃ | 2-pyrimidyl | 4-morpholino |
| 276 | SCH₃ | 2-pyrimidyl | 2-(1'-CF₃-tetrazol-2-yl)phenyl |
| 277 | SCH₃ | 2-pyrimidyl | 4-morpholinocarbonyl |
| 278 | SCH₃ | 2-pyrimidyl | 2-methyl-1-imidazolyl |
| 279 | SCH₃ | 2-pyrimidyl | 5-methyl-1-imidazolyl |
| 280 | SCH₃ | 2-pyrimidyl | 2-methylsulfonyl-1-imidazolyl |
| 281 | SCH₃ | 5-pyrimidyl | 2-(aminosulfonyl)phenyl |
| 282 | SCH₃ | 5-pyrimidyl | 2-(methylaminosulfonyl)phenyl |
| 283 | SCH₃ | 5-pyrimidyl | 1-pyrrolidinocarbonyl |
| 284 | SCH₃ | 5-pyrimidyl | 2-(methylsulfonyl)phenyl |
| 285 | SCH₃ | 5-pyrimidyl | 4-morpholino |
| 286 | SCH₃ | 5-pyrimidyl | 2-(1'-CF₃-tetrazol-2-yl)phenyl |
| 287 | SCH₃ | 5-pyrimidyl | 4-morpholinocarbonyl |
| 288 | SCH₃ | 5-pyrimidyl | 2-methyl-1-imidazolyl |
| 289 | SCH₃ | 5-pyrimidyl | 5-methyl-1-imidazolyl |
| 290 | SCH₃ | 5-pyrimidyl | 2-methylsulfonyl-1-imidazolyl |
| 291 | SCH₃ | 2-Cl-phenyl | 2-(aminosulfonyl)phenyl |
| 292 | SCH₃ | 2-Cl-phenyl | 2-(methylaminosulfonyl)phenyl |
| 293 | SCH₃ | 2-Cl-phenyl | 1-pyrrolidinocarbonyl |
| 294 | SCH₃ | 2-Cl-phenyl | 2-(methylsulfonyl)phenyl |
| 295 | SCH₃ | 2-Cl-phenyl | 4-morpholino |
| 296 | SCH₃ | 2-Cl-phenyl | 2-(1'-CF₃-tetrazol-2-yl)phenyl |
| 297 | SCH₃ | 2 -Cl-phenyl | 4-morpholinocarbonyl |
| 298 | SCH₃ | 2-Cl-phenyl | 2-methyl-1-imidazolyl |
| 299 | SCH₃ | 2-Cl-phenyl | 5-methyl-1-imidazolyl |
| 300 | SCH₃ | 2-Cl-phenyl | 2-methylsulfonyl-1-imidazolyl |
| 301 | SCH₃ | 2-F-phenyl | 2-(aminosulfonyl)phenyl |
| 302 | SCH₃ | 2-F-phenyl | 2-(methylaminosulfonyl)phenyl |
| 303 | SCH₃ | 2-F-phenyl | 1-pyrrolidinocarbonyl |
| 304 | SCH₃ | 2-F-phenyl | 2-(methylsulfonyl)phenyl |
| 305 | SCH₃ | 2-F-phenyl | 4-morpholino |
| 306 | SCH₃ | 2-F-phenyl | 2-(1'-CF₃-tetrazol-2-yl)phenyl |
| 307 | SCH₃ | 2-F-phenyl | 4-morpholinocarbonyl |
| 308 | SCH₃ | 2-F-phenyl | 2-methyl-1-imidazolyl |
| 309 | SCH₃ | 2-F-phenyl | 5-methyl-1-imidazolyl |
| 310 | SCH₃ | 2-F-phenyl | 2-methylsulfonyl-1-imidazolyl |
| 311 | SCH₃ | 2,6-diF-phenyl | 2-(aminosulfonyl)phenyl |
| 312 | SCH₃ | 2,6-diF-phenyl | 2-(methylaminosulfonyl)phenyl |
| 313 | SCH₃ | 2,6-diF-phenyl | 1-pyrrolidinocarbonyl |
| 314 | SCH₃ | 2,6-diF-phenyl | 2-(methylsulfonyl)phenyl |
| 315 | SCH₃ | 2,6-diF-phenyl | 4-morpholino |
| 316 | SCH₃ | 2,6-diF-phenyl | 2-(1'-CF₃-tetrazol-2-yl)phenyl |
| 317 | SCH₃ | 2,6-diF-phenyl | 4-morpholinocarbonyl |
| 318 | SCH₃ | 2,6-diF-phenyl | 2-methyl-1-imidazolyl |
| 319 | SCH₃ | 2,6-diF-phenyl | 5-methyl-1-imidazolyl |
| 320 | SCH₃ | 2,6-diF-phenyl | 2-methylsulfonyl-1-imidazolyl |
| 321 | SOCH₃ | phenyl | 2-(aminosulfonyl)phenyl |
| 322 | SOCH₃ | phenyl | 2-(methylaminosulfonyl)phenyl |
| 323 | SOCH₃ | phenyl | 1-pyrrolidinocarbonyl |
| 324 | SOCH₃ | phenyl | 2-(methylsulfonyl)phenyl |
| 325 | SOCH₃ | phenyl | 4-morpholino |
| 326 | SOCH₃ | phenyl | 2-(1'-CF₃-tetrazol-2-yl)phenyl |
| 327 | SOCH₃ | phenyl | 4-morpholinocarbonyl |
| 328 | SOCH₃ | phenyl | 2-methyl-1-imidazolyl |
| 329 | SOCH₃ | phenyl | 5-methyl-1-imidazolyl |
| 330 | SOCH₃ | phenyl | 2-methylsulfonyl-1-imidazolyl |
| 331 | SOCH₃ | 2-pyridyl | 2-(aminosulfonyl)phenyl |
| 332 | SOCH₃ | 2-pyridyl | 2-(methylaminosulfonyl)phenyl |
| 333 | SOCH₃ | 2-pyridyl | 1-pyrrolidinocarbonyl |
| 334 | SOCH₃ | 2-pyridyl | 2-(methylsulfonyl)phenyl |
| 335 | SOCH₃ | 2-pyridyl | 4-morpholino |
| 336 | SOCH₃ | 2-pyridyl | 2-(1'-CF₃-tetrazol-2-yl)phenyl |
| 337 | SOCH₃ | 2-pyridyl | 4-morpholinocarbonyl |
| 338 | SQCH₃ | 2-pyridyl | 2-methyl-1-imidazolyl |
| 339 | SOCH₃ | 2-pyridyl | 5-methyl-1-imidazolyl |
| 340 | SOCH₃ | 2-pyridyl | 2-methylsulfonyl-1-imidazolyl |
| 341 | SOCH₃ | 3-pyridyl | 2-(aminosulfonyl)phenyl |
| 342 | SOCH₃ | 3-pyridyl | 2-(methylaminosulfonyl)phenyl |
| 343 | SOCH₃ | 3-pyridyl | 1-pyrrolidinocarbonyl |
| 344 | SOCH₃ | 3-pyridyl | 2-(methylsulfonyl)phenyl |
| 345 | SOCH₃ | 3-pyridyl | 4-morpholino |
| 346 | SOCH₃ | 3-pyridyl | 2-(1'-CF₃-tetrazol-2-yl)phenyl |
| 347 | SOCH₃ | 3-pyridyl | 4-morpholinocarbonyl |
| 348 | SOCH₃ | 3-pyridyl | 2-methyl-1-imidazolyl |
| 349 | SOCH₃ | 3-pyridyl | 5-methyl-1-imidazolyl |
| 350 | SOCH₃ | 3-pyridyl | 2-methylsulfonyl-1-imidazolyl |
| 351 | SOCH₃ | 2-pyrimidyl | 2-(aminosulfonyl)phenyl |
| 352 | SOCH₃ | 2-pyrimidyl | 2-(methylaminosulfonyl)phenyl |
| 353 | SOCH₃ | 2-pyrimidyl | 1-pyrrolidinocarbonyl |
| 354 | SOCH₃ | 2-pyrimidyl | 2-(methylsulfonyl)phenyl |
| 355 | SOCH₃ | 2-pyrimidyl | 4-morpholino |
| 356 | SOCH₃ | 2-pyrimidyl | 2-(1'-CF₃-tetrazol-2-yl)phenyl |
| 357 | SQCH₃ | 2-pyrimidyl | 4-morpholinocarbonyl |
| 358 | SOCH₃ | 2-pyrimidyl | 2-methyl-1-imidazolyl |
| 359 | SOCH₃ | 2-pyrimidyl | 5-methyl-1-imidazolyl |
| 360 | SOCH₃ | 2-pyrimidyl | 2-methylsulfonyl-1-imidazolyl |
| 3 61 | SOCH₃ | 5-pyrimidyl | 2-(aminosulfonyl)phenyl |
| 3 62 | SOCH₃ | 5-pyrimidyl | 2-(methylaminosulfonyl)phenyl |
| 363 | SOCH₃ | 5-pyrimidyl | 1-pyrrolidinocarbonyl |
| 3 64 | SOCH₃ | 5-pyrimidyl | 2-(methylsulfonyl)phenyl |
| 365 | SOCH₃ | 5-pyrimidyl | 4-morpholino |
| 366 | SOCH₃ | 5-pyrimidyl | 2-(1'-CF₃-tetrazol-2-yl)phenyl |
| 367 | SQCH₃ | 5-pyrimidyl | 4-morpholinocarbonyl |
| 368 | SOCH₃ | 5-pyrimidyl | 2-methyl-1-imidazolyl |
| 369 | SOCH₃ | 5-pyrimidyl | 5-methyl-1-imidazolyl |
| 370 | SOCH₃ | 5-pyrimidyl | 2-methylsulfonyl-1-imidazolyl |
| 371 | SOCH₃ | 2-Cl-phenyl | 2-(aminosulfonyl)phenyl |
| 372 | SOCH₃ | 2-Cl-phenyl | 2-(methylaminosulfonyl)phenyl |
| 373 | SOCH₃ | 2-Cl-phenyl | 1-pyrrolidinocarbonyl |
| 374 | SOCH₃ | 2-Cl-phenyl | 2-(methylsulfonyl)phenyl |
| 375 | SOCH₃ | 2-Cl-phenyl | 4-morpholino |
| 376 | SOCH₃ | 2-Cl-phenyl | 2-(1'-CF₃-tetrazol-2-yl)phenyl |
| 377 | SOCH₃ | 2-Cl-phenyl | 4-morpholinocarbonyl |
| 378 | SOCH₃ | 2-Cl-phenyl | 2-methyl-1-imidazolyl |

TABLE 4-continued

| | | | |
|---|---|---|---|
| 379 | SOCH$_3$ | 2-Cl-phenyl | 5-methyl-1-imidazolyl |
| 380 | SOCH$_3$ | 2-Cl-phenyl | 2-methylsulfonyl-1-imidazolyl |
| 381 | SOCH$_3$ | 2-F-phenyl | 2-(aminosulfonyl)phenyl |
| 382 | SOCH$_3$ | 2-F-phenyl | 2-(methylaminosulfonyl)phenyl |
| 383 | SOCH$_3$ | 2-F-phenyl | 1-pyrrolidinocarbonyl |
| 384 | SOCH$_3$ | 2-F-phenyl | 2-(methylsulfonyl)phenyl |
| 385 | SOCH$_3$ | 2-F-phenyl | 4-morpholino |
| 386 | SOCH$_3$ | 2-F-phenyl | 2-(1'-CF$_3$-tetrazol-2-yl)phenyl |
| 387 | SOCH$_3$ | 2-F-phenyl | 4-morpholinocarbonyl |
| 388 | SOCH$_3$ | 2-F-phenyl | 2-methyl-1-imidazolyl |
| 389 | SOCH$_3$ | 2-F-phenyl | 5-methyl-1-imidazolyl |
| 390 | SOCH$_3$ | 2-F-phenyl | 2-methylsulfonyl-1-imidazolyl |
| 391 | SOCH$_3$ | 2,6-diF-phenyl | 2-(aminosulfonyl)phenyl |
| 392 | SOCH$_3$ | 2,6-diF-phenyl | 2-(methylaminosulfonyl)phenyl |
| 393 | SOCH$_3$ | 2,6-diF-phenyl | 1-pyrrolidinocarbonyl |
| 394 | SOCH$_3$ | 2,6-diF-phenyl | 2-(methylsulfonyl)phenyl |
| 395 | SOCH$_3$ | 2,6-diF-phenyl | 4-morpholino |
| 396 | SOCH$_3$ | 2,6-diF-phenyl | 2-(1'-CF$_3$-tetrazol-2-yl)phenyl |
| 397 | SOCH$_3$ | 2,6-diF-phenyl | 4-morpholinocarbonyl |
| 398 | SOCH$_3$ | 2,6-diF-phenyl | 2-methyl-1-imidazolyl |
| 399 | SOCH$_3$ | 2,6-diF-phenyl | 5-methyl-1-imidazolyl |
| 400 | SOCH$_3$ | 2,6-diF-phenyl | 2-methylsulfonyl-1-imidazolyl |
| 401 | SO$_2$CH$_3$ | phenyl | 2-(aminosulfonyl)phenyl |
| 402 | SO$_2$CH$_3$ | phenyl | 2-(methylaminosulfonyl)phenyl |
| 403 | SO$_2$CH$_3$ | phenyl | 1-pyrrolidinocarbonyl |
| 404 | SO$_2$CH$_3$ | phenyl | 2-(methylsulfonyl)phenyl |
| 405 | SO$_2$CH$_3$ | phenyl | 4-morpholino |
| 406 | SO$_2$CH$_3$ | phenyl | 2-(1'-CF$_3$-tetrazol-2-yl)phenyl |
| 407 | SO$_2$CH$_3$ | phenyl | 4-morpholinocarbonyl |
| 408 | SO$_2$CH$_3$ | phenyl | 2-methyl-1-imidazolyl |
| 409 | SO$_2$CH$_3$ | phenyl | 5-methyl-1-imidazolyl |
| 410 | SO$_2$CH$_3$ | phenyl | 2-methylsulfonyl-1-imidazolyl |
| 411 | SO$_2$CH$_3$ | 2-pyridyl | 2-(aminosulfonyl)phenyl |
| 412 | SO$_2$CH$_3$ | 2-pyridyl | 2-(methylaminosulfonyl)phenyl |
| 413 | SO$_2$CH$_3$ | 2-pyridyl | 1-pyrrolidinocarbonyl |
| 414 | SO$_2$CH$_3$ | 2-pyridyl | 2-(methylsulfonyl)phenyl |
| 415 | SO$_2$CH$_3$ | 2-pyridyl | 4-morpholino |
| 416 | SO$_2$CH$_3$ | 2-pyridyl | 2-(1'-CF$_3$-tetrazol-2-yl)phenyl |
| 417 | SO$_2$CH$_3$ | 2-pyridyl | 4-morpholinocarbonyl |
| 418 | SO$_2$CH$_3$ | 2-pyridyl | 2-methyl-1-imidazolyl |
| 419 | SO$_2$CH$_3$ | 2-pyridyl | 5-methyl-1-imidazolyl |
| 420 | SO$_2$CH$_3$ | 2-pyridyl | 2-methylsulfonyl-1-imidazolyl |
| 421 | SO$_2$CH$_3$ | 3-pyridyl | 2-(aminosulfonyl)phenyl |
| 422 | SO$_2$CH$_3$ | 3-pyridyl | 2-(methylaminosulfonyl)phenyl |
| 423 | SO$_2$CH$_3$ | 3-pyridyl | 1-pyrrolidinocarbonyl |
| 424 | SO$_2$CH$_3$ | 3-pyridyl | 2-(methylsulfonyl)phenyl |
| 425 | SO$_2$CH$_3$ | 3-pyridyl | 4-morpholino |
| 426 | SO$_2$CH$_3$ | 3-pyridyl | 2-(1'-CF$_3$-tetrazol-2-yl)phenyl |
| 427 | SO$_2$CH$_3$ | 3-pyridyl | 4-morpholinocarbonyl |
| 428 | SO$_2$CH$_3$ | 3-pyridyl | 2-methyl-1-imidazolyl |
| 429 | SO$_2$CH$_3$ | 3-pyridyl | 5-methyl-1-imidazolyl |
| 430 | SO$_2$CH$_3$ | 3-pyridyl | 2-methylsulfonyl-1-imidazolyl |
| 431 | SO$_2$CH$_3$ | 2-pyrimidyl | 2-(aminosulfonyl)phenyl |
| 432 | SO$_2$CH$_3$ | 2-pyrimidyl | 2-(methylaminosulfonyl)phenyl |
| 433 | SO$_2$CH$_3$ | 2-pyrimidyl | 1-pyrrolidinocarbonyl |
| 434 | SO$_2$CH$_3$ | 2-pyrimidyl | 2-(methylsulfonyl)phenyl |
| 435 | SO$_2$CH$_3$ | 2-pyrimidyl | 4-morpholino |
| 436 | SO$_2$CH$_3$ | 2-pyrimidyl | 2-(1'-CF$_3$-tetrazol-2-yl)phenyl |
| 437 | SO$_2$CH$_3$ | 2-pyrimidyl | 4-morpholinocarbonyl |
| 438 | SO$_2$CH$_3$ | 2-pyrimidyl | 2-methyl-1-imidazolyl |
| 439 | SO$_2$CH$_3$ | 2-pyrimidyl | 5-methyl-1-imidazolyl |
| 440 | SO$_2$CH$_3$ | 2-pyrimidyl | 2-methylsulfonyl-1-imidazolyl |
| 441 | SO$_2$CH$_3$ | 5-pyrimidyl | 2-(aminosulfonyl)phenyl |
| 442 | SO$_2$CH$_3$ | 5-pyrimidyl | 2-(methylaminosulfonyl)phenyl |
| 443 | SO$_2$CH$_3$ | 5-pyrimidyl | 1-pyrrolidinocarbonyl |
| 444 | SO$_2$CH$_3$ | 5-pyrimidyl | 2-(methylsulfonyl)phenyl |
| 445 | SO$_2$CH$_3$ | 5-pyrimidyl | 4-morpholino |
| 446 | SO$_2$CH$_3$ | 5-pyrimidyl | 2-(1'-CF$_3$-tetrazol-2-yl)phenyl |
| 447 | SO$_2$CH$_3$ | 5-pyrimidyl | 4-morpholinocarbonyl |
| 448 | SO$_2$CH$_3$ | 5-pyrimidyl | 2-methyl-1-imidazolyl |
| 449 | SO$_2$CH$_3$ | 5-pyrimidyl | 5-methyl-1-imidazolyl |
| 450 | SO$_2$CH$_3$ | 5-pyrimidyl | 2-methylsulfonyl-1-imidazolyl |
| 451 | SO$_2$CH$_3$ | 2-Cl-phenyl | 2-(aminosulfonyl)phenyl |
| 452 | SO$_2$CH$_3$ | 2-Cl-phenyl | 2-(methylaminosulfonyl)phenyl |
| 453 | SO$_2$CH$_3$ | 2-Cl-phenyl | 1-pyrrolidinocarbonyl |
| 454 | SO$_2$CH$_3$ | 2-Cl-phenyl | 2-(methylsulfonyl)phenyl |
| 455 | SO$_2$CH$_3$ | 2-Cl-phenyl | 4-morpholino |
| 456 | SO$_2$CH$_3$ | 2-Cl-phenyl | 2-(1'-CF$_3$-tetrazol-2-yl)phenyl |
| 457 | SO$_2$CH$_3$ | 2-Cl-phenyl | 4-morpholinocarbonyl |
| 458 | SO$_2$CH$_3$ | 2-Cl-phenyl | 2-methyl-1-imidazolyl |
| 459 | SO$_2$CH$_3$ | 2-Cl-phenyl | 5-methyl-1-imidazolyl |
| 460 | SO$_2$CH$_3$ | 2-Cl-phenyl | 2-methylsulfonyl-1-imidazolyl |
| 461 | SO$_2$CH$_3$ | 2-F-phenyl | 2-(aminosulfonyl)phenyl |
| 462 | SO$_2$CH$_3$ | 2-F-phenyl | 2-(methylaminosulfonyl)phenyl |
| 463 | SO$_2$CH$_3$ | 2-F-phenyl | 1-pyrrolidinocarbonyl |
| 464 | SO$_2$CH$_3$ | 2-F-phenyl | 2-(methylsulfonyl)phenyl |
| 465 | SO$_2$CH$_3$ | 2-F-phenyl | 4-morpholino |
| 466 | SO$_2$CH$_3$ | 2-F-phenyl | 2-(1'-CF$_3$-tetrazol-2-yl)phenyl |
| 467 | SO$_2$CH$_3$ | 2-F-phenyl | 4-morpholinocarbonyl |
| 468 | SO$_2$CH$_3$ | 2-F-phenyl | 2-methyl-1-imidazolyl |
| 469 | SO$_2$CH$_3$ | 2-F-phenyl | 5-methyl-1-imidazolyl |
| 470 | SO$_2$CH$_3$ | 2-F-phenyl | 2-methylsulfonyl-1-imidazolyl |
| 471 | SO$_2$CH$_3$ | 2,6-diF-phenyl | 2-(aminosulfonyl)phenyl |
| 472 | SO$_2$CH$_3$ | 2,6-diF-phenyl | 2-(methylaminosulfonyl)phenyl |
| 473 | SO$_2$CH$_3$ | 2,6-diF-phenyl | 1-pyrrolidinocarbonyl |
| 474 | SO$_2$CH$_3$ | 2,6-diF-phenyl | 2-(methylsulfonyl)phenyl |
| 475 | SO$_2$CH$_3$ | 2,6-diF-phenyl | 4-morpholino |
| 476 | SO$_2$CH$_3$ | 2,6-diF-phenyl | 2-(1'-CF$_3$-tetrazol-2-yl)phenyl |
| 477 | SO$_2$CH$_3$ | 2,6-diF-phenyl | 4-morpholinocarbonyl |
| 478 | SO$_2$CH$_3$ | 2,6-diF-phenyl | 2-methyl-1-imidazolyl |
| 479 | SO$_2$CH$_3$ | 2,6-diF-phenyl | 5-methyl-1-imidazolyl |
| 480 | SO$_2$CH$_3$ | 2,6-diF-phenyl | 2-methylsulfonyl-1-imidazolyl |
| 481 | CH$_2$NH—SO$_2$CH$_3$ | phenyl | 2-(aminosulfonyl)phenyl |
| 482 | CH$_2$NH—SO$_2$CH$_3$ | phenyl | 2-(methylaminosulfonyl)phenyl |
| 483 | CH$_2$NH—SO$_2$CH$_3$ | phenyl | 1-pyrrolidinocarbonyl |
| 484 | CH$_2$NH—SO$_2$CH$_3$ | phenyl | 2-(methylsulfonyl)phenyl |
| 485 | CH$_2$NH—SO$_2$CH$_3$ | phenyl | 4-morpholino |
| 486 | CH$_2$NH—SO$_2$CH$_3$ | phenyl | 2-(1'-CF$_3$-tetrazol-2-yl)phenyl |
| 487 | CH$_2$NH—SO$_2$CH$_3$ | phenyl | 4-morpholinocarbonyl |
| 488 | CH$_2$NH—SO$_2$CH$_3$ | phenyl | 2-methyl-1-imidazolyl |
| 489 | CH$_2$NH—SO$_2$CH$_3$ | phenyl | 5-methyl-1-imidazolyl |
| 490 | CH$_2$NH—SO$_2$CH$_3$ | phenyl | 2-methylsulfonyl-1-imidazolyl |
| 491 | CH$_2$NH—SO$_2$CH$_3$ | 2-pyridyl | 2-(aminosulfonyl)phenyl |
| 492 | CH$_2$NH—SO$_2$CH$_3$ | 2-pyridyl | 2-(methylaminosulfonyl)phenyl |
| 493 | CH$_2$NH—SO$_2$CH$_3$ | 2-pyridyl | 1-pyrrolidinocarbonyl |
| 494 | CH$_2$NH—SO$_2$CH$_3$ | 2-pyridyl | 2-(methylsulfonyl)phenyl |
| 495 | CH$_2$NH—SO$_2$CH$_3$ | 2-pyridyl | 4-morpholino |
| 496 | CH$_2$NH—SO$_2$CH$_3$ | 2-pyridyl | 2-(1'-CF$_3$-tetrazol-2-yl)phenyl |
| 497 | CH$_2$NH—SO$_2$CH$_3$ | 2-pyridyl | 4-morpholinocarbonyl |
| 498 | CH$_2$NH—SO$_2$CH$_3$ | 2-pyridyl | 2-methyl-1-imidazolyl |
| 499 | CH$_2$NH—SO$_2$CH$_3$ | 2-pyridyl | 5-methyl-1-imidazolyl |
| 500 | CH$_2$NH—SO$_2$CH$_3$ | 2-pyridyl | 2-methylsulfonyl-1-imidazolyl |
| 501 | CH$_2$NH—SO$_2$CH$_3$ | 3-pyridyl | 2-(aminosulfonyl)phenyl |
| SO$_2$ | CH$_2$NH—SO$_2$CH$_3$ | 3-pyridyl | 2-(methylaminosulfonyl)phenyl |
| 503 | CH$_2$NH—SO$_2$CH$_3$ | 3-pyridyl | 1-pyrrolidinocarbonyl |
| 504 | CH$_2$NH—SO$_2$CH$_3$ | 3-pyridyl | 2-(methylsulfonyl)phenyl |
| 505 | CH$_2$NH—SO$_2$CH$_3$ | 3-pyridyl | 4-morpholino |
| 506 | CH$_2$NH—SO$_2$CH$_3$ | 3-pyridyl | 2-(1'-CF$_3$-tetrazol-2-yl)phenyl |
| 507 | CH$_2$NH—SO$_2$CH$_3$ | 3-pyridyl | 4-morpholinocarbonyl |
| 508 | CH$_2$NH—SO$_2$CH$_3$ | 3-pyridyl | 2-methyl-1-imidazolyl |

TABLE 4-continued

| | | | |
|---|---|---|---|
| 509 | CH$_2$NH—SO$_2$CH$_3$ | 3-pyridyl | 5-methyl-1-imidazolyl |
| 510 | CH$_2$NH—SO$_2$CH$_3$ | 3-pyridyl | 2-methylsulfonyl-1-imidazolyl |
| 511 | CH$_2$NH—SO$_2$CH$_3$ | 2-pyrimidyl | 2-(aminosulfonyl)phenyl |
| 512 | CH$_2$NH—SO$_2$CH$_3$ | 2-pyrimidyl | 2-(methylaminosulfonyl)phenyl |
| 513 | CH$_2$NH—SO$_2$CH$_3$ | 2-pyrimidyl | 1-pyrrolidinocarbonyl |
| 514 | CH$_2$NH—SO$_2$CH$_3$ | 2-pyrimidyl | 2-(methylsulfonyl)phenyl |
| 515 | CH$_2$NH—SO$_2$CH$_3$ | 2-pyrimidyl | 4-morpholino |
| 516 | CH$_2$NH—SO$_2$CH$_3$ | 2-pyrimidyl | 2-(1'-CF$_3$-tetrazol-2-yl)phenyl |
| 517 | CH$_2$NH—SO$_2$CH$_3$ | 2-pyrimidyl | 4-morpholinocarbonyl |
| 518 | CH$_2$NH—SO$_2$CH$_3$ | 2-pyrimidyl | 2-methyl-1-imidazolyl |
| 519 | CH$_2$NH—SO$_2$CH$_3$ | 2-pyrimidyl | 5-methyl-1-imidazolyl |
| 520 | CH$_2$NH—SO$_2$CH$_3$ | 2-pyrimidyl | 2-methylsulfonyl-1-imidazolyl |
| 521 | CH$_2$NH—SO$_2$CH$_3$ | 5-pyrimidyl | 2-(aminosulfonyl)phenyl |
| 522 | CH$_2$NH—SO$_2$CH$_3$ | 5-pyrimidyl | 2-(methylaminosulfonyl)phenyl |
| 523 | CH$_2$NH—SO$_2$CH$_3$ | 5-pyrimidyl | 1-pyrrolidinocarbonyl |
| 524 | CH$_2$NH—SO$_2$CH$_3$ | 5-pyrimidyl | 2-(methylsulfonyl)phenyl |
| 525 | CH$_2$NH—SO$_2$CH$_3$ | 5-pyrimidyl | 4-morpholino |
| 526 | CH$_2$NH—SO$_2$CH$_3$ | 5-pyrimidyl | 2-(1'-CF$_3$-tetrazol-2-yl)phenyl |
| 527 | CH$_2$NH—SO$_2$CH$_3$ | 5-pyrimidyl | 4-morpholinocarbonyl |
| 528 | CH$_2$NH—SO$_2$CH$_3$ | 5-pyrimidyl | 2-methyl-1-imidazolyl |
| 529 | CH$_2$NH—SO$_2$CH$_3$ | 5-pyrimidyl | 5-methyl-1-imidazolyl |
| 530 | CH$_2$NH—SO$_2$CH$_3$ | 5-pyrimidyl | 2-methylsulfonyl-1-imidazolyl |
| 531 | CH$_2$NH—SO$_2$CH$_3$ | 2-Cl-phenyl | 2-(aminosulfonyl)phenyl |
| 532 | CH$_2$NH—SO$_2$CH$_3$ | 2-Cl-phenyl | 2-(methylaminosulfonyl)phenyl |
| 533 | CH$_2$NH—SO$_2$CH$_3$ | 2-Cl-phenyl | 1-pyrrolidinocarbonyl |
| 534 | CH$_2$NH—SO$_2$CH$_3$ | 2-Cl-phenyl | 2-(methylsulfonyl)phenyl |
| 535 | CH$_2$NH—SO$_2$CH$_3$ | 2-Cl-phenyl | 4-morpholino |
| 536 | CH$_2$NH—SO$_2$CH$_3$ | 2-Cl-phenyl | 2-(1'-CF$_3$-tetrazol-2-yl)phenyl |
| 537 | CH$_2$NH—SO$_2$CH$_3$ | 2-Cl-phenyl | 4-morpholinocarbonyl |
| 538 | CH$_2$NH—SO$_2$CH$_3$ | 2-Cl-phenyl | 2-methyl-1-imidazolyl |
| 539 | CH$_2$NH—SO$_2$CH$_3$ | 2-Cl-phenyl | 5-methyl-1-imidazolyl |
| 540 | CH$_2$NH—SO$_2$CH$_3$ | 2-Cl-phenyl | 2-methylsulfonyl-1-imidazolyl |
| 541 | CH$_2$NH—SO$_2$CH$_3$ | 2-F-phenyl | 2-(aminosulfonyl)phenyl |
| 542 | CH$_2$NH—SO$_2$CH$_3$ | 2-F-phenyl | 2-(methylaminosulfonyl)phenyl |
| 543 | CH$_2$NH—SO$_2$CH$_3$ | 2-F-phenyl | 1-pyrrolidinocarbonyl |
| 544 | CH$_2$NH—SO$_2$CH$_3$ | 2-F-phenyl | 2-(methylsulfonyl)phenyl |
| 545 | CH$_2$NH—SO$_2$CH$_3$ | 2-F-phenyl | 4-morpholino |
| 546 | CH$_2$NH—SO$_2$CH$_3$ | 2-F-phenyl | 2-(1'-CF$_3$-tetrazol-2-yl)phenyl |
| 547 | CH$_2$NH—SO$_2$CH$_3$ | 2-F-phenyl | 4-morpholinocarbonyl |
| 548 | CH$_2$NH—SO$_2$CH$_3$ | 2-F-phenyl | 2-methyl-1-imidazolyl |
| 549 | CH$_2$NH—SO$_2$CH$_3$ | 2-F-phenyl | 5-methyl-1-imidazolyl |
| 550 | CH$_2$NH—SO$_2$CH$_3$ | 2-F-phenyl | 2-methylsulfonyl-1-imidazolyl |
| 551 | CH$_2$NH—SO$_2$CH$_3$ | 2,6-diF-phenyl | 2-(aminosulfonyl)phenyl |
| 552 | CH$_2$NH—SO$_2$CH$_3$ | 2,6-diF-phenyl | 2-(methylaminosulfonyl)phenyl |
| 553 | CH$_2$NH—SO$_2$CH$_3$ | 2,6-diF-phenyl | 1-pyrrolidinocarbonyl |
| 554 | CH$_2$NH—SO$_2$CH$_3$ | 2,6-diF-phenyl | 2-(methylsulfonyl)phenyl |
| 555 | CH$_2$NH—SO$_2$CH$_3$ | 2,6-diF-phenyl | 4-morpholino |
| 556 | CH$_2$NH—SO$_2$CH$_3$ | 2, 6-diF-phenyl | 2-(1'-CF$_3$-tetrazol-2-yl)phenyl |
| 557 | CH$_2$NH—SO$_2$CH$_3$ | 2,6-diF-phenyl | 4-morpholinocarbonyl |
| 558 | CH$_2$NH—SO$_2$CH$_3$ | 2,6-diF-phenyl | 2-methyl-1-imidazolyl |
| 559 | CH$_2$NH—SO$_2$CH$_3$ | 2, 6-diF-phenyl | 5-methyl-1-imidazolyl |
| 560 | CH$_2$NH—SO$_2$CH$_3$ | 2,6-diF-phenyl | 2-methylsulfonyl-1-imidazolyl |
| 561 | Cl | phenyl | 2-(aminosulfonyl)phenyl |
| 562 | Cl | phenyl | 2-(methylaminosulfonyl)phenyl |
| 563 | Cl | phenyl | 1-pyrrolidinocarbonyl |
| 564 | Cl | phenyl | 2-(methylsulfonyl)phenyl |
| 565 | Cl | phenyl | 4-morpholino |
| 566 | Cl | phenyl | 2-(1'-CF$_3$-tetrazol-2-yl)phenyl |
| 567 | Cl | phenyl | 4-morpholinocarbonyl |
| 568 | Cl | phenyl | 2-methyl-1-imidazolyl |
| 569 | Cl | phenyl | 5-methyl-1-imidazolyl |
| 570 | Cl | phenyl | 2-methylsulfonyl-1-imidazolyl |
| 571 | Cl | 2-pyridyl | 2-(aminosulfonyl)phenyl |
| 572 | Cl | 2-pyridyl | 2-(methylaminosulfonyl)phenyl |
| 573 | Cl | 2-pyridyl | 1-pyrrolidinocarbonyl |
| 574 | Cl | 2-pyridyl | 2-(methylsulfonyl)phenyl |
| 575 | Cl | 2-pyridyl | 4-morpholino |
| 576 | Cl | 2-pyridyl | 2-(1'-CF$_3$-tetrazol-2-yl)phenyl |
| 577 | Cl | 2-pyridyl | 4-morpholinocarbonyl |
| 578 | Cl | 2-pyridyl | 2-methyl-1-imidazolyl |
| 579 | Cl | 2-pyridyl | 5-methyl-1-imidazolyl |
| 580 | Cl | 2-pyridyl | 2-methylsulfonyl-1-imidazolyl |
| 581 | Cl | 3-pyridyl | 2-(aminosulfonyl)phenyl |
| 582 | Cl | 3-pyridyl | 2-(methylaminosulfonyl)phenyl |
| 583 | Cl | 3-pyridyl | 1-pyrrolidinocarbonyl |
| 584 | Cl | 3-pyridyl | 2-(methylsulfonyl)phenyl |
| 585 | Cl | 3-pyridyl | 4-morpholino |
| 586 | Cl | 3-pyridyl | 2-(1'-CF$_3$-tetrazol-2-yl)phenyl |
| 587 | Cl | 3-pyridyl | 4-morpholinocarbonyl |
| 588 | Cl | 3-pyridyl | 2-methyl-1-imidazolyl |
| 589 | Cl | 3-pyridyl | 5-methyl-1-imidazolyl |
| 590 | Cl | 3-pyridyl | 2-methylsulfonyl-1-imidazolyl |
| 591 | Cl | 2-pyrimidyl | 2-(aminosulfonyl)phenyl |
| 592 | Cl | 2-pyrimidyl | 2-(methylaminosulfonyl)phenyl |
| 593 | Cl | 2-pyrimidyl | 1-pyrrolidinocarbonyl |
| 594 | Cl | 2-pyrimidyl | 2-(methylsulfonyl)phenyl |
| 595 | Cl | 2-pyrimidyl | 4-morpholino |
| 596 | Cl | 2-pyrimidyl | 2-(1'-CF$_3$-tetrazol-2-yl)phenyl |
| 597 | Cl | 2-pyrimidyl | 4-morpholinocarbonyl |
| 598 | Cl | 2-pyrimidyl | 2-methyl-1-imidazolyl |
| 599 | Cl | 2-pyrimidyl | 5-methyl-1-imidazolyl |
| 600 | Cl | 2-pyrimidyl | 2-methylsulfonyl-1-imidazolyl |
| 601 | Cl | 5-pyrimidyl | 2-(aminosulfonyl)phenyl |
| 602 | Cl | 5-pyrimidyl | 2-(methylaminosulfonyl)phenyl |
| 603 | Cl | 5-pyrimidyl | 1-pyrrolidinocarbonyl |
| 604 | Cl | 5-pyrimidyl | 2-(methylsulfonyl)phenyl |
| 605 | Cl | 5-pyrimidyl | 4-morpholino |
| 606 | Cl | 5-pyrimidyl | 2-(1'-CF$_3$-tetrazol-2-yl)phenyl |
| 607 | Cl | 5-pyrimidyl | 4-morpholinocarbonyl |
| 608 | Cl | 5-pyrimidyl | 2-methyl-1-imidazolyl |
| 609 | Cl | 5-pyrimidyl | 5-methyl-1-imidazolyl |
| 610 | Cl | 5-pyrimidyl | 2-methylsulfonyl-1-imidazolyl |
| 611 | Cl | 2-Cl-phenyl | 2-(aminosulfonyl)phenyl |
| 612 | Cl | 2-Cl-phenyl | 2-(methylaminosulfonyl)phenyl |
| 613 | Cl | 2-Cl-phenyl | 1-pyrrolidinocarbonyl |
| 614 | Cl | 2-Cl-phenyl | 2-(methylsulfonyl)phenyl |

TABLE 4-continued

| | | | |
|---|---|---|---|
| 615 | Cl | 2-Cl-phenyl | 4-morpholino |
| 616 | Cl | 2-Cl-phenyl | 2-(1'-$CF_3$-tetrazol-2-yl)phenyl |
| 617 | Cl | 2-Cl-phenyl | 4-morpholinocarbonyl |
| 618 | Cl | 2-Cl-phenyl | 2-methyl-1-imidazolyl |
| 619 | Cl | 2-Cl-phenyl | 5-methyl-1-imidazolyl |
| 620 | Cl | 2-Cl-phenyl | 2-methylsulfonyl-1-imidazolyl |
| 621 | Cl | 2-F-phenyl | 2-(aminosulfonyl)phenyl |
| 622 | Cl | 2-F-phenyl | 2-(methylaminosulfonyl)phenyl |
| 623 | Cl | 2-F-phenyl | 1-pyrrolidinocarbonyl |
| 624 | Cl | 2-F-phenyl | 2-(methylsulfonyl)phenyl |
| 625 | Cl | 2-F-phenyl | 4-morpholino |
| 626 | Cl | 2-F-phenyl | 2-(1'-$CF_3$-tetrazol-2-yl)phenyl |
| 627 | Cl | 2-F-phenyl | 4-morpholinocarbonyl |
| 628 | Cl | 2-F-phenyl | 2-methyl-1-imidazolyl |
| 629 | Cl | 2-F-phenyl | 5-methyl-1-imidazolyl |
| 630 | Cl | 2-F-phenyl | 2-methylsulfonyl-1-imidazolyl |
| 631 | Cl | 2,6-diF-phenyl | 2-(aminosulfonyl)phenyl |
| 632 | Cl | 2,6-diF-phenyl | 2-(methylaminosulfonyl)phenyl |
| 633 | Cl | 2,6-diF-phenyl | 1-pyrrolidinocarbonyl |
| 634 | Cl | 2,6-diF-phenyl | 2-(methylsulfonyl)phenyl |
| 635 | Cl | 2,6-diF-phenyl | 4-morpholino |
| 636 | Cl | 2,6-diF-phenyl | 2-(1'-$CF_3$-tetrazol-2-yl)phenyl |
| 637 | Cl | 2,6-diF-phenyl | 4-morpholinocarbonyl |
| 638 | Cl | 2,6-diF-phenyl | 2-methyl-1-imidazolyl |
| 639 | Cl | 2,6-diF-phenyl | 5-methyl-1-imidazolyl |
| 640 | Cl | 2,6-diF-phenyl | 2-methylsulfonyl-1-imidazolyl |
| 641 | F | phenyl | 2-(aminosulfonyl)phenyl |
| 642 | F | phenyl | 2-(methylaminosulfonyl)phenyl |
| 643 | F | phenyl | 1-pyrrolidinocarbonyl |
| 644 | F | phenyl | 2-(methylsulfonyl)phenyl |
| 645 | F | phenyl | 4-morpholino |
| 646 | F | phenyl | 2-(1'-$CF_3$-tetrazol-2-yl)phenyl |
| 647 | F | phenyl | 4-morpholinocarbonyl |
| 648 | F | phenyl | 2-methyl-1-imidazolyl |
| 649 | F | phenyl | 5-methyl-1-imidazolyl |
| 650 | F | phenyl | 2-methylsulfonyl-1-imidazolyl |
| 651 | F | 2-pyridyl | 2-(aminosulfonyl)phenyl |
| 652 | F | 2-pyridyl | 2-(methylaminosulfonyl)phenyl |
| 653 | F | 2-pyridyl | 1-pyrrolidinocarbonyl |
| 654 | F | 2-pyridyl | 2-(methylsulfonyl)phenyl |
| 655 | F | 2-pyridyl | 4-morpholino |
| 656 | F | 2-pyridyl | 2-(1'-$CF_3$-tetrazol-2-yl)phenyl |
| 657 | F | 2-pyridyl | 4-morpholinocarbonyl |
| 658 | F | 2-pyridyl | 2-methyl-1-imidazolyl |
| 659 | F | 2-pyridyl | 5-methyl-1-imidazolyl |
| 660 | F | 2-pyridyl | 2-methylsulfonyl-1-imidazolyl |
| 661 | F | 3-pyridyl | 2-(aminosulfonyl)phenyl |
| 662 | F | 3-pyridyl | 2-(methylaminosulfonyl)phenyl |
| 663 | F | 3-pyridyl | 1-pyrrolidinocarbonyl |
| 664 | F | 3-pyridyl | 2-(methylsulfonyl)phenyl |
| 665 | F | 3-pyridyl | 4-morpholino |
| 666 | F | 3-pyridyl | 2-(1'-$CF_3$-tetrazol-2-yl)phenyl |
| 667 | F | 3-pyridyl | 4-morpholinocarbonyl |
| 668 | F | 3-pyridyl | 2-methyl-1-imidazolyl |
| 669 | F | 3-pyridyl | 5-methyl-1-imidazolyl |
| 670 | F | 3-pyridyl | 2-methylsulfonyl-1-imidazolyl |
| 671 | F | 2-pyrimidyl | 2-(aminosulfonyl)phenyl |
| 672 | F | 2-pyrimidyl | 2-(methylaminosulfonyl)phenyl |
| 673 | F | 2-pyrimidyl | 1-pyrrolidinocarbonyl |
| 674 | F | 2-pyrimidyl | 2-(methylsulfonyl)phenyl |
| 675 | F | 2-pyrimidyl | 4-morpholino |
| 676 | F | 2-pyrimidyl | 2-(1'-$CF_3$-tetrazol-2-yl)phenyl |
| 677 | F | 2-pyrimidyl | 4-morpholinocarbonyl |
| 678 | F | 2-pyrimidyl | 2-methyl-1-imidazolyl |
| 679 | F | 2-pyrimidyl | 5-methyl-1-imidazolyl |
| 680 | F | 2-pyrimidyl | 2-methylsulfonyl-1-imidazolyl |
| 681 | F | 5-pyrimidyl | 2-(aminosulfonyl)phenyl |
| 682 | F | 5-pyrimidyl | 2-(methylaminosulfonyl)phenyl |
| 683 | F | 5-pyrimidyl | 1-pyrrolidinocarbonyl |
| 684 | F | 5-pyrimidyl | 2-(methylsulfonyl)phenyl |
| 685 | F | 5-pyrimidyl | 4-morpholino |
| 686 | F | 5-pyrimidyl | 2-(1'-$CF_3$-tetrazol-2-yl)phenyl |
| 687 | F | 5-pyrimidyl | 4-morpholinocarbonyl |
| 688 | F | 5-pyrimidyl | 2-methyl-1-imidazolyl |
| 689 | F | 5-pyrimidyl | 5-methyl-1-imidazolyl |
| 690 | F | 5-pyrimidyl | 2-methylsulfonyl-1-imidazolyl |
| 691 | F | 2-Cl-phenyl | 2-(aminosulfonyl)phenyl |
| 692 | F | 2-Cl-phenyl | 2-(methylaminosulfonyl) phenyl |
| 693 | F | 2-Cl-phenyl | 1-pyrrolidinocarbonyl |
| 694 | F | 2-Cl-phenyl | 2-(methylsulfonyl)phenyl |
| 695 | F | 2-Cl-phenyl | 4-morpholino |
| 696 | F | 2-Cl-phenyl | 2-(1'-$CF_3$-tetrazol-2-yl)phenyl |
| 697 | F | 2-Cl-phenyl | 4-morpholinocarbonyl |
| 698 | F | 2-Cl-phenyl | 2-methyl-1-imidazolyl |
| 699 | F | 2-Cl-phenyl | 5-methyl-1-imidazolyl |
| 700 | F | 2-Cl-phenyl | 2-methylsulfonyl-1-imidazolyl |
| 701 | F | 2-F-phenyl | 2-(aminosulfonyl)phenyl |
| 702 | F | 2-F-phenyl | 2-(methylaminosulfonyl)phenyl |
| 703 | F | 2-F-phenyl | 1-pyrrolidinocarbonyl |
| 704 | F | 2-F-phenyl | 2-(methylsulfonyl)phenyl |
| 705 | F | 2-F-phenyl | 4-morpholino |
| 706 | F | 2-F-phenyl | 2-(1'-$CF_3$-tetrazol-2-yl)phenyl |
| 707 | F | 2-F-phenyl | 4-morpholinocarbonyl |
| 708 | F | 2-F-phenyl | 2-methyl-1-imidazolyl |
| 709 | F | 2-F-phenyl | 5-methyl-1-imidazolyl |
| 710 | F | 2-F-phenyl | 2-methylsulfonyl-1-imidazolyl |
| 711 | F | 2,6-diF-phenyl | 2-(aminosulfonyl)phenyl |
| 712 | F | 2,6-diF-phenyl | 2-(methylaminosulfonyl)phenyl |
| 713 | F | 2,6-diF-phenyl | 1-pyrrolidinocarbonyl |
| 714 | F | 2,6-diF-phenyl | 2-(methylsulfonyl)phenyl |
| 715 | F | 2,6-diF-phenyl | 4-morpholino |
| 716 | F | 2,6-diF-phenyl | 2-(1'-$CF_3$-tetrazol-2-yl)phenyl |
| 717 | F | 2,6-diF-phenyl | 4-morpholinocarbonyl |
| 718 | F | 2,6-diF-phenyl | 2-methyl-1-imidazolyl |
| 719 | F | 2,6-diF-phenyl | 5-methyl-1-imidazolyl |
| 720 | F | 2,6-diF-phenyl | 2-methylsulfonyl-1-imidazolyl |
| 721 | $CO_2CH_3$ | phenyl | 2-(aminosulfonyl)phenyl |
| 722 | $CO_2CH_3$ | phenyl | 2-(methylaminosulfonyl)phenyl |
| 723 | $CO_2CH_3$ | phenyl | 1-pyrrolidinocarbonyl |
| 724 | $CO_2CH_3$ | phenyl | 2-(methylsulfonyl)phenyl |
| 725 | $CO_2CH_3$ | phenyl | 4-morpholino |
| 726 | $CO_2CH_3$ | phenyl | 2-(1'-$CF_3$-tetrazol-2-yl)phenyl |
| 727 | $CO_2CH_3$ | phenyl | 4-morpholinocarbonyl |
| 728 | $CO_2CH_3$ | phenyl | 2-methyl-1-imidazolyl |
| 729 | $CO_2CH_3$ | phenyl | 5-methyl-1-imidazolyl |
| 730 | $CO_2CH_3$ | phenyl | 2-methylsulfonyl-1-imidazolyl |
| 731 | $CO_2CH_3$ | 2-pyridyl | 2-(aminosulfonyl)phenyl |
| 732 | $CO_2CH_3$ | 2-pyridyl | 2-(methylaminosulfonyl)phenyl |
| 733 | $CO_2CH_3$ | 2-pyridyl | 1-pyrrolidinocarbonyl |
| 734 | $CO_2CH_3$ | 2-pyridyl | 2-(methylsulfonyl)phenyl |
| 735 | $CO_2CH_3$ | 2-pyridyl | 4-morpholino |
| 736 | $CO_2CH_3$ | 2-pyridyl | 2-(1'-$CF_3$-tetrazol-2-yl)phenyl |
| 737 | $CO_2CH_3$ | 2-pyridyl | 4-morpholinocarbonyl |
| 738 | $CO_2CH_3$ | 2-pyridyl | 2-methyl-1-imidazolyl |
| 739 | $CO_2CH_3$ | 2-pyridyl | 5-methyl-1-imidazolyl |
| 740 | $CO_2CH_3$ | 2-pyridyl | 2-methylsulfonyl-1-imidazolyl |
| 741 | $CO_2CH_3$ | 3-pyridyl | 2-(aminosulfonyl)phenyl |
| 742 | $CO_2CH_3$ | 3-pyridyl | 2-(methylaminosulfonyl)phenyl |
| 743 | $CO_2CH_3$ | 3-pyridyl | 1-pyrrolidinocarbonyl |
| 744 | $CO_2CH_3$ | 3-pyridyl | 2-(methylsulfonyl)phenyl |
| 745 | $CO_2CH_3$ | 3-pyridyl | 4-morpholino |
| 746 | $CO_2CH_3$ | 3-pyridyl | 2-(1'-$CF_2$-tetrazol-2-yl)phenyl |
| 747 | $CO_2CH_3$ | 3-pyridyl | 4-morpholinocarbonyl |
| 748 | $CO_2CH_3$ | 3-pyridyl | 2-methyl-1-imidazolyl |
| 749 | $CO_2CH_3$ | 3-pyridyl | 5-methyl-1-imidazolyl |
| 750 | $CO_2CH_3$ | 3-pyridyl | 2-methylsulfonyl-1-imidazolyl |
| 751 | $CO_2CH_3$ | 2-pyrimidyl | 2-(aminosulfonyl)phenyl |
| 752 | $CO_2CH_3$ | 2-pyrimidyl | 2-(methylaminosulfonyl)phenyl |
| 753 | $CO_2CH_3$ | 2-pyrimidyl | 1-pyrrolidinocarbonyl |
| 754 | $CO_2CH_3$ | 2-pyrimidyl | 2-(methylsulfonyl)phenyl |
| 755 | $CO_2CH_3$ | 2-pyrimidyl | 4-morpholino |
| 756 | $CO_2CH_3$ | 2-pyrimidyl | 2-(1'-$CF_2$-tetrazol-2-yl)phenyl |
| 757 | $CO_2CH_3$ | 2-pyrimidyl | 4-morpholinocarbonyl |
| 758 | $CO_2CH_3$ | 2-pyrimidyl | 2-methyl-1-imidazolyl |
| 759 | $CO_2CH_3$ | 2-pyrimidyl | 5-methyl-1-imidazolyl |
| 760 | $CO_2CH_3$ | 2-pyrimidyl | 2-methylsulfonyl-1-imidazolyl |
| 761 | $CO_2CH_3$ | 5-pyrimidyl | 2-(aminosulfonyl)phenyl |
| 762 | $CO_2CH_3$ | 5-pyrimidyl | 2-(methylaminosulfonyl)phenyl |
| 763 | $CO_2CH_3$ | 5-pyrimidyl | 1-pyrrolidinocarbonyl |
| 764 | $CO_2CH_3$ | 5-pyrimidyl | 2-(methylsulfonyl)phenyl |
| 765 | $CO_2CH_3$ | 5-pyrimidyl | 4-morpholino |
| 766 | $CO_2CH_3$ | 5-pyrimidyl | 2-(1'-$CF_2$-tetrazol-2-yl)phenyl |
| 767 | $CO_2CH_3$ | 5-pyrimidyl | 4-morpholinocarbonyl |
| 768 | $CO_2CH_3$ | 5-pyrimidyl | 2-methyl-1-imidazolyl |
| 769 | $CO_2CH_3$ | 5-pyrimidyl | 5-methyl-1-imidazolyl |
| 770 | $CO_2CH_3$ | 5-pyrimidyl | 2-methylsulfonyl-1-imidazolyl |
| 771 | $CO_2CH_3$ | 2-Cl-phenyl | 2-(aminosulfonyl)phenyl |
| 772 | $CO_2CH_3$ | 2-Cl-phenyl | 2-(methylaminosulfonyl)phenyl |

TABLE 4-continued

| | | | |
|---|---|---|---|
| 773 | $CO_2CH_3$ | 2-Cl-phenyl | 1-pyrrolidinocarbonyl |
| 774 | $CO_2CH_3$ | 2-Cl-phenyl | 2-(methylsulfonyl)phenyl |
| 775 | $CO_2CH_3$ | 2-Cl-phenyl | 4-morpholino |
| 776 | $CO_2CH_3$ | 2-Cl-phenyl | 2-(1'-$CF_2$-tetrazol-2-yl)phenyl |
| 777 | $CO_2CH_3$ | 2-Cl-phenyl | 4-morpholinocarbonyl |
| 778 | $CO_2CH_3$ | 2-Cl-phenyl | 2-methyl-1-imidazolyl |
| 779 | $CO_2CH_3$ | 2-Cl-phenyl | 5-methyl-1-imidazolyl |
| 780 | $CO_2CH_3$ | 2-Cl-phenyl | 2-methylsulfonyl-1-imidazolyl |
| 781 | $CO_2CH_3$ | 2-F-phenyl | 2-(aminosulfonyl)phenyl |
| 782 | $CO_2CH_3$ | 2-F-phenyl | 2-(methylaminosulfonyl)phenyl |
| 783 | $CO_2CH_3$ | 2-F-phenyl | 1-pyrrolidinocarbonyl |
| 784 | $CO_2CH_3$ | 2-F-phenyl | 2-(methylsulfonyl)phenyl |
| 785 | $CO_2CH_3$ | 2-F-phenyl | 4-morpholino |
| 786 | $CO_2CH_3$ | 2-F-phenyl | 2-(1'-$CF_2$-tetrazol-2-yl)phenyl |
| 787 | $CO_2CH_3$ | 2-F-phenyl | 4-morpholinocarbonyl |
| 788 | $CO_2CH_3$ | 2-F-phenyl | 2-methyl-1-imidazolyl |
| 789 | $CO_2CH_3$ | 2-F-phenyl | 5-methyl-1-imidazolyl |
| 790 | $CO_2CH_3$ | 2-F-phenyl | 2-methylsulfonyl-1-imidazolyl |
| 791 | $CO_2CH_3$ | 2,6-diF-phenyl | 2-(aminosulfonyl)phenyl |
| 792 | $CO_2CH_3$ | 2,6-diF-phenyl | 2-(methylaminosulfonyl)phenyl |
| 793 | $CO_2CH_3$ | 2,6-diF-phenyl | 1-pyrrolidinocarbonyl |
| 794 | $CO_2CH_3$ | 2,6-diF-phenyl | 2-(methylsulfonyl)phenyl |
| 795 | $CO_2CH_3$ | 2,6-diF-phenyl | 4-morpholino |
| 796 | $CO_2CH_3$ | 2,6-diF-phenyl | 2-(1'-$CF_2$-tetrazol-2-yl)phenyl |
| 797 | $CO_2CH_3$ | 2,6-diF-phenyl | 4-morpholinocarbonyl |
| 798 | $CO_2CH_3$ | 2,6-diF-phenyl | 2-methyl-1-imidazolyl |
| 799 | $CO_2CH_3$ | 2,6-diF-phenyl | 5-methyl-1-imidazolyl |
| 800 | $CO_2CH_3$ | 2,6-diF-phenyl | 2-methylsulfonyl-1-imidazolyl |
| 801 | $CH_2OCH_3$ | phenyl | 2-(aminosulfonyl)phenyl |
| 802 | $CH_2OCH_3$ | phenyl | 2-(methylaminosulfonyl)phenyl |
| 803 | $CH_2OCH_3$ | phenyl | 1-pyrrolidinocarbonyl |
| 804 | $CH_2OCH_3$ | phenyl | 2-(methylsulfonyl)phenyl |
| 805 | $CH_2OCH_3$ | phenyl | 4-morpholino |
| 806 | $CH_2OCH_3$ | phenyl | 2-(1'-$CF_2$-tetrazol-2-yl)phenyl |
| 807 | $CH_2OCH_3$ | phenyl | 4-morpholinocarbonyl |
| 808 | $CH_2OCH_3$ | phenyl | 2-methyl-1-imidazolyl |
| 809 | $CH_2OCH_3$ | phenyl | 5-methyl-1-imidazolyl |
| 810 | $CH_2OCH_3$ | phenyl | 2-methylsulfonyl-1-imidazolyl |
| 811 | $CH_2OCH_3$ | 2-pyridyl | 2-(aminosulfonyl)phenyl |
| 812 | $CH_2OCH_3$ | 2-pyridyl | 2-(methylaminosulfonyl)phenyl |
| 813 | $CH_2OCH_3$ | 2-pyridyl | 1-pyrrolidinocarbonyl |
| 814 | $CH_2OCH_3$ | 2-pyridyl | 2-(methylsulfonyl)phenyl |
| 815 | $CH_2OCH_3$ | 2-pyridyl | 4-morpholino |
| 816 | $CH_2OCH_3$ | 2-pyridyl | 2-(1'-$CF_2$-tetrazol-2-yl)phenyl |
| 817 | $CH_2OCH_3$ | 2-pyridyl | 4-morpholinocarbonyl |
| 818 | $CH_2OCH_3$ | 2-pyridyl | 2-methyl-1-imidazolyl |
| 819 | $CH_2OCH_3$ | 2-pyridyl | 5-methyl-1-imidazolyl |
| 820 | $CH_2OCH_3$ | 2-pyridyl | 2-methylsulfonyl-1-imidazolyl |
| 821 | $CH_2OCH_3$ | 3-pyridyl | 2-(aminosulfonyl)phenyl |
| 822 | $CH_2OCH_3$ | 3-pyridyl | 2-(methylaminosulfonyl)phenyl |
| 823 | $CH_2OCH_3$ | 3-pyridyl | 1-pyrrolidinocarbonyl |
| 824 | $CH_2OCH_3$ | 3-pyridyl | 2-(methylsulfonyl)phenyl |
| 825 | $CH_2OCH_3$ | 3-pyridyl | 4-morpholino |
| 826 | $CH_2OCH_3$ | 3-pyridyl | 2-(1'-$CF_2$-tetrazol-2-yl)phenyl |
| 827 | $CH_2OCH_3$ | 3-pyridyl | 4-morpholinocarbonyl |
| 828 | $CH_2OCH_3$ | 3-pyridyl | 2-methyl-1-imidazolyl |
| 829 | $CH_2OCH_3$ | 3-pyridyl | 5-methyl-1-imidazolyl |
| 830 | $CH_2OCH_3$ | 3-pyridyl | 2-methylsulfonyl-1-imidazolyl |
| 831 | $CH_2OCH_3$ | 2-pyrimidyl | 2-(aminosulfonyl)phenyl |
| 832 | $CH_2OCH_3$ | 2-pyrimidyl | 2-(methylaminosulfonyl)phenyl |
| 833 | $CH_2OCH_3$ | 2-pyrimidyl | 1-pyrrolidinocarbonyl |
| 834 | $CH_2OCH_3$ | 2-pyrimidyl | 2-(methylsulfonyl)phenyl |
| 835 | $CH_2OCH_3$ | 2-pyrimidyl | 4-morpholino |
| 836 | $CH_2OCH_3$ | 2-pyrimidyl | 2-(1'-$CF_2$-tetrazol-2-yl)phenyl |
| 837 | $CH_2OCH_3$ | 2-pyrimidyl | 4-morpholinocarbonyl |
| 838 | $CH_2OCH_3$ | 2-pyrimidyl | 2-methyl-1-imidazolyl |
| 839 | $CH_2OCH_3$ | 2-pyrimidyl | 5-methyl-1-imidazolyl |
| 840 | $CH_2OCH_3$ | 2-pyrimidyl | 2-methylsulfonyl-1-imidazolyl |
| 841 | $CH_2OCH_3$ | 5-pyrimidyl | 2-(aminosulfonyl)phenyl |
| 842 | $CH_2OCH_3$ | 5-pyrimidyl | 2-(methylaminosulfonyl)phenyl |
| 843 | $CH_2OCH_3$ | 5-pyrimidyl | 1-pyrrolidinocarbonyl |
| 844 | $CH_2OCH_3$ | 5-pyrimidyl | 2-(methylsulfonyl)phenyl |
| 845 | $CH_2OCH_3$ | 5-pyrimidyl | 4-morpholino |
| 846 | $CH_2OCH_3$ | 5-pyrimidyl | 2-(1'-$CF_2$-tetrazol-2-yl)phenyl |
| 847 | $CH_2OCH_3$ | 5-pyrimidyl | 4-morpholinocarbonyl |
| 848 | $CH_2OCH_3$ | 5-pyrimidyl | 2-methyl-1-imidazolyl |
| 849 | $CH_2OCH_3$ | 5-pyrimidyl | 5-methyl-1-imidazolyl |
| 850 | $CH_2OCH_3$ | 5-pyrimidyl | 2-methylsulfonyl-1-imidazolyl |
| 851 | $CH_2OCH_3$ | 2-Cl-phenyl | 2-(aminosulfonyl)phenyl |
| 852 | $CH_2OCH_3$ | 2-Cl-phenyl | 2-(methylaminosulfonyl)phenyl |
| 853 | $CH_2OCH_3$ | 2-Cl-phenyl | 1-pyrrolidinocarbonyl |
| 854 | $CH_2OCH_3$ | 2-Cl-phenyl | 2-(methylsulfonyl)phenyl |
| 855 | $CH_2OCH_3$ | 2-Cl-phenyl | 4-morpholino |
| 856 | $CH_2OCH_3$ | 2-Cl-phenyl | 2-(1'-$CF_2$-tetrazol-2-yl)phenyl |
| 857 | $CH_2OCH_3$ | 2-Cl-phenyl | 4-morpholinocarbonyl |
| 858 | $CH_2OCH_3$ | 2-Cl-phenyl | 2-methyl-1-imidazolyl |
| 859 | $CH_2OCH_3$ | 2-Cl-phenyl | 5-methyl-1-imidazolyl |
| 860 | $CH_2OCH_3$ | 2-Cl-phenyl | 2-methylsulfonyl-1-imidazolyl |
| 861 | $CH_2OCH_3$ | 2-F-phenyl | 2-(aminosulfonyl)phenyl |
| 862 | $CH_2OCH_3$ | 2-F-phenyl | 2-(methylaminosulfonyl)phenyl |
| 863 | $CH_2OCH_3$ | 2-F-phenyl | 1-pyrrolidinocarbonyl |
| 864 | $CH_2OCH_3$ | 2-F-phenyl | 2-(methylsulfonyl)phenyl |
| 865 | $CH_2OCH_3$ | 2-F-phenyl | 4-morpholino |
| 866 | $CH_2OCH_3$ | 2-F-phenyl | 2-(1'-$CF_2$-tetrazol-2-yl)phenyl |
| 867 | $CH_2OCH_3$ | 2-F-phenyl | 4-morpholinocarbonyl |
| 868 | $CH_2OCH_3$ | 2-F-phenyl | 2-methyl-1-imidazolyl |
| 869 | $CH_2OCH_3$ | 2-F-phenyl | 5-methyl-1-imidazolyl |
| 870 | $CH_2OCH_3$ | 2-F-phenyl | 2-methylsulfonyl-1-imidazolyl |
| 871 | $CH_2OCH_3$ | 2,6-diF-phenyl | 2-(aminosulfonyl)phenyl |
| 872 | $CH_2OCH_3$ | 2,6-diF-phenyl | 2-(methylaminosulfonyl)phenyl |
| 873 | $CH_2OCH_3$ | 2,6-diF-phenyl | 1-pyrrolidinocarbonyl |
| 874 | $CH_2OCH_3$ | 2,6-diF-phenyl | 2-(methylsulfonyl)phenyl |
| 875 | $CH_2OCH_3$ | 2,6-diF-phenyl | 4-morpholino |
| 876 | $CH_2OCH_3$ | 2,6-diF-phenyl | 2-(1'-$CF_2$-tetrazol-2-yl)phenyl |
| 877 | $CH_2OCH_3$ | 2,6-diF-phenyl | 4-morpholinocarbonyl |
| 878 | $CH_2OCH_3$ | 2,6-diF-phenyl | 2-methyl-1-imidazolyl |
| 879 | $CH_2OCH_3$ | 2,6-diF-phenyl | 5-methyl-1-imidazolyl |
| 880 | $CH_2OCH_3$ | 2,6-diF-phenyl | 2-methylsulfonyl-1-imidazolyl |
| 881 | $CONH_2$ | phenyl | 2-(aminosulfonyl)phenyl |
| 882 | $CONH_2$ | phenyl | 2-(methylaminosulfonyl)phenyl |
| 883 | $CONH_2$ | phenyl | 1-pyrrolidinocarbonyl |
| 884 | $CONH_2$ | phenyl | 2-(methylsulfonyl)phenyl |
| 885 | $CONH_2$ | phenyl | 4-morpholino |
| 886 | $CONH_2$ | phenyl | 2-(1'-$CF_2$-tetrazol-2-yl)phenyl |
| 887 | $CONH_2$ | phenyl | 4-morpholinocarbonyl |
| 888 | $CONH_2$ | phenyl | 2-methyl-1-imidazolyl |
| 889 | $CONH_2$ | phenyl | 5-methyl-1-imidazolyl |
| 890 | $CONH_2$ | phenyl | 2-methylsulfonyl-1-imidazolyl |
| 891 | $CONH_2$ | 2-pyridyl | 2-(aminosulfonyl)phenyl |
| 892 | $CONH_2$ | 2-pyridyl | 2-(methylaminosulfonyl)phenyl |
| 893 | $CONH_2$ | 2-pyridyl | 1-pyrrolidinocarbonyl |
| 894 | $CONH_2$ | 2-pyridyl | 2-(methylsulfonyl)phenyl |
| 895 | $CONH_2$ | 2-pyridyl | 4-morpholino |
| 896 | $CONH_2$ | 2-pyridyl | 2-(1'-$CF_2$-tetrazol-2-yl)phenyl |
| 897 | $CONH_2$ | 2-pyridyl | 4-morpholinocarbonyl |
| 898 | $CONH_2$ | 2-pyridyl | 2-methyl-1-imidazolyl |
| 899 | $CONH_2$ | 2-pyridyl | 5-methyl-1-imidazolyl |
| 900 | $CONH_2$ | 2-pyridyl | 2-methylsulfonyl-1-imidazolyl |
| 901 | $CONH_2$ | 3-pyridyl | 2-(aminosulfonyl)phenyl |
| 902 | $CONH_2$ | 3-pyridyl | 2-(methylaminosulfonyl)phenyl |
| 903 | $CONH_2$ | 3-pyridyl | 1-pyrrolidinocarbonyl |
| 904 | $CONH_2$ | 3-pyridyl | 2-(methylsulfonyl)phenyl |
| 905 | $CONH_2$ | 3-pyridyl | 4-morpholino |
| 906 | $CONH_2$ | 3-pyridyl | 2-(1'-$CF_2$-tetrazol-2-yl)phenyl |
| 907 | $CONH_2$ | 3-pyridyl | 4-morpholinocarbonyl |
| 908 | $CONH_2$ | 3-pyridyl | 2-methyl-1-imidazolyl |
| 909 | $CONH_2$ | 3-pyridyl | 5-methyl-1-imidazolyl |
| 910 | $CONH_2$ | 3-pyridyl | 2-methylsulfonyl-1-imidazolyl |
| 911 | $CONH_2$ | 2-pyrimidyl | 2-(aminosulfonyl)phenyl |
| 912 | $CONH_2$ | 2-pyrimidyl | 2-(methylaminosulfonyl)phenyl |
| 913 | $CONH_2$ | 2-pyrimidyl | 1-pyrrolidinocarbonyl |
| 914 | $CONH_2$ | 2-pyrimidyl | 2-(methylsulfonyl)phenyl |
| 915 | $CONH_2$ | 2-pyrimidyl | 4-morpholino |
| 916 | $CONH_2$ | 2-pyrimidyl | 2-(1'-$CF_2$-tetrazol-2-yl)phenyl |
| 917 | $CONH_2$ | 2-pyrimidyl | 4-morpholinocarbonyl |
| 918 | $CONH_2$ | 2-pyrimidyl | 2-methyl-1-imidazolyl |
| 919 | $CONH_2$ | 2-pyrimidyl | 5-methyl-1-imidazolyl |
| 920 | $CONH_2$ | 2-pyrimidyl | 2-methylsulfonyl-1-imidazolyl |
| 921 | $CONH_2$ | 5-pyrimidyl | 2-(aminosulfonyl)phenyl |
| 922 | $CONH_2$ | 5-pyrimidyl | 2-(methylaminosulfonyl)phenyl |
| 923 | $CONH_2$ | 5-pyrimidyl | 1-pyrrolidinocarbonyl |
| 924 | $CONH_2$ | 5-pyrimidyl | 2-(methylsulfonyl)phenyl |
| 925 | $CONH_2$ | 5-pyrimidyl | 4-morpholino |
| 926 | $CONH_2$ | 5-pyrimidyl | 2-(1'-$CF_2$-tetrazol-2-yl)phenyl |
| 927 | $CONH_2$ | 5-pyrimidyl | 4-morpholinocarbonyl |
| 928 | $CONH_2$ | 5-pyrimidyl | 2-methyl-1-imidazolyl |
| 929 | $CONH_2$ | 5-pyrimidyl | 5-methyl-1-imidazolyl |
| 930 | $CONH_2$ | 5-pyrimidyl | 2-methylsulfonyl-1-imidazolyl |

TABLE 4-continued

| | | | |
|---|---|---|---|
| 931 | CONH₂ | 2-Cl-phenyl | 2-(aminosulfonyl)phenyl |
| 932 | CONH₂ | 2-Cl-phenyl | 2-(methylaminosulfonyl)phenyl |
| 933 | CONH₂ | 2-Cl-phenyl | 1-pyrrolidinocarbonyl |
| 934 | CONH₂ | 2-Cl-phenyl | 2-(methylsulfonyl)phenyl |
| 935 | CONH₂ | 2-Cl-phenyl | 4-morpholino |
| 936 | CONH₂ | 2-Cl-phenyl | 2-(1'-CF₂-tetrazol-2-yl)phenyl |
| 937 | CONH₂ | 2-Cl-phenyl | 4-morpholinocarbonyl |
| 938 | CONH₂ | 2-Cl-phenyl | 2-methyl-1-imidazolyl |
| 939 | CONH₂ | 2-Cl-phenyl | 5-methyl-1-imidazolyl |
| 940 | CONH₂ | 2-Cl-phenyl | 2-methylsulfonyl-1-imidazolyl |
| 941 | CONH₂ | 2-F-phenyl | 2-(aminosulfonyl)phenyl |
| 942 | CONH₂ | 2-F-phenyl | 2-(methylaminosulfonyl)phenyl |
| 943 | CONH₂ | 2-F-phenyl | 1-pyrrolidinocarbonyl |
| 944 | CONH₂ | 2-F-phenyl | 2-(methylsulfonyl)phenyl |
| 945 | CONH₂ | 2-F-phenyl | 4-morpholino |
| 946 | CONH₂ | 2-F-phenyl | 2-(1'-CF₂-tetrazol-2-yl)phenyl |
| 947 | CONH₂ | 2-F-phenyl | 4-morpholinocarbonyl |
| 948 | CONH₂ | 2-F-phenyl | 2-methyl-1-imidazolyl |
| 949 | CONH₂ | 2-F-phenyl | 5-methyl-1-imidazolyl |
| 950 | CONH₂ | 2-F-phenyl | 2-methylsulfonyl-1-imidazolyl |
| 951 | CONH₂ | 2,6-diF-phenyl | 2-(aminosulfonyl)phenyl |
| 952 | CONH₂ | 2,6-diF-phenyl | 2-(methylaminosulfonyl)phenyl |
| 953 | CONH₂ | 2,6-diF-phenyl | 1-pyrrolidinocarbonyl |
| 954 | CONH₂ | 2,6-diF-phenyl | 2-(methylsulfonyl)phenyl |
| 955 | CONH₂ | 2,6-diF-phenyl | 4-morpholino |
| 956 | CONH₂ | 2,6-diF-phenyl | 2-(1'-CF₂-tetrazol-2-yl)phenyl |
| 957 | CONH₂ | 2,6-diF-phenyl | 4-morpholinocarbonyl |
| 958 | CONH₂ | 2,6-diF-phenyl | 2-methyl-1-imidazolyl |
| 959 | CONH₂ | 2,6-diF-phenyl | 5-methyl-1-imidazolyl |
| 960 | CONH₂ | 2,6-diF-phenyl | 2-methylsulfonyl-1-imidazolyl |

TABLE 5

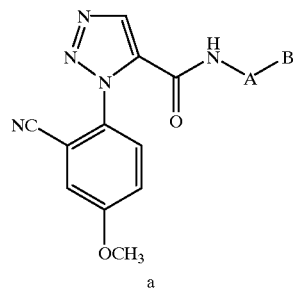

a

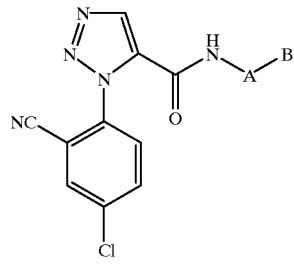

b

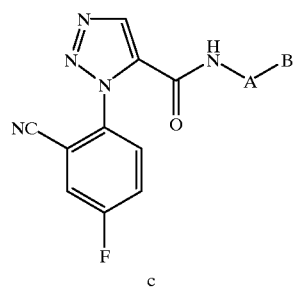

c

TABLE 5-continued

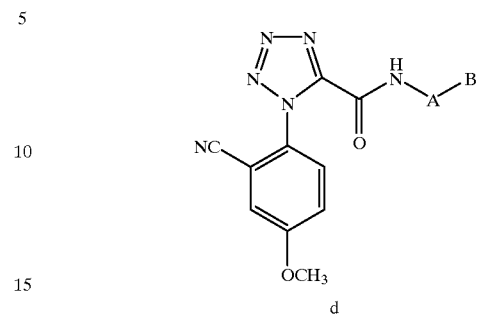

d

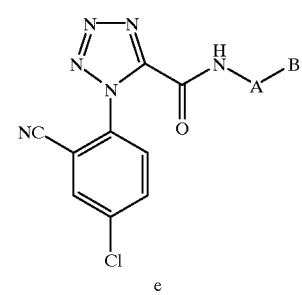

e

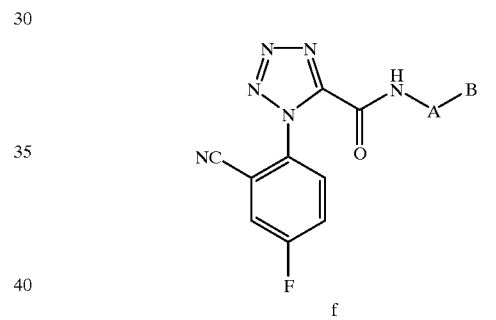

f

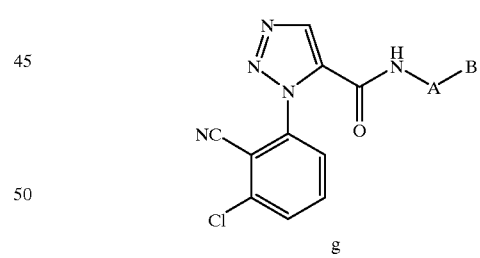

g

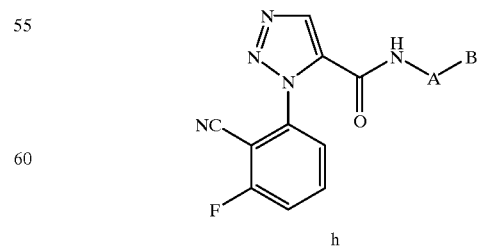

h

TABLE 5-continued
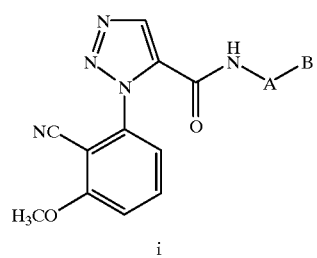
i
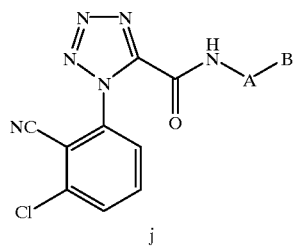
j
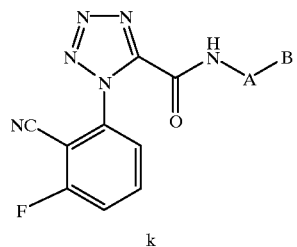
k
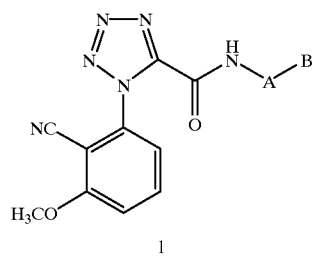
l
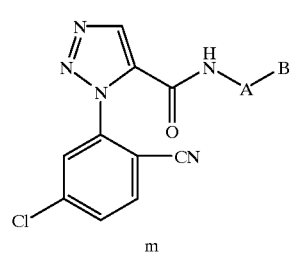
m
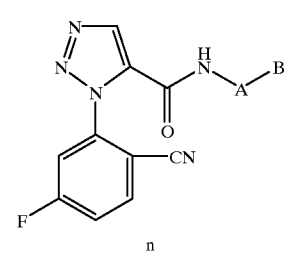
n
TABLE 5-continued
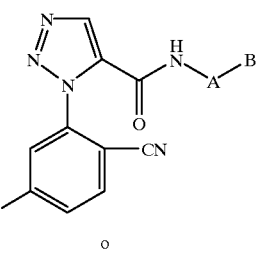
o
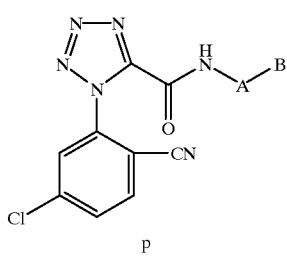
p
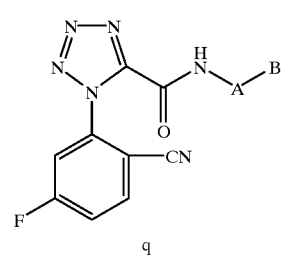
q
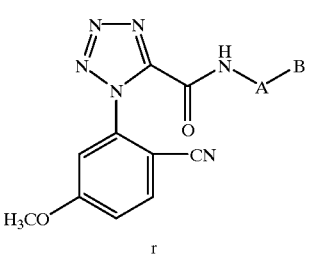
r
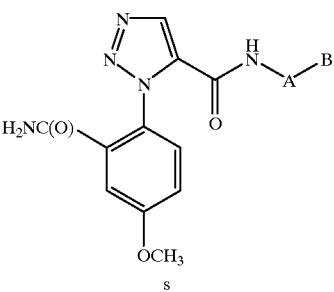
s TABLE 5-continued
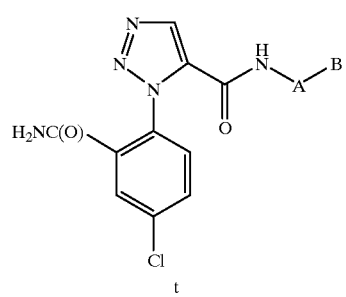
t
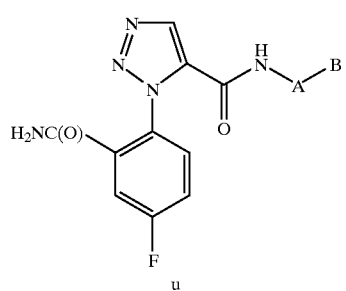
u
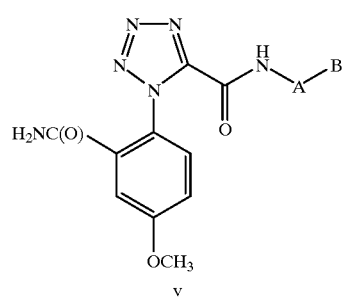
v
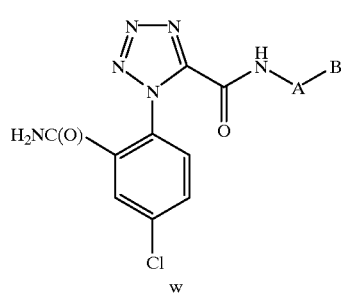
w
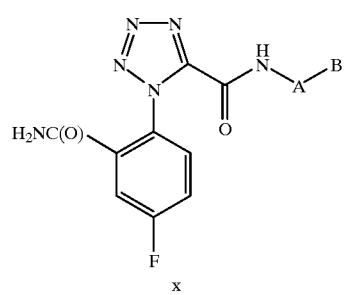
x
TABLE 5-continued
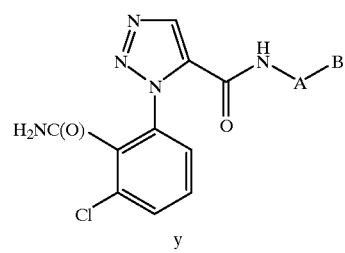
y
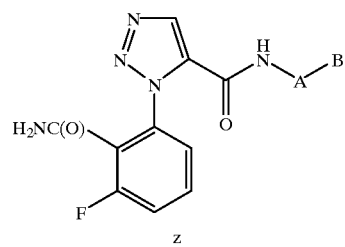
z
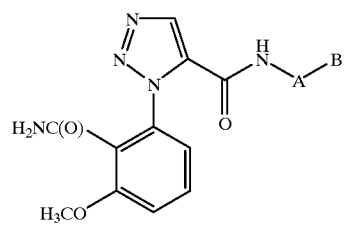
aa
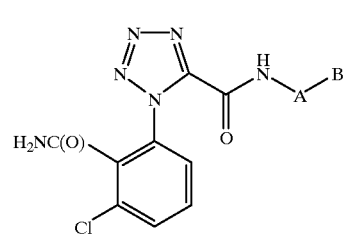
bb
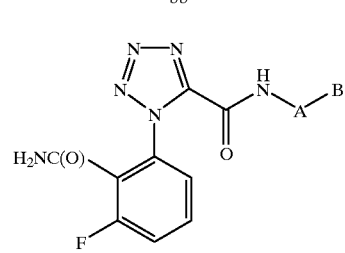
cc
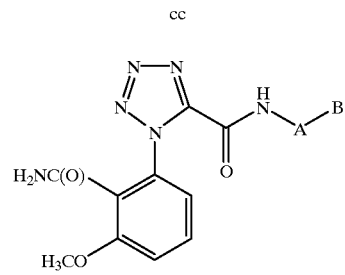
dd TABLE 5-continued
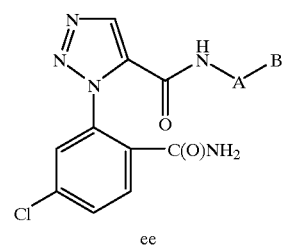
ee
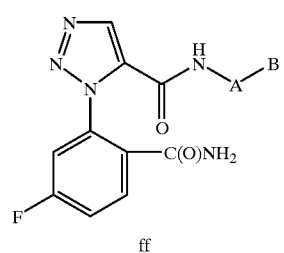
ff
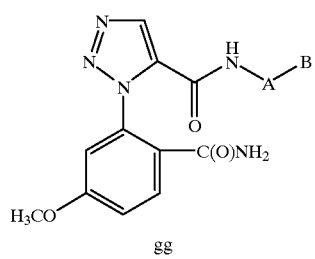
gg
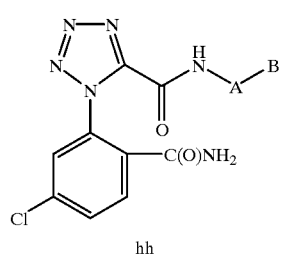
hh
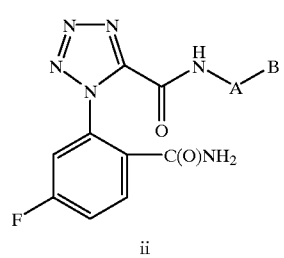
ii
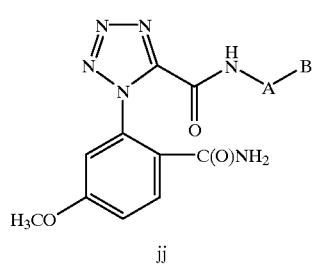
jj
TABLE 5-continued
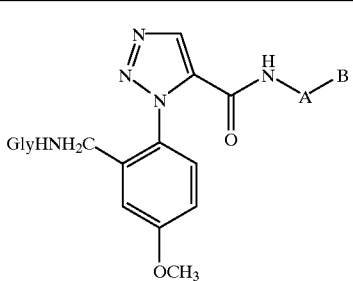
kk
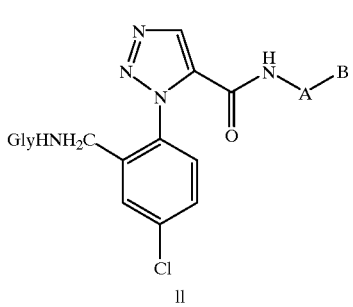
ll
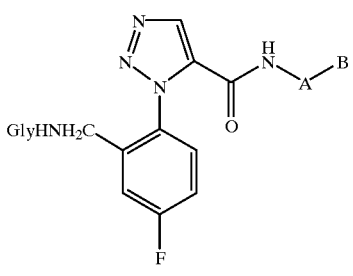
mm
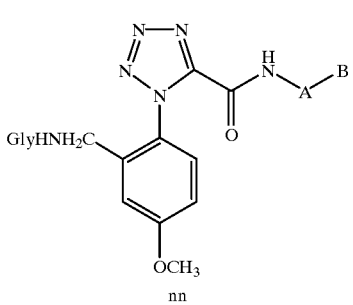
nn
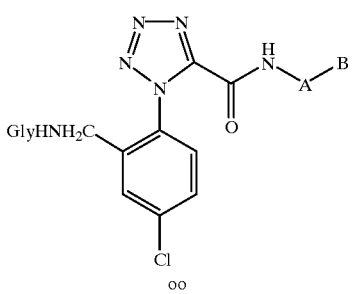
oo TABLE 5-continued
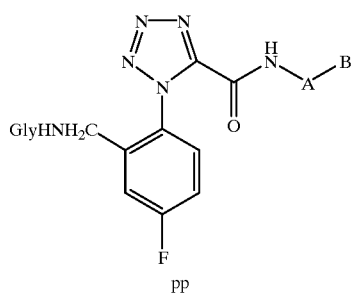
pp
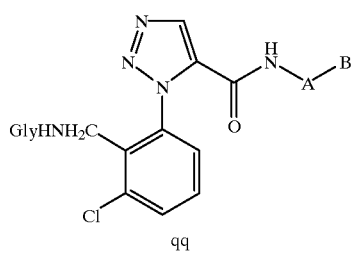
qq
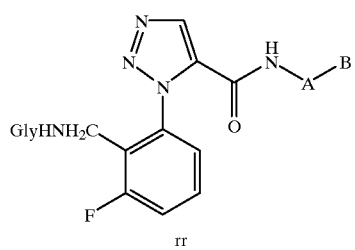
rr
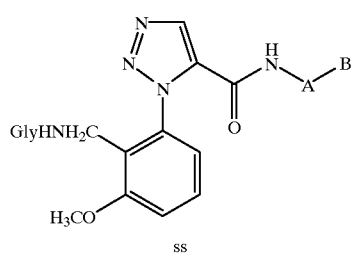
ss
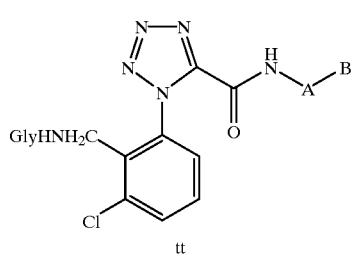
tt
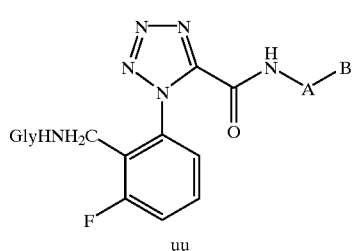
uu
TABLE 5-continued
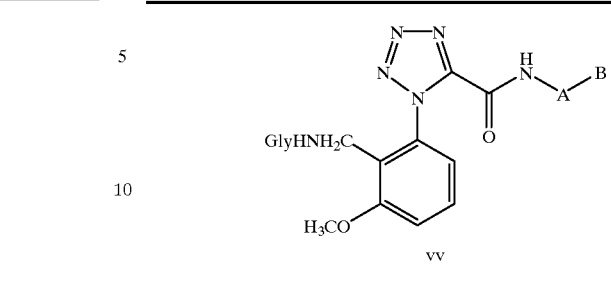
vv
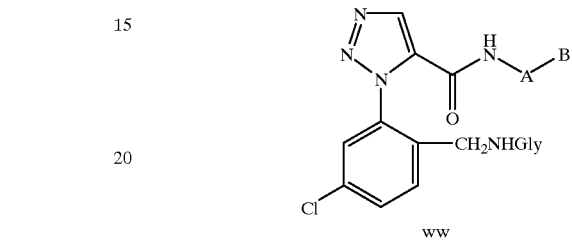
ww
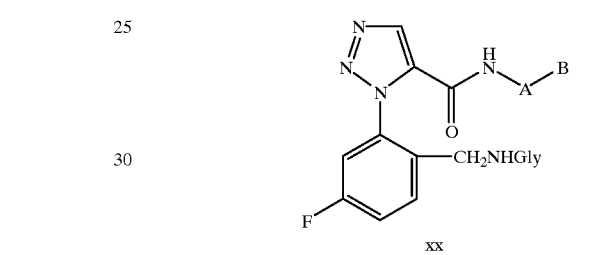
xx
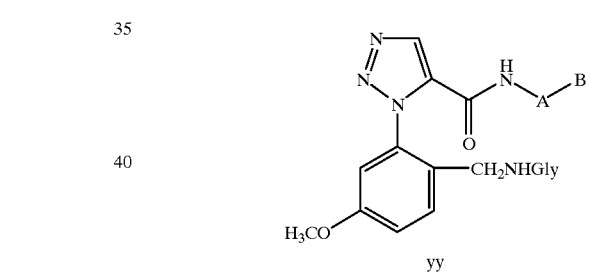
yy
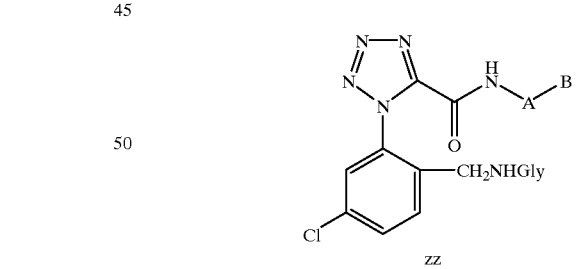
zz
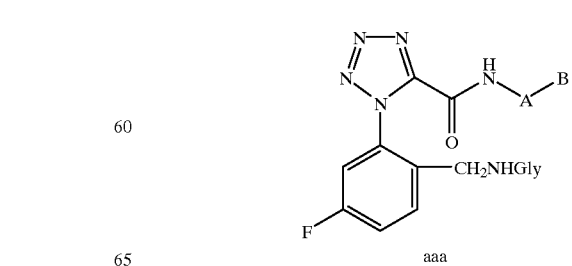
aaa TABLE 5-continued

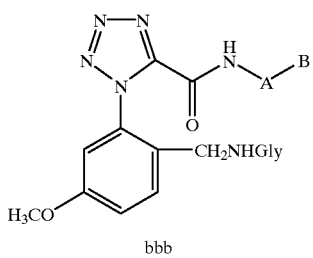

bbb

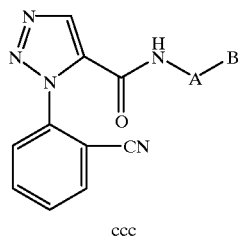

ccc

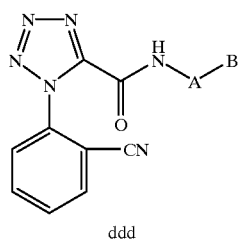

ddd

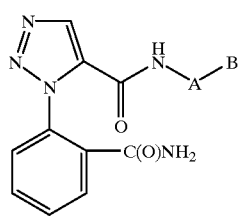

eee

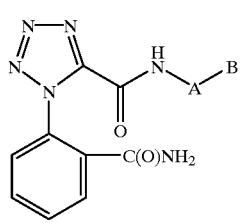

fff

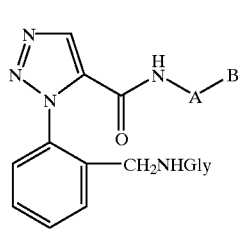

ggg

TABLE 5-continued

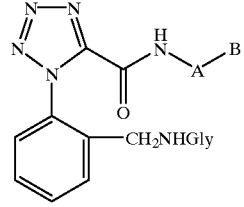

hhh

| EX # | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-$CF_3$-tetrazol-2-yl)phenyl |
| 7 | phenyl | 4-morpholinocarbonyl |
| 8 | phenyl | 2-methyl-1-imidazolyl |
| 9 | phenyl | 5-methyl-1-imidazolyl |
| 10 | phenyl | 2-methylsulfonyl-1-imidazolyl |
| 11 | 2-pyridyl | 2-(aminosulfonyl)phenyl |
| 12 | 2-pyridyl | 2-(methylaminosulfonyl)phenyl |
| 13 | 2-pyridyl | 1-pyrrolidinocarbonyl |
| 14 | 2-pyridyl | 2-(methylsulfonyl)phenyl |
| 15 | 2-pyridyl | 4-morpholino |
| 16 | 2-pyridyl | 2-(1'-$CF_3$-tetrazol-2-yl)phenyl |
| 17 | 2-pyridyl | 4-morpholinocarbonyl |
| 18 | 2-pyridyl | 2-methyl-1-imidazolyl |
| 19 | 2-pyridyl | 5-methyl-1-imidazolyl |
| 20 | 2-pyridyl | 2-methylsulfonyl-1-imidazolyl |
| 21 | 3-pyridyl | 2-(aminosulfonyl)phenyl |
| 22 | 3-pyridyl | 2-(methylaminosulfonyl)phenyl |
| 23 | 3-pyridyl | 1-pyrrolidinocarbonyl |
| 24 | 3-pyridyl | 2-(methylsulfonyl)phenyl |
| 25 | 3-pyridyl | 4-morpholino |
| 26 | 3-pyridyl | 2-(1'-$CF_3$-tetrazol-2-yl)phenyl |
| 27 | 3-pyridyl | 4-morpholinocarbonyl |
| 28 | 3-pyridyl | 2-methyl-1-imidazolyl |
| 29 | 3-pyridyl | 5-methyl-1-imidazolyl |
| 30 | 3-pyridyl | 2-methylsulfonyl-1-imidazolyl |
| 31 | 2-pyrimidyl | 2-(aminosulfonyl)phenyl |
| 32 | 2-pyrimidyl | 2-(methylaminosulfonyl)phenyl |
| 33 | 2-pyrimidyl | 1-pyrrolidinocarbonyl |
| 34 | 2-pyrimidyl | 2-(methylsulfonyl)phenyl |
| 35 | 2-pyrimidyl | 4-morpholino |
| 36 | 2-pyrimidyl | 2-(1'-$CF_3$-tetrazol-2-yl)phenyl |
| 37 | 2-pyrimidyl | 4-morpholinocarbonyl |
| 38 | 2-pyrimidyl | 2-methyl-1-imidazolyl |
| 39 | 2-pyrimidyl | 5-methyl-1-imidazolyl |
| 40 | 2-pyrimidyl | 2-methylsulfonyl-1-imidazolyl |
| 41 | 5-pyrimidyl | 2-(aminosulfonyl)phenyl |
| 42 | 5-pyrimidyl | 2-(methylaminosulfonyl)phenyl |
| 43 | 5-pyrimidyl | 1-pyrrolidinocarbonyl |
| 44 | 5-pyrimidyl | 2-(methylsulfonyl)phenyl |
| 45 | 5-pyrimidyl | 4-morpholino |
| 46 | 5-pyrimidyl | 2-(1'-$CF_3$-tetrazol-2-yl)phenyl |
| 47 | 5-pyrimidyl | 4-morpholinocarbonyl |
| 48 | 5-pyrimidyl | 2-methyl-1-imidazolyl |
| 49 | 5-pyrimidyl | 5-methyl-1-imidazolyl |
| 50 | 5-pyrimidyl | 2-methylsulfonyl-1-imidazolyl |
| 51 | 2-Cl-phenyl | 2-(aminosulfonyl)phenyl |
| 52 | 2-Cl-phenyl | 2-(methylaminosulfonyl)phenyl |
| 53 | 2-Cl-phenyl | 1-pyrrolidinocarbonyl |
| 54 | 2-Cl-phenyl | 2-(methylsulfonyl)phenyl |
| 55 | 2-Cl-phenyl | 4-morpholino |
| 56 | 2-Cl-phenyl | 2-(1'-$CF_3$-tetrazol-2-yl)phenyl |
| 57 | 2-Cl-phenyl | 4-morpholinocarbonyl |
| 58 | 2-Cl-phenyl | 2-methyl-1-imidazolyl |
| 59 | 2-Cl-phenyl | 5-methyl-1-imidazolyl |
| 60 | 2-Cl-phenyl | 2-methylsulfonyl-1-imidazolyl |
| 61 | 2-F-phenyl | 2-(aminosulfonyl)phenyl |
| 62 | 2-F-phenyl | 2-(methylaminosulfonyl)phenyl |
| 63 | 2-F-phenyl | 1-pyrrolidinocarbonyl |
| 64 | 2-F-phenyl | 2-(methylsulfonyl)phenyl |

TABLE 5-continued

| 65 | 2-F-phenyl | 4-morpholino |
| 66 | 2-F-phenyl | 2-(1'-CF$_3$-tetrazol-2-yl)phenyl |
| 67 | 2-F-phenyl | 4-morpholinocarbonyl |
| 68 | 2-F-phenyl | 2-methyl-1-imidazolyl |
| 69 | 2-F-phenyl | 5-methyl-1-imidazolyl |
| 70 | 2-F-phenyl | 2-methylsulfonyl-1-imidazolyl |
| 71 | 2,6-diF-phenyl | 2-(aminosulfonyl)phenyl |
| 72 | 2,6-diF-phenyl | 2-(methylaminosulfonyl)phenyl |
| 73 | 2,6-diF-phenyl | 1-pyrrolidinocarbonyl |
| 74 | 2,6-diF-phenyl | 2-(methylsulfonyl)phenyl |
| 75 | 2,6-diF-phenyl | 4-morpholino |
| 76 | 2,6-diF-phenyl | 2-(1'-CF$_3$-tetrazol-2-yl)phenyl |
| 77 | 2,6-diF-phenyl | 4-morpholinocarbonyl |
| 78 | 2,6-diF-phenyl | 2-methyl-1-imidazolyl |
| 79 | 2,6-diF-phenyl | 5-methyl-1-imidazolyl |
| 80 | 2,6-diF-phenyl | 2-methylsulfonyl-1-imidazolyl |

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, OH) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s=I/(K_i(1+S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Using the methodology described above, a number of compounds of the present invention were found to exhibit a $K_i$ of ≦10 μm, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing which contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al, U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Reminaton's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed is:
1. A compound of formula I:

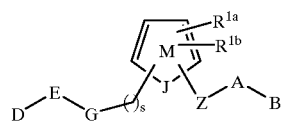

or a stereoisomer or pharmaceutically acceptable salt thereof, wherein;
ring M contains, in addition to J, 1 N atom;
J is N or NH;
D is selected from CN, $C(=NR^8)NR^7R^9$, $NHC(=NR^8)NR^7R^9$, $NR^8CH(=NR^7)$, $C(O)NR^7R^8$, and $(CR^8R^9)_rNR^7R^8$, provided that D is substituted ortho to G on E;
E is phenyl substituted with 1–2 R;
R is selected from H, Cl, F, Br, I, $(CH_2)_rOR^3$, $C_{1-4}$ alkyl, $OCF_3$, $CF_3$, $C(O)NR^7R^8$, and $(CR^8R^9)_rNR^7R^8$;
G is absent or is selected from $NHCH_2$, $OCH_2$, and $SCH_2$, provided that when s is 0, then G is attached to a carbon atom on ring M;
Z is selected from a $C_{1-4}$ alkylene, $(CH_2)_rO(CH_2)_r$, $(CH_2)_r NR^3(CH_2)_r$, $(CH_2)_rC(O)(CH_2)_r$, $(CH_2)_rC(O)O(CH_2)_r$, $(CH_2)_rOC(O)(CH_2)_r$, $(CH_2)_rC(O)NR^3(CH_2)_r$, $(CH_2)_r NR^3C(O)(CH_2)_r$, $(CH_2)_rOC(O)O(CH_2)_r$, $(CH_2)_r OC(O)NR^3(CH_2)_r$, $(CH_2)_rNR^3C(O)O(CH_2)_r$, $(CH_2)_r NR^3C(O)NR^3(CH_2)_r$, $(CH_2)_rS(O)_p(CH_2)_r$, $(CH_2)_r SO_2NR^3(CH_2)_r$, $(CH_2)_rNR^3SO_2(CH_2)_r$, and $(CH_2)_r NR^3SO_2NR^3(CH_2)_r$, provided that Z does not form a N—N, N—O, N—S, $NCH_2N$, $NCH_2O$, or $NCH_2S$ bond with ring M or group A;
$R^{1a}$ and $R^{1b}$ are independently absent or selected from $—(CH_2)_r—R^{1'}$, $—CH=CH—R^{1'}$, $NCH_2R^{1''}$, $OCH_2R^{1''}$, $SCH_2R^{1''}$, $NH(CH_2)_2(CH_2)_rR^{1'}$, $O(CH_2)_2(CH_2)_rR^{1'}$, and $S(CH_2)_2(CH_2)_rR^{1'}$;
alternatively, $R^{1a}$ and $R^{1b}$, when attached to adjacent carbon atoms, together with the atoms to which they are attached form a 5–8 membered saturated, partially saturated or unsaturated ring substituted with 0–2 $R^4$ and which contains from 0–2 heteroatoms selected from the group consisting of N, O, and S;
$R^{1'}$ is selected from H, $C_{1-3}$ alkyl, F, Cl, Br, I, —CN, —CHO, $(CF_2)_rCF_3$, $(CH_2)_rOR^2$, $NR^2R^{2a}$, $C(O)R^{2c}$, $OC(O)R^2$, $(CF_2)_rCO_2R^{2c}$, $S(O)_pR^{2b}$, $NR^2(CH_2)_rOR^2$, $C(=NR^{2c})NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-6}$ carbocyclic residue substituted with 0–2 $R^4$, and 5–10 membered heterocyclic system containing from 1–4 heteroatoms selected from the group consisting of N, O, and S substituted with 0–2 $R^4$;
$R^{1''}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;
$R^2$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;
$R^{2a}$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;
$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

alternatively, $R^2$ and $R^{2a}$ combine to form a 5 or 6 membered saturated, partially saturated or unsaturated ring substituted with 0–2 $R^{4b}$ which contains from 0–1 additional heteroatoms selected from the group consisting of N, O, and S;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

$R^{3c}$, at each occurrence, is selected from $C_{1-4}$ alkyl, and phenyl;

A is selected from:
 $C_{3-10}$ carbocyclic residue substituted with 0–2 $R^4$, and
 5–10 membered heterocyclic system containing from 1–4 heteroatoms selected from the group consisting of N, O, and S substituted with 0–2 $R^4$;

B is selected from:
 Y, X—Y, $NR^2R^{2a}$, $C(=NR^2)NR^2R^{2a}$, $NR^2C(=NR^2)NR^2R^{2a}$,
 $C_{3-10}$ carbocyclic residue substituted with 0–2 $R^{4a}$, and
 5–10 membered heterocyclic system containing from 1–4 heteroatoms selected from the group consisting of N, O, and S substituted with 0–2 $R^{4a}$;

X is selected from $C_{1-4}$ alkylene, —$CR^2(CR^2R^{2b})(CH_2)_t$—, —C(O)—, —C(=$NR^{1"}$)—, —$CR^2(NR^{1"}R^2)$—, —$CR^2(OR^2)$—, —$CR^2(SR^2)$—, —$C(O)CR^2R^{2a}$—, —$CR^2R^{2a}C(O)$, —$S(O)_p$—, —$S(O)_pCR^2R^{2a}$—, —$CR^2R^{2a}S(O)_p$—, —$S(O)_2NR^2$—, —$NR^2S(O)_2$—, —$NR^2S(O)_2CR^2R^{2a}$—, —$CR^2R^{2a}S(O)_2NR^2$—, —$NR^2S(O)_2NR^2$—, —$C(O)NR^2$—, —$NR^2C(O)$—, —$C(O)NR^2CR^2R^{2a}$—, —$NR^2C(O)CR^2R^{2a}$—, —, —$CR^2R^{2a}C(O)NR^2$—, —$CR^2R^{2a}NR^2C(O)$—, —$NR^2C(O)O$—, —$OC(O)NR^2$—, —$NR^2C(O)NR^2$—, —$NR^2$—, —$NR^2CR^2R^{2a}$—, $CR^2R^{2a}NR^2$—, O, —$CR^2R^{2a}O$—, and —$OCR^2R^{2a}$—;

Y is selected from:
 $(CH_2)_rNR^2R^{2a}$, provided that X—Y do not form a N—N, O—N, or S—N bond,
 $C_{3-10}$ carbocyclic residue substituted with 0–2 $R^{4a}$, and
 5–10 membered heterocyclic system containing from 1–4 heteroatoms selected from the group consisting of N, O, and S substituted with 0–2 $R^{4a}$;

$R^4$, at each occurrence, is selected from H, =O, $(CH_2)_rOR^2$, F, Cl, Br, I, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)NR^2R^{2a}$, $C(=NR^2)NR^2R^{2a}$, $C(=NS(O)_2R^5)NR^2R^{2a}$, $NC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $(CF_2)_rCF_3$, $NCH_2R^{1"}$, $OCH_2R^{1"}$, $SCH_2R^{1"}$, $N(CH_2)_2(CH_2)_tR^{1"}$, $O(CH_2)_2(CH_2)_tR^{1"}$, and $S(CH_2)_2(CH_2)_tR^{1"}$, alternatively, one $R^4$ is a 5–6 membered aromatic heterocycle containing from 1–4 heteroatoms selected from the group consisting of N, O, and S;

$R^{4a}$, at each occurrence, is selected from H, =O, $(CH_2)_rOR^2$, $(CH_2)_r$—F, $(CH_2)_r$—Br, $(CH_2)_r$—Cl, Cl, Br, F, I, $C_{1-4}$ aLkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $C(O)NH(CH_2)_2NR^2R^{2a}$, $NR^2C(O)NR^2R^{2a}$, $C(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $C(O)NHSO_2$-$C_{1-4}$ alkyl, $NR^2SO_2R^5$, $S(O)_pR^5$, and $(CF_2)_rCF_3$; p1 alternatively, one $R^{4a}$ is a 5–6 membered aromatic heterocycle containing from 1–4 heteroatoms selected from the group consisting of N, O, and S substituted with 0–1 $R^5$;

$R^{4b}$, at each occurrence, is selected from H, =O, $(CH_2)_rOR^3$, F, Cl, Br, I, $C_{1-4}$ alkyl, —CN, $NO_2$, $(CH_2)_rNR^3R^{3a}$, $(CH_2)_rC(O)R^3$, $(CH_2)_rC(O)OR^{3c}$, $NR^3C(O)R^{3a}$, $C(O)NR^3R^{3a}$, $NR^3C(O)NR^3R^{3a}$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$-$C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

alternatively, $R^7$ and $R^8$ combine to form a 5 or 6 membered saturated, ring which contains from 0–1 additional heteroatoms selected from the group consisting of N, O, and S;

$R^9$, at each occurrence, is selected from H, $C_{1-6}$ alkyl and $(CH_2)_n$-phenyl;

n, at each occurrence, is selected from 0, 1, 2, and 3;

p, at each occurrence, is selected from 0, 1, and 2;

r, at each occurrence, is selected from 0, 1, 2, and 3;

s, at each occurrence, is selected from 0, 1, and 2; and, t, at each occurrence, is selected from 0, 1, 2, and 3;

provided that D—E—G—$(CH_2)_s$— and —Z—A—B are not both benzamidines.

2. A compound according to claim 1, wherein the compound is of formula Ib:

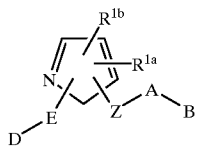

Ib wherein, groups D—E— and —Z—A—B are attached to adjacent atoms on the ring;

R is selected from H, Cl, F, Br, I, $(CH_2)_tOR^3$, $C_{1-4}$ alkyl, $OCF_3$, $CF_3$, $C(O)NR^7R^8$, and $(CR^8R^9)_tNR^7R^8$;

Z is selected from a $CH_2O$, $OCH_2$, $CH_2NH$, $NHCH_2$, $C(O)$, $CH_2C(O)$, $C(O)CH_2$, $NHC(O)$, $C(O)NH$, $CH_2S(O)_2$, $S(O)_2(CH_2)$, $SO_2NH$, and $NHSO_2$, provided that Z does not form a N—N, N—O, $NCH_2N$, or $NCH_2O$ bond with ring M or group A;

A is selected from one of the following carbocyclic and heterocyclic systems which are substituted with 0–2 $R^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is selected from: Y, X—Y, $NR^2R^{2a}$, $C(=NR^2)NR^2R^{2a}$, and $NR^2C(=NR^2)NR^2R^{2a}$;

X is selected from $C_{1-4}$ alkylene, —C(O)—, —C(=NR)—, —$CR^2(NR^2R^{2a})$—, —$C(O)CR^2R^{2a}$—, —$CR^2R^{2a}C(O)$—, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is $NR^2R^{2a}$, provided that X—Y do not form a N—N or O—N bond;

alternatively, Y is selected from one of the following carbocyclic and heterocyclic systems which are substituted with 0–2 $R^{4a}$;

cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, irnidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

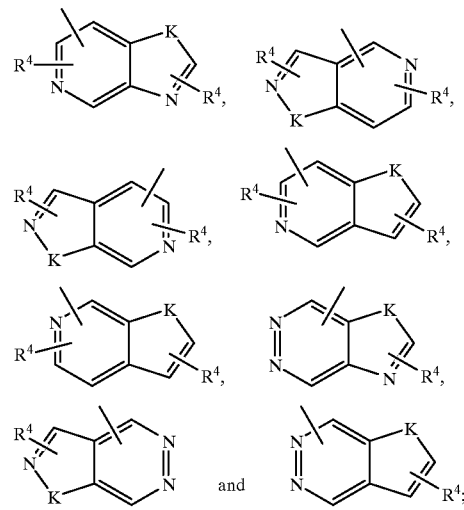

K is selected from O, S, NH, and N.

3. A compound according to claim 2, wherein the compound is of formula IIa:

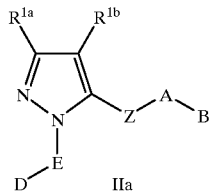

IIa wherein;

Z is selected from a C(O), $CH_2C(O)$, $C(O)CH_2$, NHC(O), C(O)NH, $C(O)N(CH_3)$, $CH_2S(O)_2$, $S(O)_2(CH_2)$, $SO_2NH$, and $NHSO_2$, provided that Z does not form a N—N or $NCH_2N$ bond with ring M or group A.

4. A compound according to claim 3, wherein;

E is phenyl substituted with R;

D is selected from $NH_2$, $NHCH_3$, $CH_2NH_2$, $CH_2NHCH_3$, $CH(CH_3)NH_2$, and $C(CH_3)_2NH_2$, provided that D is substituted ortho to ring M on E; and, R is selected from H, $OCH_3$, Cl, and F.

5. A compound according to claim 4, wherein;

D—E is selected from 2-aminophenyl, 2-methylaminophenyl, 2-aminomethylphenyl, 4-methoxy-2-aminophenyl, 4-methoxy-2-(methylamino)phenyl, 4-methoxy-2-aminomethylphenyl, 4-methoxy-2-(methylaminomethyl)phenyl, 4-methoxy-2-(1-aminoethyl)phenyl, 4-methoxy-2-(2-amino-2-propyl)phenyl, 4-Cl-2-aminophenyl, 4-Cl-2-(methylamino)phenyl, 4-Cl-2-aminomethylphenyl, 4-Cl-2-(methylaminomethyl)phenyl, 4-Cl-2-(1-aminoethyl)phenyl, 4-Cl-2-(2-amino-2-propyl)phenyl, 4-F-2-aminophenyl, 4-F-2-(methylamino)phenyl, 4-F-2-aminomethylphenyl, 4-F-2-(methylaminomethyl)phenyl, 4-F-2-(1-aminoethyl)phenyl, and 4-F-2-(2-amino-2-propyl)phenyl.

6. A compound according to claim 3, wherein;

Z is $C(O)CH_2$ and CONH, provided that Z does not form a N—N bond with group A;

A is selected from phenyl, pyridyl, and pyrimidyl, and is substituted with 0–2 $R^4$; and, B is selected from X—Y, phenyl, pyrrolidino, morpholino, 1,2,3-triazolyl, and imidazolyl, and is substituted with 0–1 $R^{4a}$;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from $C_{1-4}$ alkyl, $(CH_2)_rNR^2R^{2a}$, $CF_3$, $S(O)_pR^5$, $SO_2NR^2R^{2a}$, and 1-$CF_3$-tetrazol-2-yl;

$R^5$, at each occurrence, is selected from $CF_3$, $C_{1-6}$ alkyl, phenyl, and benzyl;

X is $CH_2$ or C(O); and,

Y is selected from pyrrolidino and morpholino.

7. A compound according to claim 6, wherein;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-$CF_3$-phenyl, 2-(aminosulfonyl)phenyl, 2-(methylaminosulfonyl)phenyl, 2-(dimethylaminosulfonyl)phenyl, 1-pyrrolidinocarbonyl, 2-(methylsulfonyl)phenyl, 4-morpholino, 2-(1'-$CF_3$-tetrazol-2-yl)phenyl, 4-morpholinocarbonyl, 2-methyl-1-imidazolyl, 5-methyl-1-imidazolyl, 2-methylsulfonyl-1-imidazolyl and, 5-methyl-1,2,3-triazolyl.

8. A compound according to claim 3, wherein;

E is phenyl substituted with R;

D is selected from $NH_2$, $NHCH_3$, $CH_2NH_2$, $CH_2NHCH_3$, $CH(CH_3)NH_2$, and $C(CH_3)_2NH_2$, provided that D is substituted ortho to ring M on E; and, R is selected from H, $OCH_3$, Cl, and F;

Z is $C(O)CH_2$ or CONH, provided that Z does not form a N—N bond with group A;

A is selected from phenyl, pyridyl, and pyiimidyl, and is substituted with 0–2 $R^4$; and, B is selected from X—Y, phenyl, pyrrolidino, morpholino, 1,2,3-triazolyl, and imidazolyl, and is substituted with 0–1 $R^{4a}$;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from $C_{1-4}$ alkyl, $(CH_2)_rNR^2R^{2a}$, $CF_3$, $S(O)_pR^5$, $SO_2NR^2R^{2a}$, and 1-$CF_3$-tetrazol-2-yl;

$R^5$, at each occurrence, is selected from $CF_3$, $C_{1-6}$ alkyl, phenyl, and benzyl;

X is $CH_2$ or C(O); and,

Y is selected from pyrrolidino and morpholino.

9. A compound according to claim 8, wherein;

D—E is selected from 2-aminophenyl, 2-methylaminophenyl, 2-aminomethylphenyl, 4-methoxy-2-aminophenyl, 4-methoxy-2-(methylamino)phenyl, 4-methoxy-2-aminomethylphenyl, 4-methoxy-2-(methylaminomethyl)phenyl, 4-methoxy-2-(1-aminoethyl)phenyl, 4-methoxy-2-(2-amino-2-propyl) phenyl, 4-Cl-2-aminophenyl, 4-Cl-2-(methylamino)phenyl, 4-Cl-2-aminomethylphenyl, 4-Cl-2-(methylaminomethyl)phenyl, 4-Cl-2-(1-aminoethyl) phenyl, 4-Cl-2-(2-amino-2-propyl)phenyl, 4-F-2-aminophenyl, 4-F-2-(methylamino)phenyl, 4-F-2-aminomethylphenyl, 4-F-2-(methylaminomethyl) phenyl, 4-F-2-(1-aminoethyl)phenyl, and 4-F-2-(2-amino-2-propyl)phenyl;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-$CF_3$-phenyl, 2-(aminosulfonyl)phenyl, 2-(methylaminosulfonyl)phenyl, 2-(dimethylaminosulfonyl)phenyl, 1-pyrrolidinocarbonyl, 2-(methylsulfonyl)phenyl, 4-morpholino, 2-(1'-$CF_3$-tetrazol-2-yl)phenyl, 4-morpholinocarbonyl, 2-methyl-1-imidazolyl, 5-methyl-1-imidazolyl, 2-methylsulfonyl-1-imidazolyl and, 5-methyl-1,2,3-triazolyl.

10. A compound according to claim 3, wherein;

D is selected from —CN, $C(=NR^8)NR^7R^9$, $C(O)NR^7R^8$, $NR^7R^8$, and $CH_2NR^7R^8$, provided that D is substituted ortho to ring M on E;

E is phenyl substituted with R;

R is selected from H, Cl, F, $OR^3$, $CH_3$, $CH_2CH_3$, $OCF_3$, $CF_3$, $NR^7R^8$, and $CH_2NR^7R^8$;

Z is selected from C(O), $CH_2C(O)$, $C(O)CH_2$, NHC(O), and C(O)NH, provided that Z does not form a N—N bond with ring M or group A;

$R^{1a}$ and $R^{1b}$ are independently absent or selected from $-(CH_2)_r-R^{1'}$, $NCH_2R^{1'}$, $OCH_2R^{1'}$, $SCH_2R^{1'}$, $N(CH_2)_2(CH_2)_rR^{1'}$, $O(CH_2)_2(CH_2)_rR^{1'}$, and $S(CH_2)_2(CH_2)_rR^{1'}$, or combine to form a 5–8 membered saturated, partially saturated or unsaturated ring substituted with 0–2 $R^4$ and which contains from 0–2 heteroatoms selected from the group consisting of N, O, and S;

$R^{1'}$, at each occurrence, is selected from H, $C_{1-3}$ alkyl, halo, $(CF_2)_rCF_3$, $OR^2$, $NR^2R^{2a}$, $C(O)R^{2c}$, $(CF_2)_rCO_2R^{2c}$, $S(O)_pR^{2b}$, $NR^2(CH_2)_rOR^2$, $NR^2C(O)R^{2b}$, $NR^2C(O)_2R^{2b}$, $C(O)NR^2R^{2a}$, $SO_2NR^2R^{2a}$, and $NR^2SO_2R^{2b}$;

A is selected from one of the following carbocyclic and heterocyclic systems which are substituted with 0–2 $R^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, and imidazolyl;

B is selected from: Y, X—Y, $NR^2R^{2a}$, $C(=NR^2)NR^2R^{2a}$, and $NR^2C(=NR^2)NR^2R^{2a}$;

X is selected from $CH_2$, $-CR^2(CR^2R^{2b})(CH_2)_r-$, —C(O)—, —C(=NR)—, —CH$(NR^2R^{2a})$—, —C(O)NR$^2$—, —NR$^2$C(O)—, —NR$^2$C(O)NR$^2$—, —NR$^2$—, and O;

Y is $NR^2R^{2a}$, provided that X—Y do not form a N—N or O—N bond;

alternatively, Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

$R^4$, at each occurrence, is selected from =O, OH, Cl, F, $C_{1-4}$ alkyl, $(CH_2)_rNR^2R^{2a}$, $(CH_2)_rC(O)R^{2b}$, $NR^2C(O)R^{2b}$, $C(O)NR^2R^{2a}$, $C(=NH)NH_2$, $NHC(=NH)NH_2$, $SO_2NR^2R^{2a}$, $NR^2SO_2-C_{1-4}$ alkyl, $NR^2SO_2R^5$, $S(O)_pR^5$, and $(CF_2)_rCF_3$;

$R^{4a}$, at each occurrence, is selected from =O, OH, Cl, F, $C_{1-4}$ alkyl, $(CH_2)_rNR^2R^{2a}$, $(CH_2)_rC(O)R^{2b}$, $NR^2C(O)$

199

$R^{2b}$, $C(O)NR^2R^{2a}$, $C(=NH)NH_2$, $NHC(=NH)NH_2$, $SO_2NR^2R^{2a}$, $NR^2SO_2$—$C_{1-4}$ alkyl, $NR^2SO_2R^5$, $S(O)_p R^5$, $(CF_2)_rCF_3$, and 1-$CF_3$-tetrazol-2-yl;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, =O, OH, $OR^2$, Cl, F, $CH_3$, CN, $NO_2$, $(CH_2)_rNR^2R^{2a}$, $(CH_2)_rC(O)R^{2b}$, $NR^2C(O)R^{2b}$, $C(=NH)NH_2$, $NHC(=NH)NH_2$, and $So_2NR^2R^{2a}$;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, benzyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and benzyl;

alternatively, $R^7$ and $R^8$ combine to form a morpholino group; and, $R^9$, at each occurrence, is selected from H, $C_{1-6}$ alkyl and benzyl.

11. A compound according to claim 10, wherein;

E is phenyl substituted with R;

R is selected from H, Cl, F, $OCH_3$, $CH_3$, $OCF_3$, $CF_3$, $NH_2$, and $CH_2NH_2$;

Z is selected from $C(O)CH_2$ and $C(O)NH$, provided that Z does not form a N—N bond with group A;

$R^{1a}$ is selected from H, $CH_3$, $CH_2CH_3$, Cl, F, $CF_3$, $OCH_3$, $NR^2R^{2a}$, $S(O)_pR^{2b}$, $CH_2S(O)_pR^{2b}$, $CH_2NR^2S(O)_pR^{2b}$, $C(O)R^{2c}$, $CH_2C(O)R^{2c}$, $C(O)NR^2R^{2a}$, and $SO_2NR^2R^{2a}$;

$R^{1b}$ is selected from H, $CH_3$, $CH_2CH_3$, Cl, F, $CF_3$, $OCH_3$, $NR^2R^{2a}$, $S(O)_pR^{2b}$, $CH_2S(O)_pR^{2b}$, $CH_2NR^2S(O)_pR^{2b}$, $C(O)R^{2c}$, $CH_2C(O)R^{2c}$, $C(O)NR^2R^{2a}$, and $SO_2NR^2R^{2a}$;

A is selected from one of the following carbocyclic and heterocyclic systems which are substituted with 0–1 $R^4$;

phenyl, pyridyl, pyrimidyl, furanyl, thiophenyl, pyrrolyl, oxazolyl, isoxazolyl, thiazolyl, isothiazolyl, pyrazolyl, and imidazolyl;

B is selected from: Y and X—Y;

X is selected from $CH_2$, —$CR^2(CR^2R^{2b})$—, —$C(O)$—, —$C(=NR)$—, —$CH(NR^2R^{2a})$—, —$C(O)NR^2$—, —$NR^2C(O)$—, —$NR^2C(O)NR^2$—, —$NR^2$—, and O;

Y is $NR^2R^{2a}$, provided that X—Y do not form a N—N or O—N bond;

alternatively, Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

$R^2$, at each occurrence, is selected from H, $CF_3$, $CH_3$, benzyl, and phenyl;

200

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^{2a}$ combine to form a 5 or 6 membered saturated, partially unsaturated, or unsaturated ring which contains from 0–1 additional heteroatoms selected from the group consisting of N, O, and S;

$R^3$, at each occurrence, is selected from H, $CH_3$, $CH_2CH_3$, and phenyl;

$R^{3a}$, at each occurrence, is selected from H, $CH_3$, $CH_2CH_3$, and phenyl;

$R^4$, at each occurrence, is selected from OH, Cl, F, $CH_3$, $CH_2CH_3$, $NR^2R^{2a}$, $CH_2NR^2R^{2a}$, $C(O)R^{2b}$, $NR^2C(O)R^{2b}$, $C(O)NR^2R^{2a}$, and $CF_3$;

$R^{4a}$, at each occurrence, is selected from OH, Cl, F, $CH_3$, $CH_2CH_3$, $NR^2R^{2a}$, $CH_2NR^2R^{2a}$, $C(O)R^{2b}$, $C(O)NR^2R^{2a}$, $SO_2NR^2R^{2a}$, $S(O)_pR^5$, $CF_3$, and 1-$CF_3$-tetrazol-2-yl;

$R^5$, at each occurrence, is selected from $CF_3$, $C_{1-6}$ alkyl, phenyl substituted with 0–2 $R^6$, and benzyl substituted with 1 $R^6$;

$R^6$, at each occurrence, is selected from H, OH, $OCH_3$, Cl, F, $CH_3$, CN, $NO_2$, $NR^2R^{2a}$, $CH_2NR^2R^{2a}$, and $SO_2NR^2R^{2a}$;

$R^7$, at each occurrence, is selected from H and $C_{1-3}$ alkyl;

$R^8$, at each occurrence, is selected from H, $CH_3$, and benzyl;

$R^9$, at each occurrence, is selected from H, $CH_3$, and benzyl; and, t, at each occurrence, is selected from 0 and 1.

12. A compound according to claim 11, wherein;

D is selected from $NR^7R^8$, and $CH_2NR^7R^8$, provided that D is substituted ortho to ring M on E;

$R^{1a}$ is absent or is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $CH_2NR^2S(O)_pR^{2b}$, $C(O)R^{2c}$, $CH_2C(O)R^{2c}$, and $SO_2NR^2R^{2a}$;

$R^{1b}$ is absent or is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $CH_2NR^2S(O)_pR^{2b}$, $C(O)R^{2b}$, $CH_2C(O)R^{2b}$, and $SO_2NR^2R^{2a}$;

A is selected from one of the following carbocyclic and heterocyclic systems which are substituted with 0–2 $R^4$;

phenyl, pyridyl, and pyrimidyl;

B is selected from: Y and X—Y;

X is selected from —$C(O)$— and O;

Y is $NR^2R^{2a}$, provided that X—Y do not form a O—N bond;

alternatively, Y is selected from one of the following carbocyclic and heterocyclic systems which are substituted with 0–2 $R^{4a}$;

phenyl, piperazinyl, pyridyl, pyrimidyl, morpholinyl, pyrrolidinyl, imidazolyl, and 1,2,3-triazolyl;

$R^2$, at each occurrence, is selected from H, $CF_3$, $CH_3$, benzyl, and phenyl;

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^{2a}$ combine to form a ring system selected from pyrrolidinyl, piperazinyl and morpholino;

$R^4$, at each occurrence, is selected from Cl, F, $CH_3$, $NR^2R^{2a}$, and $CF_3$;

$R^{4a}$, at each occurrence, is selected from Cl, F, $CH_3$, $CH_2NR^2R^{2a}$, $SO_2NR^2R^{2a}$, $S(O)_pR^5$, and $CF_3$;

$R^5$, at each occurrence, is selected from $CF_3$ and $CH_3$;

$R^7$, at each occurrence, is selected from H, $CH_3$, and $CH_2CH_3$; and, $R^8$, at each occurrence, is selected from H and $CH_3$.

13. A compound according to claim 1, wherein the compound is selected from:

3-Methyl-1-(2-aminomethyl-4-methoxyphenyl)-1H-pyrazole-5-(N-(2'-sulfamido-[1,1']-biphen-4-yl))carboxyamide;

3-Ethyl-1-(2-aminomethyl-4-methoxyphenyl)-1H-pyrazole-5-(N-(2'-sulfamido-[1,1']-biphen-4-yl))carboxyamide;

3-Trifluoromethyl-1-(2-aminomethyl-4-methoxyphenyl)-1H-pyrazole-5-(N-(2'-sulfamido-[1,1']-biphen-4-yl))carboxyamide;

3-Methyl-1-(2-N-methylaminomethyl-4-methoxyphenyl)-1H-pyrazole-5-(N-(2'-sulfamido-[1,1']-biphen-4-yl))carboxyamide;

3-Ethyl-1-(2-N-methylaminomethyl-4-methoxyphenyl)-1H-pyrazole-5-(N-(2'-sulfamido-[1,1']-biphen-4-yl))carboxyamide;

3-Trifluoromethyl-1-(2-N-methylaminomethyl-4-methoxyphenyl)-1H-pyrazole-5-(N-(2'-sulfamido-[1,1']-biphen-4-yl))carboxyamide;

3-Methyl-1-(2-aminomethyl-4-methoxyphenyl)-1H-pyrazole-5-(N-(2'-methylsulfonyl-[1,1']-biphen-4-yl))carboxyamide;

3-Ethyl-1-(2-aminomethyl-4-methoxyphenyl)-1H-pyrazole-5-(N-(2'-methylsulfonyl-[1,1']-biphen-4-yl))carboxyamide;

3-Trifluoromethyl-1-(2-aminomethyl-4-methoxyphenyl)-1H-pyrazole-5-(N-(2'-methylsulfonyl-[1,1']-biphen-4-yl))carboxyamide;

3-Methyl-1-(2-N-methylaminomethyl-4-methoxyphenyl)-1H-pyrazole-5-(N-(2'-methylsulfonyl-[1,1']-biphen-4-yl))carboxyamide;

3-Ethyl-1-(2-N-methylaminomethyl-4-methoxyphenyl)-1H-pyrazole-5-(N-(2'-methylsulfonyl-[1,1']-biphen-4-yl))carboxyamide;

3-Trifluoromethyl-1-(2-N-methylaminomethyl-4-methoxyphenyl)-1H-pyrazole-5-(N-(2'-methylsulfonyl-[1,1']-biphen-4-yl))carboxyamide;

3-Methyl-1-(2-aminomethyl-4-methoxyphenyl)-1H-pyrazole-5-(N-(3-fluoro-2'-sulfamido-[1,1']-biphen-4-yl))carboxyamide;

3-Ethyl-1-(2-aminomethyl-4-methoxyphenyl)-1H-pyrazole-5-(N-(3-fluoro-2'-sulfamido-[1,1']-biphen-4-yl))carboxyamide;

3-Trifluoromethyl-1-(2-aminomethyl-4-methoxyphenyl)-1H-pyrazole-5-(N-(3-fluoro-2'-sulfamido-[1,1']-biphen-4-yl))carboxyamide;

3-Methyl-1-(2-N-methylaminomethyl-4-methoxyphenyl)-1H-pyrazole-5-(N-(3-fluoro-2'-sulfamido-[1,1']-biphen-4-yl))carboxyamide;

3-Ethyl-1-(2-N-methylaminomethyl-4-methoxyphenyl)-1H-pyrazole-5-(N-(3-fluoro-2'-sulfamido-[1,1']-biphen-4-yl))carboxyamide;

3-Trifluoromethyl-1-(2-N-methylaminomethyl-4-methoxyphenyl)-1H-pyrazole-5-(N-(3-fluoro-2'-sulfamido-[1,1']-biphen-4-yl))carboxyamide;

3-Methyl-1-(2-aminomethyl-4-methoxyphenyl)-1H-pyrazole-5-(N-(3-fluoro-2'-methylsulfonyl-[1,1']-biphen-4-yl))carboxyamide;

3-Ethyl-1-(2-aminomethyl-4-methoxyphenyl)-1H-pyrazole-5-(N-(3-fluoro-2'-methylsulfonyl-[1,1']-biphen-4-yl))carboxyamide;

3-Trifluoromethyl-1-(2-aminomethyl-4-methoxyphenyl)-1H-pyrazole-5-(N-(3-fluoro-2'-methylsulfonyl-[1,1']-biphen-4-yl))carboxyamide;

3-Methyl-1-(2-N-methylaminomethyl-4-methoxyphenyl)-1H-pyrazole-5-(N-(3-fluoro-2'-methylsulfonyl-[1,1']-biphen-4-yl))carboxyamide;

3-Ethyl-1-(2-N-methylaminomethyl-4-methoxyphenyl)-1H-pyrazole-5-(N-(3-fluoro-2'-methylsulfonyl-[1,1']-biphen-4-yl))carboxyamide;

3-Trifluoromethyl-1-(2-N-methylaminomethyl-4-methoxyphenyl)-1H-pyrazole-5-(N-(3-fluoro-2'-methylsulfonyl-[1,1']-biphen-4-yl))carboxyamide;

3-Methyl-1-(2-aminomethyl-4-methoxyphenyl)-1H-pyrazole-5-(N-(4-(1-pyrrolidinocarbonyl)phenyl)carboxyamide;

3-Ethyl-1-(2-aminomethyl-4-methoxyphenyl)-1H-pyrazole-5-(N-(4-(1-pyrrolidinocarbonyl)phenyl)carboxyamide;

3-Trifluoromethyl-1-(2-aminomethyl-4-methoxyphenyl)-1H-pyrazole-5-(N-(4-(1-pyrrolidinocarbonyl)phenyl)carboxyamide;

3-Methyl-1-(2-N-methylaminomethyl-4-methoxyphenyl)-1H-pyrazole-5-(N-(4-(1-pyrrolidinocarbonyl)phenyl)carboxyamide;

3-Ethyl-1-(2-N-methylaminomethyl-4-methoxyphenyl)-1H-pyrazole-5-(N-(4-(1-pyrrolidinocarbonyl)phenyl)carboxyamide;

3-Trifluoromethyl-1-(2-N-methylaminomethyl-4-methoxyphenyl)-1H-pyrazole-5-(N-(4-(1-pyrrolidinocarbonyl)phenyl)carboxyamide;

3-Methyl-1-(2-aminomethyl-4-methoxyphenyl)-1H-pyrazole-5-(N-(2-fluoro-4-(1-pyrrolidinocarbonyl)phenyl)carboxyamide;

3-Ethyl-1-(2-aminomethyl-4-methoxyphenyl)-1H-pyrazole-5-(N-(2-fluoro-4-(1-pyrrolidinocarbonyl)phenyl)carboxyamide;

3-Trifluoromethyl-1-(2-aminomethyl-4-methoxyphenyl)-1H-pyrazole-5-(N-(2-fluoro-4-(1-pyrrolidinocarbonyl)phenyl)carboxyamide;

3-Methyl-1-(2-N-methylaminomethyl-4-methoxyphenyl)-1H-pyrazole-5-(N-(2-fluoro-4-(1-pyrrolidinocarbonyl)phenyl)carboxyamide;

3-Ethyl-1-(2-N-methylaminomethyl-4-methoxyphenyl)-1H-pyrazole-5-(N-(2-fluoro-4-(1-pyrrolidinocarbonyl)phenyl)carboxyamide;

3-Trifluoromethyl-1-(2-N-methylaminomethyl-4-methoxyphenyl)-1H-pyrazole-5-(N-(2-fluoro-4-(1-pyrrolidinocarbonyl)phenyl)carboxyamide;

3-Methyl-1-(2-aminomethyl-4-methoxyphenyl)-1H-pyrazole-5-(N-(5-((2-sulfamido)phenyl)pyridin-2-yl)carboxyamide;

3-Ethyl-1-(2-aminomethyl-4-methoxyphenyl)-1H-pyrazole-5-(N-(5-((2-sulfamido)phenyl)pyridin-2-yl)carboxyamide;

3-Trifluoromethyl-1-(2-aminomethyl-4-methoxyphenyl)-1H-pyrazole-5-(N-(5-((2-sulfamido)phenyl)pyridin-2-yl)carboxyamide;

3-Methyl-1-(2-N-methylaminomethyl-4-methoxyphenyl)-1H-pyrazole-5-(N-(5-((2-sulfamido)phenyl)pyridin-2-yl)carboxyamide;

3-Ethyl-1-(2-N-methylaminomethyl-4-methoxyphenyl)-1H-pyrazole-5-(N-(5-((2-sulfamido)phenyl)pyridin-2-yl)carboxyamide;

3-Trifluoromethyl-1-(2-N-methylaminomethyl-4-methoxyphenyl)-1H-pyrazole-5-(N-(5-((2-sulfamido)phenyl)pyridin-2-yl)carboxyamide;
3-Methyl-1-(2-aminomethyl-4-methoxyphenyl)-1H-pyrazole-5-(N-(5-((2-methylsulphonyl)phenyl)pyridin-2-yl)carboxyamide;
3-Ethyl-1-(2-aminomethyl-4-methoxyphenyl)-1H-pyrazole-5-(N-(5-(2-methylsulphonyl)phenyl)pyridin-2-yl)carboxyamide;
3-Trifluoromethyl-1-(2-aminomethyl-4-methoxyphenyl)-1H-pyrazole-5-(N-(5-((2-methylsulphonyl)phenyl)pyridin-2-yl)carboxyamide;
3-Methyl-1-(2-N-methylaminomethyl-4-methoxyphenyl)-1H-pyrazole-5-(N-(5-((2-methylsulphonyl)phenyl)pyridin-2-yl)carboxyamide;
3-Ethyl-1-(2-N-methylaminomethyl-4-methoxyphenyl)-1H-pyrazole-5-(N-(5-((2-methylsulphonyl)phenyl)pyridin-2-yl)carboxyamide;
3-Trifluoromethyl-1-(2-N-methylaminomethyl-4-methoxyphenyl)-1H-pyrazole-5-(N-(5-((2-methylsulphonyl)phenyl)pyridin-2-yl) carboxyamide;
3-Methyl-1-(2-aminomethyl-4-methoxyphenyl)-1H-pyrazole-5-(N-(5-((2-sulfamido)phenyl)pyrimidin-2-yl)carboxyamide;
3-Ethyl-1-(2-aminomethyl-4-methoxyphenyl)-1H-pyrazole-5-(N-(5-((2-sulfamido)phenyl)pyrimidin-2-yl)carboxyamide;
3-Trifluoromethyl-1-(2-aminomethyl-4-methoxyphenyl)-1H-pyrazole-5-(N-(5-((2-sulfamido)phenyl)pyrimidin-2-yl)carboxyamide;
3-Methyl-1-(2-N-methylaminomethyl-4-methoxyphenyl)-1H-pyrazole-5-(N-(5-((2-sulfamido)phenyl)pyrimidin-2-yl)carboxyamide;
3-Ethyl-1-(2-N-methylaminomethyl-4-methoxyphenyl)-1H-pyrazole-5-(N-(5-((2-sulfamido)phenyl)pyrimidin-2-yl)carboxyamide;
3-Trifluoromethyl-1-(2-N-methylaminomethyl-4-methoxyphenyl)-1H-pyrazole-5-(N-(5-((2-sulfamido)phenyl)pyrimidin-2-yl)carboxyamide;
3-Methyl-1-(2-aminomethyl-4-methoxyphenyl)-1H-pyrazole-5-(N-(5-((2-methylsulphonyl)phenyl)pyrimidin-2-yl)carboxyamide;
3-Ethyl-1-(2-aminomethyl-4-methoxyphenyl)-1H-pyrazole-5-(N-(5-(2-methylsulphonyl)phenyl)pyrimidin-2-yl)carboxyamide;
3-Trifluoromethyl-1-(2-aminomethyl-4-methoxyphenyl)-1H-pyrazole-5-(N-(5-((2-methylsulphonyl)phenyl)pyrimidin-2-yl)carboxyamide;
3-Methyl-1-(2-N-methylaminomethyl-4-methoxyphenyl)-1H-pyrazole-5-(N-(5-((2-methylsulphonyl)phenyl)pyrimidin-2-yl)carboxyamide;
3-Ethyl-1-(2-N-methylaminomethyl-4-methoxyphenyl)-1H-pyrazole-5-(N-(5-((2-methylsulphonyl)phenyl)pyrimidin-2-yl)carboxyamide;
3-Trifluoromethyl-1-(2-N-methylaminomethyl-4-methoxyphenyl)-1H-pyrazole-5-(N-(5-((2-methylsulphonyl)phenyl)pyrimidin-2-yl)carboxyamide;
3-Methyl-1-(2-aminomethyl-4-methoxyphenyl)-1H-pyrazole-5-(N-(4-((2-methyl)imidazo-1-yl)phenyl)carboxyamide;
3-Ethyl-1-(2-aminomethyl-4-methoxyphenyl)-1H-pyrazole-5-(N-(4-((2-methyl)imidazo-1-yl)phenyl)carboxyamide;
3-Trifluoromethyl-1-(2-aminomethyl-4-methoxyphenyl)-1H-pyrazole-5-(N-(4-((2-methyl)imidazo-1-yl)phenyl)carboxyamide;
3-Methyl-1-(2-N-methylaminomethyl-4-methoxyphenyl)-1H-pyrazole-5-(N-(4-((2-methyl)imidazo-1-yl)phenyl)carboxyamide;
3-Ethyl-1-(2-N-methylaminomethyl-4-methoxyphenyl)-1H-pyrazole-5-(N-(4-((2-methyl)imidazo-1-yl)phenyl)carboxyamide;
3-Trifluoromethyl-1-(2-N-methylaminomethyl-4-methoxyphenyl)-1H-pyrazole-5-(N-(4-((2-methyl)imidazo-1-yl)phenyl)carboxyamide;
3-Methyl-1-(2-aminomethyl-4-methoxyphenyl)-1H-pyrazole-5-(N-(4-((5-methyl)imidazo-1-yl)phenyl)carboxyamide;
3-Ethyl-1-(2-aminomethyl-4-methoxyphenyl)-1H-pyrazole-5-(N-(4-((5-methyl)imidazo-1-yl)phenyl)carboxyamide;
3-Trifluoromethyl-1-(2-aminomethyl-4-methoxyphenyl)-1H-pyrazole-5-(N-(4-((5-methyl)imidazo-1-yl)phenyl)carboxyamide;
3-Methyl-1-(2-N-methylaminomethyl-4-methoxyphenyl)-1H-pyrazole-5-(N-(4-((5-methyl)imidazo-1-yl)phenyl)carboxyamide;
3-Ethyl-1-(2-N-methylaminomethyl-4-methoxyphenyl)-1H-pyrazole-5-(N-(4-((5-methyl)imidazo-1-yl)phenyl)carboxyamide;
3-Trifluoromethyl-1-(2-N-methylaminomethyl-4-methoxyphenyl)-1H-pyrazole-5-(N-(4-((5-methyl)imidazo-1-yl)phenyl)carboxyamide;
3-Methyl-1-(2-aminomethyl-4-methoxyphenyl)-1H-pyrazole-5-(N-(2-fluoro-4-((2-methyl)imidazo-1-yl)phenyl)carboxyamide;
3-Ethyl-1-(2-aminomethyl-4-methoxyphenyl)-1H-pyrazole-5-(N-(2-fluoro-4-((2-methyl)imidazo-1-yl)phenyl)carboxyamide;
3-Trifluoromethyl-1-(2-aminomethyl-4-methoxyphenyl)-1H-pyrazole-5-(N-(2-fluoro-4-((2-methyl)imidazo-1-yl)phenyl)carboxyamide;
3-Methyl-1-(2-N-methylaminomethyl-4-methoxyphenyl)-1H-pyrazole-5-(N-(2-fluoro-4-((2-methyl)imidazo-1-yl)phenyl)carboxyamide;
3-Ethyl-1-(2-N-methylaminomethyl-4-methoxyphenyl)-1H-pyrazole-5-(N-(2-fluoro-4-((2-methyl)imidazo-1-yl )phenyl)carboxyamide;
3-Trifluoromethyl-1-(2-N-methylaminomethyl-4-methoxyphenyl)-1H-pyrazole-5-(N-(2-fluoro-4-((2-methyl)imidazo-1-yl)phenyl)carboxyamide;
3-Methyl-1-(2-aminomethyl-4-methoxyphenyl)-1H-pyrazole-5-(N-(2-fluoro-4-((5-methyl)imidazo-1-yl)phenyl)carboxyamide;
3-Ethyl-1-(2-aminomethyl-4-methoxyphenyl)-1H-pyrazole-5-(N-(2-fluoro-4-((5-methyl)imidazo-1-yl)phenyl)carboxyamide;
3-Trifluoromethyl-1-(2-aminomethyl-4-methoxyphenyl)-1H-pyrazole-5-(N-(2-fluoro-4-((5-methyl)imidazo-1-yl)phenyl)carboxyamide;
3-Methyl-1-(2-N-methylaminomethyl-4-methoxyphenyl)-1H-pyrazole-5-(N-(2-fluoro-4-((5-methyl)imidazo-1-yl)phenyl)carboxyamide;
3-Ethyl-1-(2-N-methylaminomethyl-4-methoxyphenyl)-1H-pyrazole-5-(N-(2-fluoro-4-((5-methyl)imidazo-1-yl)phenyl)carboxyamide; and,
3-Trifluoromethyl-1-(2-N-methylaminomethyl-4-methoxyphenyl)-1H-pyrazole-5-(N-(2-fluoro-4-((5-methyl)imidazo-1-yl)phenyl)carboxyamide;
and pharmaceutically acceptable salts thereof.

14. A compound according to claim 1, wherein the compound is selected from:
3-Methyl-1-(2-aminomethyl-4-methoxyphenyl)-1H-pyrazole-5-(N-(2'-sulfamido-[1,1']-biphen-4-yl))carboxyamnide;
5-Methyl-1-(2-aminomethyl-4-methoxyphenyl)-1H-pyrazole-3-(N-(2'-sulfamido-[1,1']-biphen-4-yl))carboxyamide;

3-Methyl-1-(2-N,N-dimethylaminomethyl-4-methoxyphenyl)-1H-pyrazole-5-(N-(2'-N-methylsulfamido-[1,1']-biphen-4-yl))carboxyamide;
3-Trifluoromethyl-1-(2-aminomethyl-4-methoxyphenyl)-1H-pyrazole-5-(N-(3-fluoro-2'-sulfamido-[1,1]-biphen-4-yl))carboxyamide;
3-Trifluoromethyl-1-(2-aminomethyl-4-methoxyphenyl)-1H-pyrazole-5-(N-(3-fluoro-2'-methylsulfonyl-[1,1]-biphen-4-yl))carboxyamide;
3-Trifluoromethyl-1-(2-aminomethyl-4-methoxyphenyl)-1H-pyrazole-5-(N-(2'-methylsulfonyl-[1,1]-biphen-4-yl))carboxyamide;
3-Trifluoromethyl-1-(2-aminomethyl-4-methoxyphenyl)-1H-pyrazole-5-(N-(2'-sulfamido-[1,1]-biphen-4-yl))carboxyamide;
3-Trifluoromethyl-1-(2-aminomethyl-4-methoxyphenyl)-1H-pyrazole-5-(N-(4-N-pyrrolidinocarbonyl)phenyl)carboxyamide;
N-Benzylsulfonyl-4-(3-trifluoromethyl-1-(2-aminomethyl-4-methoxyphenyl)-1H-pyrazole-5-carboxyamido)piperidine;
3-Trifluoromethyl-1-(2-aminomethyl-4-metboxyphenyl)-1H-pyrazole-5-(N-(5-(2'-sulfonamido)phenyl)pyrid-2-yl)carboxyamide;
3-Trifluoromethyl-1-(2-aminomethyl-4-methoxyphenyl)-1H-pyrazole-5-(N-(5-(pyrid-2-yl))pyrid-2-yl)carboxyamide;
N-Benzyl-4-(3-trifluoromethyl-1-(2-aminomethyl-4-methoxyphenyl)-1H-pyrazole-5-carboxyamido)piperidine;
N-Phenylsulfonyl-4-(3-trifluoromethyl-1-(2-aminomethyl-4-methoxyphenyl)-1H-pyrazole-5-carboxyamido)piperidine;
3-Trifluoromethyl-1-(2-aminomethyl-4-chlorophenyl)-1H-pyrazole-5-(N-(3-fluoro-2'-methylsulfonyl-[1,1']-biphen-4-yl))carboxyamide;
3-Trifluoromethyl-1-(2-aminomethyl-4-chlorophenyl)-1H-pyrazole-5-(N-(3-fluoro-2'-sulfamido[1,1']-biphen-4-yl))carboxyamide;
3-Trifluoromethyl-1-(2-aminomethyl-5chlorophenyl)-1H-pyrazole-5-(N-(3-fluoro-2'-methylsulfonyl-[1,1']-biphen-4-yl))carboxyamide;
3-Trifluoromethyl-1-(2-aminomethyl-4-chlorophenyl)-1H-pyrazole-5-(N-(3-fluoro-2'-sulfamido-[1,1']-biphen-4-yl))carboxyamide;
3-Trifluoromethyl-1-(2-aminomethyl-4-fluorophenyl)-1H-pyrazole-5-(N-(3-fluoro-2'-methylsulfonyl-[1,1']-biphen-4-yl))carboxyamide;
3-Trifluoromethyl-1-(2-aminomethyl-1-fluorophenyl)-1H-pyrazole-5-(N-(3-fluoro-2'-sulfamido-[1,1']-biphen-4-yl))carboxyamide;
3-Trifluoromethyl-1-(2-aminomethyl-5-fluorophenyl)-1H-pyrazole-5-(N-(3-fluoro-2'-methylsulfonyl-[1,1']-biphen-4-yl))carboxyamide;
3-Trifluoromethyl-1-(2-aminomethyl-5-fluorophenyl)-1H-pyrazole-5-(N-(3-fluoro-2'-sulfaniido-[1,1']-biphen-4-yl))carboxyamide;
3-Trifluoromethyl-1-(2-aminomethyl-4,5-difluorophenyl)-1H-pyrazole-5-(N-(3-fluoro-2'-methylsulfonyl-[1,1']-biphen-4-yl))carboxyamide;
3-Trifluoromethyl-1-(2-aminomethyl-4,5-difluorophenyl)-1H-pyrazole-5-(N-(3-fluoro-2'-sulfamido-[1,1']-biphen-4-yl))carboxyamide;
3-Trifluoromethyl-1-(2-aminomethyl-3-fluorophenyl)-1H-pyrazole-5-(N-(3-fluoro-2'-methylsulfonyl-[1,1']-biphen-4fyl))carboxyamide;
3-Trifluoromethyl-1-(2-aminomethyl-3-fluorophenyl)-1H-pyrazole-5-(N-(3-fluoro-2'-sulfamido[1,1']-biphen-4-yl))carboxyamide;
3-Trifluoromethyl-1-(2-aminomethyl-4-fluorophenyl)-1H-pyrazole-5-(N-(4-(2-methylsulfonyl-[1,1']-biphen-4-yl))carboxyamide;
3-Trifluorornethyl-1-(2-aminomethyl-4-fluorophenyl)-1H-pyrazole-5-(N-(4-(2-sulfamido-[1,1']-biphen-4-yl))carboxyamide;
3-Trifluoromethyl-1-(2-aminomethyl-4-fluorophenyl)-1H-pyrazole-5-(N-(4-(N-((N'-methylsulfonyl)imninoly)pyrrolidino))phenyl)carboxyamide;
3-Trifluoromethyl-1-(2-(N-glycyl)aminomethyl-4-methoxyphenyl)-1H-pyrazole-5-(N-(3-fluoro-2'-methylsulfonyl-[1,1']-biphen-4-yl))carboxyamide;
3-Trifluoromethyl-1-(2-(N-phenylacetyl)aminomethyl-4-methoxyphenyl)-1H-pyrazole-5-(N-(3-fluoro-2'-methylsulfonyl-[1,1']-biphen-4-yl))carboxyamide;
3-(Trifluoromethyl)-1-(2-(aminomethyl)phenyl)-1H-pyrazole-5-(N-(2'-methylsulfonyl-[1,1']-biphen-4-yl))carboxyamide;
3-Trifluoromethyl-1-(2-(aminomethyl)phenyl)-1H-pyrazole-5-(N-(2'-aminosulfonyl-[1,1']-biphen-4-yl))carboxyamide;
3-Trifluoromethyl-1-(2-(aminomethyl)phenyl)-1H-pyrazole-5-(N-(3-fluoro-2'-aminosulfonyl-[1,1']-biphen-4-yl))carboxyamide;
3-Trifluoromethyl-1-(2-(aminomethyl)phenyl)-1H-pyrazole-5-(N-(3-fluoro-2'-methylsulfonyl-[1,1']-biphen-4-yl)carboxyamide;
3-Trifluoromethyl-1-(2-(N-(glycyl)aminomethyl)phenyl)-1H-pyrazole-5-(N-(3-fluoro-2'-methylsulfonyl-[1,1']-biphen-4-yl))carboxyamide;
3-Trifluoromethyl-1-(2-((N-(N-methylglycyl)aminomethyl)phenyl)-1H-pyrazole-5-(N-(3-fluoro-2'-methylsulfonyl-[1,1']-biphen-4-yl))carboxyamide;
3-Trifluoromethyl-1-(2-carboxamidophenyl)-1H-pyrazole-5-(N-(3-fluoro-2'-methylsulfonyl-[1,1']-biphen-4-yl))carboxyamide;
3-Trifluoromethyl-1-(2-cyanophenyl)-1H-pyrazole-5-(N-(3-fluoro-2'-methylsulfonyl-[1,1']-biphen-4-yl))carboxyamide;
1-[2-(Aminomethyl)phenyl]-3-thiomethoxy-5-[(2-fluoro)-(2'-methylsulfonyl-[1,1']-biphen-4-yl)aminocarbonyl]pyrazole;
1-[2-(Aminomethyl)phenyl]-3-methysulfonyl-5-[(2-fluoro)-(2'-methylsulfonyl-[1,1']-biphen-4-yl)aminocarbonyl]pyrazole;
1-[2-(Aminomethyl)phenyl]-5-[(2-fluoro)-(2'-methylsulfonyl-[1,1']-biphen-4-yl)aminocarbonyl]pyrazole;
1-[2-(Aminomethyl)phenyl]-3-trifluoromethyl-5-[((2-fluoro)-(2'-pyrrolidinomethyl)-[1,1']-biphen-4-yl)aminocarbonyl]pyrazole; and,
1-[2-(Aminomethyl)phenyl]-3-trifluoromethyl-5-[((2-fluoro)-(2'-hydroxymethyl)-[1,1']-biphen-4-yl)aminocarbonyl]pyrazole;
and pharmaceutically acceptable salts thereof.

15. A pharmaceutical composition, comprising: a pharmaceutically acceptable carrier and a therapeutically effective amount of a compound according to claim 1 or a pharmaceutically acceptable salt thereof.

16. A pharmaceutical composition, comprising: a pharmaceutically acceptable carrier and a therapeutically effective amount of a compound according to claim 2 or a pharmaceutically acceptable salt thereof.

17. A pharmaceutical composition, comprising: a pharmaceutically acceptable carrier and a therapeutically effective amount of a compound according to claim 3 or a pharmaceutically acceptable salt thereof.

18. A pharmaceutical composition, comprising: a pharmaceutically acceptable carrier and a therapeutically effective amount of a compound according to claim 4 or a pharmaceutically acceptable salt thereof.

19. A pharmaceutical composition, comprising: a pharmaceutically acceptable carrier and a therapeutically effective amount of a compound according to claim 5 or a pharmaceutically acceptable salt thereof.

20. A pharmaceutical composition, comprising: a pharmaceutically acceptable carrier and a therapeutically effective amount of a compound according to claim 6 or a pharmaceutically acceptable salt thereof.

21. A pharmaceutical composition, comprising: a pharmaceutically acceptable carrier and a therapeutically effective amount of a compound according to claim 7 or a pharmaceutically acceptable salt thereof.

22. A pharmaceutical composition, comprising: a pharmaceutically acceptable carrier and a therapeutically effective amount of a compound according to claim 8 or a pharmaceutically acceptable salt thereof.

23. A pharmaceutical composition, comprising: a pharmaceutically acceptable carrier and a therapeutically effective amount of a compound according to claim 9 or a pharmaceutically acceptable salt thereof.

24. A pharmaceutical composition, comprising: a pharmaceutically acceptable carrier and a therapeutically effective amount of a compound according to claim 10 or a pharmaceutically acceptable salt thereof.

25. A pharmaceutical composition, comprising: a pharmaceutically acceptable carrier and a therapeutically effective amount of a compound according to claim 11 or a pharmaceutically acceptable salt thereof.

26. A pharmaceutical composition, comprising: a pharmaceutically acceptable canier and a therapeutically effective amount of a compound according to claim 12 or a pharmaceutically acceptable salt thereof.

27. A pharmaceutical composition, comprising: a pharmaceutically acceptable carier and a therapeutically effective amount of a compound according to claim 13 or a pharmaceutically acceptable salt thereof.

28. A pharmaceutical composition, comprising: a pharmaceutically acceptable carrier and a therapeutically effective amount of a compound according to claim 14 or a pharmaceutically acceptable salt thereof.

29. A method for treating a thromboembolic disorder, comprising: administering to a patient in need thereof a therapeutically effective amount of a compound according to claim 1 or a pharmaceutically acceptable salt thereof.

30. A method for treating a thromboembolic disorder, comprising: administering to a patient in need thereof a therapeutically effective amount of a compound according to claim 2 or a pharmaceutically acceptable salt thereof.

31. A method for treating a thromboembolic disorder, comprising: administering to a patient in need thereof a therapeutically effective amount of a compound according to claim 3 or a pharmaceutically acceptable salt thereof.

32. A method for treating a thromboembolic disorder, comprising: administering to a patient in need thereof a therapeutically effective amount of a compound according to claim 4 or a pharmaceutically acceptable salt thereof.

33. A method for treating a thromboembolic disorder, comprising: administering to a patient in need thereof a therapeutically effective amount of a compound according to claim 5 or a pharmaceutically acceptable salt thereof.

34. A method for treating a thromboembolic disorder, comprising: administering to a patient in need thereof a therapeutically effective amount of a compound according to claim 6 or a pharmaceutically acceptable salt thereof.

35. A method for treating a thromboembolic disorder, comprising: administering to a patient in need thereof a therapeutically effective amount of a compound according to claim 7 or a pharmaceutically acceptable salt thereof.

36. A method for treating a thromboembolic disorder, comprising: administering to a patient in need thereof a therapeutically effective amount of a compound according to claim 8 or a pharmaceutically acceptable salt thereof.

37. A method for treating a thromboembolic disorder, comprising: administering to a patient in need thereof a therapeutically effective amount of a compound according to claim 9 or a pharmaceutically acceptable salt thereof.

38. A method for treating a thromboembolic disorder, comprising: administering to a patient in need thereof a therapeutically effective amount of a compound according to claim 10 or a pharmaceutically acceptable salt thereof.

39. A method for treating a thromboembolic disorder, comprising: administering to a patient in need thereof a therapeutically effective amount of a compound according to claim 11 or a pharmaceutically acceptable salt thereof.

40. A method for treating a thromboembolic disorder, comprising: administering to a patient in need thereof a therapeutically effective amount of a compound according to claim 12 or a pharmaceutically acceptable salt thereof.

41. A method for treating a thromboembolic disorder, comprising: administering to a patient in need thereof a therapeutically effective amount of a compound according to claim 13 or a pharmaceutically acceptable salt thereof.

42. A method for treating a thromboembolic disorder, comprising: administering to a patient in need thereof a therapeutically effective amount of a compound according to claim 14 or a pharmaceutically acceptable salt thereof.

* * * * *